US012590322B2

(12) United States Patent
Wu et al.

(10) Patent No.: US 12,590,322 B2
(45) **Date of Patent: \*Mar. 31, 2026**

(54) DEVICES AND METHODS FOR MITOCHONDRIA REPLACEMENT AND FOR GENERATING CELLULAR THERAPEUTICS

(71) Applicant: NanoCav, LLC, Culver City, CA (US)

(72) Inventors: Ting-Hsiang Sherry Wu, Culver City, CA (US); Artin Mehrabi, Burbank, CA (US); Jon Thomas Van Lew, Los Angeles, CA (US)

(73) Assignee: NanoCav, LLC, Culver City, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 18/117,915

(22) Filed: Mar. 6, 2023

(65) Prior Publication Data

US 2023/0304043 A1     Sep. 28, 2023

Related U.S. Application Data

(63) Continuation of application No. 16/517,017, filed on Jul. 19, 2019, now Pat. No. 11,639,510.

(60) Provisional application No. 62/700,649, filed on Jul. 19, 2018.

(51) Int. Cl.
| | |
|---|---|
| *C12N 15/87* | (2006.01) |
| *B01L 3/00* | (2006.01) |
| *C12N 5/0775* | (2010.01) |

(52) U.S. Cl.
CPC ........ *C12N 15/87* (2013.01); *B01L 3/502715* (2013.01); *B01L 3/50273* (2013.01); *C12N 5/0662* (2013.01); *B01L 2300/041* (2013.01); *B01L 2300/06* (2013.01); *B01L 2400/0481* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 5,586,982 | A | 12/1996 | Abela |
| 10,081,816 | B1 | 9/2018 | Wu |
| 2017/0037357 | A1 | 2/2017 | Cattaruzzi et al. |
| 2017/0175139 | A1 | 6/2017 | Wu et al. |
| 2020/0087685 | A1 | 3/2020 | Wu et al. |

FOREIGN PATENT DOCUMENTS

| | | |
|---|---|---|
| WO | WO-2015148842 A1 | 10/2015 |
| WO | WO-2016008937 A1 | 1/2016 |

OTHER PUBLICATIONS

Lui et al., Design and Characterization of a Compact Voice Coil for a Needle-free Injection Device (2006), 50 pages (Year: 2006).*

Acin-Perez, R., et al., "Respiratory Complex III Is Required to Maintain Complex I in Mammalian Mitochondria," Molecular Cell, 13: 805-815 (2004).

Benjamini, Y. and Hochberg, Y., "Controlling the False Discovery Rate: A Practical and Powerful Approach to Multiple Testing," Journal of the Royal Statistical Society. Series B (Methodological), 57(1): 289-300 (1995).

Bharathan, S.P., et al., "Systematic evaluation of markers used for the identification of human induced pluripotent stem cells," The Company of Biologists, 6: 100-108 (2017).

Billing, A.M., et al., "Comprehensive transcriptomic and proteomic characterization of human mesenchymal stem cells reveals source specific cellular markers," Scientific Reports v6, p. 21507 (2016).

Brinkmann, C.R., et al., "Mitochondria and the Lectin Pathway of Complement," The Journal of Biological Chemistry, 22(12): 8016-8027 (2013).

Calvo, S.E., et al., "MitoCarta2.0: an updated inventory of mammalian mitochondrial proteins," Nucleic Acids Research, 44: D1251-D1257 (2016).

David, L. and Polo, J.M., "Phases of reprogramming," Stem Cell Research, 12: 754-761 (2014).

Denu, R.A., et al., "Fibroblasts and Mesenchymal Stromal/Stem Cells Are Phenotypically Indistinguishable," Acta Haematol, 136: 85-97 (2016).

Grégoire, M., et al., "On auxotrophy for pyrimidines of respiration-deficient chick embryo cells," Eur. J. Biochem, 142: 49-55 (1984).

Halfon, S., et al., "Markers Distinguishing Mesenchymal Stem Cells from Fibroblasts Are Downregulated with Passaging," Stem Cells and Development, 20(1): 53-66 (2011).

Harrow, J., et al., "GENCODE: The reference human genome annotation for The ENCODE Project," Genome Research, 22: 1760-1774 (2012).

(Continued)

*Primary Examiner* — Evelyn Y Pyla
(74) *Attorney, Agent, or Firm* — Harness Dickey & Pierce P.L.C.

(57) ABSTRACT

Devices and methods are presented for delivery of various macrostructures into cells, such as depleted cells as well as methods of generating engineered cells using said devices and methods. Cells are placed on a porous membrane. A force is applied by a configurable actuator to a deformable fluid reservoir that generates an applied pressure to macrostructures in a solution, causing the macrostructures to pass through the porous membrane and triggering uptake of at least some of the macrostructures into the cells to form transfected cells. Said devices and methods may be used in a process to replace defective endogenous mtDNA with corrected mtDNA to generate cellular-based therapeutics for administration to a patient. The customizable actuator may be configured with parameters to optimize efficiency for a given cell type and material to be transfected. Machine learning techniques also may be utilized to optimize transfection parameters.

10 Claims, 84 Drawing Sheets

Specification includes a Sequence Listing.

(56)          References Cited

OTHER PUBLICATIONS

Hsu, P., et al., "Assessment of the Immunomodulatory Properties of Human Mesenchymal Stem Cells (MSCs)," J. Vis. Exp., 106: e53265 (2015).

Huber, W., et al., "Orchestrating high-throughput genomic analysis with Bioconductor," Nat Methods, 12(2): 115-121 (2015).

Hänzelmann, S., et al., "GSVA: gene set variation analysis for microarray and RNA-Seq data," BMC Bioinformatics, 14: 7 (2013).

Jaiswal, R.K., et al., "Adult Human Mesenchymal Stem Cell Differentiation to the Osteogenic or Adipogenic Lineage Is Reulated by Mitogen-activated protein Kinase*," The Journal of Biological Chemistry, 275(13): 9645-9652 (2000).

Kanehisa, M., et al., "KEGG for integration and interpretation of large-scale molecular data sets," Nucleic Acids Research, 40: D109-D114 (2012).

Kankainen, M., et al., "MPEA-metabolite pathway enrichment analysis," BioInformatics, 27(13): 1878-1879 (2011).

Kenney, M.C., et al., "Inherited mitochondrial DNA variants can affect complement, inflammation and apoptosis pathways: insights into mitochondrial—nuclear interactions," Human Molecular Genetics, 23(13): 3537-3551 (2014).

Kumar, L. and Futschik, M., "Mfuzz: A software package for soft clustering of microarray data," Bioinformation, 2(1): 5-7 (2007).

Latorre-Pellicer, A., et al., "Mitochondrial and nuclear DNA matching shapes metabolism and healthy ageing," Nature, 535: 561-565 (2016).

Levinson, H.J., and Arnold, W.H. (1997). Optical Lithography. In Handbook of Microlithography, Micromachining, and Microfabrication; vol. 1: Microlithography (pp. 13-138). Bellingham, Washington and London, United Kingdom: The International Society for Optical Engineering and The Institution of Electrical Engineers.

Lorenz, C., et al., "Human iPSC-Derived Neural Progenitors Are an Effective Drug Discovery Model for Neurological mtDNA Disorders," Cell Stem Cell, 20: 659-674 (2017).

Love, M., et al., "Moderated estimation of fold change and dispersion for RNA-seq data with DESeq2," Genome Biology, 15: 550 (2014).

Lv, F., et al., "Consise Review: The Surface Markers and Identify of Human Mesenchymal Stem Cells," Stem Cells, 32: 1408-1419 (2014).

Mandal, P.K., and Rossi, D.J., "Reprogramming human fibroblasts to pluripotency using modified mRNA," Nature Protocols, 8(3): 568-582 (2013).

Mercer, T.R., et al., "The Human Mitochondrial Transcriptome," Cell, 146: 645-658 (2011).

Miyata, N., et al., "Pharmacologic rescue of an enzyme-trafficking defect in primary hyperoxaluria 1," PNAS Early Edition, p. 1-6 (2014).

Mudge, J.M. and Harrow, J., "Creating reference gene annotation for the mouse C57BL6/J genome assembly," Mamm Genome, 26: 366-378 (2015).

Nashine, S., et al., "Differential Expression of Complement Markers in Normal and AMD Transmitochondrial Cybrids," PLoS One, 11(8): e0159828 (2016).

Patro, R., et al., "Salmon: fast and bias-aware quantification of transcript expression using dual-phase inference," Nat Methods, 14(4): 417-419 (2017).

Pfeffer, G., et al., "New treatments for mitochondrial disease—no time to drop our standards," Nat Rev Neurol, 9(8): 474-481 (2013).

Ritchie, M.E., et al., "Iimma powers differential expression analyses for RNA-sequencing and microarray studies," Nucleic Acids Research, 43(7): e47 (2015).

Schaefer, A.M., et al., "Prevalence of Mitochondrial DNA Disease in Adults," Ann Neurol, 63: 35-39 (2008).

Sheyn, D., et al., "Human Induced Pluripotent Stem Cells Differentiate Into Functional Mesenchymal Stem Cells and Repair Bone Defects," Stem Cells Translational Medicine, 5: 1447-1460 (2016).

Smith, A.C., and Robinson, A.J., "MitoMiner v3.1, an update on the mitochondrial proteomics database," Nucleic Acids Research, 44: D1258-D1261 (2016).

Soneson, C., et al., "Differential analyses for RNA-seq: transcript-level estimates improve gene-level inferences [version 2; peer review: 2 approved]," F1000Research, 4: 1521 (2016).

Tachibana, M., et al., "Towards germline gene therapy of inherited mitochondrial diseases," Nature, 493(7434): 627-631 (2013).

Takahashi, K., and Yamanaka, S., "Induction of Pluripotent Stem Cells from Mouse Embryonic and Adult Fibroblast Cultures by Defined Factors," Cell, 126: 663-676 (2006).

Venkatesh, S., and Workman, J.L., "Histone exchange, chromatin structure and the regulation of transcription," Nature, 16: 178-189 (2015).

Warren, L., et al., "Highly Efficient Reprogramming to Pluripotency and Directed Differentiation of Human Cells with Synthetic Modified mRNA," Cell Stem Cell, 7: 618-630 (2010).

Wu, T.H., et al., "Mitochondrial Transfer by Photothermal Nanoblade Restores Metabolite Profile in Mammalian Cells," Cell Metabolism, 23: 921-929 (2016).

Xiao, G., et al., "B-Cell-Specific Diversion of Glucose Carbon Utilization Reveals a Unique Vulnerability in B Cell Malignancies," Cell, 173: 470-484 (2018).

Yu, G. and He, Q., "ReactomePA: an R/Bioconductor package for reactome pathway analysis and visualization," Mol. BioSyst., 12: 477-479 (2016).

Yu, G., et al., "clusterProfiler: an R Package for Comparing Biological Themes Among Gene Clusters," Omics, 16(5): 284-287 (2012).

Mombo, B.Z., et al., "MitoCeption: Transferring Isolated Human MSC Mitochondria to Glioblastoma Stem Cells," Journal of Visualized Experiments, 120: e55245 (2017).

McNamara, Jim., "Voice coil actuation technology for medical devices," XP-00795133, Dec. 7, 2016.

Wu, Y.C., et al., "Massively parallel delivery of large cargo into mammalian cells with light pulses," Nature Methods, 12(5), 439-444 (2015).

Caicedo, A., et al., "Artificial Mitochondria Transfer: Current Challenges, Advances, and Future Applications," Stem Cells International, p. 1-23, XP055500942 (2017).

Tachibana, M., et al., "Towards germline gene therapy of inherited mitochondrial diseases," Nature, 493: 627-631 (2013).

Shi, J., et al., "Pressure Regulated Biomolecule Injection Into NIH 3T3 Cells Through Integrated Nano/Mesopores," 14th International Conference on Miniaturized Systems for Chemistry and Life Sciences, 491-493 (2010).

International Search Report from PCT Application No. PCT/US2019/042672 dated Nov. 8, 2019.

Written Opinion from PCT Application No. PCT/US2019/042672 dated Nov. 8, 2019.

R Core Team., Statistical language package Metabolomics data processing, The R Foundation, 2017.

Genome Reference Consortium, "Genome Reference Consortium Human Build 38 patch release 12 (GRCh38.p12)," Dec. 21, 2017.

International Preliminary Report on Patentability issued in PCT Application No. PCT/US2019/042672 dated Sep. 4, 2020.

Office Action from corresponding US Application No. U.S. Appl. No. 16/517,017 dated Aug. 26, 2022.

Examination Report from European Application No. 19749128.5-1118 dated Feb. 17, 2025.

* cited by examiner

Deformable Fluid
Reservoir
120

Top Layer: Pliable to allow sealing
engagement with container wall(s)
with sufficient thickness to contain
macrostructure in fluid Top Layer
121

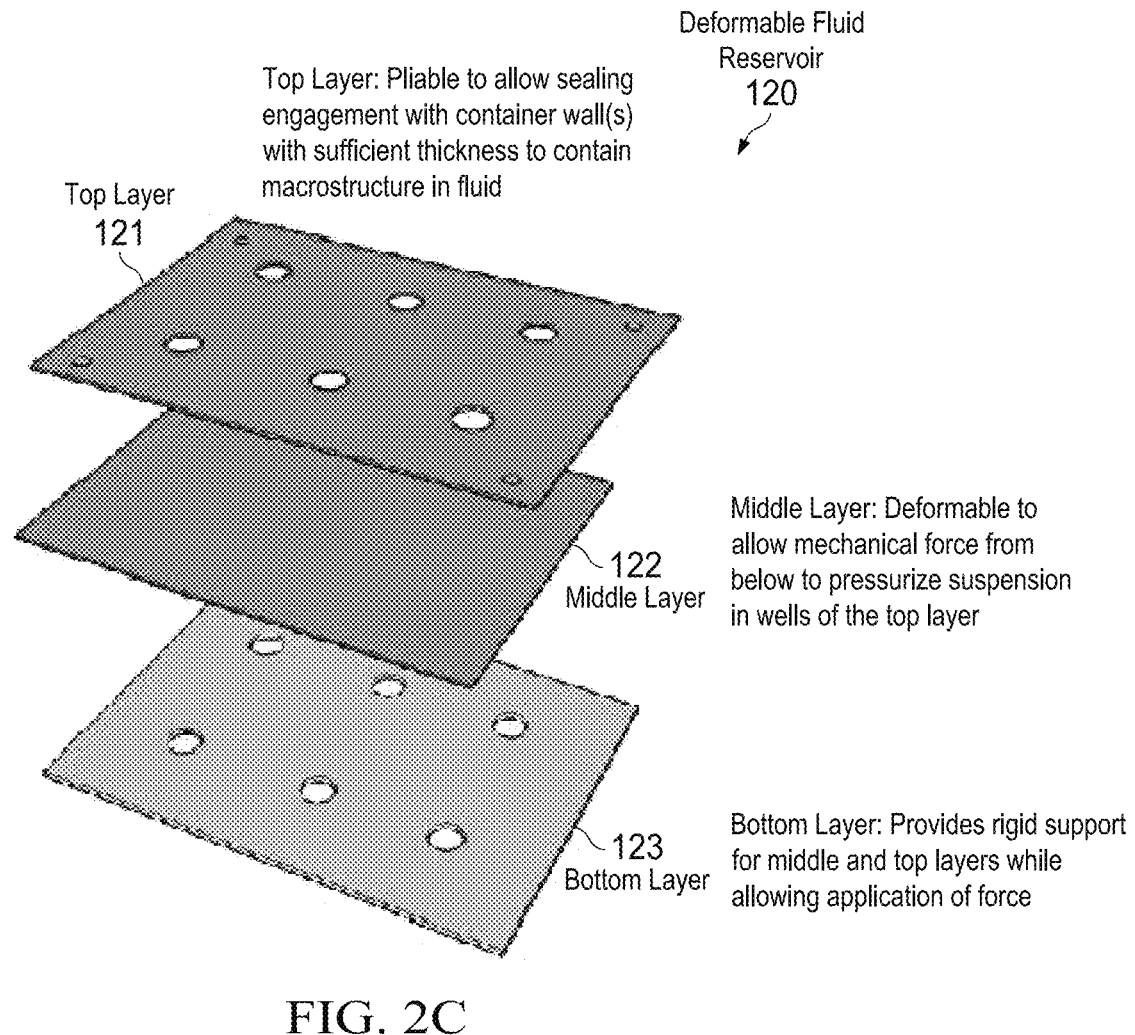

122
Middle Layer

Middle Layer: Deformable to
allow mechanical force from
below to pressurize suspension
in wells of the top layer 123
Bottom Layer Bottom Layer: Provides rigid support
for middle and top layers while
allowing application of force

FIG. 2C

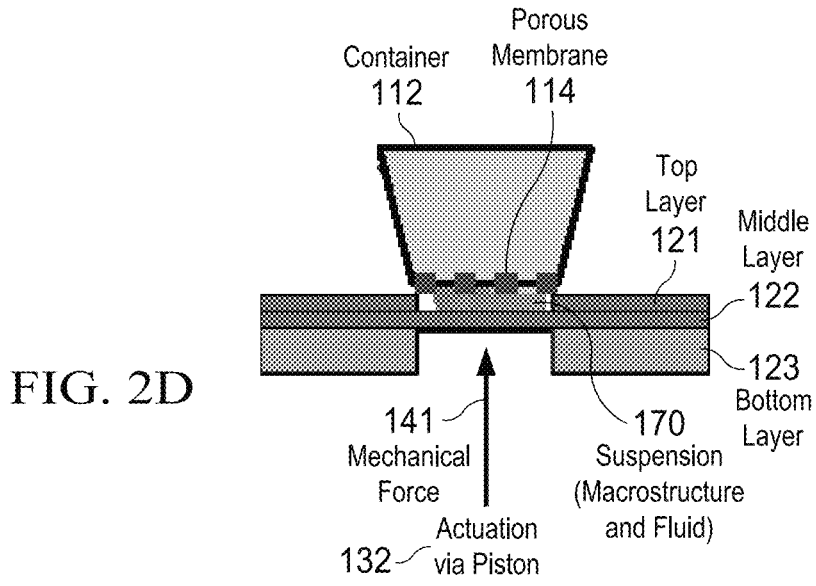

Porous
Container    Membrane
112          114

Top
Layer
121      Middle
        Layer
        122

123
        Bottom
        Layer

FIG. 2D

141
Mechanical
Force

170
Suspension
(Macrostructure
and Fluid)

Actuation
132  via Piston

Single Well Side View of Deformable Fluid Reservoir mtDNA delivery small voice coil actuator mtDNA delivery medium voice coil actuator

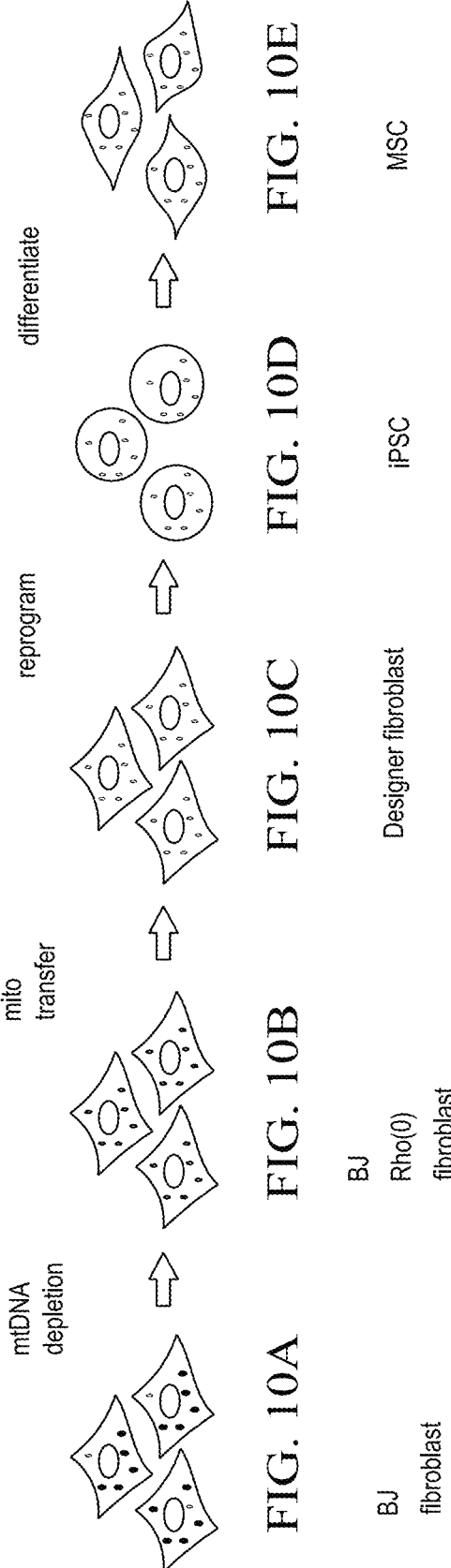

0: 1kb+ Ladder

MITOCHONDRIAL:
1: HDF Adult 5uM ddC, day 0
2: HDF Adult 5uM ddC, day 16
3: HDF Adult 5uM ddC, day 30
4: HDF Neonatal 5uM ddC, Day 0
5: HDF Neonatal 5uM ddC, Day 16
6: HDF Neonatal 5uM ddC, Day 30
7: 143 Rho Null
8: No-Template Control (NTC)

GAPDH:
9: HDF Adult 5uM ddC, day 0
10: HDF Adult 5uM ddC, day 16
11: HDF Adult 5uM ddC, day 30
12: HDF Neonatal 5uM ddC, Day 0
13: HDF Neonatal 5uM ddC, Day 16
14: HDF Neonatal 5uM ddC, Day 30
15: 143 Rho Null
16: No-Template Control (NTC)

|  |  | % GAPDH-Referenced mtDNA after 5uM 2', 3' ddC Treatment | | |
|---|---|---|---|---|
|  | Days from treatment | HDF Adult | HDF Neonatal | 143 Rho Null |
| 21-Apr | Day 0 | 100 | 100 | 0.15027963 |
| 4/21-5/7 | Day 16 | 0.17349223 | 0.009478548 | 0.15027963 |
| 4/21-5/15 | Day 30 | 0.009663171 | 0.002344969 | 0.15027963 |

Engineer fibroblast lines with donor mtDNA

| Recipient cell | Mitochondria donor | # of colonies from $10^5$ recipient cells |
|---|---|---|
| BJ (Human newborn fibroblast) | HEK (human embryonic kidney) | 23 |
| | PBMC LP351 | 10 |
| | PBMC LP298 | 5 |
| | | |
| Human dermal fibroblast, neonatal | HEK | 23 |
| | PBMC LP351 | 10 |
| | PBMC LP298 | 2 |
| | | |
| Human dermal fibroblast, adult | HEK | 13 |
| | PBMC LP351 | 5 |
| | PBMC LP298 | 0 |

Aligned to donor pbmc LP298

Pbmc LP298 CAATCCCACATCAAAACCCTCTCCCCATGCTTACAAGCAAGTACAGCAATCAACCTTCAA

0329BJ_LP298mito CAATCCGACATCAAAACCCTCTCCCCATGCTTACAAGCAAGTACAGCAATCAACCTTCAA

0526 HDF neo_LP298mito CAATCCCACATCAAAACCCTCTCCCCATGCTTACAAGCAAGTACAGCAATCAACCTTCAA

BJ CAATCCCACATCAAAACCCCTCCCCATGCTTACAAGCAAGTACAACCCCAA

HDF adult CAATCCCACATCAAAACCCCCTCCCCATGCTTACAAGCAAGTACAGCAATCAACCTTCAA

HDF neo CAATCCCACATCAAAACCCCCTCCCCATGCTTACAAGCAAGTACAACAATCAACCTTCAA

FIG. 14E mtDNA position I         mtDNA position II

BJ AAGCCACCCCTCACCCCACTAGGATACCAACAAACCTACCCCACCCTTAACAGTACACATAGCACATA

HEK AAGTCACCCCTCACCCATTAGGATACCAACAAACCTACCCCACCCTTAACAGTACATAGTACACATA

BJ with HEK mitochondria AAGTCACCCCTCACCCATTAGGATACCAACAAACCTACCCCACCCTTAACAGTACATAGTACACATA

PBMC, LP351 AAGCCACCCCTCACCCCACTAGGATACCAACAAACCTACCCCACCCTTAACAGTACATAGTACACATA

BJ with LP351 mitochondria AAGCCACCCCTCACCCCACTAGGATACCAACAAACCTACCCCACCCTTAACAGTACATAGTACACATA

FIG. 14F mtDNA position I
BJ

HEK

BJ with HEK mitochondria mtDNA position II
BJ

PBMC, LP351

BJ with LP351 mitochondria

| Result | | |
|---|---|---|
| | | Tra 1-60+ colonies from $10^5$ cells |
| 1st trial | 0609BJ_BJmito | 0 |
| | 0329BJ_HEKmito | 5 |
| | 0329BJ_LP351mito | 11 |
| | 0329BJ_LP298mito | 0 |
| | | Tra 1-60+ colonies from $10^5$ cells |
| 2nd trial | 0609BJ_BJmito | 0 |
| | 0329BJ_HEKmito | 1 |
| | 0329BJ_LP351mito | 31 |
| | 0329BJ_LP298mito | 0 |

Bright field                    Tra 1-60 mtDNA analysis of derived iPS

DsRed HEK (mito donor)    ATCAAAACCCCCTCCTCCTCATGCTTACAAGCAAGTACAGCAATCAACCCTCAACTATCACACATCAACTGCAACTCCAAAGTCACCCCT>293

BJ iPS P3M1               ATCAAAACCCCCTCC[C]CATGCTTACAAGCAAGTACAGCAATCAACCC[C]CAACTATCACACATCAACTGCAACTCCAAAG[C]CACCCCT>296

032917BJ_HEKmito_iPS 1    ATCAAAACCCCCTCCTCCTCATGCTTACAAGCAAGTACAGCAATCAACCCTCAACTATCACACATCACACATCAACTGCAACTCCAAAGTCACCCCT>295

032917BJ_HEKmito_iPS 2    ATCAAAACCCCCTCCTCCTCATGCTTACAAGCAAGTACAGCAATCAACCCTCAACTATCACACATCAACTGCAACTCCAAAGTCACCCCT>293

032917BJ_HEKmito_iPS 4    ATCAAAACCCCCTCCTCCTCATGCTTACAAGCAAGTACAGCAATCAACCCTCAACTATCACACATCAACTGCAACTCCAAAGTCACCCCT>293

032917BJ_HEKmito_iPS 5    ATCAAAACCCCCTCCTCCTCATGCTTACAAGCAAGTACAGCAATCAACCCTCAACTATCACACATCACACATCAACTGCAACTCCAAAGTCACCCCT>295

294>CACCCATTAGGATACCAACAAACCTACCCACCCTTAACAGTACATAGTACATAAAGCCATTTACCGTACATAGCACATTACAGTCAAATCCCTTCTCGTC>393

297>CACCCA[C]TAGGATACCAACAAACCTACCCACCCTTAACAGTACATAGTACATAG[C]ACATAAAGCCATTTACCGTACATAGCACATTACAGTCAAATCCCTTCTCGTC>396

296>CACCCATTAGGATACCAACAAACCTACCCACCCTTAACAGTACATAGTACATAGCACATAAAGCCATTTACCGTACATAGCACATTACAGTCAAATCCCTTCTCGTC>395

294>CACCCATTAGGATACCAACAAACCTACCCACCCTTAACAGTACATAGTACATAGCACATAAAGCCATTTACCGTACATAGCACATTACAGTCAAATCCCTTCTCGTC>393

294>CACCCATTAGGATACCAACAAACCTACCCACCCTTAACAGTACATAGTACATAGCACATAAAGCCATTTACCGTACATAGCACATTACAGTCAAATCCCTTCTCGTC>393

296>CACCCATTAGGATACCAACAAACCTACCCACCCTTAACAGTACATAGTACATAGCACATAAAGCCATTTACCGTACATAGCACATTACAGTCAAATCCCTTCTCGTC>395

394>CCCATGGATGACCCCCCTCAGATAGGGGTCCCTTGGCCACCATCCTCCGTGAAATCAATATCCCGCACAAGAGTGCTACTCTCCTCGCTCCGGGCCCATA>493

397>CCCATGGATGACCCCCCTCAGATAGGGGTCCCTTG[A]CCACCATCCTCCGTGAAATCAATATCCCGCACAAGAGTGCTACTCTCCTCGCTCCGGGCCCATA>496

396>CCCATGGATGACCCCCCTCAGATAGGGGTCCCTTGGCCACCATCCTCCGTGAAATCAATATCCCGCACAAGAGTGCTACTCTCCTCGCTCCGGGCCCATA>495

394>CCCATGGATGACCCCCCTCAGATAGGGGTCCCTTGGCCACCATCCTCCGTGAAATCAATATCCCGCACAAGAGTGCTACTCTCCTCGCTCCGGGCCCATA>493

394>CCCATGGATGACCCCCCTCAGATAGGGGTCCCTTGGCCACCATCCTCCGTGAAATCAATATCCCGCACAAGAGTGCTACTCTCCTCGCTCCGGGCCCATA>493

396>CCCATGGATGACCCCCCTCAGATAGGGGTCCCTTGGCCACCATCCTCCGTGAAATCAATATCCCGCACAAGAGTGCTACTCTCCTCGCTCCGGGCCCATA>495

FIG. 16C

PBMC LP351 (mito donor)    ATCAAAAACCCCCTCCCCATGCTTACAAGCAAGTACAGCAATCAACCCTCAACTATCACACATCAACTGCAACTCCAAAGCCACC>294

BJ iPS P3M1    ATCAAAAACCCCCTCCCCATGCTTACAAGCAAGTACAGCAATCAACCCTCAACTATCACACATCAACTGCAACTCCAAAGCCACC>293

032917BJ_LP351mito_iPS 1    ATCAAAAACCCCCTCCCCATGCTTACAAGCAAGTACAGCAATCAACCCTCAACTATCACACATCAACTGCAACTCCAAAGCCACC>291

032917BJ_LP351mito_iPS 2    ATCAAAAACCCCCTCCCCATGCTTACAAGCAAGTACAGCAATCAACCCTCAACTATCACACATCAACTGCAACTCCAAAGCCACC>290

032917BJ_LP351mito_iPS 3    ATCAAAAACCCCCTCCCCATGCTTACAAGCAAGTACAGCAATCAACCCTCAACTATCACACATCAACTGCAACTCCAAAGCCACC>291

032917BJ_LP351mito_iPS 4    ATCAAAAACCCCCTCCCCATGCTTACAAGCAAGTACAGCAATCAACCCTCAACTATCACACATCAACTGCAACTCCAAAGCCACC>291

032917BJ_LP351mito_iPS 8    ATCAAAAACCCCCTCCCCATGCTTACAAGCAAGTACAGCAATCAACCCTCAACTATCACACATCAACTGCAACTCCAAAGCCACC>293

032917BJ_LP351mito_iPS 9    ATCAAAAACCCCCTCCCCATGCTTACAAGCAAGTACAGCAATCAACCCTCAACTATCACACATCAACTGCAACTCCAAAGCCACC>291

032917BJ_LP351mito_iPS 10    ATCAAAAACCCCCTCCCCATGCTTACAAGCAAGTACAGCAATCAACCCTCAACTATCACACATCAACTGCAACTCCAAAGCCACC>291

032917BJ_LP351mito_iPS 11    ATCAAAAACCCCCTCCCCATGCTTACAAGCAAGTACAGCAATCAACCCTCAACTATCACACATCAACTGCAACTCCAAAGCCACC>293

295>CCTCACCCCACTAGGATACCAACAAACCTACCACCCTTAACAGTACATAGTACATAAAGCCATTTACCGTACATAGCACATTACAGTCAAATCCTTTCTC>394

294>CCTCACCCCACTAGGATACCAACAAACCTACCACCCTTAACAGTACATAGTACATAAAGCCATTTACCGTACATAGCACATTACAGTCAAATCCTTCTC>393

292>CCTCACCCCACTAGGATACCAACAAACCTACCACCCTTAACAGTACATAGTACATAAAGCCATTTACCGTACATAGCACATTACAGTCAAATCCTTTCTC>391

291>CCTCACCCCACTAGGATACCAACAAACCTACCACCCTTAACAGTACATAGTACATAAAGCCATTTACCGTACATAGCACATTACAGTCAAATCCTTTCTC>390

292>CCTCACCCCACTAGGATACCAACAAACCTACCACCCTTAACAGTACATAGTACATAAAGCCATTTACCGTACATAGCACATTACAGTCAAATCCTTTCTC>391

292>CCTCACCCCACTAGGATACCAACAAACCTACCACCCTTAACAGTACATAGTACATAAAGCCATTTACCGTACATAGCACATTACAGTCAAATCCTTTCTC>391

294>CCTCACCCCACTAGGATACCAACAAACCTACCACCCTTAACAGTACATAGTACATAAAGCCATTTACCGTACATAGCACATTACAGTCAAATCCTTTCTC>393

292>CCTCACCCCACTAGGATACCAACAAACCTACCACCCTTAACAGTACATAGTACATAAAGCCATTTACCGTACATAGCACATTACAGTCAAATCCTTTCTC>391

292>CCTCACCCCACTAGGATACCAACAAACCTACCACCCTTAACAGTACATAGTACATAAAGCCATTTACCGTACATAGCACATTACAGTCAAATCCTTTCTC>391

294>CCTCACCCCACTAGGATACCAACAAACCTACCACCCTTAACAGTACATAGTACATAAAGCCATTTACCGTACATAGCACATTACAGTCAAATCCTTTCTC>393

FIG. 16D

| Fibroblast (3) | | iPS (7) | | MSC (7) | |
|---|---|---|---|---|---|
| Unmodified BJ | | BJ P3M1 iPS | | BJ P3M1 iPS MSC | |
| 032917BJ_LP351mito | | 032917BJ_LP351mito_iPS1 | | 032917BJ_LP351mito_iPS1_MSC | |
| | | 032917BJ_LP351mito_iPS2 | | 032917BJ_LP351mito_iPS2_MSC | |
| | | 032917BJ_LP351mito_iPS11 | | 032917BJ_LP351mito_iPS11_MSC | |
| 032917BJ_HEKmito | | 032917BJ_HEKmito_iPS1 | | 032917BJ_HEKmito_iPS1_MSC | |
| | | 032917BJ_HEKmito_iPS2 | | 032917BJ_HEKmito_iPS2_MSC | |
| | | 032917BJ_HEKmito_iPS4 | | 032917BJ_HEKmito_iPS4_MSC | |

MSC mtDNA sequence verification

| | |
|---|---|
| PBMC LP351 (mito donor) | AGTACATAGTACATAAAGCCATTTACCGTACATAGCACATTACAGTCAAATCCTTTCTC |
| 032917BJ_LP351mito_iPS 1_MSC | AGTACATAGTACATAAAGCCATTTACCGTACATAGCACATTACAGTCAAATCCTTTCTC |
| 032917BJ_LP351mito_iPS 2_MSC | AGTACATAGTACATAAAGCCATTTACCGTACATAGCACATTACAGTCAAATCCTTTCTC |
| 032917BJ_LP351mito_iPS 11_MSC | AGTACATAGTACATAAAGCCATTTACCGTACATAGCACATTACAGTCAAATCCTTTCTC |
| BJ iPS P3M1 MSC | AGTACATAGCACATAAAGCCATTTACCGTACATAGCACATTACAGTCAAATCCCTTCTC |
| BJ | AGTACATAGCACATAAAGCCATTTACCGTACATAGCACATTACAGTCAAATCCCTTCTC |

| | |
|---|---|
| HEK (mito donor) | TACAAGCAAGTACAGCAATCAACCCTCAACTATCACACATCAACTGCAACTCCAAAGTC |
| 032917BJ_HEKmito_iPS 1_MSC | TACAAGCAAGTACAGCAATCAACCCTCAACTATCACACATCAACTGCAACTCCAAAGTC |
| 032917BJ_HEKmito_iPS 2_MSC | TACAAGCAAGTACAGCAATCAACCCTCAACTATCACACATCAACTGCAACTCCAAAGTC |
| BJ iPS P3M1 MSC | TACAAGCAAGTACAGCAATCAACCCCCAACTATCACACATCAACTGCAACTCCAAAGCC |
| BJ | TACAAGCAAGTACAGCAATCAACCCCCAACTATCACACATCAACTGCAACTCCAAAGCC |

FIG. 18D

| | P3M1_MSC | LP351-11_MSC | LP351-2_MSC | LP351-1_MSC | HEK-2_MSC | HEK-1_MSC |
|---|---|---|---|---|---|---|
| % GAPDH-Referenced mtDNA | 100 | 160.5972871 | 103.2555094 | 106.1200413 | 133.5382806 | 128.2132618 |
| std error | 8.269300018 | 16.1333554 | 6.969402131 | 9.516785771 | 15.65751875 | 9.965185069 | log2(TPM+1)

12

10

8

6

4

2

0

LEGEND FOR B, D, E

FATE  FIBROBLAST  iPSC  MSC

CONDITION  BJ ρ0  BJ  BJ ρ0+LP351  BJ ρ0+HEK293T

FIG. 25E

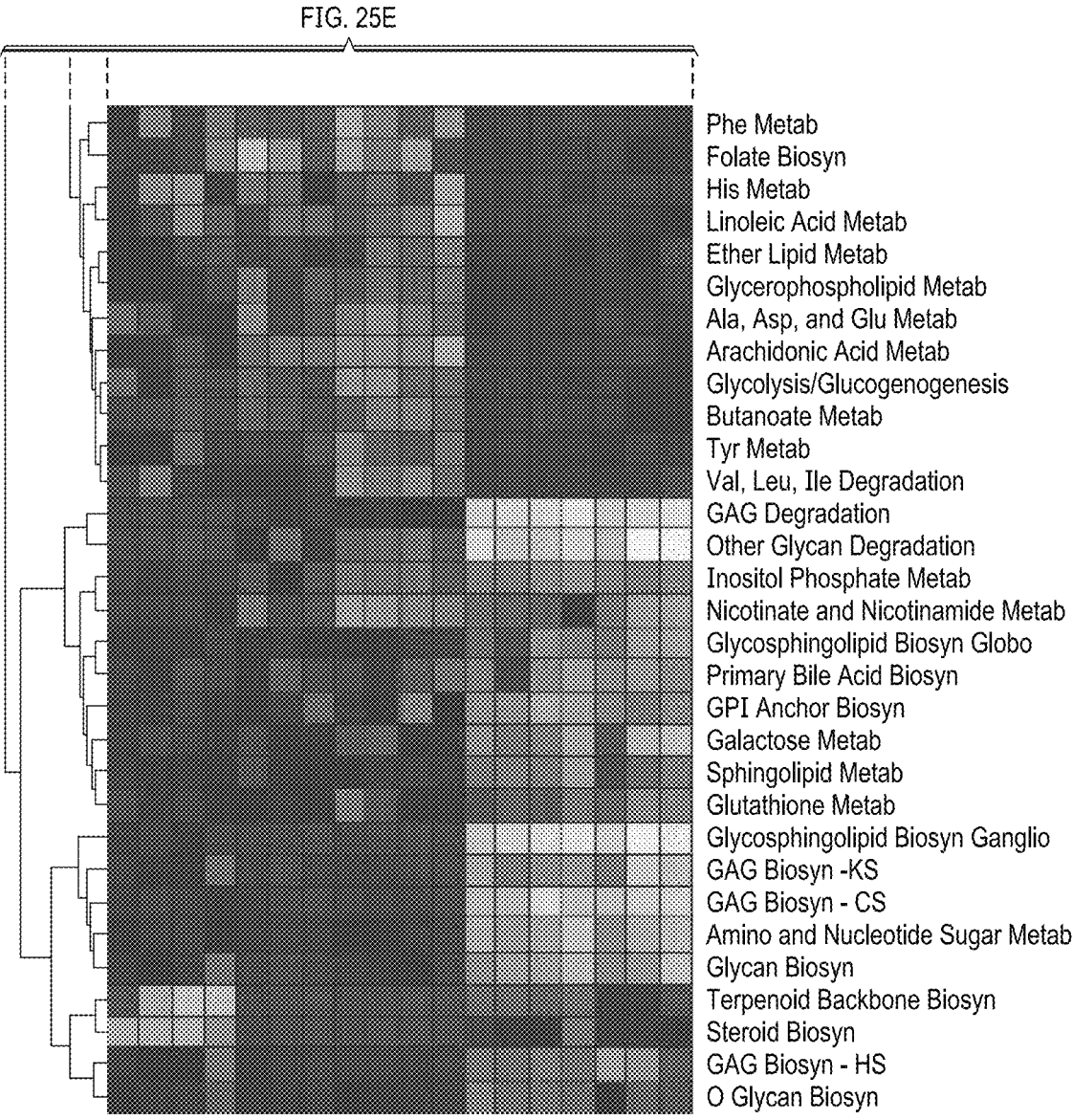

Phe Metab
Folate Biosyn
His Metab
Linoleic Acid Metab
Ether Lipid Metab
Glycerophospholipid Metab
Ala, Asp, and Glu Metab
Arachidonic Acid Metab
Glycolysis/Glucogenogenesis
Butanoate Metab
Tyr Metab
Val, Leu, Ile Degradation
GAG Degradation
Other Glycan Degradation
Inositol Phosphate Metab
Nicotinate and Nicotinamide Metab
Glycosphingolipid Biosyn Globo
Primary Bile Acid Biosyn
GPI Anchor Biosyn
Galactose Metab
Sphingolipid Metab
Glutathione Metab
Glycosphingolipid Biosyn Ganglio
GAG Biosyn -KS
GAG Biosyn - CS
Amino and Nucleotide Sugar Metab
Glycan Biosyn
Terpenoid Backbone Biosyn
Steroid Biosyn
GAG Biosyn - HS
O Glycan Biosyn

FIG. 25E
(CONTINUED)

DEVICES AND METHODS FOR MITOCHONDRIA REPLACEMENT AND FOR GENERATING CELLULAR THERAPEUTICS

CROSS REFERENCE TO RELATED APPLICATIONS

This application is a continuation of U.S. patent application Ser. No. 16/517,017 filed on 19 Jul. 2019, which claims the benefit of and priority to U.S. Provisional Patent Application Ser. No. 62/700,649, filed Jul. 19, 2018. The entire disclosures of each of the above recited applications are incorporated herein by reference.

Reference to an Electronic Sequence Listing

This application contains references to nucleic acid sequences which have been submitted herewith as the sequence listing.xml file named "ST26_SL_conversion_14_Jun_2023.xml" and was created on 14 Jun. 2023 and has a file size of 100 KB. The aforementioned sequence listing.xml file is hereby incorporated by reference in its entirety.

FIELD OF THE INVENTION

Devices and methods are provided herein for replacement of endogenous mitochondrial DNA with corrected mitochondrial DNA, which is useful for, inter alia, treatment of diseases arising from mutations in endogenous mitochondrial DNA.

BACKGROUND OF THE INVENTION

The background description includes information that may be useful in understanding the systems and methods described herein. It is not an admission that any of the information provided herein is prior art, or that any publication specifically or implicitly referenced is prior art.

Mitochondria typically are present in large numbers in a variety of different types of cells. As the energy powerhouse for cells, mitochondria conduct biochemical reactions involving respiration and energy production, including the production of ATP. Mitochondria also may have other roles, including signaling, metabolism, cellular differentiation, epigenetic remodeling, and apoptosis, as well as in regulating the cell cycle and growth. Each mitochondrion may contain multiple copies of a compact and circular 16.5 kbp genome (mtDNA) that is independent of the nuclear genome and essential for electron transport chain (ETC)-dependent processes.

Mitochondria have been implicated in a variety of diseases, including mitochondrial disorders, cardiac dysfunction, heart failure, autism, diabetes mellitus, and deafness. These diseases may arise in part because mitochondrial DNA (mtDNA) lack proofreading capability during mtDNA replication, which may lead to a high rate of mutations. Accordingly, as an individual ages, mtDNA mutations may accumulate and clonally expand in various tissues, including but not limited to nerve cells, cardiomyocytes, skeletal muscle cells, colon tissue, etc. Some estimates place the prevalence of mtDNA disease at about 1 in 5,000 individuals (Schaefer et al., *Ann Neurol* (2008) v 63:35-9) with as many as 1 in 200 people being carriers for mtDNA mutations.

Mesenchymal stem cells comprise mtDNA and are involved in the repair of a variety of different tissues. Mesenchymal stem cells secrete cytokines and growth factors, shed exosomes and micro vesicles to promote tissue repair, and demonstrate other protective cellular effects. Additionally, mesenchymal stem cells may undergo differentiation into various cell types, including osteocytes, adipocytes, chondrocytes, myocytes, astrocytes, smooth muscle, or endothelial cells. Thus, defective endogenous mtDNA in mesenchymal stem cells may be unable to repair damaged tissue, to replicate, or to differentiate into other cell types during tissue repair. Cells with defective mtDNA are associated with a variety of different types of diseases, including cardiovascular disorders, autoimmune diseases, osteoarthritis, liver disorders, graft versus host disease, respiratory disorders, kidney failure, spinal cord injuries, skin diseases, neurological diseases, etc. However, there are relatively few treatments for mitochondrial disorders.

Transfection processes are used to deliver various types of materials into a cell, and there are numerous types of transfection methods described in the art. For example, U.S. Pat. No. 5,586,982 describes a device capable of delivering genetic material or drugs into cells of a patient in vivo using heat to assist with transfection. However, this approach often results in damage to the cells. Moreover, since electroporation typically lasts for a short period of time, the amount of material delivered into the cells is small, and this amount may decrease as the size of the material increases.

Other devices having porous membranes have been used for transfecting cargos into cells (US Patent Publication No. 2017/0175139). However, such devices have limited customization capabilities, and may not achieve optimal transfection efficiency for different types of cells receiving different materials of different sizes. For example, these devices utilize solenoids that are not tunable as a consequence of having one (on/off) speed. Solenoids are typically unidirectional devices, with a short stroke.

Current methods for transferring mtDNA into cells are limited by a variety of factors, including low yield/throughput, limited cell type availability, selection difficulties, contamination from other cellular components, unreliability and/or inconsistencies in transferring and integrating mtDNA into recipient cells, or reliance on spontaneous biological processes. Additionally, correlating specific mtDNA mutations to particular phenotypes has been difficult. While techniques such as material spindle transfer have been used to generate ooctyes with particular mtDNA, the oocytes are often outcompeted by endogenous mtDNA or may fail to undergo selection (Tachibana et al., *Nature* (2013) v493, p 627-631).

Accordingly, there is a need for improved transfection devices and methods suitable for delivery of mtDNA into recipient cells, and for cellular-based therapeutics to treat diseases caused by defective mtDNA.

SUMMARY

Methods and devices are presented herein for transfecting mtDNA into cells, and for generating cellular-based therapeutics for the treatment of diseases associated with defective mtDNA. In some aspects, methods of generating engineered cells are presented. Endogenous mtDNA may be depleted from recipient cells to produce depleted cells, and corrected mtDNA may be transfected into the depleted cells using the devices and techniques described herein to produce transfected cells. The transfected cells can be reprogrammed into induced pluripotent stem cells, and the induced pluripotent stem cells can be differentiated into the engineered cells, for example, mesenchymal stem cells. Transfected cells comprising the corrected mtDNA may be cultured under conditions suitable to bring one or more characteristics of the transfected cells into a state that is similar to or the same as corresponding wild type (wt) cells. The mesenchymal stem cells may be administered to a patient to treat a mitochondrial associated disease.

A transfection device is presented that comprises a porous membrane onto which cells to be transfected are placed, such as depleted cells. The porous membrane is fluidly coupled to a solution comprising macrostructures to be transfected into the cell (e.g., depleted cells), wherein the solution is enclosed at least partially in a deformable fluid reservoir. Applied pressure causes deformation of the fluid reservoir and movement of the macrostructures in the solution, such that the macrostructures contact the surface of the cells (e.g., depleted cells) for a time and at a pressure effective to introduce the macrostructures into the cells. In some aspects, the macrostructures are taken up by the cell, e.g., through a process such as endocytosis, to produce transfected cells. The devices presented herein are characterized by their tunability and customizable features (e.g., custom waveforms, variable pressures, variable rise times, etc.), high transfection efficiency, and low rate of cell damage.

In some aspects, the device may generate applied pressure using a configurable actuator (e.g., a voice coil actuator), in which the movement of the actuator translates into applied pressure. While not intending to be limiting with regard to the present subject matter, the pressures applied to the cells for transfection, e.g., depleted cells, are generally non-ballistic in nature and may be at least 100 hPa. Typically, the applied pressure is maintained for a period of time between 10 ms and 30 s, while the cells are in a fixed position (e.g., within a microfluidic channel, adhered to the porous membrane, etc.) during the application of pressure.

Such devices provide the ability to tune and customize parameters of the transfection process described herein (also referred to as a mitoPUNCH transfection process) to specific types of recipient cells in order to achieve optimized transfection efficiencies. In other aspects, the devices and methods presented herein may use machine learning techniques to predict or identify optimal parameters for specific types of depleted cells based upon previous experimental data.

In general, the device delivers isolated, whole mitochondrion carrying mtDNA into its intended target. Thus, the mtDNA is packaged within mitochondrion for delivery, rather than delivering mtDNA alone or as part of a complex comprising mtDNA.

Various objects, features, aspects and advantages of the present subject matter will become more apparent from the following detailed description of preferred embodiments.

BRIEF DESCRIPTION OF THE DRAWINGS

FIGS. 2A-2D are schematics of an exemplary mechanical interface, according to aspects provided herein. FIG. 2A is a schematic overview of the base plate, deformable fluid reservoir and stage. FIG. 2B is a more detailed schematic of the stage of the device of FIG. 2A. FIG. 2C is a more detailed schematic of the deformable fluid reservoir of the device of FIG. 2A. FIG. 2D is a more detailed view of a container engaged with the reservoir of the device of FIG. 2A.

FIGS. 10A-10E are illustrations showing an example process for generating patient-specific mtDNA-engineered mesenchymal stem cells, according to the embodiments presented herein.

FIGS. 13A-13D show high-efficiency mtDNA integration, according to the embodiments and devices presented herein.

FIGS. 14A-14L shows various recipient cells that have been transfected with mtDNA, according to the embodiments presented herein.

FIG. 14A is a table showing various recipient cells (BJ, HDF neonatal, HDF adult) along with donor mtDNA (HEK mtDNA, PBMC LP351, and PBMC LP298).

FIG. 14B is an illustration of mtDNA, showing hypervariable regions (HVSI and HVSII), which may be used to track the lineage of mtDNA strains.

FIG. 14C shows wild type strains (BJ (SEQ ID NO: 11), HDF adult (SEQ ID NO: 12), HDF neonatal (SEQ ID NO: 13)) without transfected mtDNA (DsRed HEK (SEQ ID NO: 7) and transformed strains (0329BJ_HEKmito (SEQ ID NO: 8), 0526 HDF adult HEKmito (SEQ ID NO: 9), 0526 HDF neonatal HEKmito (SEQ ID NO: 10)) with transfected mtDNA from HEK mtDNA.

FIGS. 14D and 14E show wild type strains (BJ (SEQ ID NOs: 18 and 24), HDF adult (SEQ ID NOs: 19 and 25), HDF neonatal (SEQ ID NOs: 20 and 26)) without transfected mtDNA (SEQ ID NOs: 16, 17, and 23) and transformed strains with transfected mtDNA from PBMC LP351 (SEQ ID NOs: 14 and 21) or PBMCLP298 (SEQ ID NOs: 15 and 22), respectfully.

FIGS. 14F-14L show additional transformation results, wherein BJ cells were transformed with HEK mtDNA or LP351 mtDNA. A sequence alignment showing that endogenous mtDNA has been replaced with transfected mtDNA (SEQ ID NOs: 27-31) is shown in FIG. 14F, with corresponding sequence runs shown in FIGS. 14G-14L.

FIGS. 16A-16E show aspects of reprogramming various fibroblasts to induced pluripotent stem cells (iPSCs), according to the embodiments presented herein.

FIG. 16A shows a table summarizing two trials, in which various strains were reprogrammed to iPSCs.

FIG. 16B shows a bright field and a fluorescent image of a fibroblast after reprogramming.

FIG. 16C shows that the endogenous mtDNA in BJ-derived iPS strain (BJ iPS P3M1 (SEQ ID NO: 33)) was successfully replaced with donor HEK mtDNA (SEQ ID NO: 32) during depletion and transfection, and was retained during reprogramming (032917BJ_HEKmito_iPS 1-5 (SEQ ID NOs: 34-37)).

FIG. 16D shows that the endogenous mtDNA in BJ-derived iPS strain (BJ iPS P3M1 (SEQ ID NO: 39)) was successfully replaced with another donor mtDNA (LP351mito) (SEQ ID NO: 38) during depletion and transfection, and was retained during reprogramming (032917BJ_LP351mito_iPS 1-4, 8-11 (SEQ ID NOs: 40-47)).

FIG. 16E shows expression of proteins SSEA-4, OCT4 and NANOG, proteins known to be associated with undifferentiated stem cells, in the various reprogrammed BJ cells comprising donor mtDNA.

FIGS. 18A-18F show aspects of differentiating iPSCs into mesenchymal cells, according to the embodiments presented herein.

FIG. 18A shows a flowchart summarizing the process for differentiating iPSCs into MSCs, including passaging for about three or more weeks.

FIG. 18B is a table showing various strains that were differentiated into MSC cells. Differentiation may be achieved by any suitable technique known in the art.

FIG. 18C shows expression of various proteins including CD73, CD105, and CD146, which are proteins associated with mesenchymal stem cells, in various differentiated BJ-derived iPS cells, some of which comprise donor mtDNA from HEK or LP351 strains.

FIG. 18D shows that the endogenous mtDNA in BJ-derived iPS and differentiated cells (BJ (SEQ ID NOs: 53 and 58) or BJ iPS P3M1 (SEQ ID NOs: 52 and 57)) was successfully replaced with donor HEK mtDNA (SEQ ID NO: 54) or LP351mtDNA (SEQ ID NO: 48) during depletion and transfection, and was retained during reprogramming and differentiation (032917BJ_HEKmito_iPS 1-2 MSC (SEQ ID NOs: 55-56) and 032917BJ_LP351mito_iPS 1-2,11 MSC (SEQ ID NOs: 49-51)).

FIGS. 18E and 18F show a graph and table, respectfully, illustrating % GAPDH-referenced mtDNA (mitochondrial donors in MSCs, with P3M1-MSC as a calibrator).

FIG. 19A shows isolated mitochondria from HEK293T, LP351 PBMC, or LP298 PBMC cells that were transferred using the mitochondria delivery tool (see, e.g., FIG. 1) into BJ p0, NDF p0, or ADF p0 recipient cell lines.

Dihydroorate dehydrogenase is inactive in p0 cells caused by impaired ETC function, and depends on supplemented uridine for pyrimidine biosynthesis and proliferation (Gregoire et al., *Eur J Biochem* (1984) 142, 49-55). Therefore, mitochondrial recipient p0 cells were first incubated in uridine supplemented media for 4 days to facilitate mtDNA expansion before a 10-day selection in uridine-deficient media to isolate p0 cells that successfully integrated exogenous mtDNA (FIG. 19A).

After selection, unstained colonies were counted by brightfield microscopy. Recipient cells transferred PBS served as the negative control. Each bar represents colonies generated from mitochondrial transfer into 100,000 recipient p0 cells.

Figures 19A, 19B:
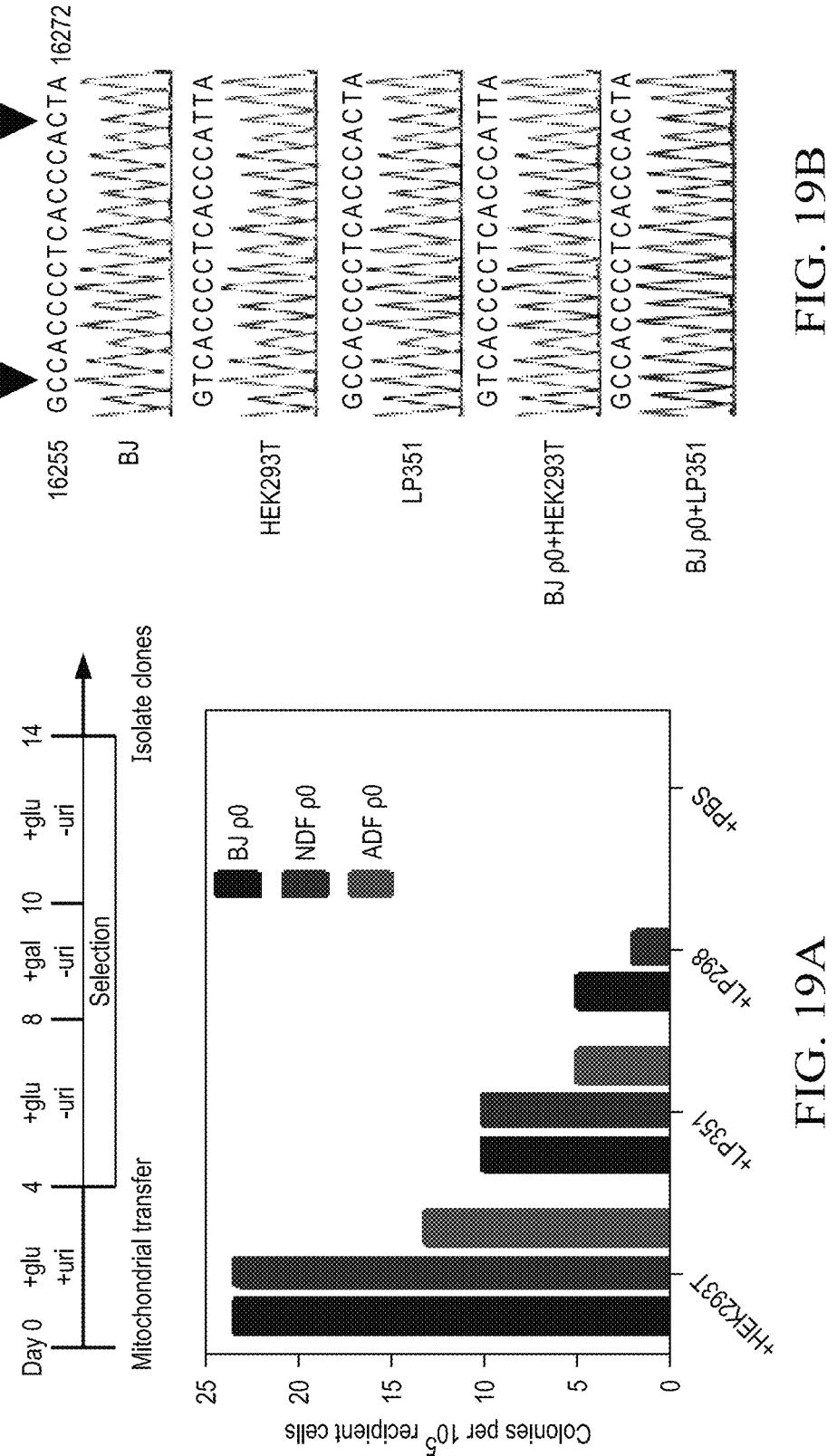
FIGS. 19A-19F show rescue of p0 fibroblasts by mitochondrial transfer according to the embodiments presented herein.

FIG. 19B shows DNA that was isolated from transferred cells in panel A, with the exception of BJ p0+LP298, and the D-loop hypervariable region was sequenced. Arrows denote regions of polymorphisms. SEQ ID NOs: 59-63 refer to the D-loop hypervariable regions of BJ, HEK293T, LP351, BJ p0+HEK293T, and BJ p0+LP35 cells, respectively.

FIGS. 19C-19F show ~15,000 BJ, BJ p0, BJ p0+HEK293T, or BJ p0+LP351 cells that were plated on a Seahorse XF96 plate. Dotted lines indicate drug injection points. Data is presented as the mean of four technical measurements+standard deviation. * P<0.05,  P<0.01, * P<0.001, **** P<0.0001.

Figure 19C:
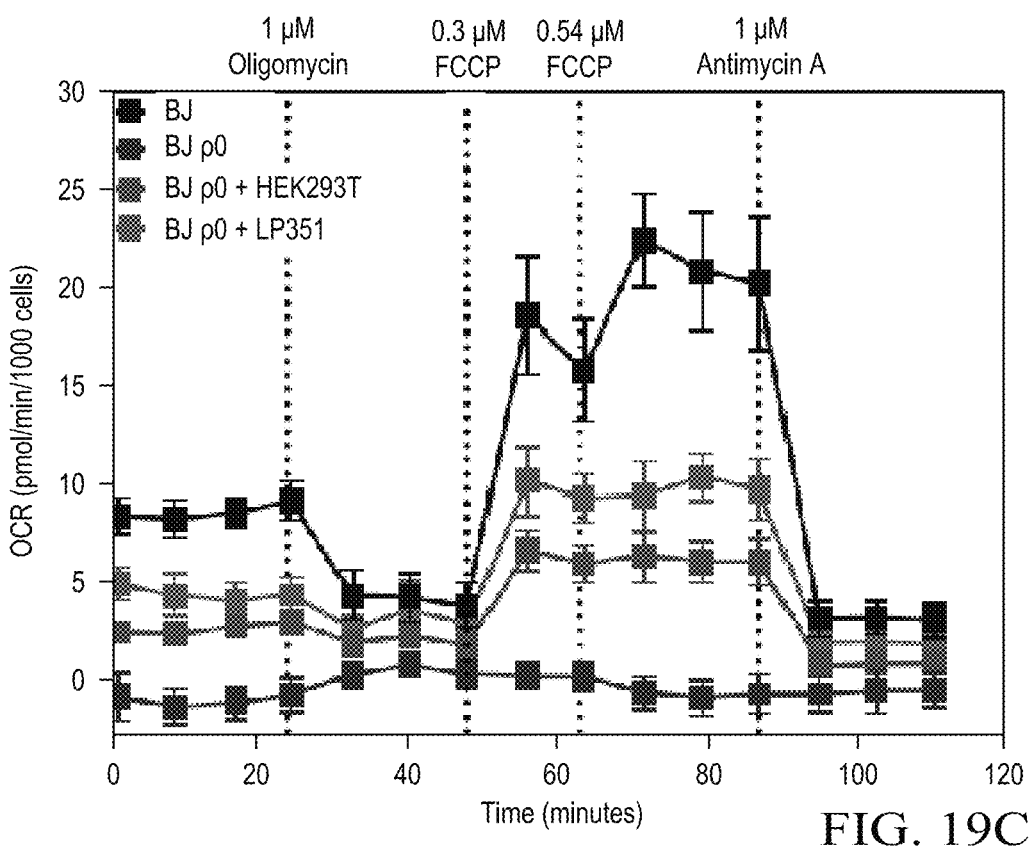
Figure 19D:
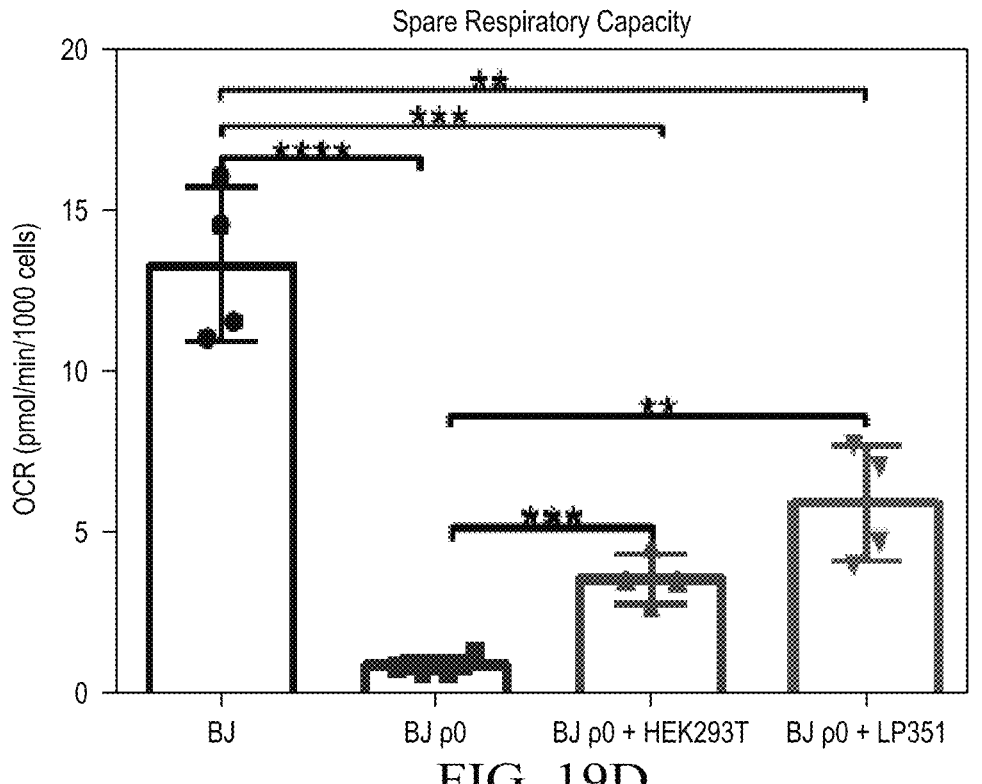
Figure 19E:
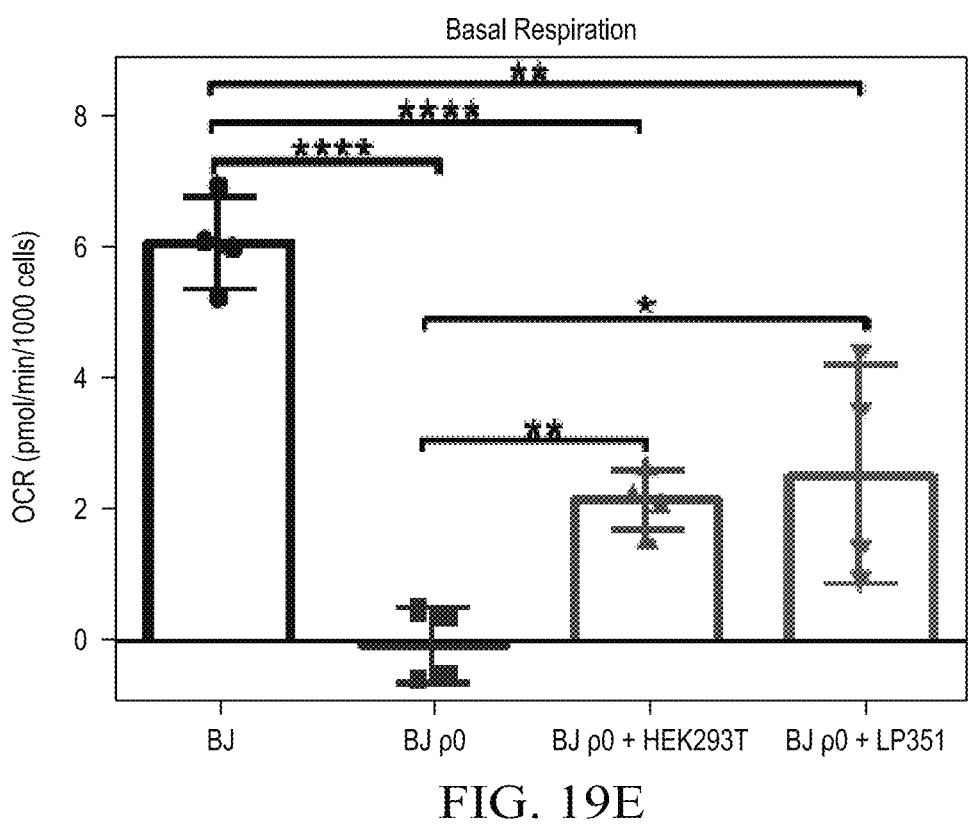
Figure 19F:
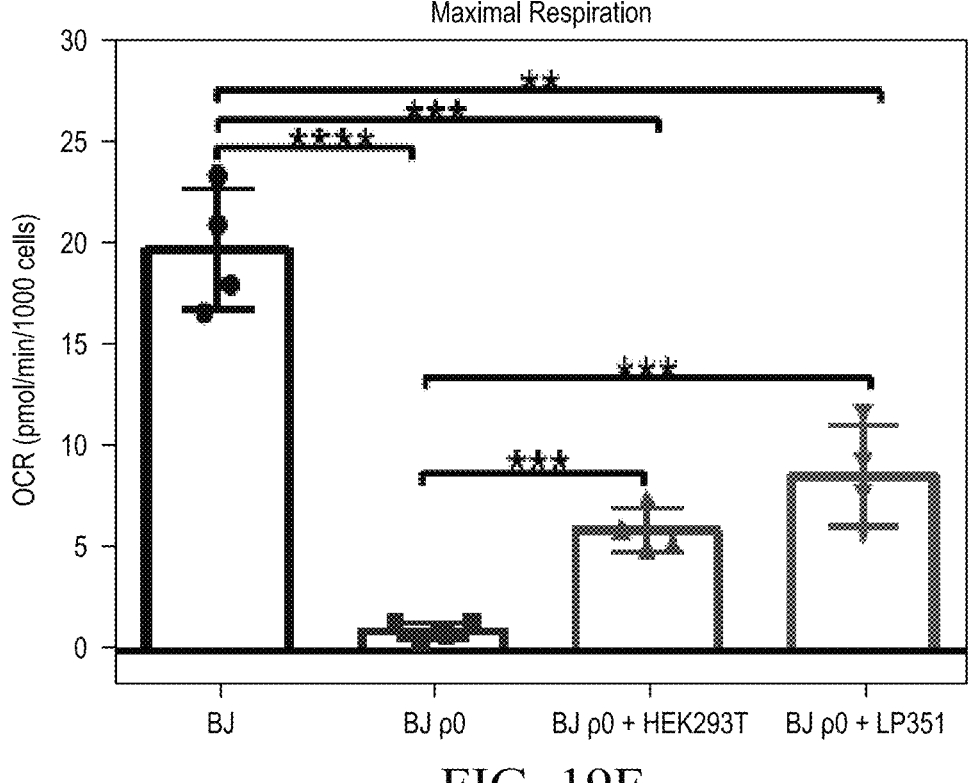

Quantification of the oxygen consumption rates showed BJ p0+HEK293T and BJ p0+LP351 had improved coupling and complex III/V activities in comparison to the BJ p0 line (FIG. 19C). Both mitochondrial recipient lines had lower spare capacity, basal, and maximal respirations in comparison to the BJ line with intact mtDNA. Although not significant, BJ p0+LP351 trended to have increased respiration compared to the BJ p0+HEK293T. Thus, the mitochondrial transfer platform provided herein may be used to rescue the ETC function of p0 fibroblasts and generate multiple cell lines with different mtDNA derived from an established cell line and a patient sample.

FIGS. 20A-20G show aspects of reprogramming mitochondrial recipient fibroblasts to iPSCs.

Figure 20A:
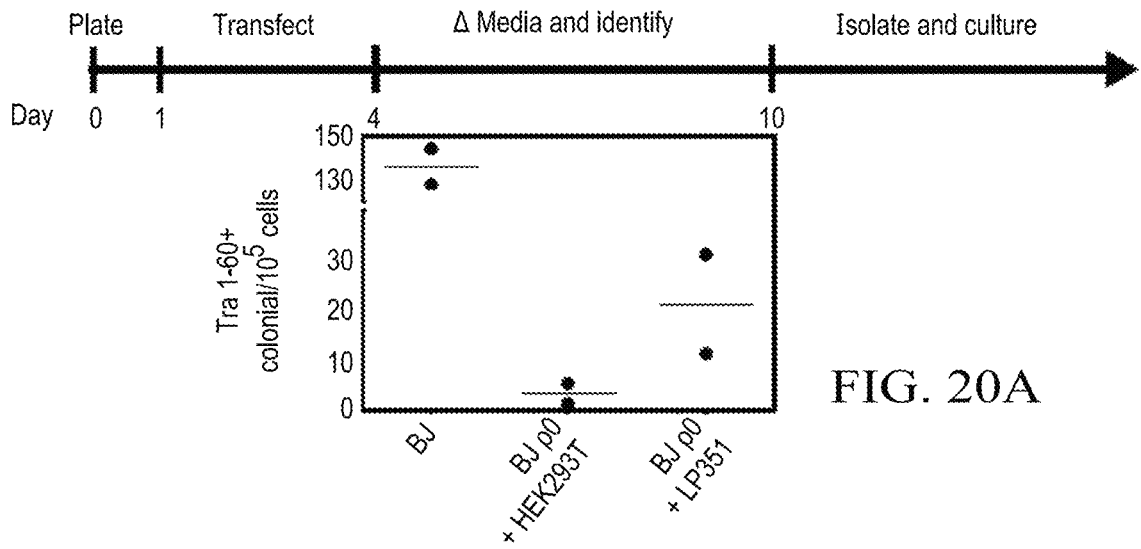

FIG. 20A shows a schematic of fibroblast reprogramming to iPSC. Tra 1-60 positive clones were counted by microscopy. Data is presented as biological duplicate and the mean is shown. After transfecting BJ, BJ p0+HEK293T, and BJ p0+LP351 cells with reprogramming (e.g., Oct4, Sox2, Klf4, cMyc, Nanog, and Ling28) and immune evasion (E3, K3, and B18R) factors, Tra 1-60 positive colonies were isolated. BJ fibroblasts yielded 136 colonies (0.068% efficiency), while approximately 21 (0.011% efficiency) and 3 (0.0015% efficiency) colonies from the BJp0+LP351 and BJp0+HEK293T lines were quantified, respectively (FIG. 20A).

Figure 20B:
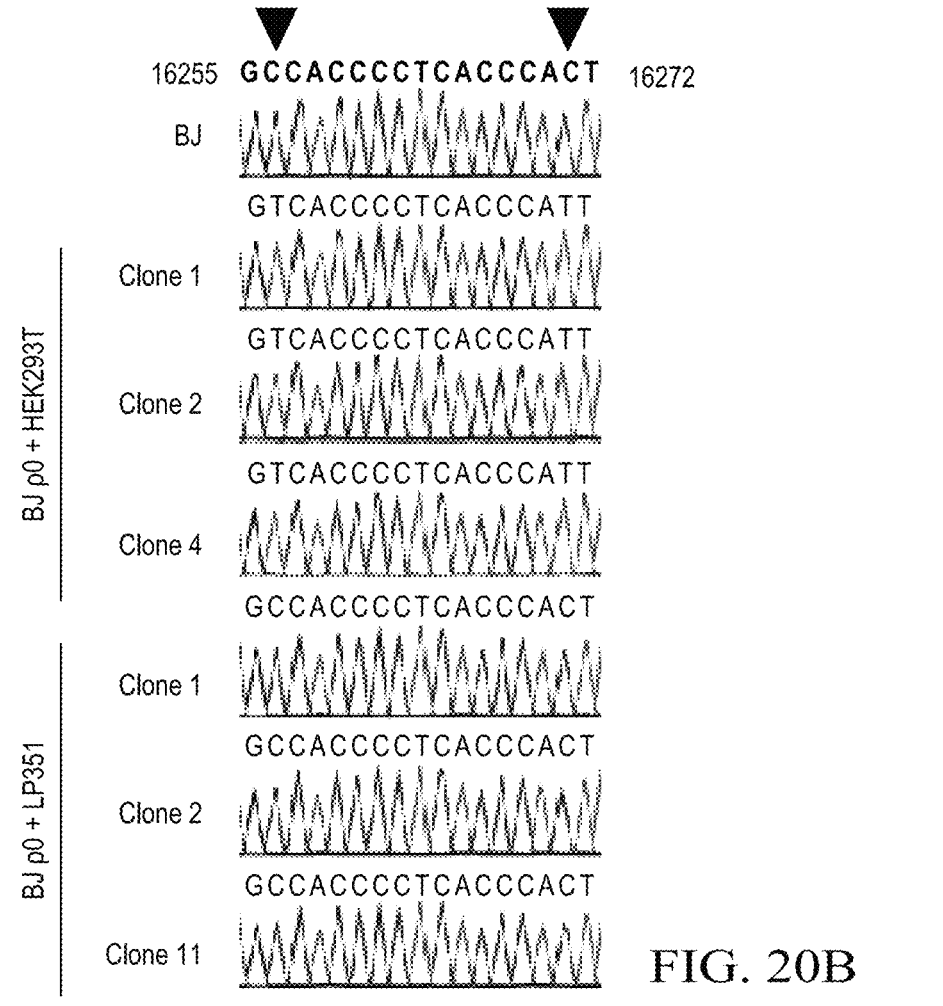

FIG. 20B shows sequences of hypervariable regions. DNA was isolated from iPSC clones and the mtDNA D-loop hypervariable region was sequenced. BJ fibroblasts that were reprogrammed to iPSCs were also sequenced. SEQ ID NOs: 64-70 refer to the D-loop hypervariable regions of BJ, BJ p0+HEK293T Clone 1, J p0+HEK293T Clone 2, J p0+HEK293T Clone 3, BJ p0+LP35 Clone 1, BJ p0+LP35 Clone 2, and BJ p0+LP35 Clone 11 cells, respectively. Arrows denote SNPs.

From FIG. 20A, three clones were selected, the BJp0+HEK293T (clones 1, 2, and 4) and BJp0+LP351 (clones 1, 2, and 11) fibroblasts, and their D-loop hypervariable regions were sequenced to confirm that the correct mtDNA sequences were present in each line (FIG. 20B).

Figure 20C:
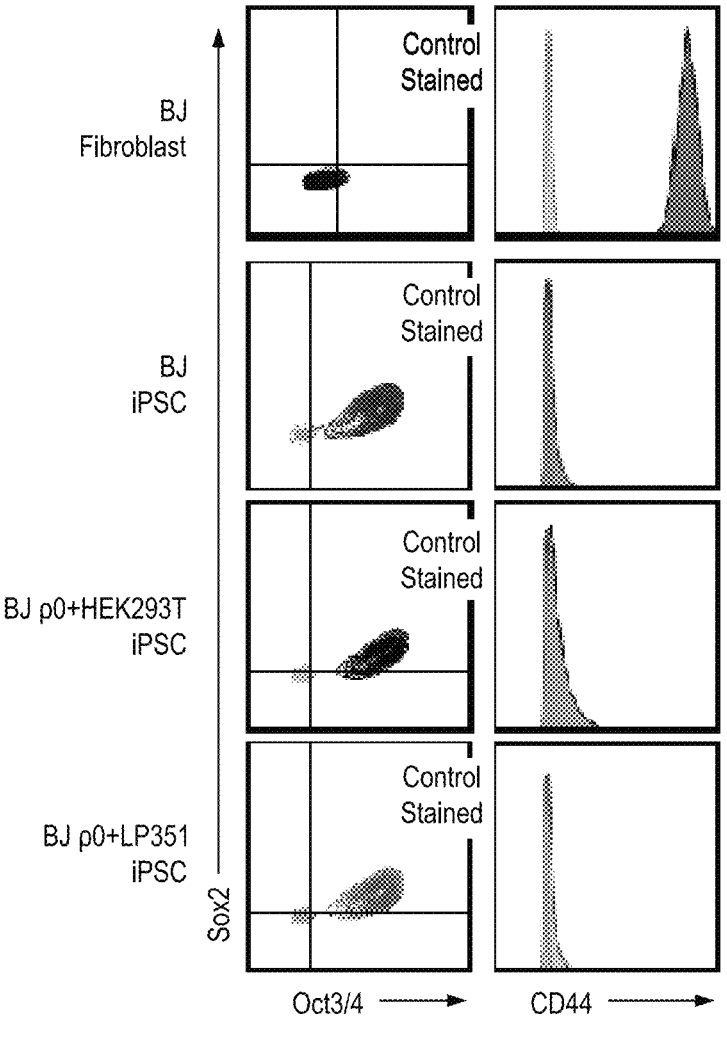
Figure 20D:
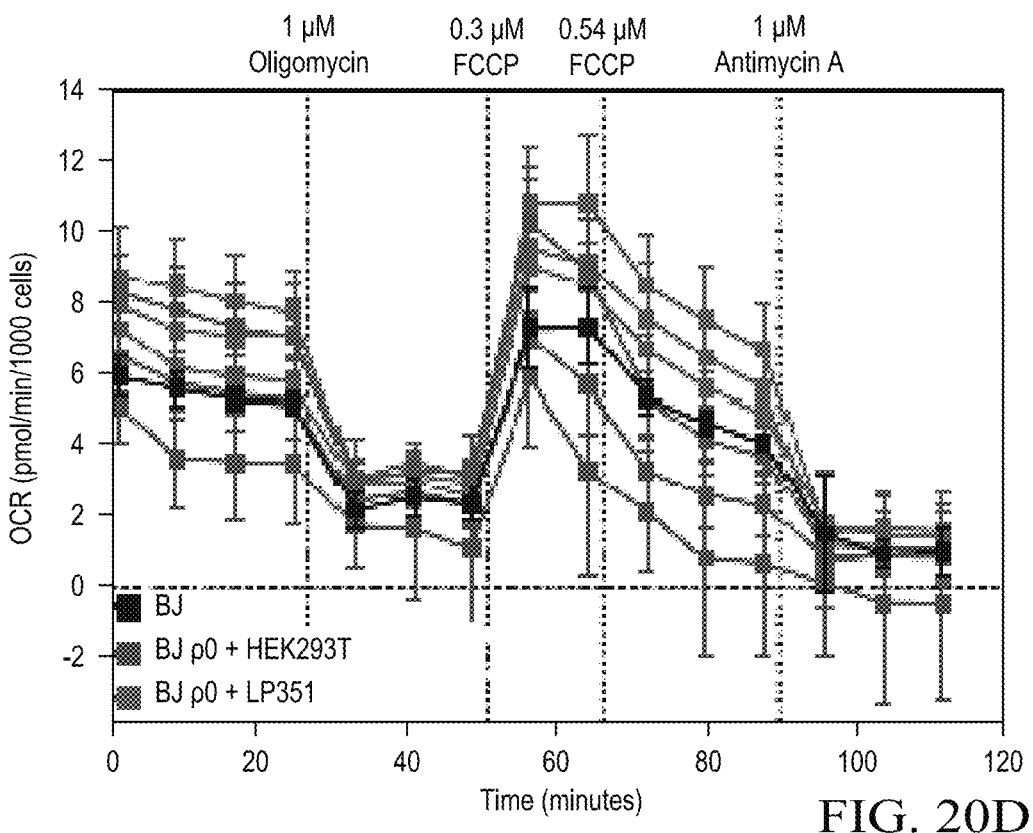
Figure 20E:
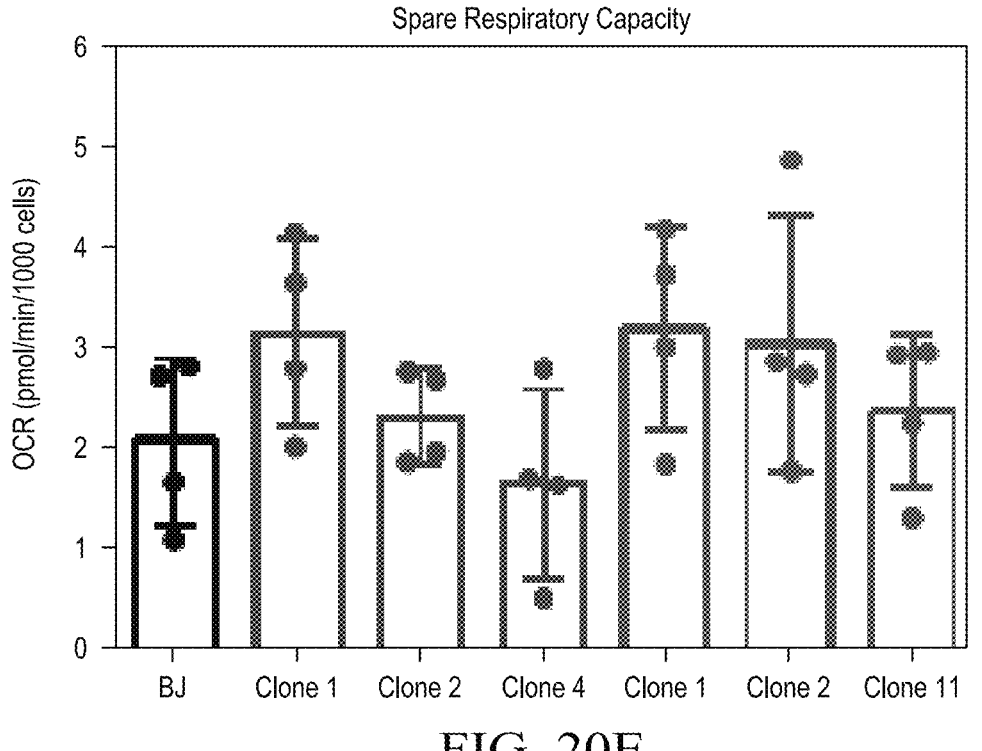
Figure 20F:
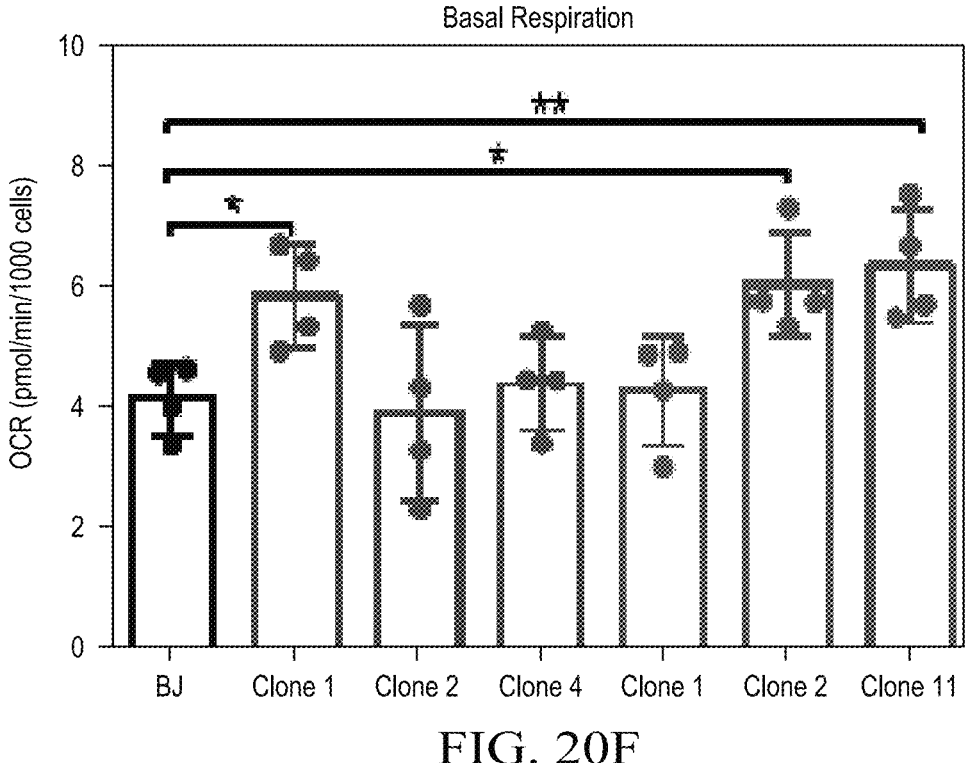
Figure 20G:
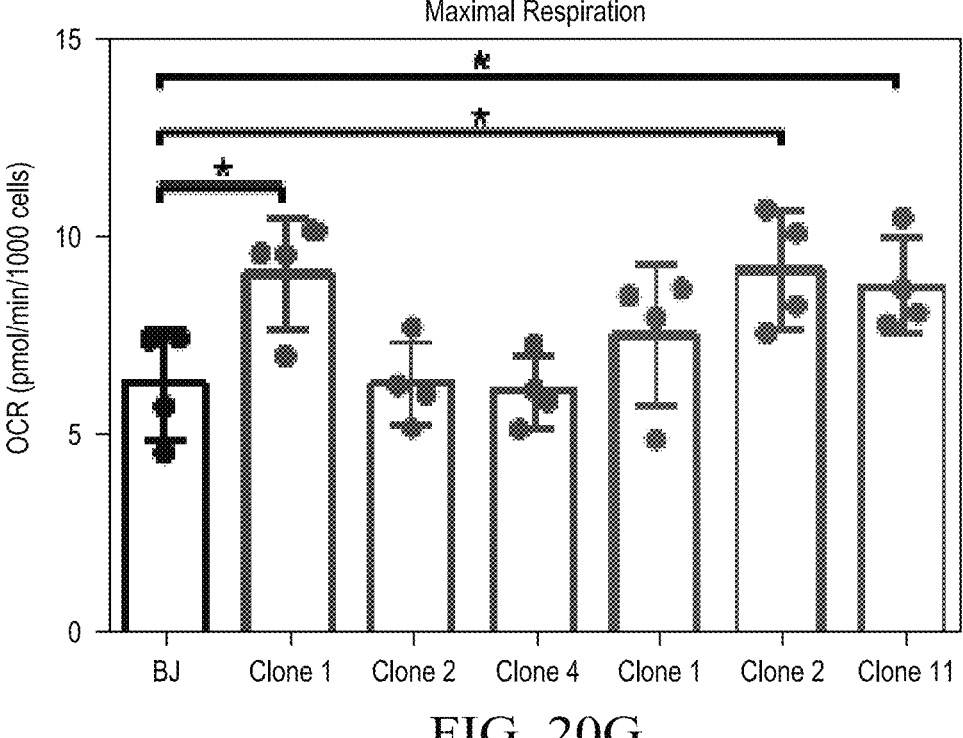

FIG. 20C shows flow cytometry quantification of pluripotency markers Sox2 and Oct3/4, and fibroblast marker CD44. Stained samples are shown in color with isotype negative controls in grey. BJ fibroblasts represent the negative control and BJ iPSCs represent the positive control. Representative data from the BJ p0+HEK293T and BJ p0+LP351 are shown. CD44, a marker for differentiated cells, was negative in all reprogrammed clones and positive only in BJ fibroblasts (FIG. 20C).

FIGS. 20D-20G show the respiratory profiles of transferred cells and the BJ iPSC control that were quantified by a Seahorse XF96 flux analyzer. About 15,000 cells were used for each condition. Data is presented as the average of four technical replicates±standard deviation. Dotted lines represent drug injection points. * P<0.05, ** P<0.01.

While slight differences in respiratory capacities were observed between the BJ, BJp0+HEK293T, and BJp0+LP351 lines, there were no dramatic population differences between the non-transferred and transferred reprogrammed cell lines.

FIGS. 21A-21F show differentiation of iPSCs into MSCs according to the embodiments presented herein.

Figure 21A:
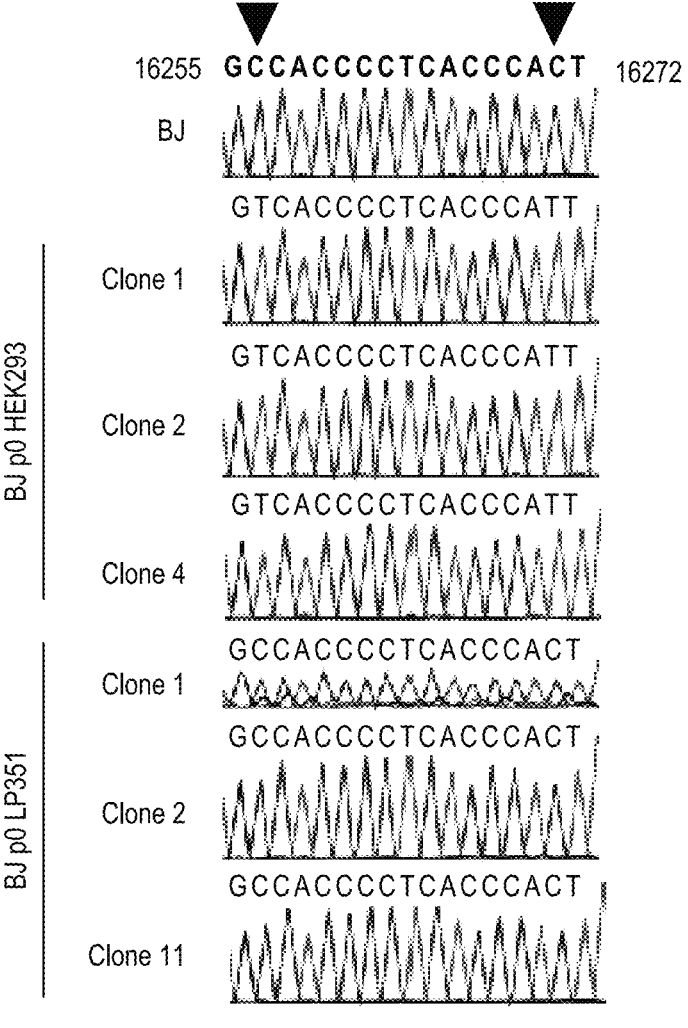

FIG. 21A shows sequences of hypervariable regions. DNA was isolated from MSCs and the mtDNA D-loop hypervariable region was sequenced. Arrows denote SNPs. SEQ ID NOs: 71-77 refer to the mtDNA D-loop hypervariable regions of BJ, BJ p0+HEK293T Clone 1. J p0+HEK293T Clone 2, J p0+HEK293T Clone 3, BJ p0+LP35 Clone 1, BJ p0+LP35 Clone 2, and BJ p0+LP35 Clone 11 cells, respectively.

Each MSC transfer clone was confirmed to retain the correct mtDNA sequence through the differentiation process (FIG. 21A).

Figure 21B:
Figure 21C:
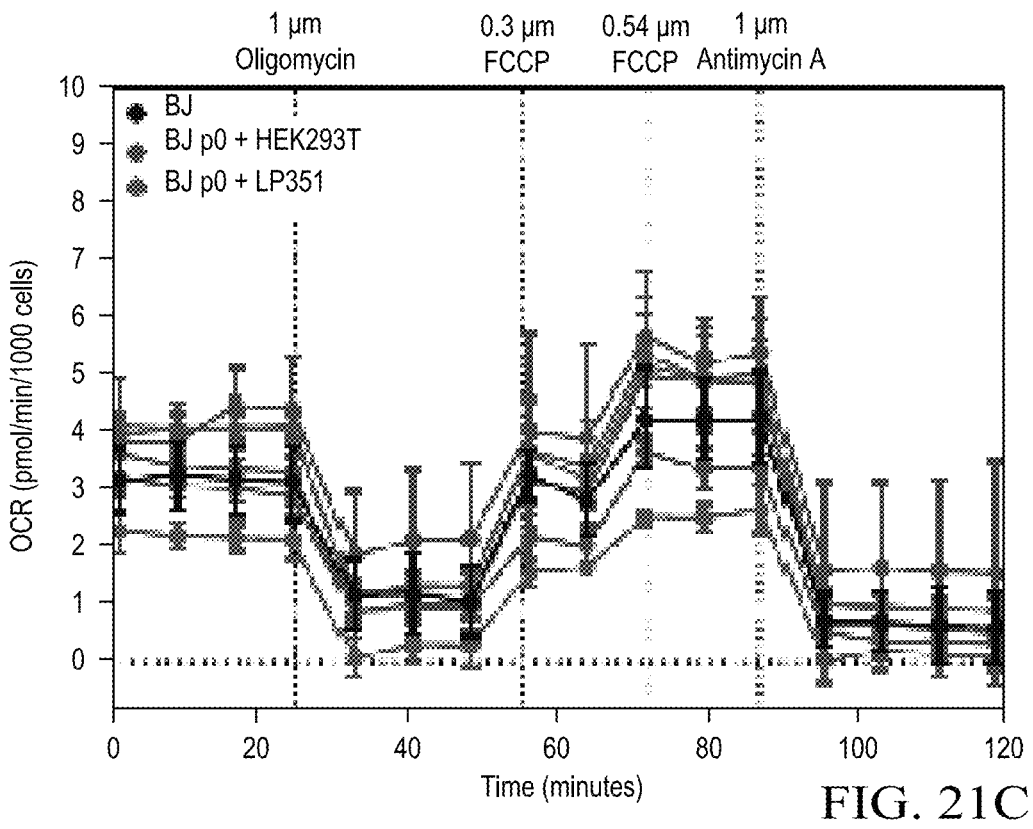
Figure 21D:
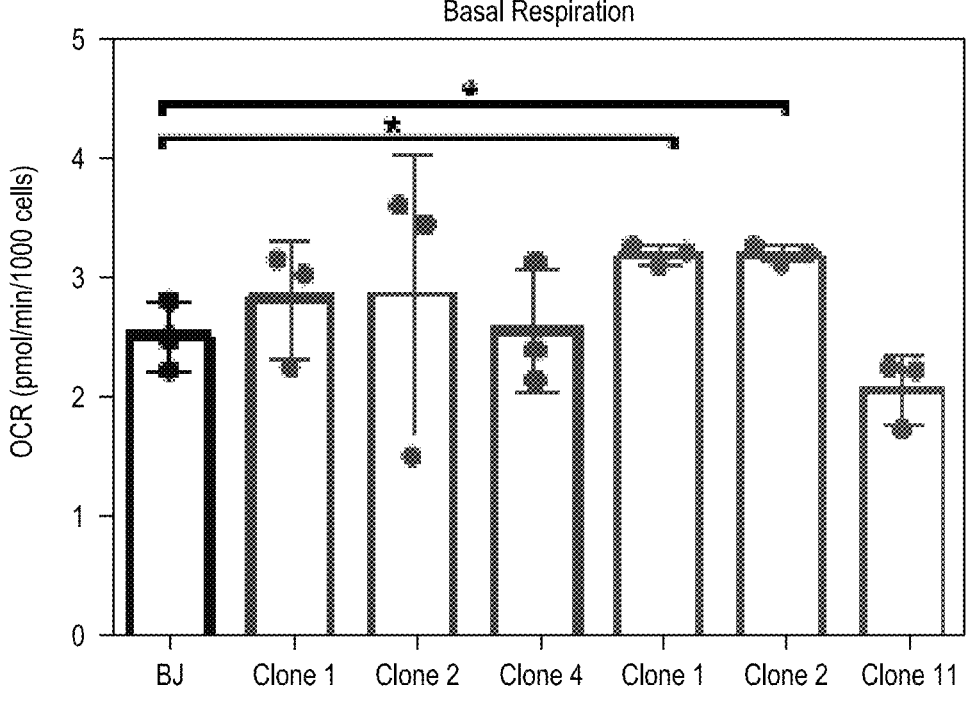
Figure 21E:
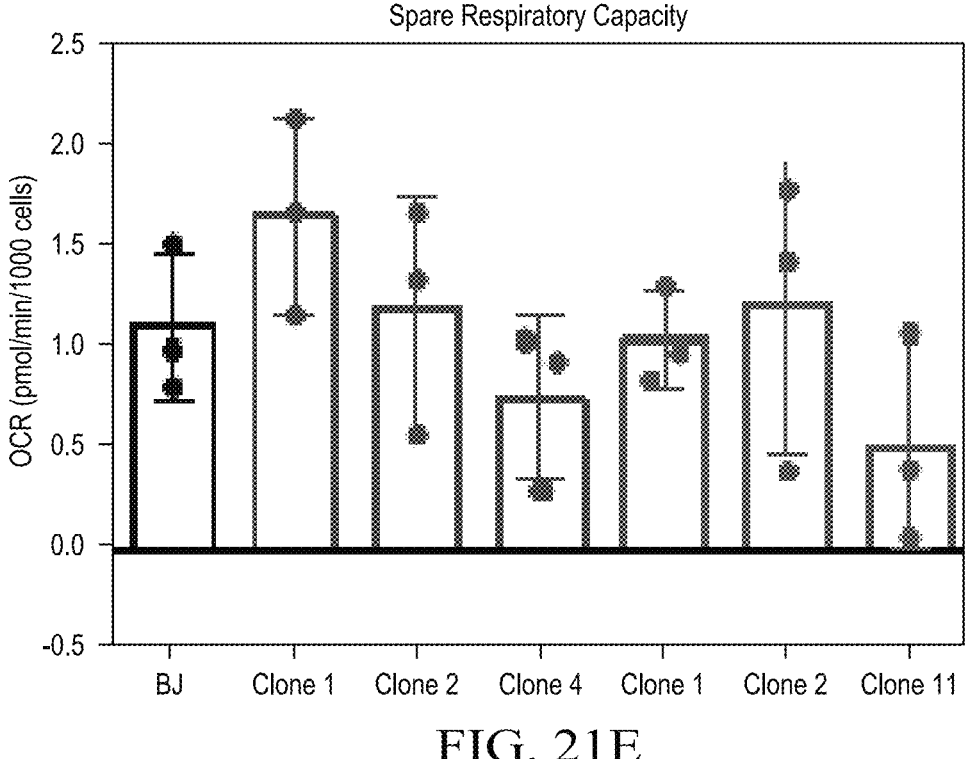
Figure 21F:
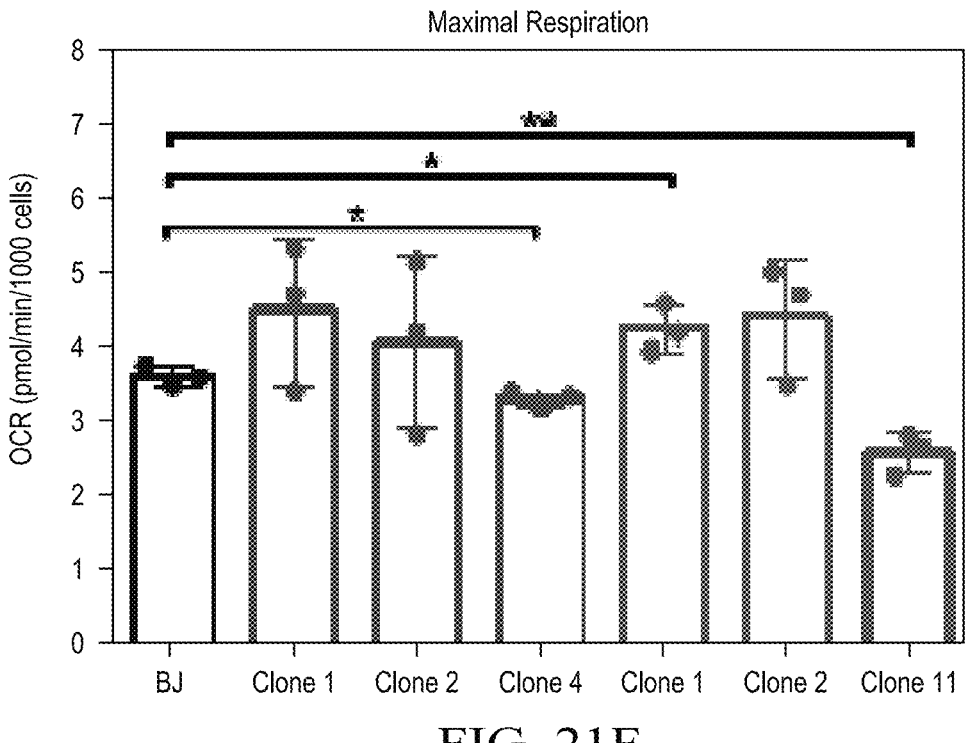

FIG. 21B shows flow cytometry of positive MSC markers CD90, CD73, and CD105, and a cocktail of negative MSC markers (CD34, CD45, CD11b, CD19, and HLA-DR). Stained samples are shown in color with isotype negative controls in grey. Representative clones from the BJ p0+HEK293T and BJ p0+LP351 are shown. BJ iPSCs that were converted to MSC represent the control.

FIGS. 21C-21F show quantification of mitochondrial respiration, by a seahorse XF96 extracellular flux analyzer, for BJ p0+HEK293T and BJ p0+LP351. About15,000 cells were plated in each well. Three biological replicates are presented for the BJ p0+HEK293T and BJ p0+LP351, and one biological replicate is presented for the BJ control. Dotted lines denote drug injection points. Data is presented as an average of three technical replicates±standard deviation. * P<0.05, ** P<0.01.

The respiratory profiles of MSC clones were characterized (FIGS. 21C-21F). In comparison to the BJ MSC control, no statically significant differences in spare respiratory capacity were observed in the BJp0+HEK293T and BJp0+LP351 lines. In addition, only slight variations in basal and maximal respiration existed in the mitochondrial recipient clones in comparison to the BJ control.

FIGS. 22A-22E show aspects of functional characterization of MSCs according to the embodiments presented herein.

Figure 22A:
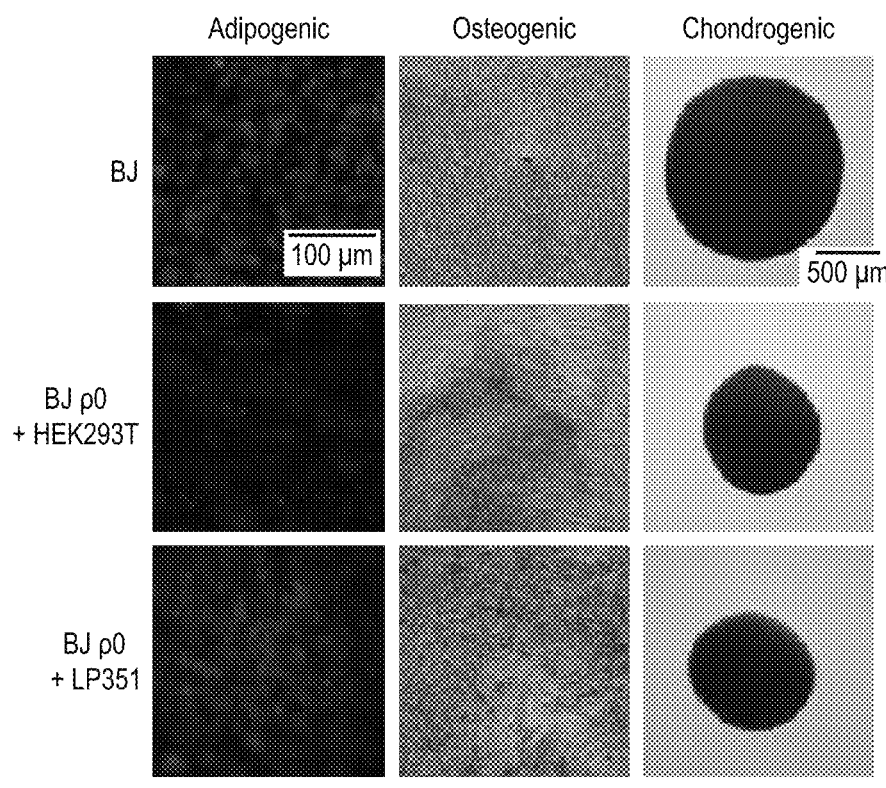

FIG. 22A shows MSCs that underwent trilineage differentiation. The resulting adipocytes, osteocytes, and chondrocytes were fixed and stained with 1 μM Bodipy 493/503, 1% alizarin red S, and 0.1% safranin O, respectively. Adipocytes were imaged at 20×. The scale bar denotes 100 μm. Osteocytes were imaged at 10×. Chondrocytes were imaged at 3.2×. Scale bar denotes 500 μm.

Figure 22B:
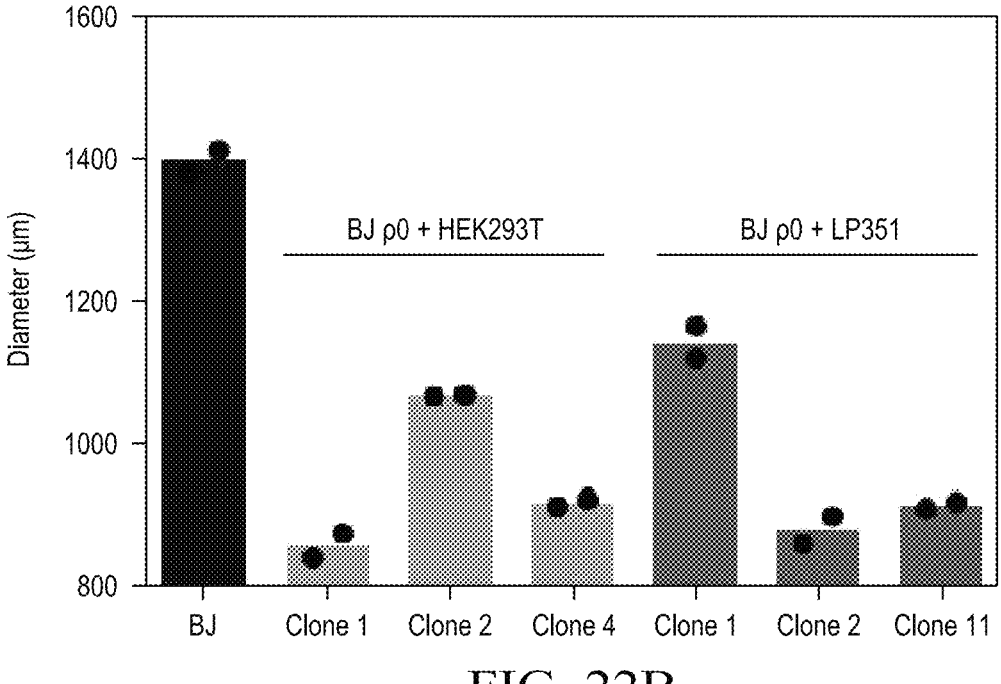

FIG. 22B shows the diameter of chondrocytes from FIG. 22A that were measured in ImageJ. Data is represented for each condition as the mean of two biological replicates.

Figure 22C:
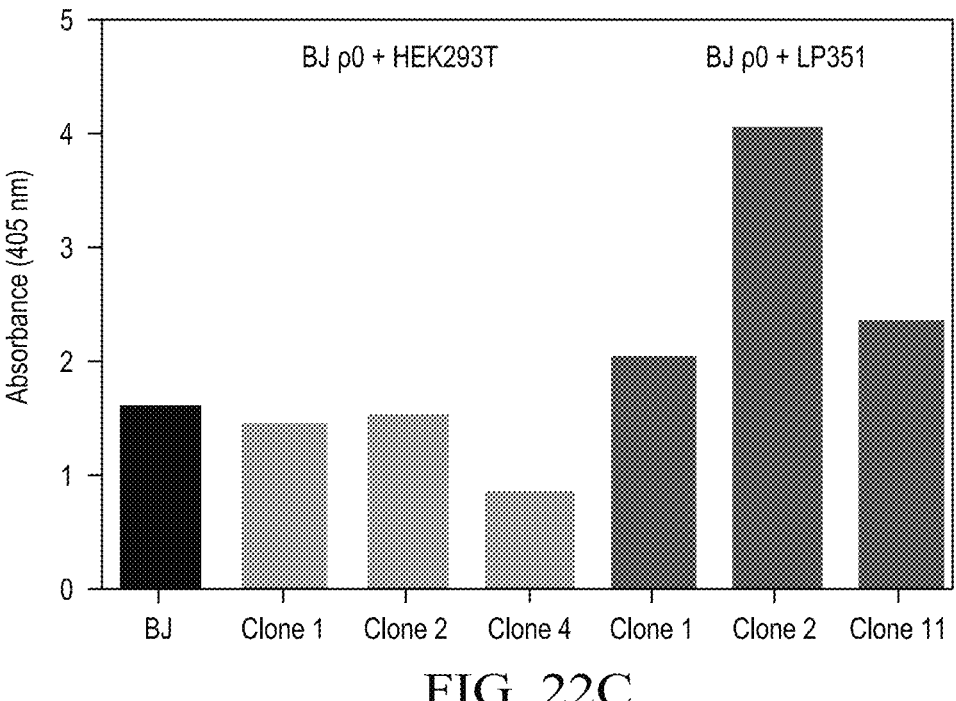

FIG. 22C shows calcium deposits from osteocytes identified in FIG. 22A that were collected and measured at 405 nm. Data represents n=1.

Figure 22D:
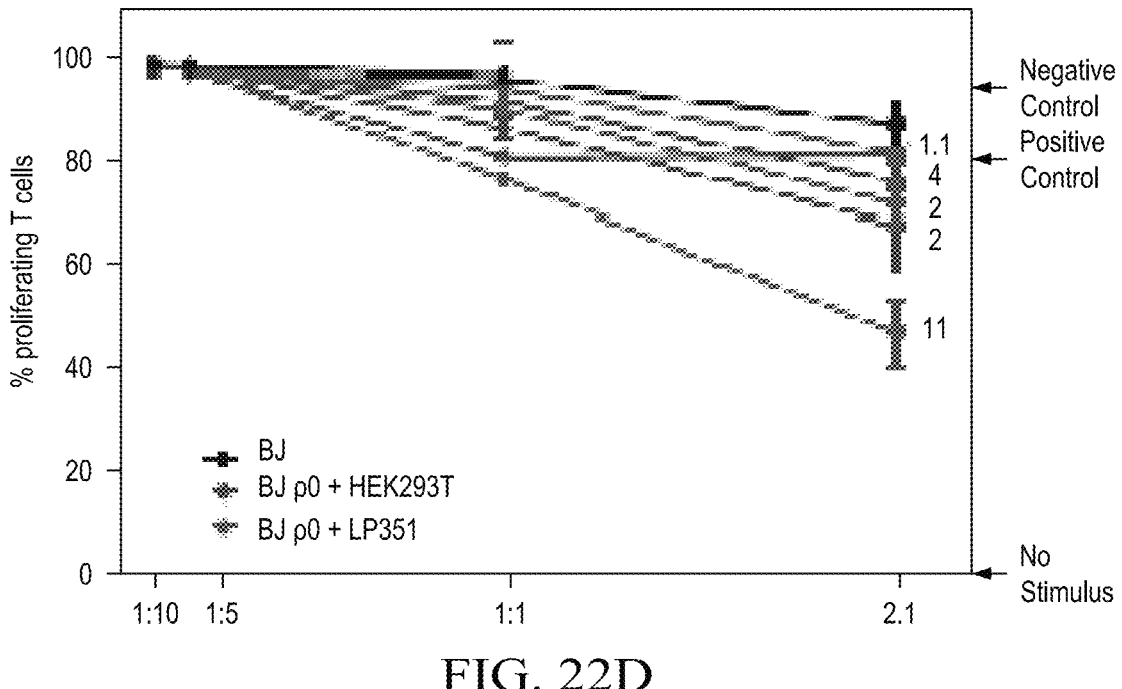

FIG. 22D shows the effect of MSC cells on T cell proliferation. T cells were added into MSC culture at the following T cell: MSC ratios: 1:2, 1:1, 5:1, and 10:1. After 5 days of co-culture, T cell proliferation was measured using CFSE signature by flow cytometry. Data was presented as the mean of three technical replicates±standard deviation.

T cells that were not stimulated with CD3/CD28 beads represent no stimulus. The addition of no MSCs to stimulated T cells represents the negative control. The 1:1 addition of MDSCs to T cells represents the positive control. In general, all mitochondria recipient MSC clones showed enhanced reduction in T cell proliferation in comparison to the BJ parental MSC (FIG. 22D). BJp0+LP351 clone 11 exhibited the greatest reduction in T cell proliferation, while the remaining clones were not significantly different.

Figure 22E:
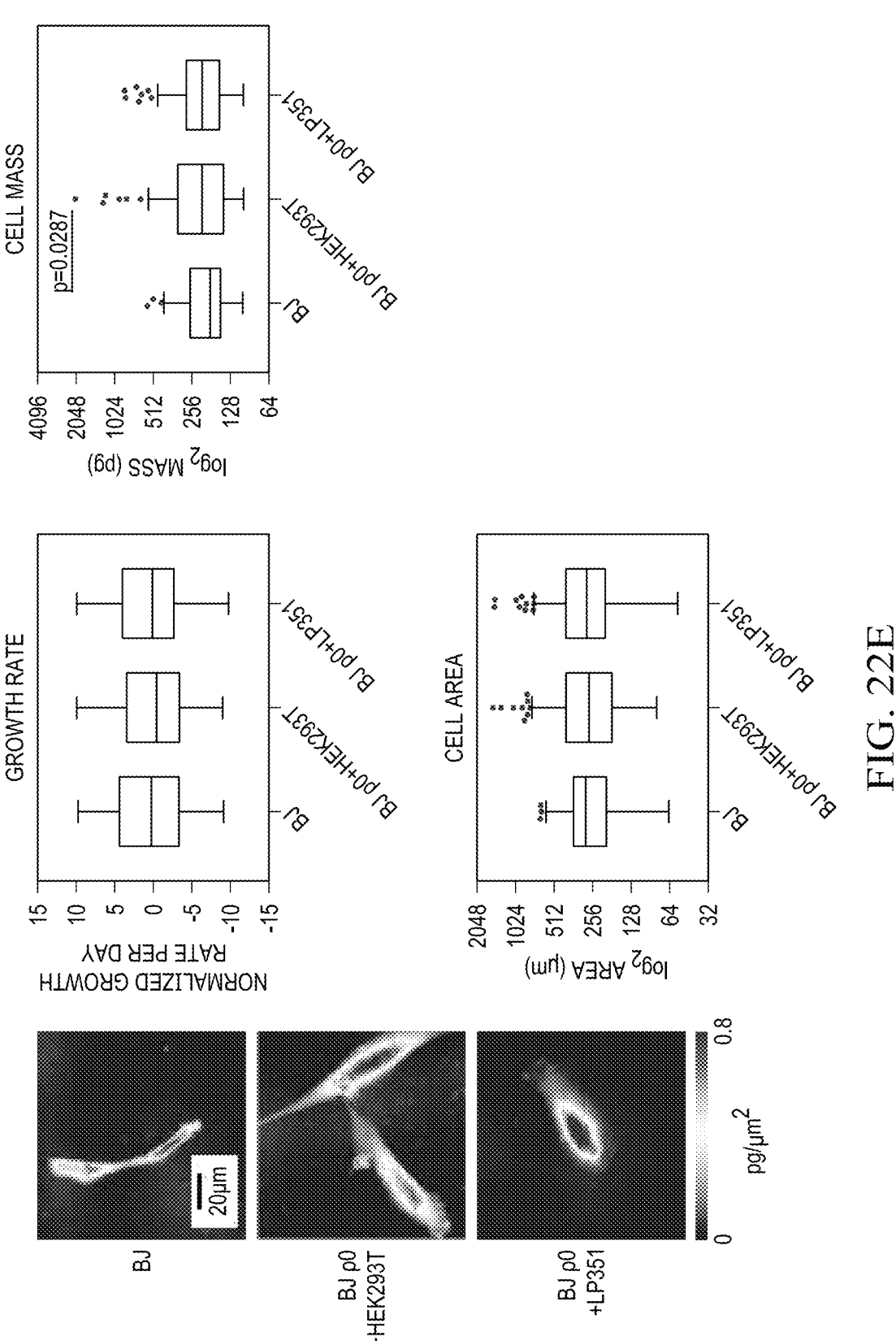

FIG. 22E shows quantitative phase microscopy (QPM) characterization of BJ, BJ p0+HEK293T, and BJ p0+LP351. Representative phase images are shown for each condition on the left. Growth rate, cell mass, and cell area are represented as box-and-whisker Tukey plots with outliers shown. Only biologically relevant cells were analyzed by removing mass increases >10 times per day. Data was obtained from 77, 124, and 172 cells for BJ, BJ p0+HEK293T, and BJ p0+LP351 conditions, respectively. Statistical significance was determined by Welch's T test.

QPM was used to analyze the biophysical characteristics of the mitochondrial recipient MSCs (FIG. 22E). No significant differences were observed in growth rate and comparison to the BJ MSC control, but a significant increase in BJp0+HEK293T mass was observed. MSCs generated by mitochondrial transfer were functional, multipotent, able to suppress T cell proliferation, and had similar biophysical properties as compared to the BJ parental control.

Figure 23A:
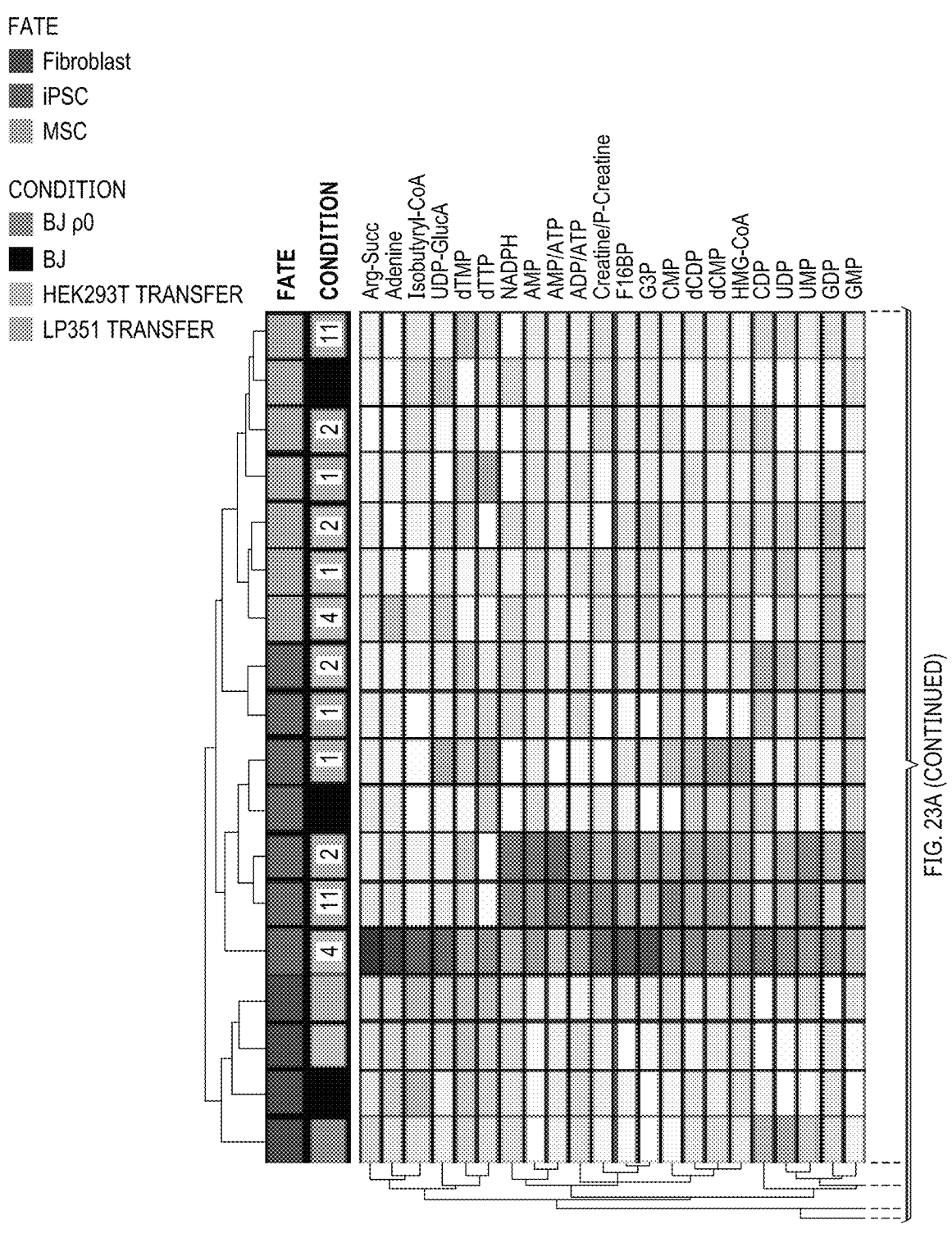
Figure 23A:
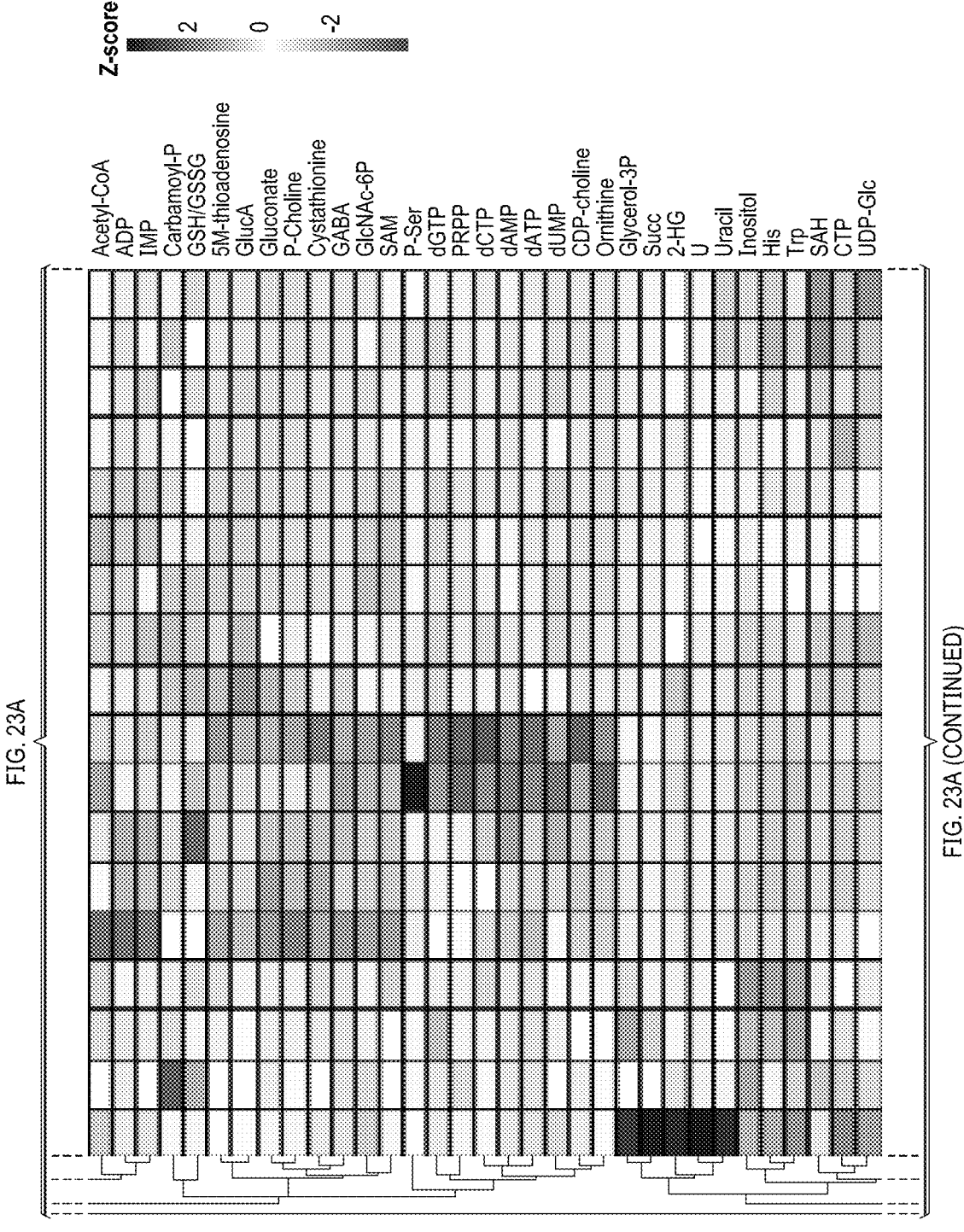
Figure 23A:
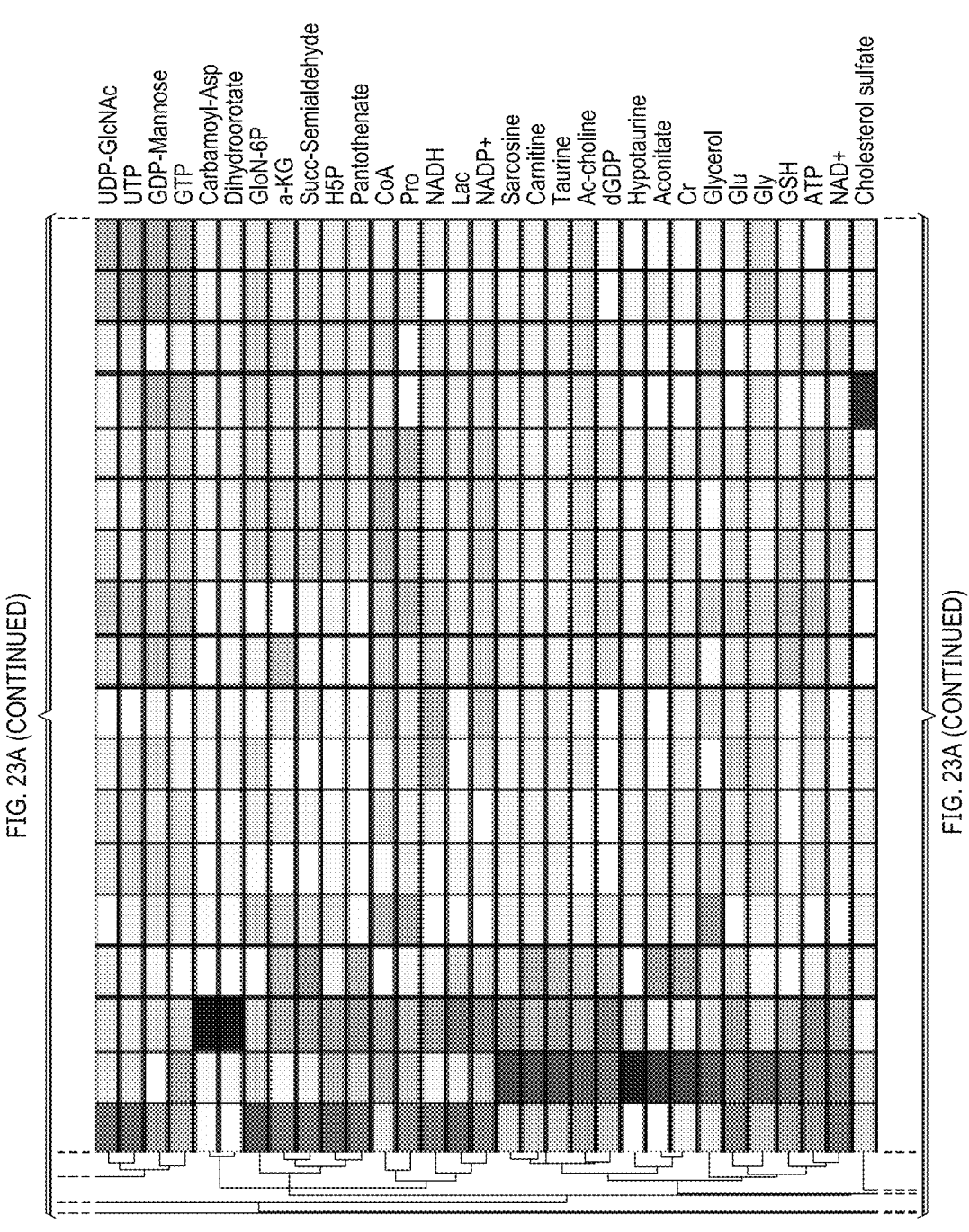
Figure 23A:
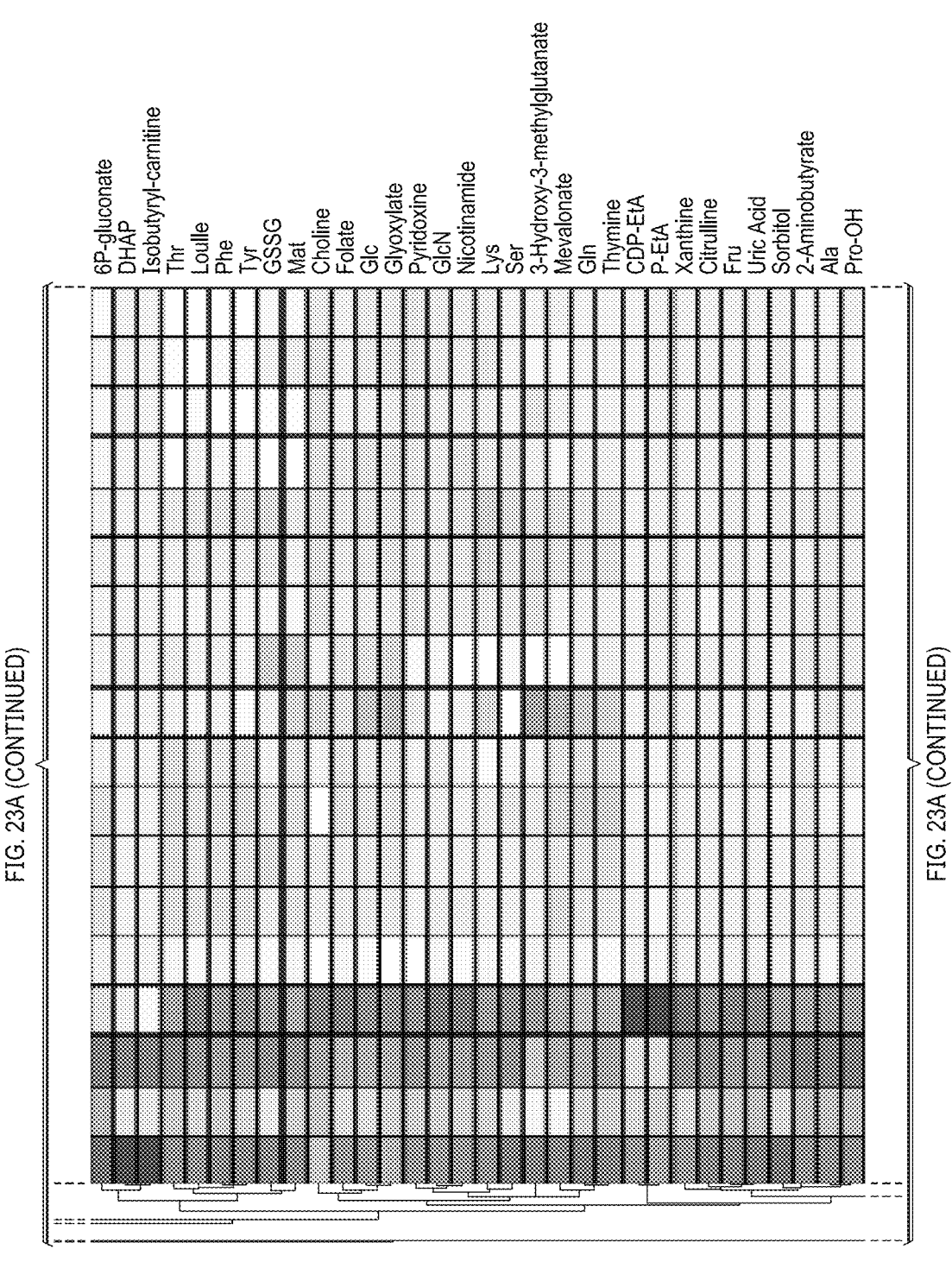
Figure 23A:
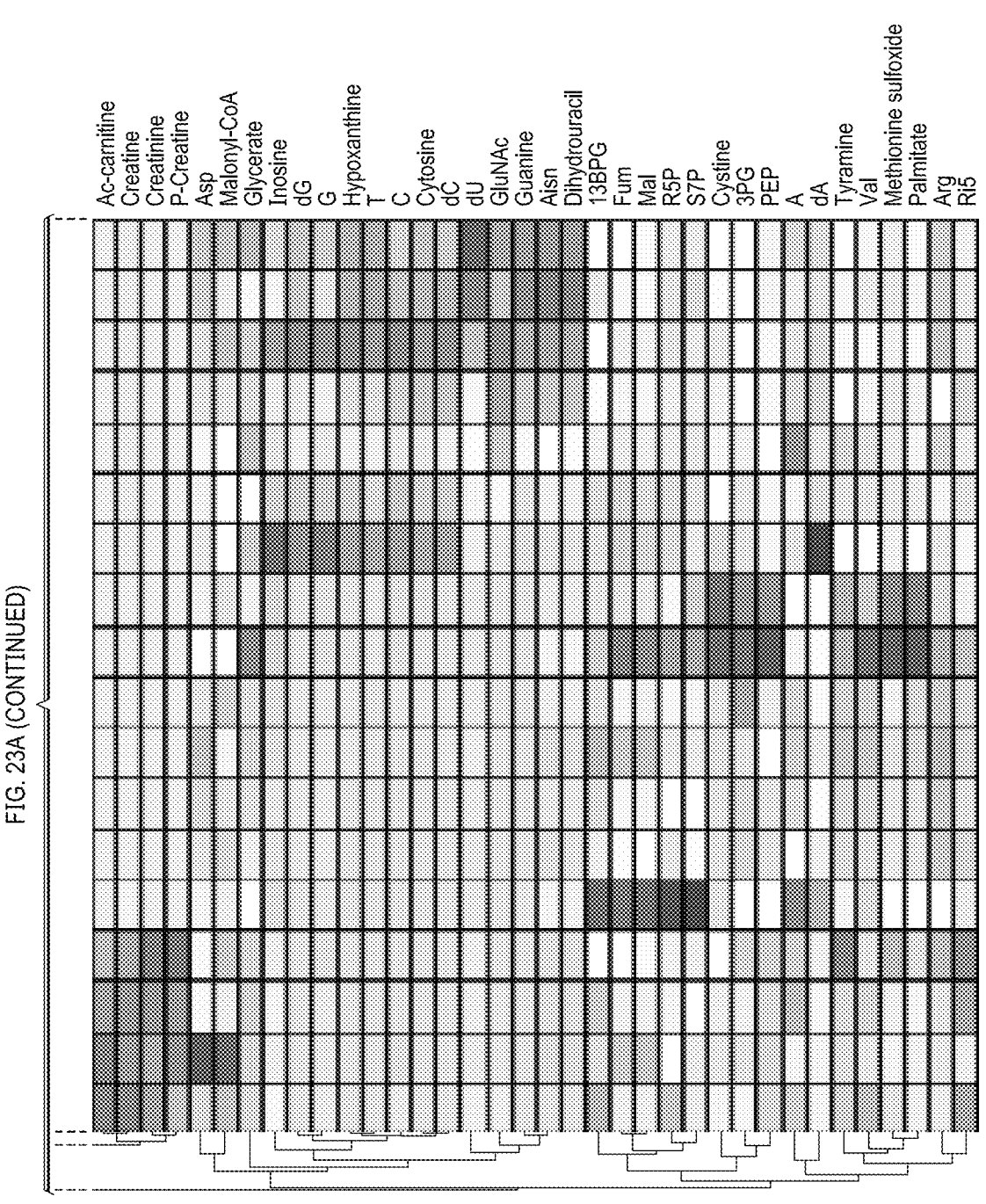
Figure 23C:
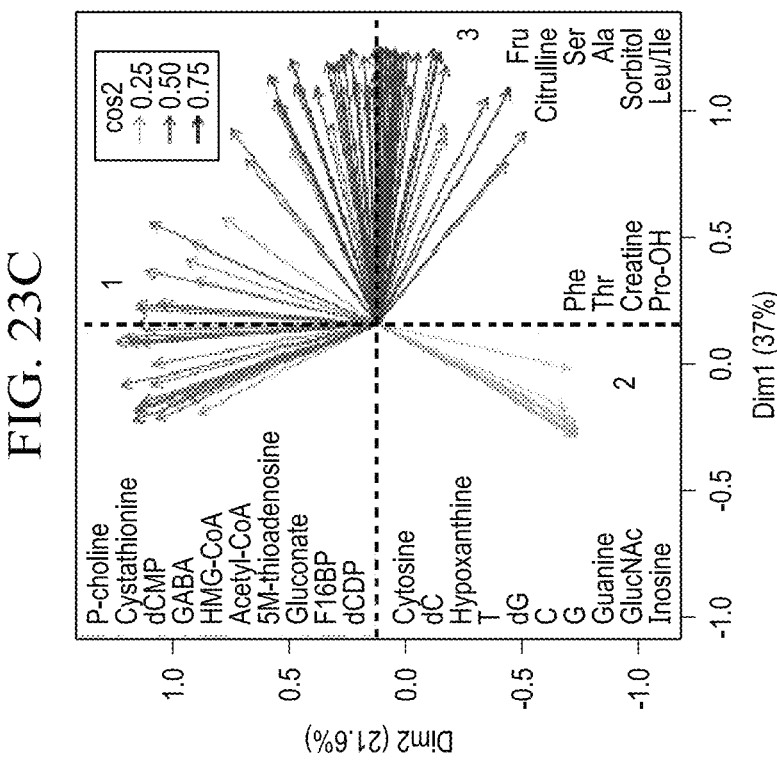
Figure 23B:
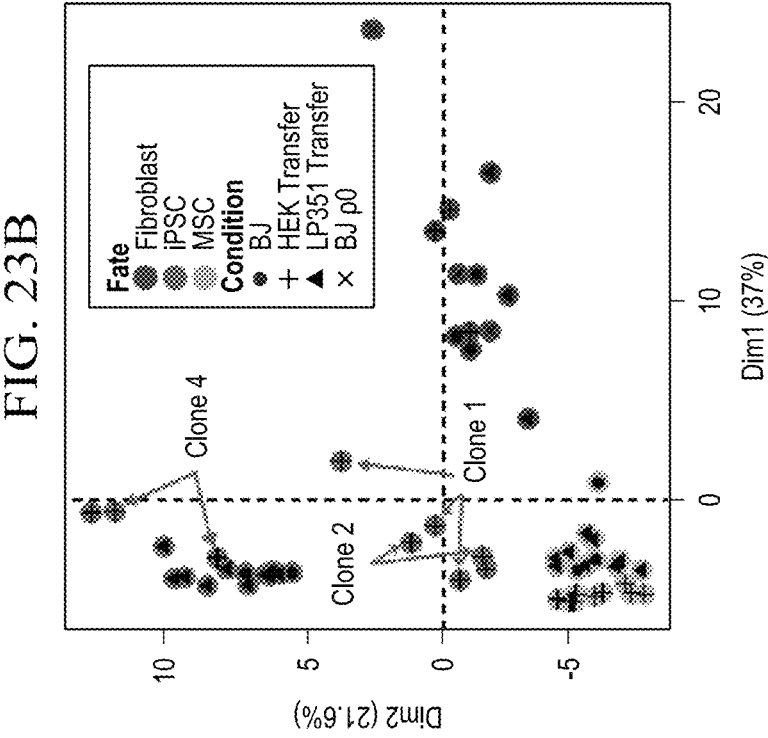

FIGS. 23A-23C show steady-state metabolomics results that revealed restored respiratory profiles of mitochondria-transferred fibroblasts and differentiated progeny according to the embodiments presented herein.

FIG. 23A shows UHPLC-MS quantification of Z-score converted normalized abundance of metabolites across averaged samples. Samples are annotated by cell fate (top row) and transfer condition (second row). Clone number for BJ p0+HEK293T and BJ p0+LP351 samples are indicated by number in the transfer condition row.

FIG. 23B shows principal components analysis (PCA) of metabolite normalized abundance across all sample replicates. Fibroblasts are indicated in red, iPSCs in green, and MSCs in yellow. BJ control cells are indicated with a circle, BJ p0 cells with an x, BJ p0+HEK293T with a plus, and BJ p0+LP351 with a triangle. Plot represents the first (Dim1) and second (Dim2) principal components along the x- and y-axes, representing the primary and secondary sources of variation across all samples, respectively.

FIG. 23C shows principal components loading plots indicating contribution of metabolites towards the variability across principal components, grouped into three clusters using k-means clustering (k=3). Tips of the arrow projections indicate Pearson correlation of the specified metabolite with Dim1 and Dim2 principal components; transparency of lines denote the cosine$^2$ value, the strength of metabolite representation on calculating the principal components. Metabolites listed represent the top 10 metabolites contributing to the variance explained by each cluster (calculated as the metabolite cosine[2] value divided by the total number of cosine[2] per principal component).

Samples represent 154 quantified metabolites that were averaged across BJ fibroblasts (n=3), BJ p0 fibroblasts (n=3), BJ p0+HEK293T fibroblasts (n=3 per clone, n=9 total), BJ p0+LP351 fibroblasts (n=3 per clone, n=9 total), BJ iPSCs (n=3), BJ p0+HEK293T iPSCs (n=3 per clone, n=9 total), BJ p0+LP351 iPSCs (n=3 per clone, n=9 total), BJ MSCs (n=3), BJ p0+HEK293T MSCs (n=3 per clone, n=9 total), and BJ p0+LP351 MSCs (n=3 per clone, n=9 total).

Figure 24A:
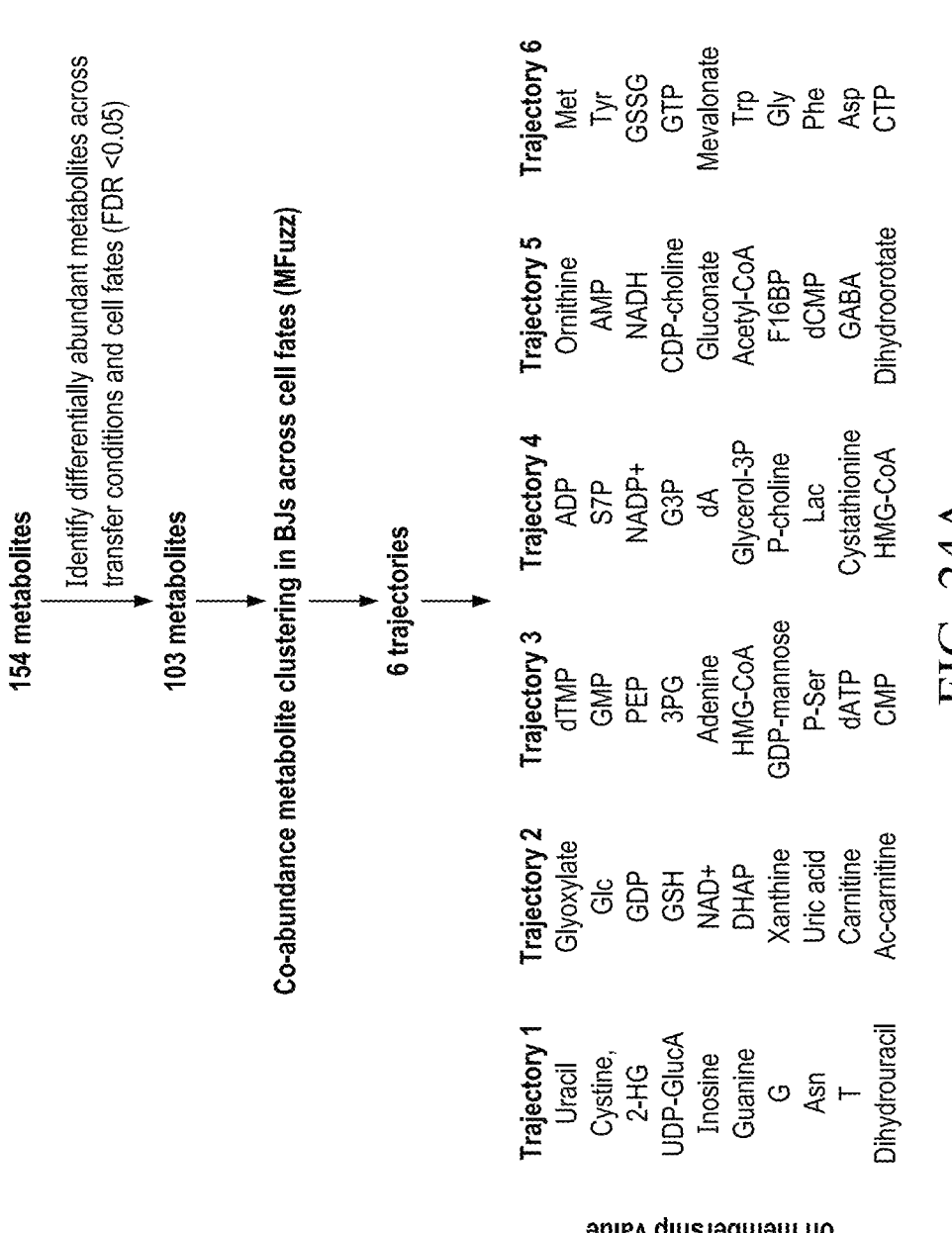
Figures 24B, 24C:
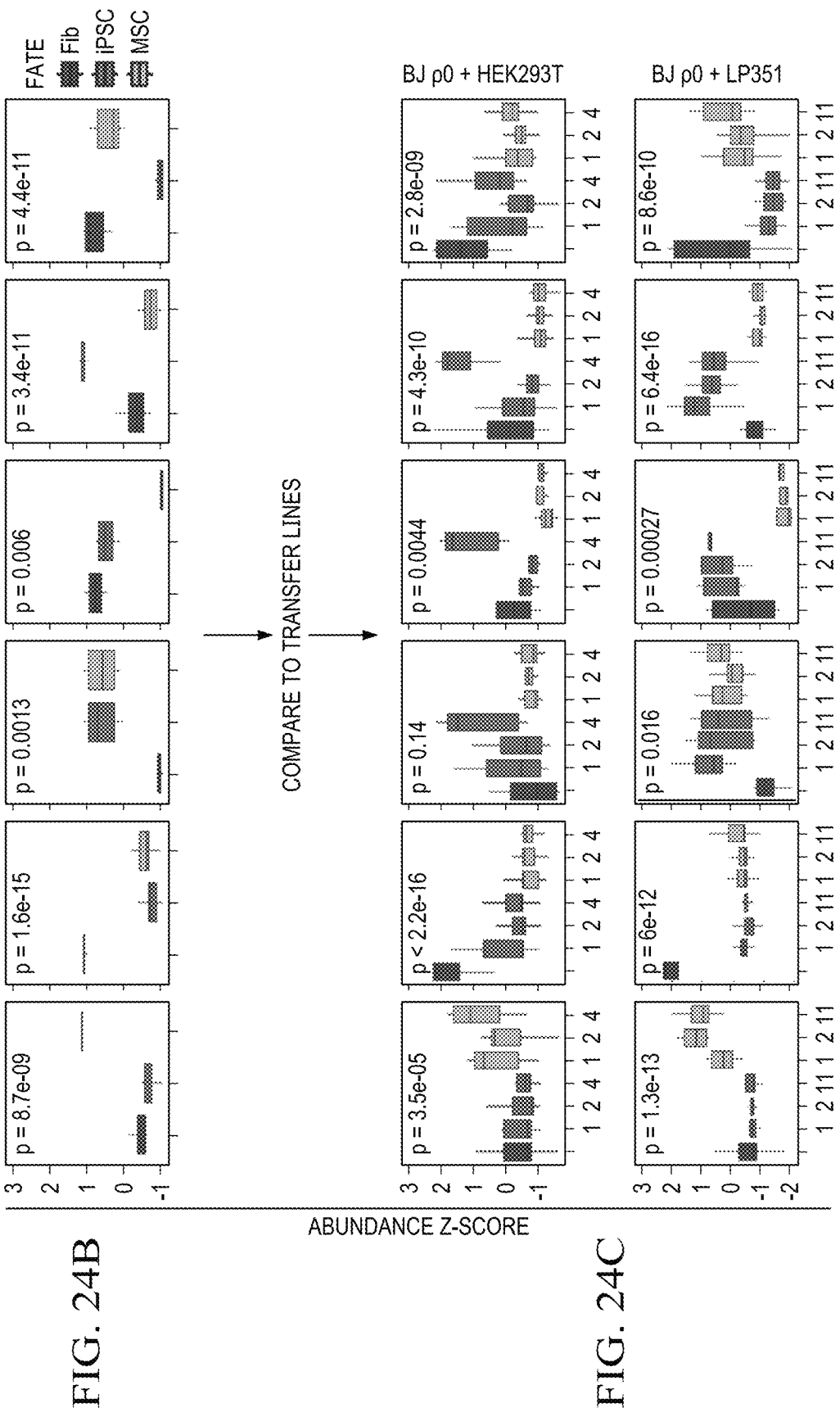

FIGS. 24A-24C show time-series clustering of metabolite data that indicates clonal variation in metabolite levels within BJ p0+HEK293T mitochondria iPSCs according to the embodiments presented herein.

FIG. 24A is a schematic for identifying BJ metabolomic time-series differentiation trajectories.

FIG. 24B shows boxplots of metabolites clustered into 6 independent BJ differentiation trajectories, averaged by transfer condition and cell fate. Red box indicates BJ fibroblast metabolite levels for metabolites binned in each trajectory: green box indicates BJ iPSC and yellow box indicates BJ MSC. Y-axis represents normalized abundance Z-scores, scaled across samples and metabolites. The metabolites listed represent the top 10 metabolites contributing to each trajectory, ranked by membership value (highest Pearson correlation coefficient).

FIG. 24C shows boxplots indicating comparison of BJ p0+HEK 293 mitochondria and BJ p0+LP351 mitochondria transfer lines to each established BJ trajectory (indicated to the right). Red box indicates transfer fibroblast metabolite levels for metabolites binned in each trajectory; green box indicates transfer of iPSC clones (denoted by number on x-axis); yellow box indicates MSC clones (denoted by number on x-axis). Y-axis represents normalized abundance Z-scores, scaled across samples and metabolites. P values indicate Kruskal-Wallis one-way analysis of variance across sample cell fate and transfer condition. Samples represent 154 quantified metabolites averaged across BJ fibroblasts (n=3), BJ p0 fibroblasts (n=3), BJ p0+HEK293 mitochondria fibroblasts (n=3 per clone, n=9 total), BJ p0+LP351 mitochondria fibroblasts (n=3 per clone, n=9 total), BJ iPSCs (n=3), BJ p0+HEK293 mitochondria iPSCs (n=3 per clone, n=9 total), BJ p0+LP351 mitochondria iPSCs (n=3 per clone, n=9 total), BJ MSCs (n=3), BJ p0+HEK293 mitochondria MSCs (n=3 per clone, n=9 total), and BJ p0+LP351 mitochondria MSCs (n=3 per clone, n=9 total).

FIGS. 25A-25E show steady-state transcriptomics that reveal conserved global transcriptional expression across mitochondrial-transferred fibroblasts and their derived progeny, according to the embodiments presented herein. Data represents bulk next generation RNA-sequencing (RNA-Seq) of whole cell extract.

Figure 25A:
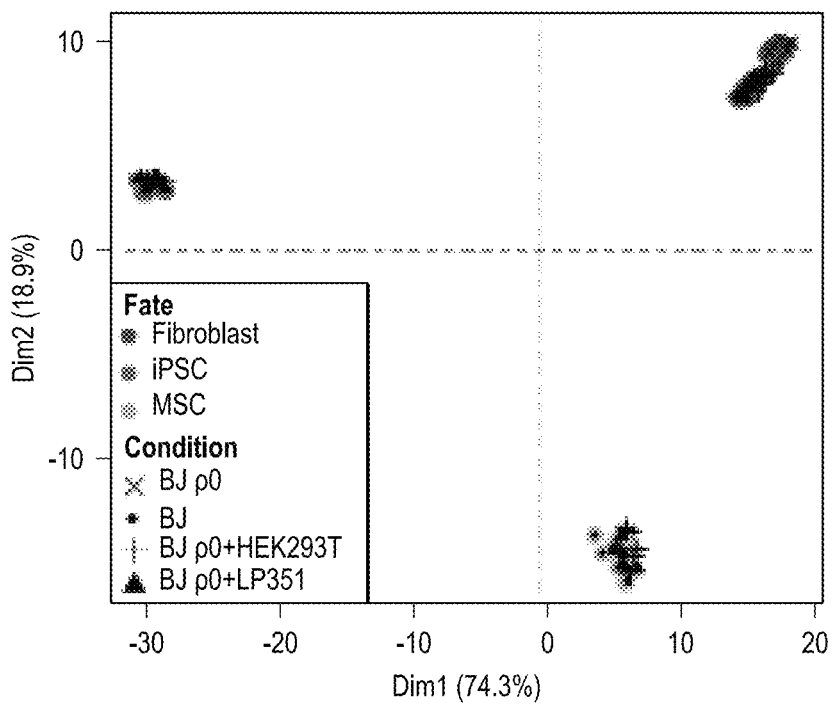

FIG. 25A shows PCA of whole transcriptome gene-level expression. Samples are labeled and plotted as indicated in the methods and FIG. 24C.

Figure 25B:
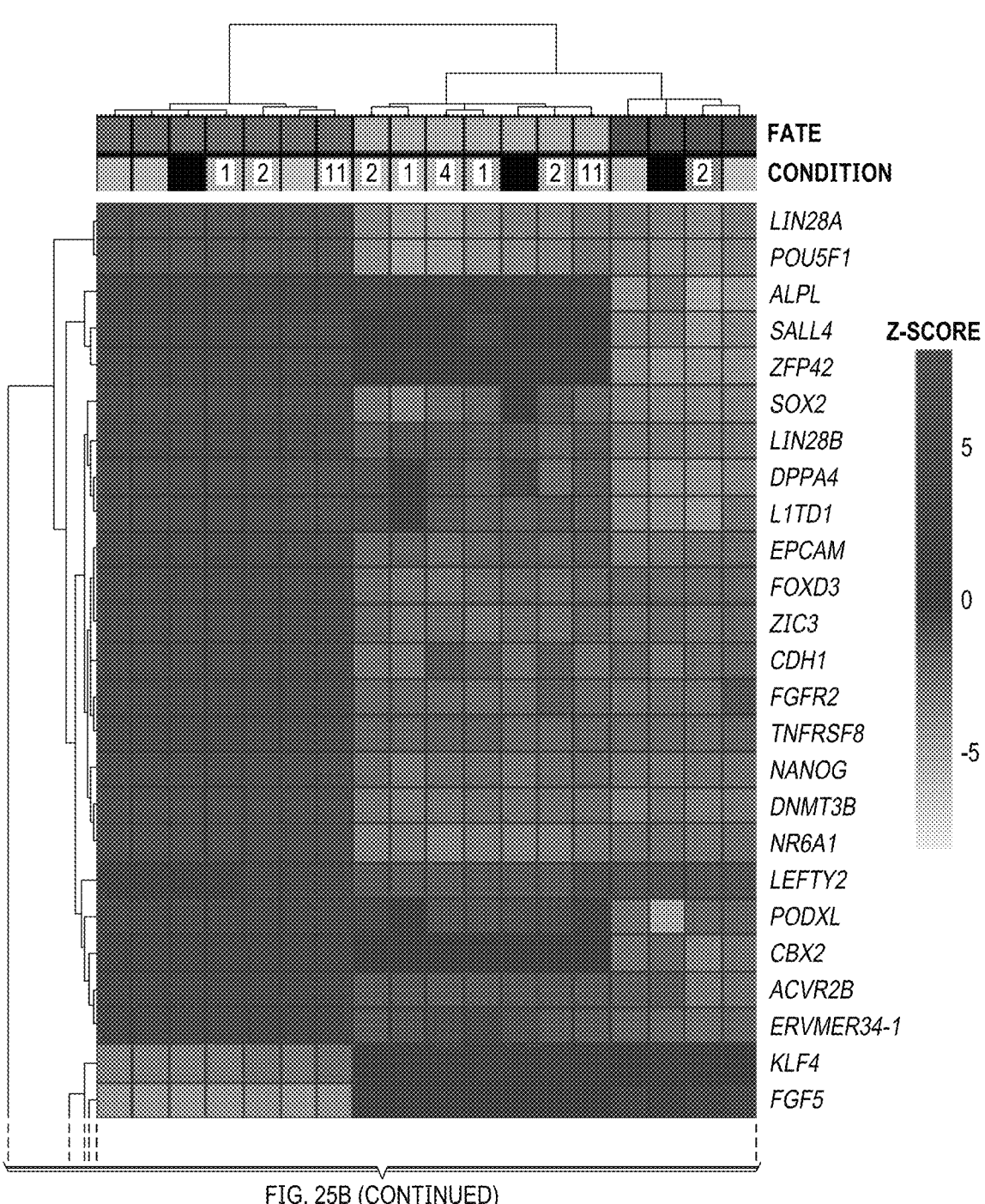
Figure 25B:
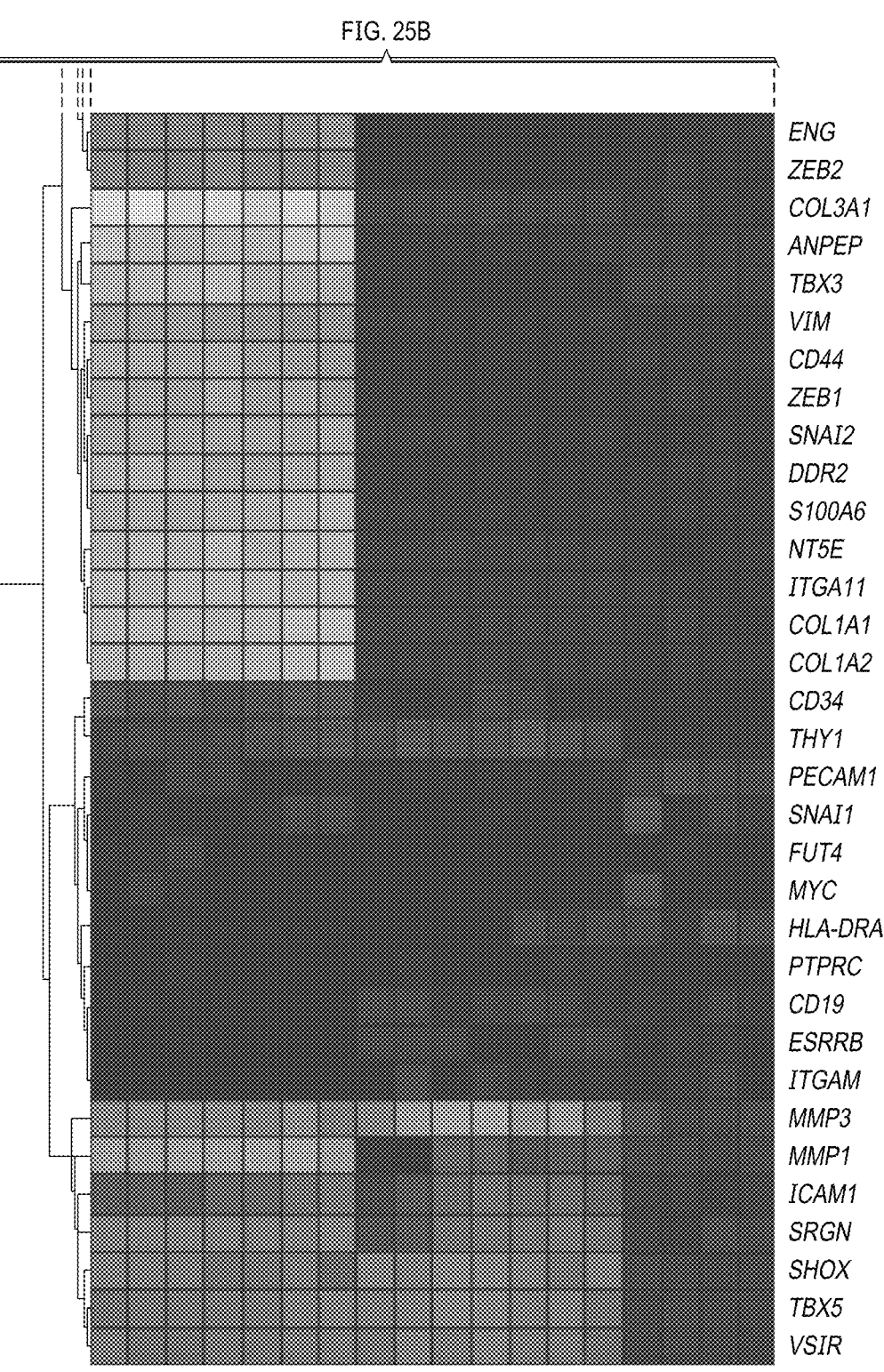

FIG. 25B shows a heatmap of gene-level expression of selected fibroblast, iPSC, and MSC markers across all samples. Data plotted represents row Z score of the variance stabilized transformation of raw read counts across samples.

Figure 25C:
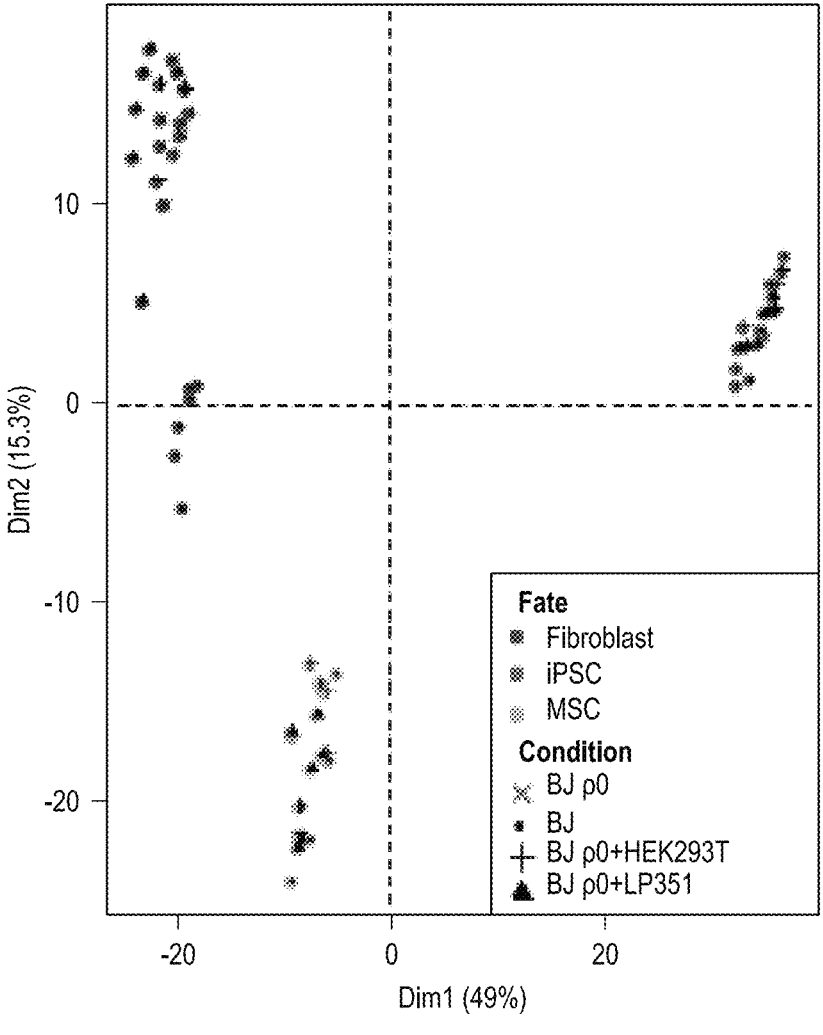

FIG. 25C shows PCA of nuclear-encoded mitochondrial transcript gene-level expression, as derived from mitochondrial localization evidence in MitoMiner v4.0. Samples are labeled and plotted as FIG. 25A.

Figure 25D:
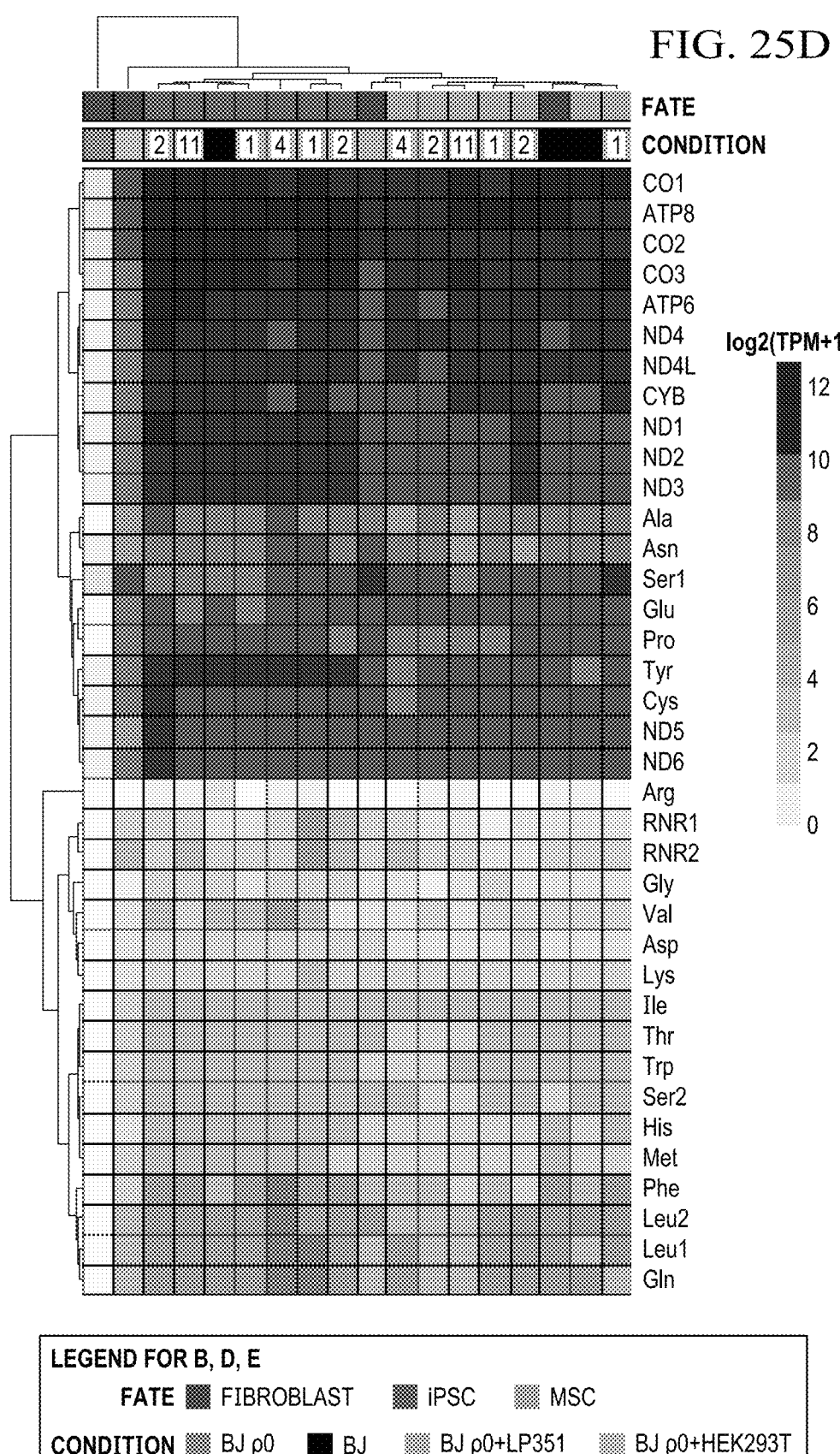

FIG. 25D shows a heatmap of gene-level expression of mitochondrial DNA (mtDNA) derived protein coding and tRNA transcripts across all samples. Data plotted represents log 2 transformation transcript per million plus one ($\log_2$ (TPM+1)) normalized expression across samples.

Figure 25E:
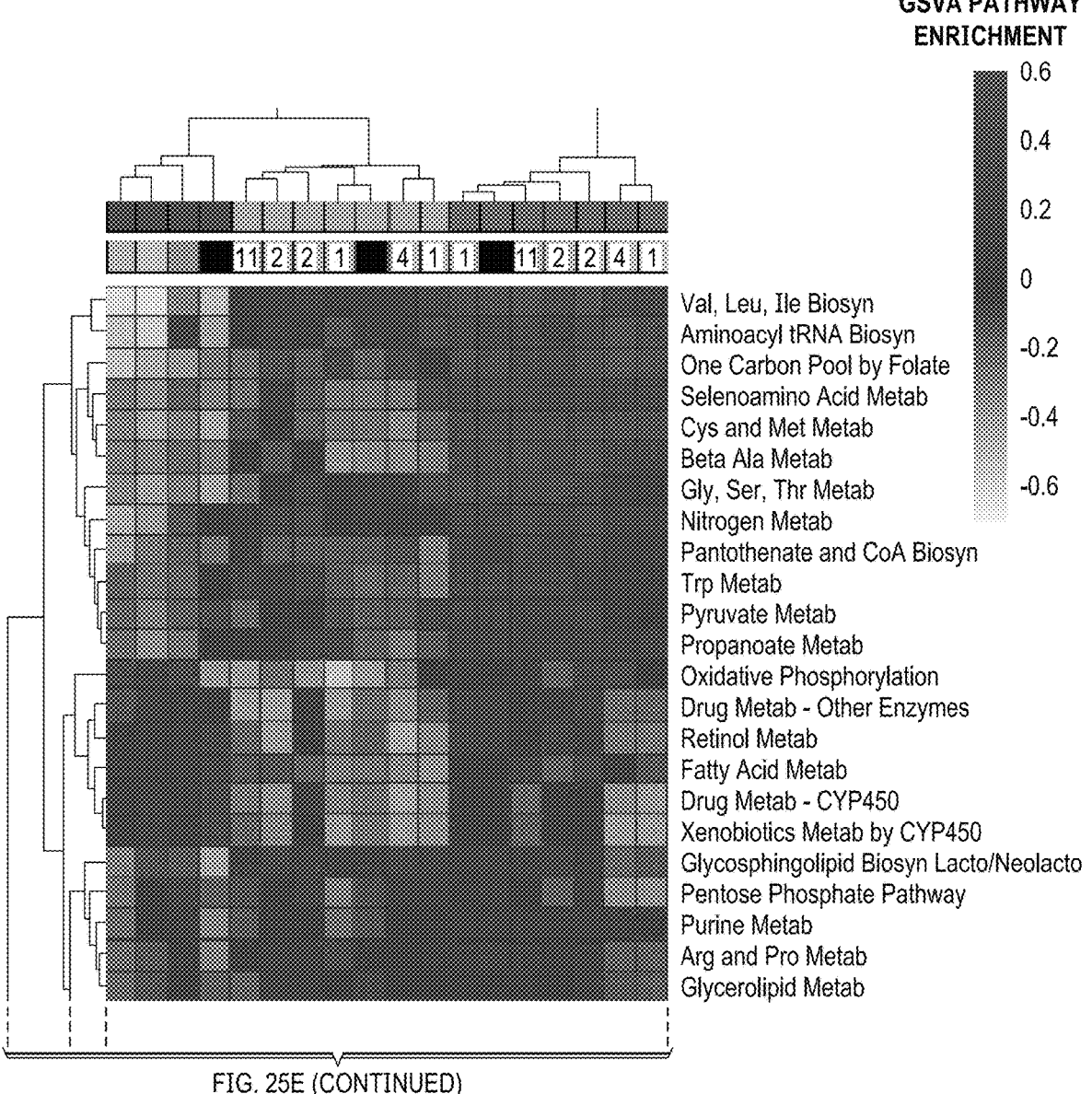

FIG. 25E shows a heatmap of gene set variation analysis (GSVA) indicating metabolic transcript pathway enrichment across averaged clonal samples. Rows indicate independent KEGG metabolic pathways analyzed (HSA01100). Clone number for BJ p0+HEK293 mitochondria and BJ p0+LP351 mitochondria samples are indicated by number in the transfer condition row. For all heatmaps, samples are annotated by cell fate (top row) and transfer condition (second row). Samples represent 37,116 quantified protein coding and non-coding gene-level summed transcripts quantified across BJ fibroblasts (n=6), BJ p0 fibroblasts (n=6), BJ p0+HEK293 mitochondria fibroblasts (n=2 per clone, n=6 total), BJ p0+LP351 mitochondria fibroblasts (n=2 per clone, n=6 total), BJ iPSCs (n=6), BJ p0+HEK293 mitochondria iPSCs (n=2 per clone, n=6 total), BJ p0+LP351 mitochondria iPSCs (n=2 per clone, n=6 total), BJ MSCs (n=6), BJ p0+HEK293 mitochondria MSCs (n=2 per clone, n=6 total), and BJ p0+LP351 mitochondria MSCs (n=2 per clone, n=6 total).

FIGS. 26A-26G show that transcriptomic alterations induced by mitochondrial transfer were reduced through differentiation according to the embodiments presented herein.

Figure 26A:
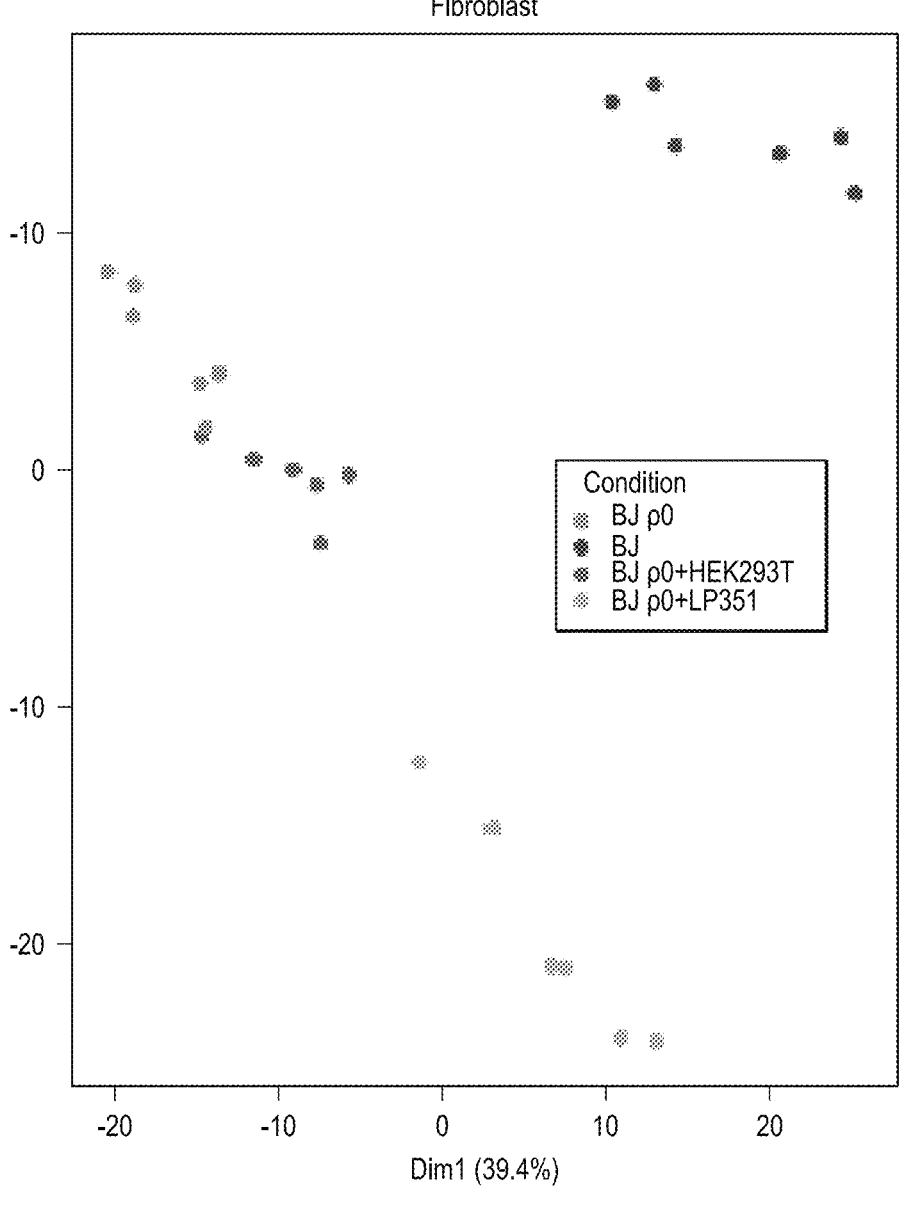
Figure 26B:
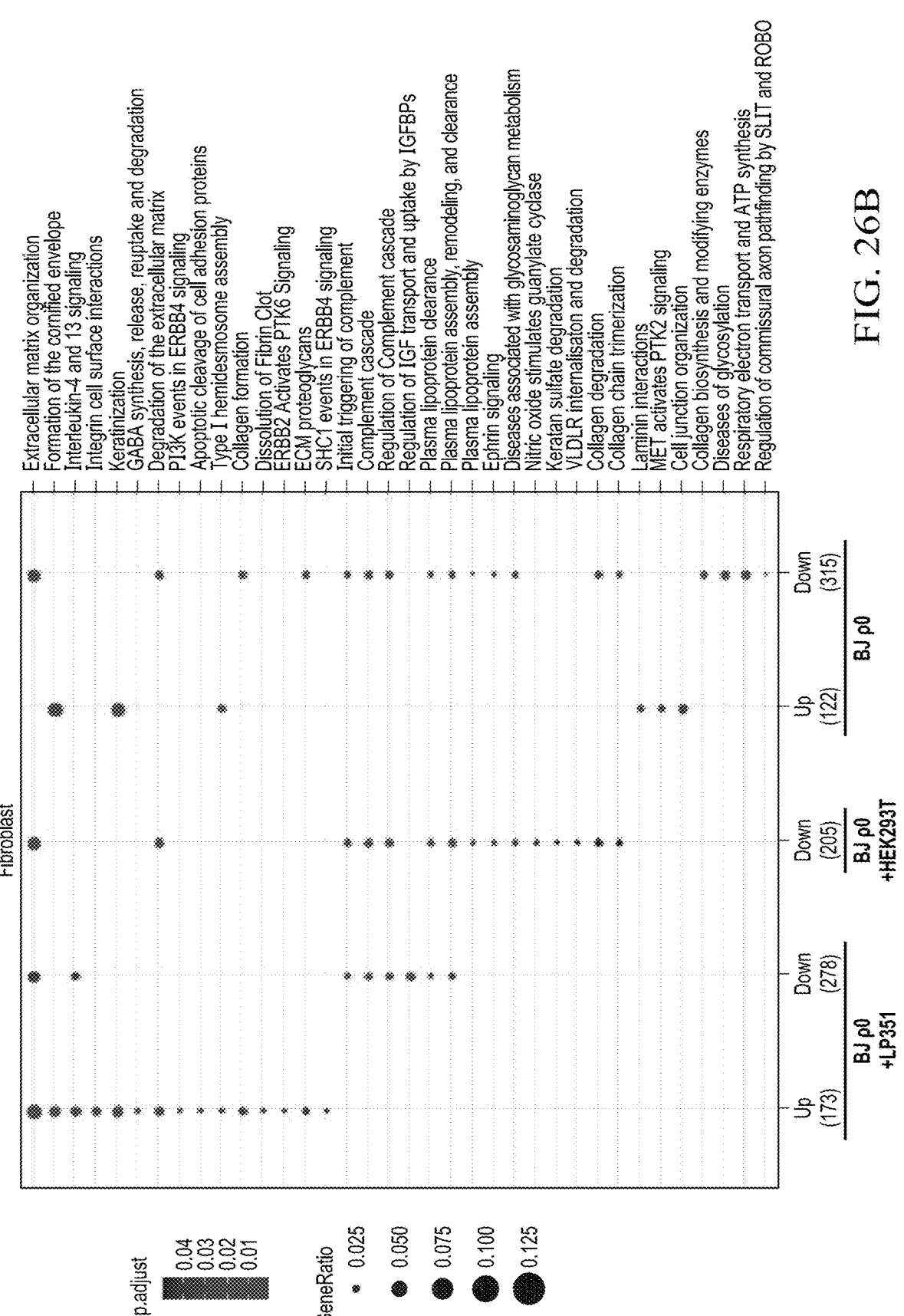
Figure 26C:
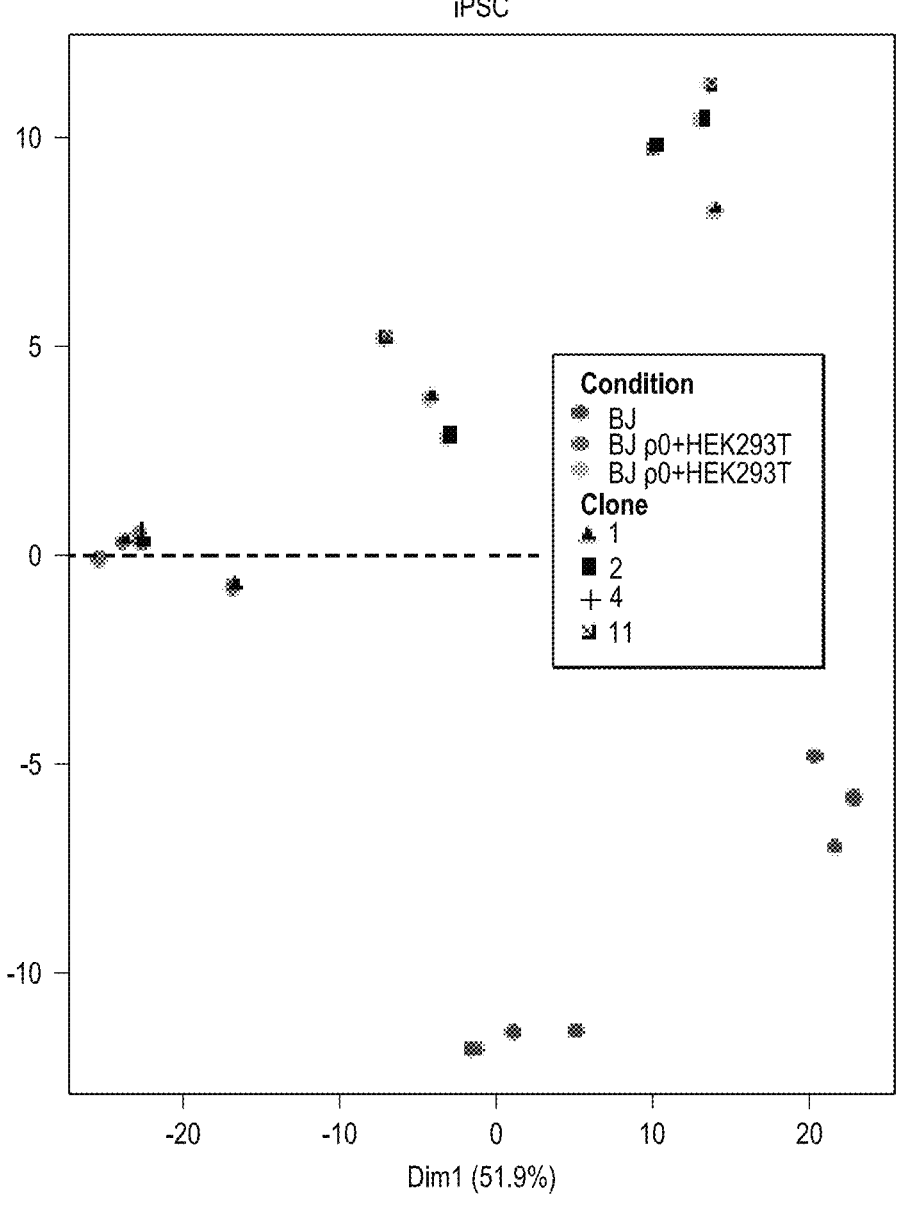
Figure 26D:
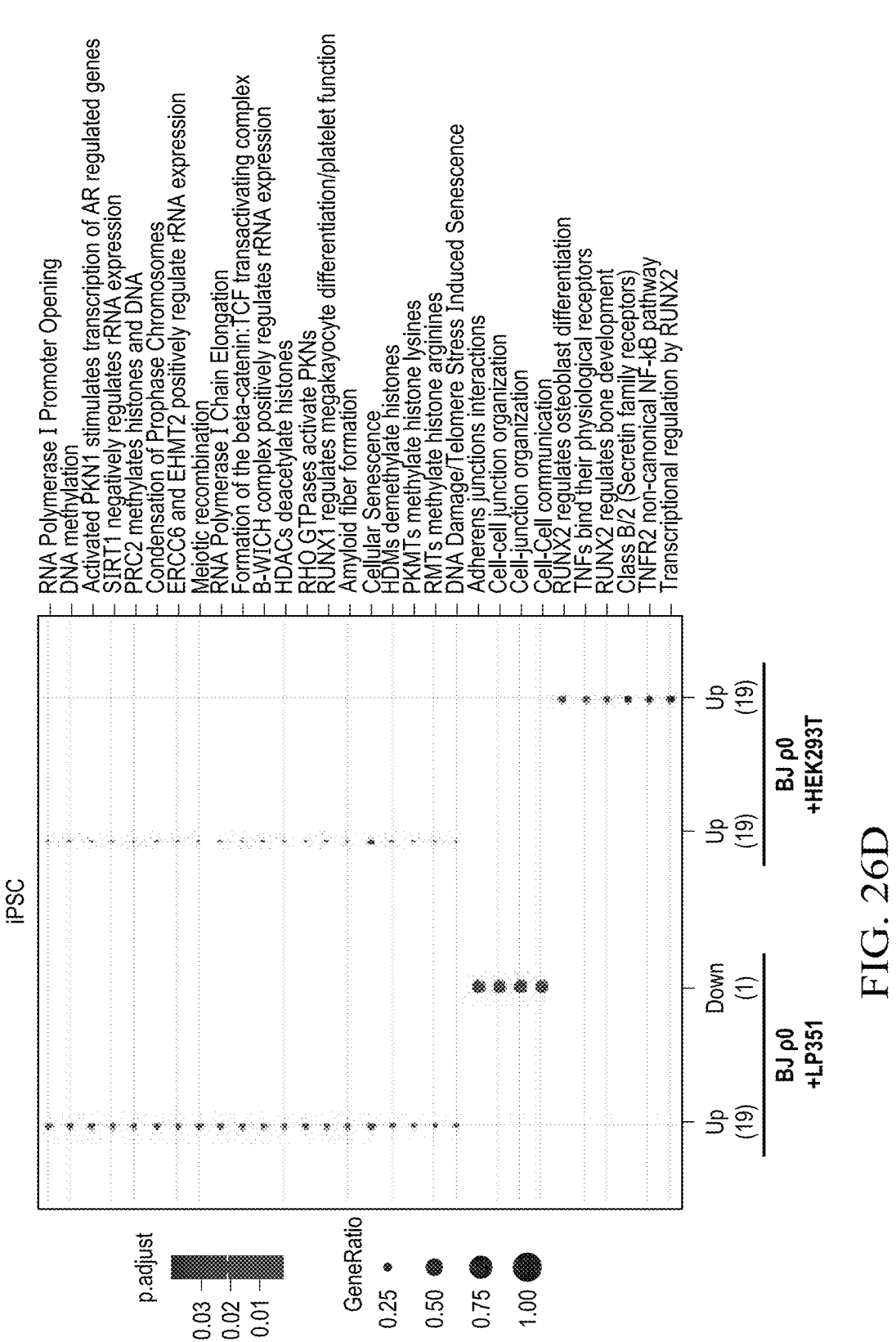
Figure 26E:
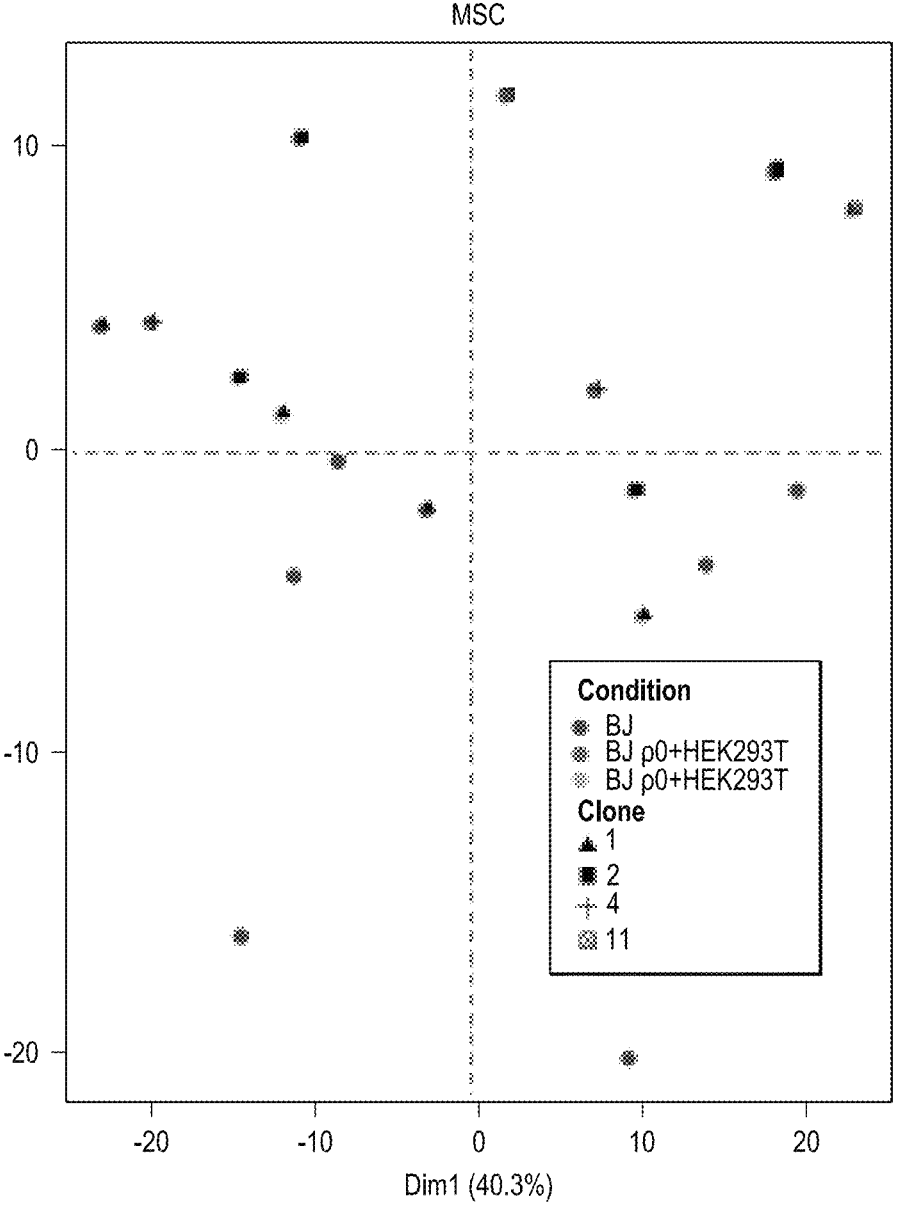

FIGS. 26A, 26C, and 26E show PCA of whole transcriptome gene-level expression across fibroblasts (i), iPSC (ii), and MSC (iii) samples. Samples are colored by transfer condition and labeled based on clonal derivation (for iPSC and MSC samples only). Samples are plotted as indicated in FIG. 25A.

Figure 26F:
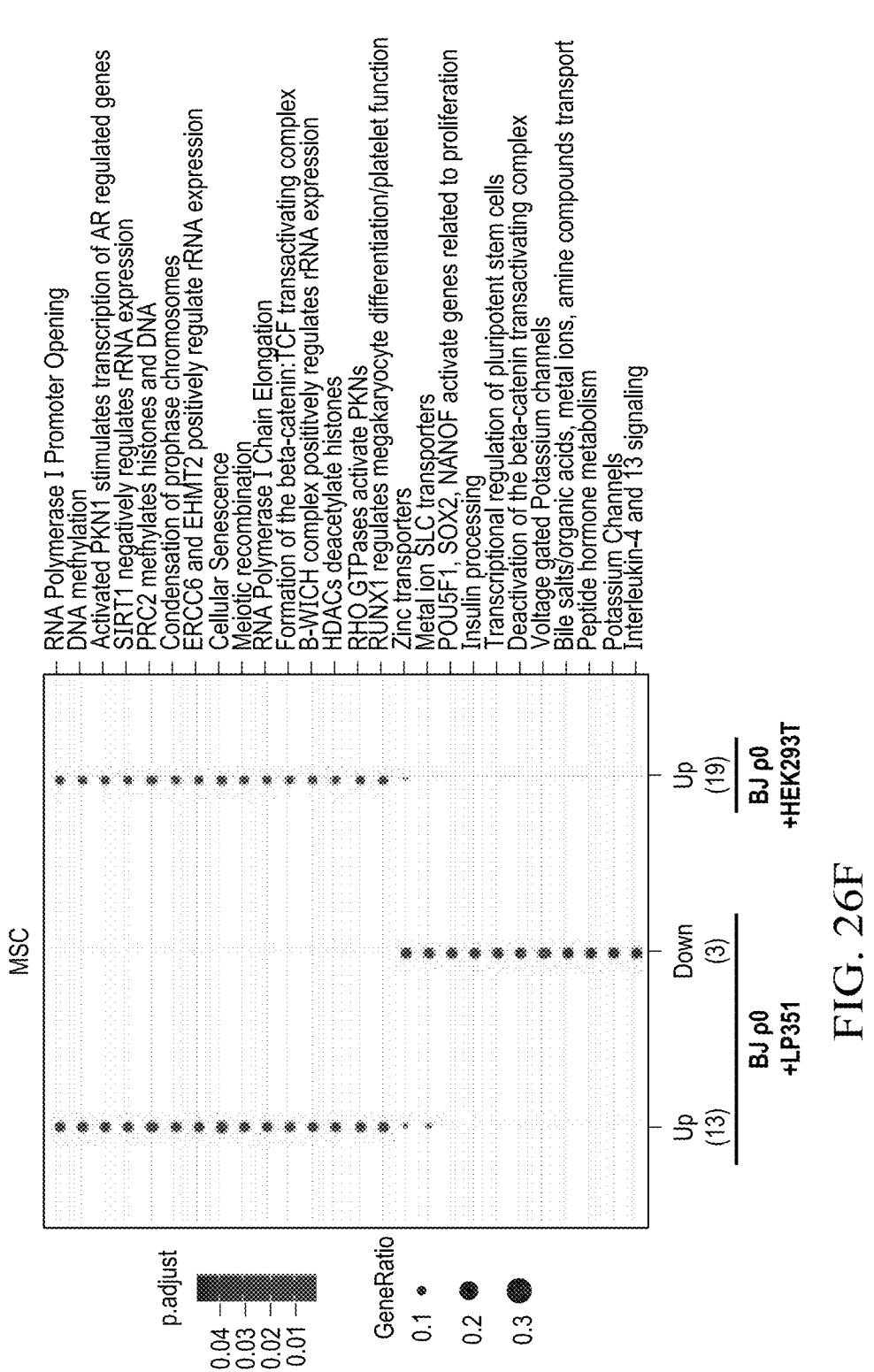

FIGS. 26B, 26D, and 26F show a reactome pathway database overrepresentation analysis (ORA) of BJ p0+HEK293 mitochondria and BJ p0+LP351 mitochondria transfers relative to BJ control in fibroblast (i), iPSC (ii), and MSC (iii) samples. Pathways are grouped based on up and down-regulation per transfer condition; size of dot indicates ratio of genes in the DEG list relative to the background genome, and color represents the adjusted P value of overrepresentation. Pathways listed represent overrepresentation below an adjusted P value threshold of 0.05. Number listed represent the number of genes annotated to any enriched Reactome pathway in the specified column.

Figure 26G:
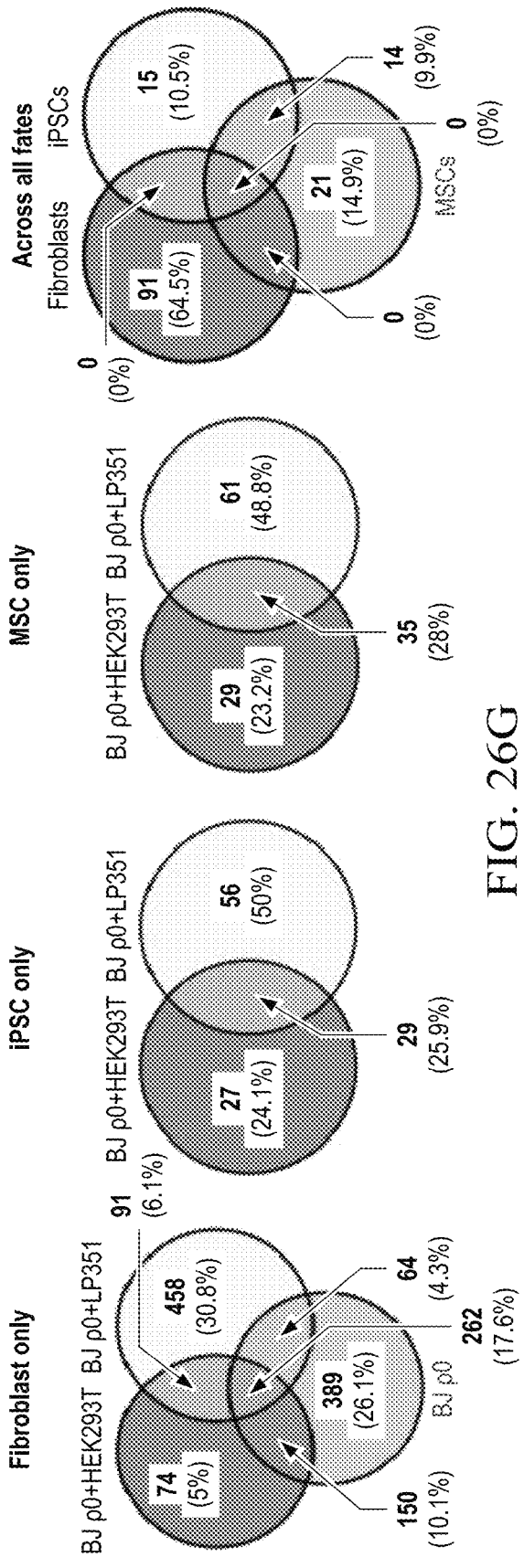

FIG. 26G shows Venn diagrams indicating the overlap of DEGs between BJ p0+HEK293 mitochondria, BJ p0+LP351 mitochondria, and BJ p0 fibroblasts relative to BJ control (i), and DEGs between BJ p0+HEK293 mitochondria and BJ p0+LP351 mitochondria relative to BJ control for the iPSC (ii) and MSC (iii) samples. Genes differentially expressed in both transfer conditions across fibroblasts (91 genes), iPSCs (29 genes), and MSCs (35 genes) were overlapped (iv) to determine transfer signatures over differentiation across all fates. Sample information is as explained in FIGS. 25A-25E.

Figure 27A:
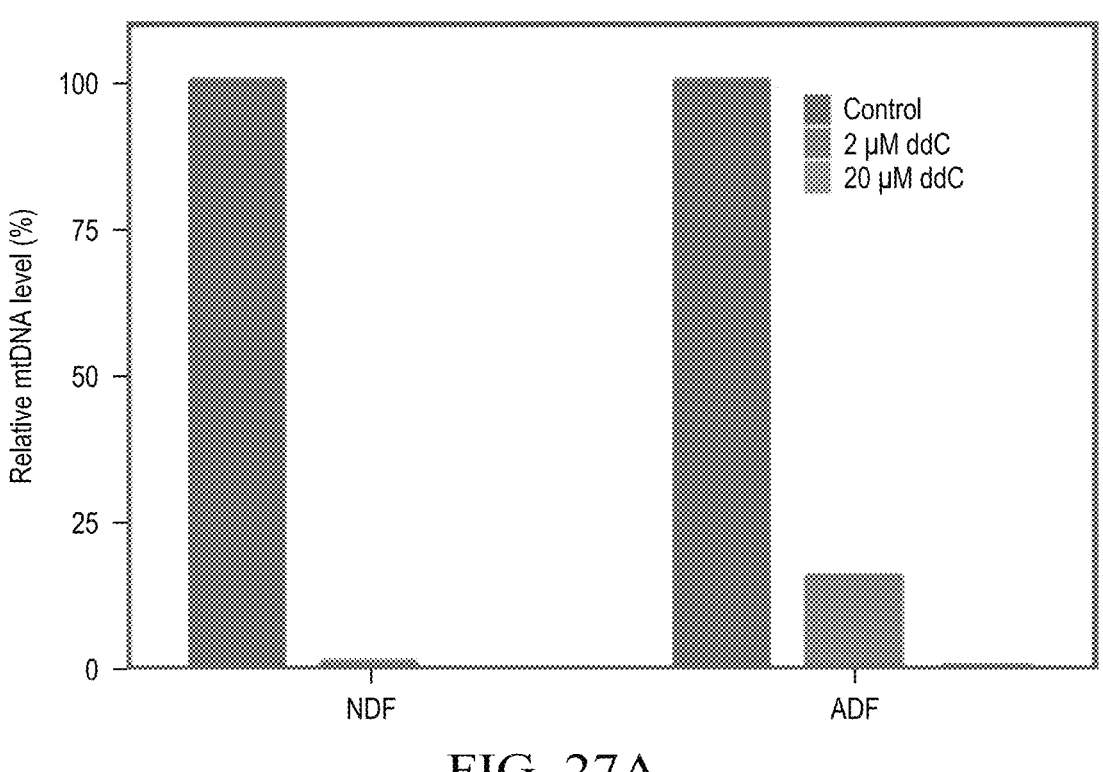
Figure 27B:
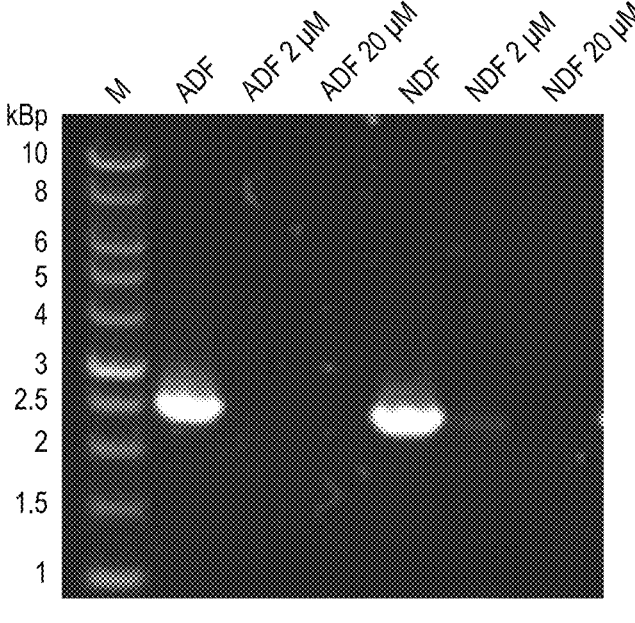
Figure 27C:
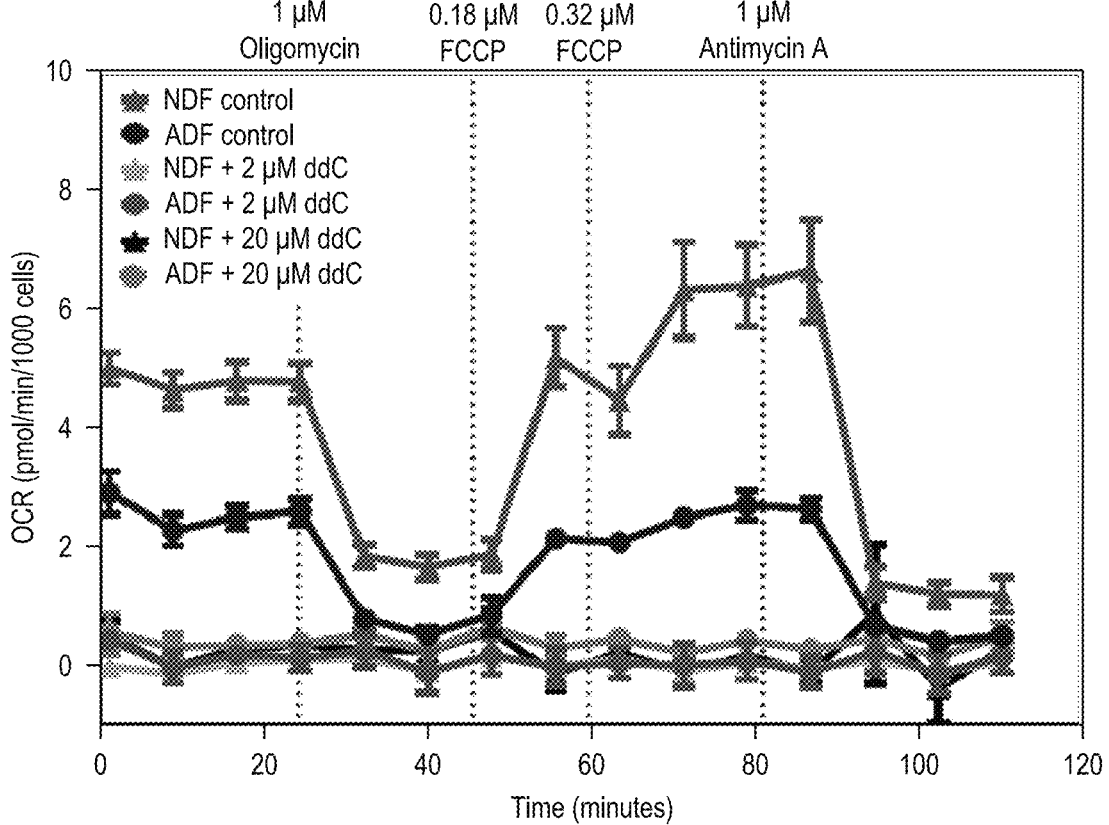

FIGS. 27A-27C show ADF and NDF mtDNA-depletion by ddC according to the embodiments presented herein.

FIG. 27A shows ADF and NDF fibroblasts that were treated with ddC at a final concentration of 2 μM and 20 μM for three weeks. At the end of ddC treatment, DNA was isolated and qPCR was performed using mitochondria (ND1) and nuclear (RPLPO)-targeted probes. Data is presented as the average of one biological replicate.

As shown in FIG. 27B, after approximately three weeks of 2 μM or 20 μM ddC treatment, ADF and NDF cells were lysed and DNA was extracted. Primers were used to amplify the region of mtDNA from 1404-3947, resulting in a fragment length of 2543 bp. PCR products and a DNA ladder were separated on a 0.5% agarose gel. Untreated ADF and NDF cells served as control samples.

FIG. 27C shows ~15,000 cells that were plated and analyzed on a Seahorse XF96 flux analyzer. Data is presented as the average of five technical replicates±standard deviation. Dotted lines denote times of drug injection.

Figure 28:
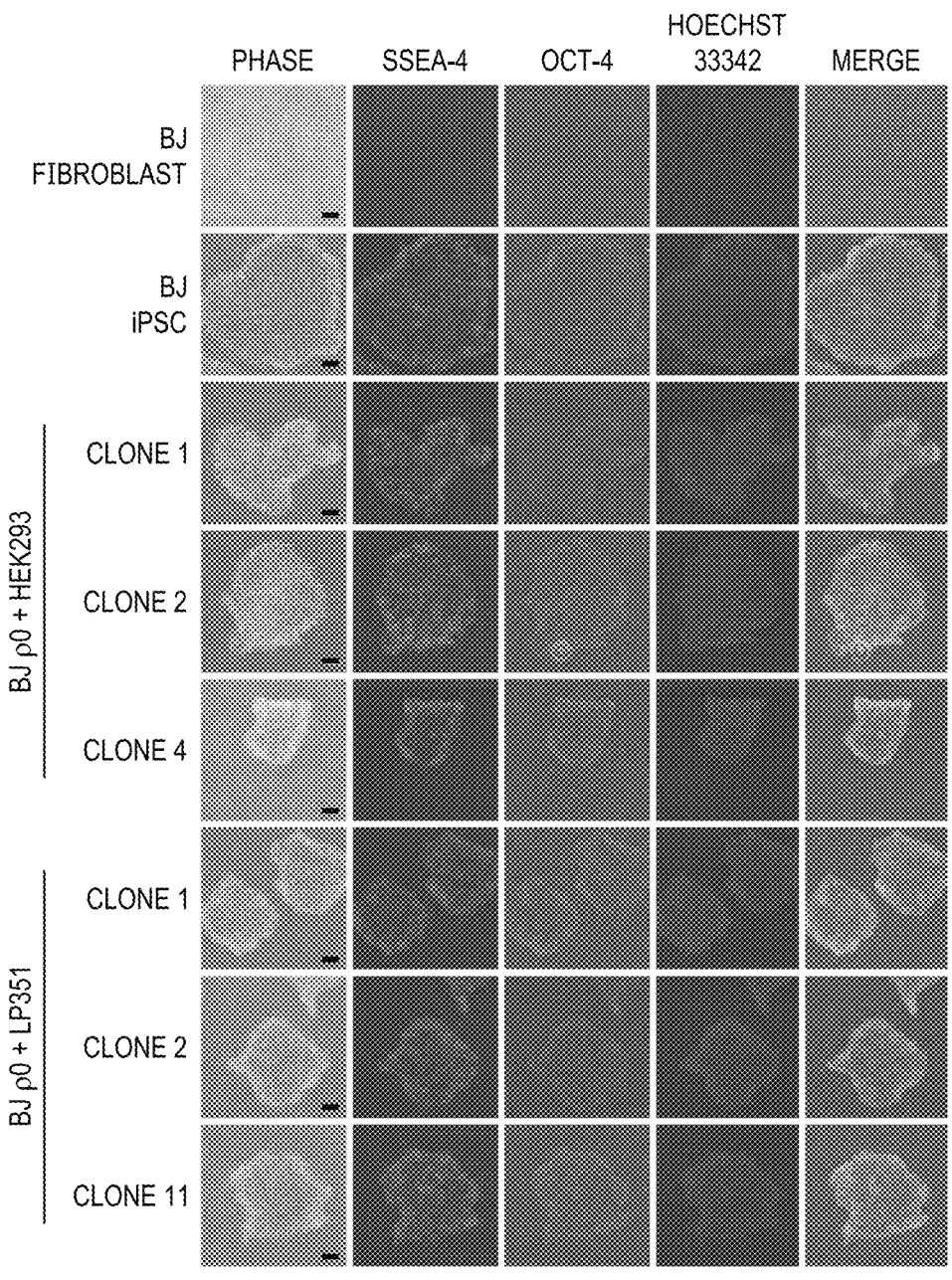

FIG. 28 shows immunofluorescence of iPSC lines according to the embodiments presented herein. BJ p0+HEK293T and BJ p0+LP351 iPSCs were cultured on matrigel-coated 6 well plates and fixed with 4% paraformaldehyde. Cells were stained with SSEA4, OCT4, and Hoechst 33342. Phase contrast and fluorescence images were taken with a Zeiss Axio Observer Z1 microscope and Hamamatsu EM CCD camera (Cat. #C9100-02) at 5× objective. Controls were represented by BJ iPSCs and BJ fibroblasts. The scale bar denotes 100 μm.

Figure 29:
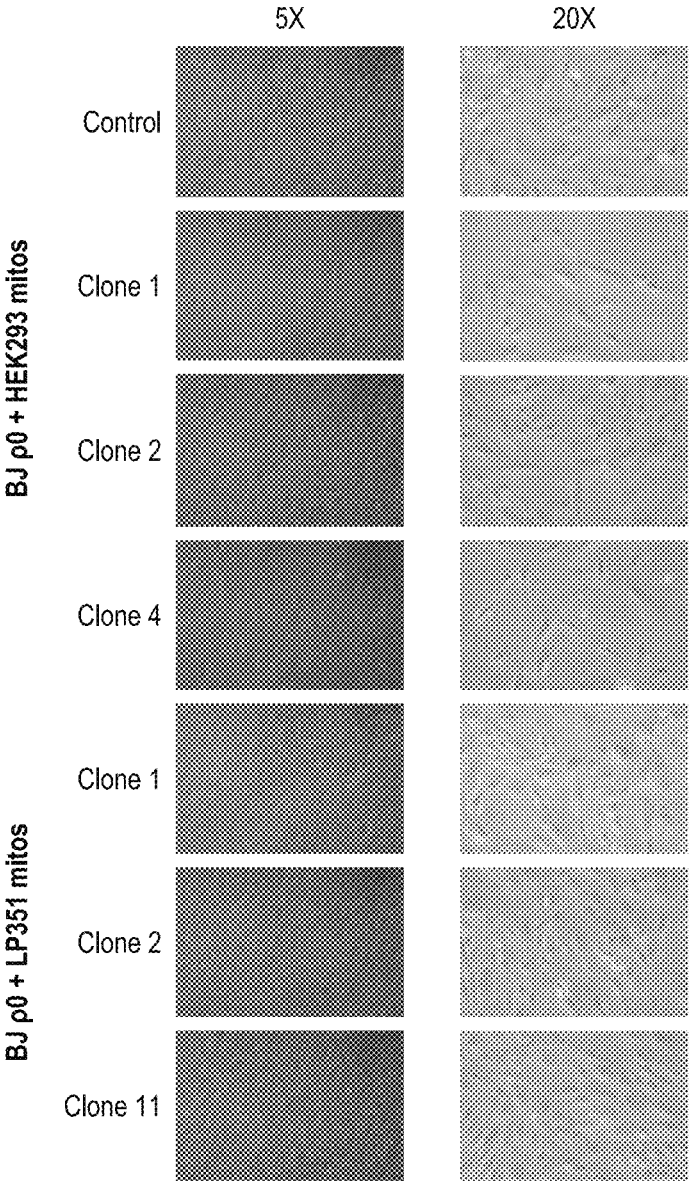

FIG. 29 shows that MSC clones adhered to plastic. BJ p0+HEK293T and BJ p0+LP351 MSC clones were imaged by brightfield microscopy at 5× and 20× according to the embodiments presented herein.

Figure 30A:
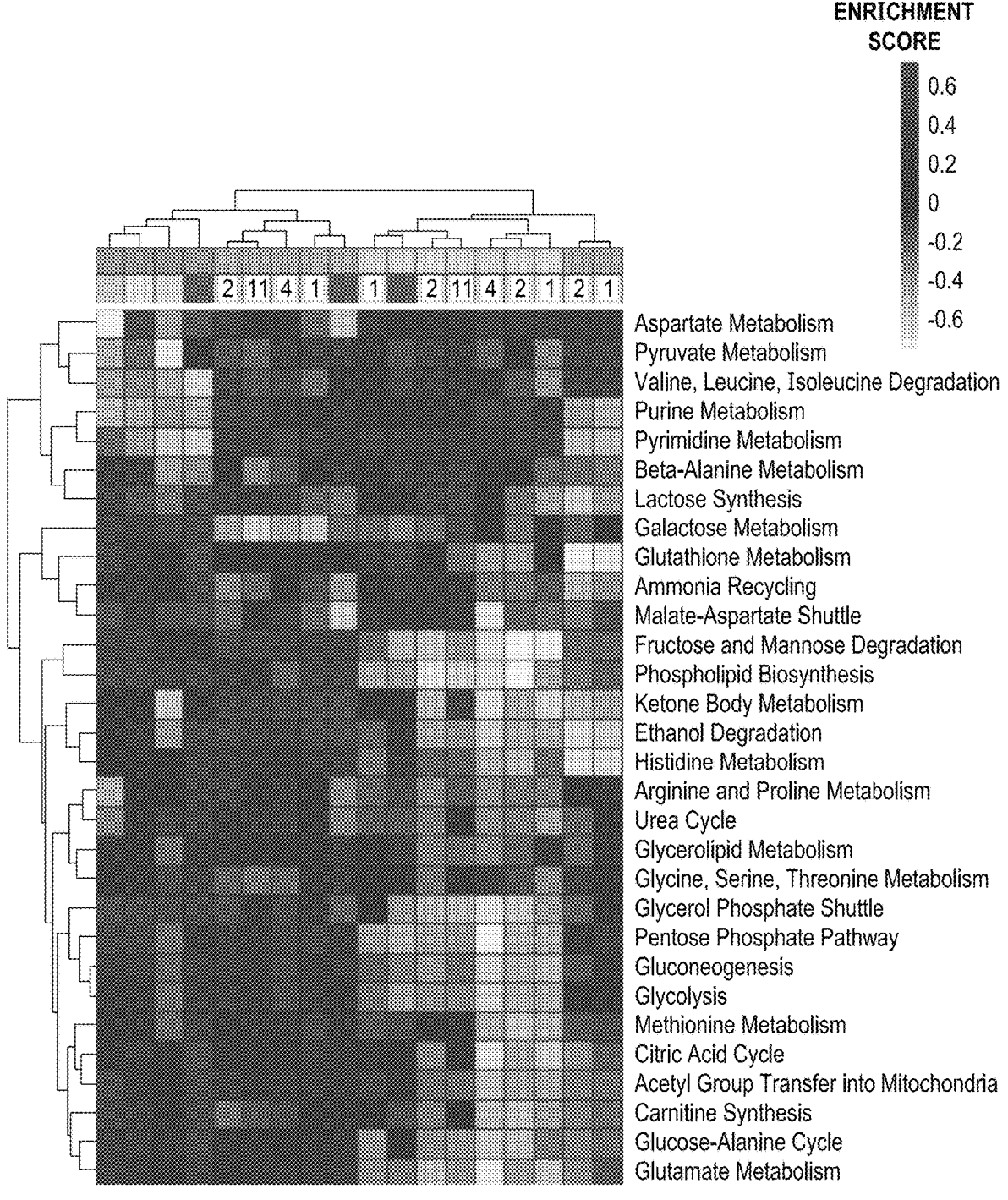
Figure 30B:
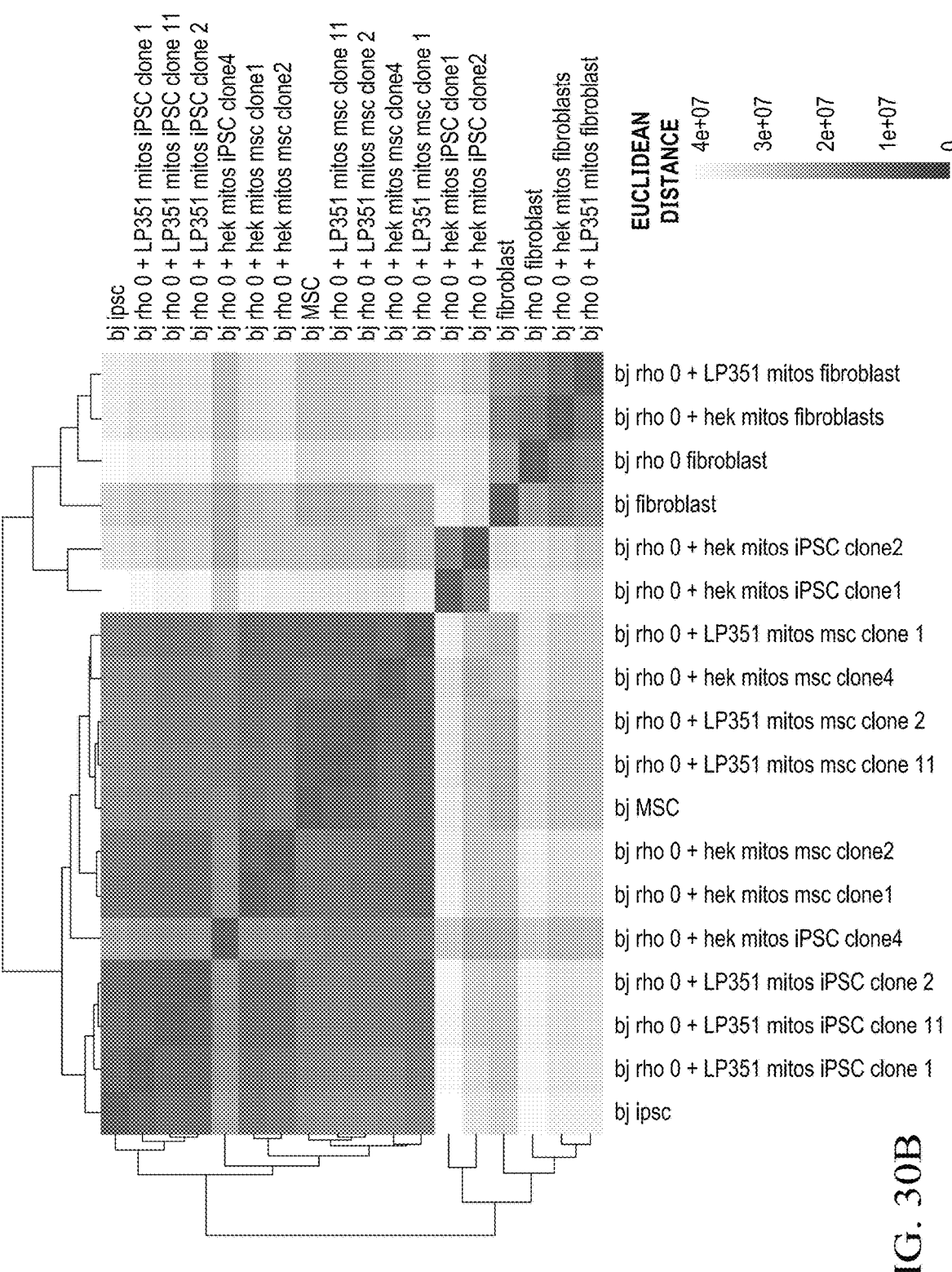

FIGS. 30A-30B show that metabolite profiles across mitochondrial transfer line differentiations are consistent with control cell fate according to the embodiments presented herein, see also FIGS. 23A-23C.

FIG. 30A shows metabolite set variation analysis (MSVA) indicating metabolite pathway enrichment across averaged samples. Rows indicate independent KEGG metabolic pathways that were analyzed. Higher MSVA enrichment scores indicate elevated pathway enrichment relative to all samples, lower MSVA enrichment score indicate reduced pathway enrichment relative to all samples. Samples are annotated by cell fate (top row) and transfer condition (second row). Clone number for BJ p0+HEK293 mitochondria and BJ p0+LP351 mitochondria samples are indicated by number in the transfer condition row.

FIG. 30B shows Euclidean distance similarity matrix of whole metabolite levels across all sample comparisons. Heatmap values indicate the Euclidean distance between the two indicated samples (n=54).

FIGS. 31A-31E show transcriptomic comparisons of mtDNA and similarity measures across mitochondrial transfer line conditions relative to control cell fate according to the embodiments presented herein, see also FIGS. 25A-25E.

Figure 31A:
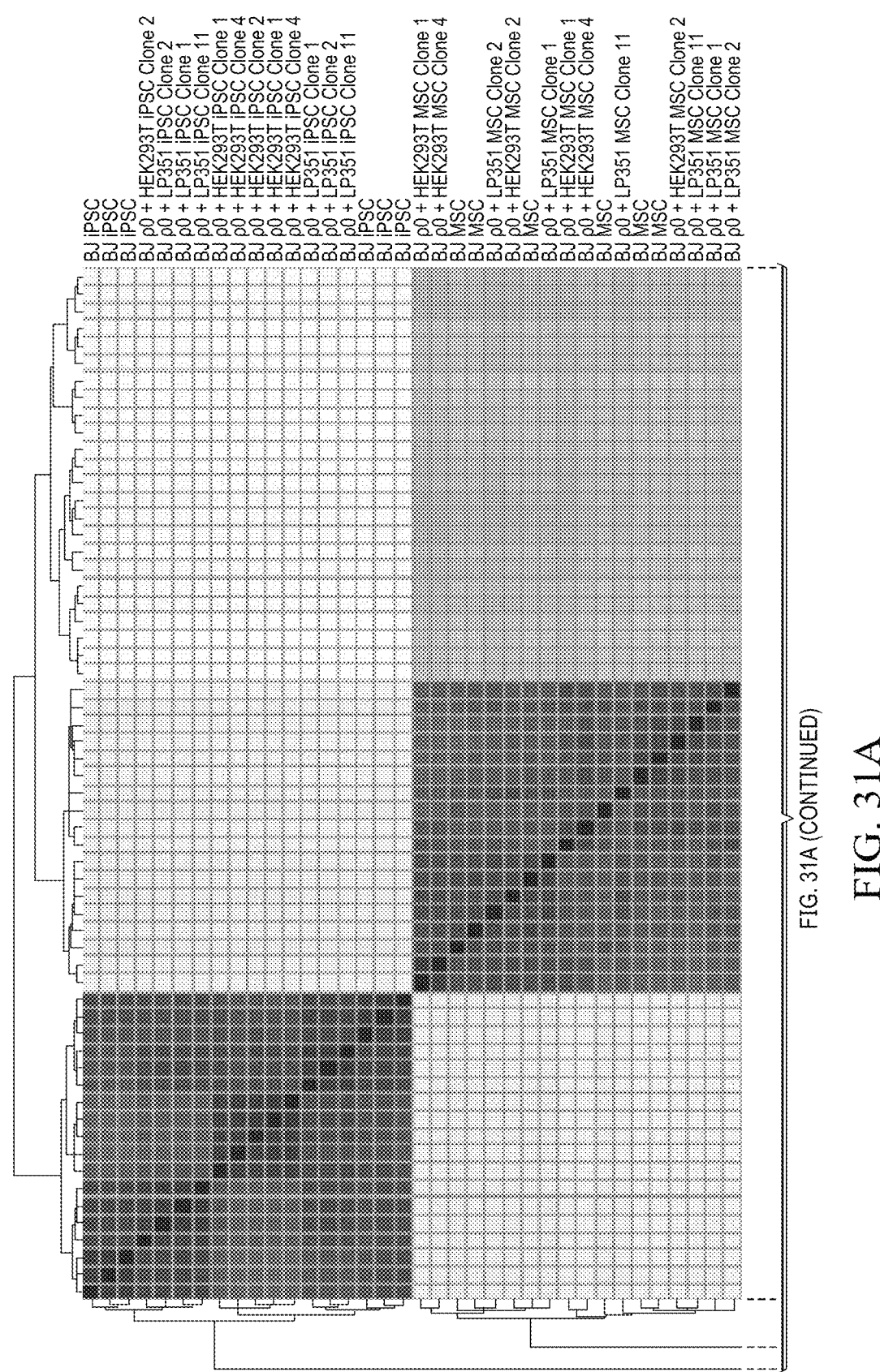
Figure 31A:
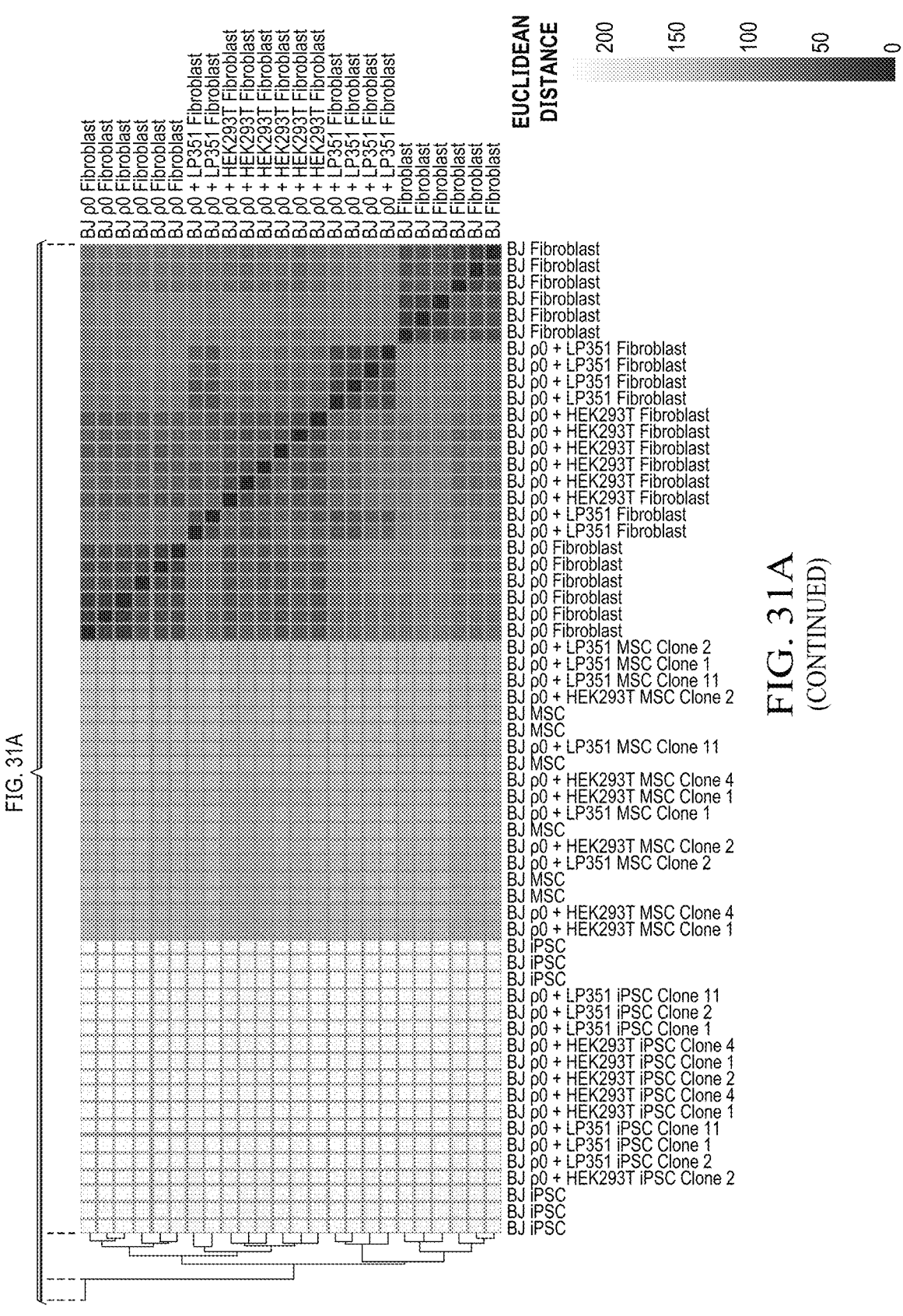

FIG. 31A shows a Euclidean distance similarity matrix of whole transcriptome levels across all sample comparisons. Heatmap values indicate the Euclidean distance between the two indicated samples (n=60).

Figure 31B:
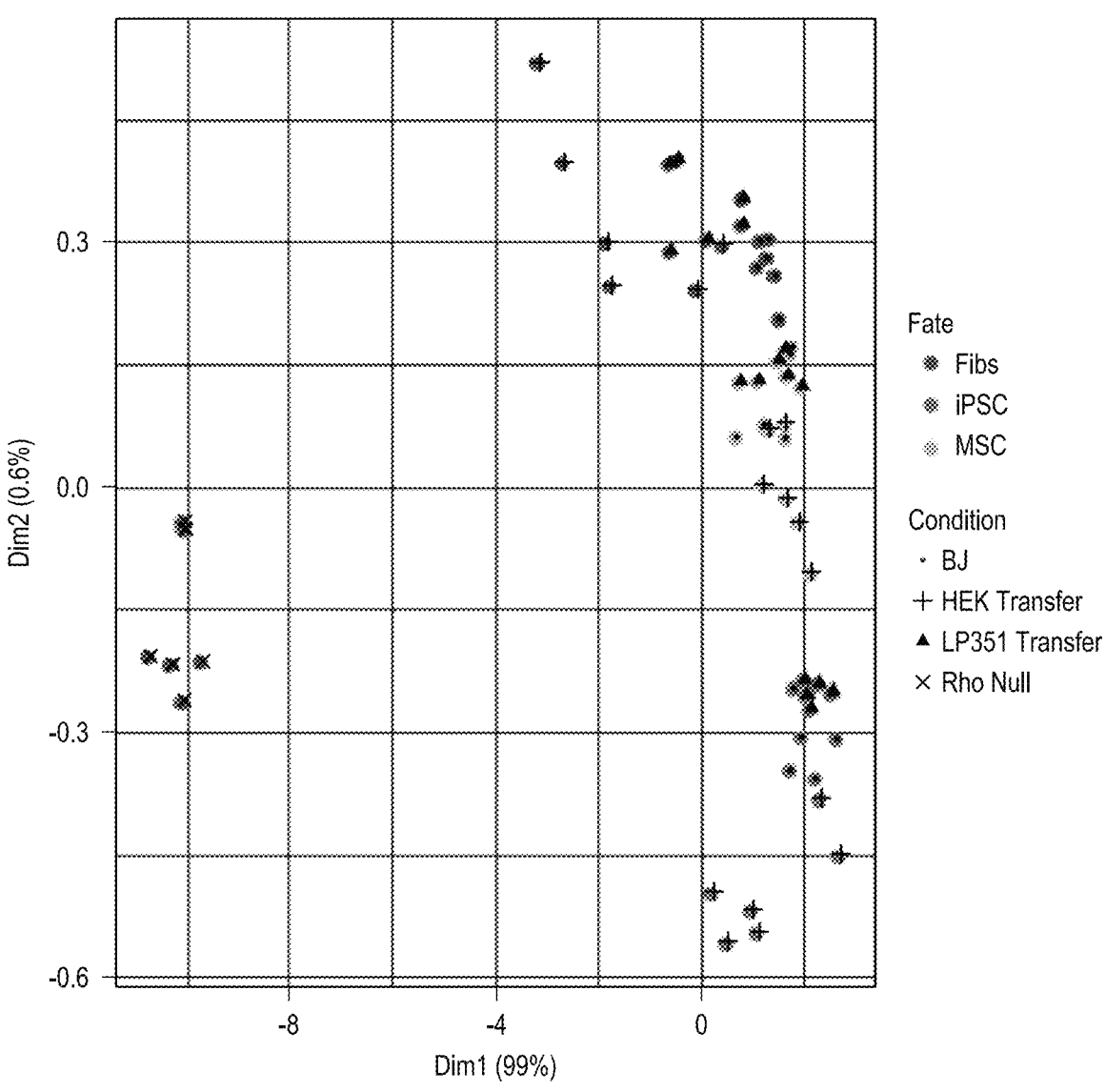
Figure 31C:
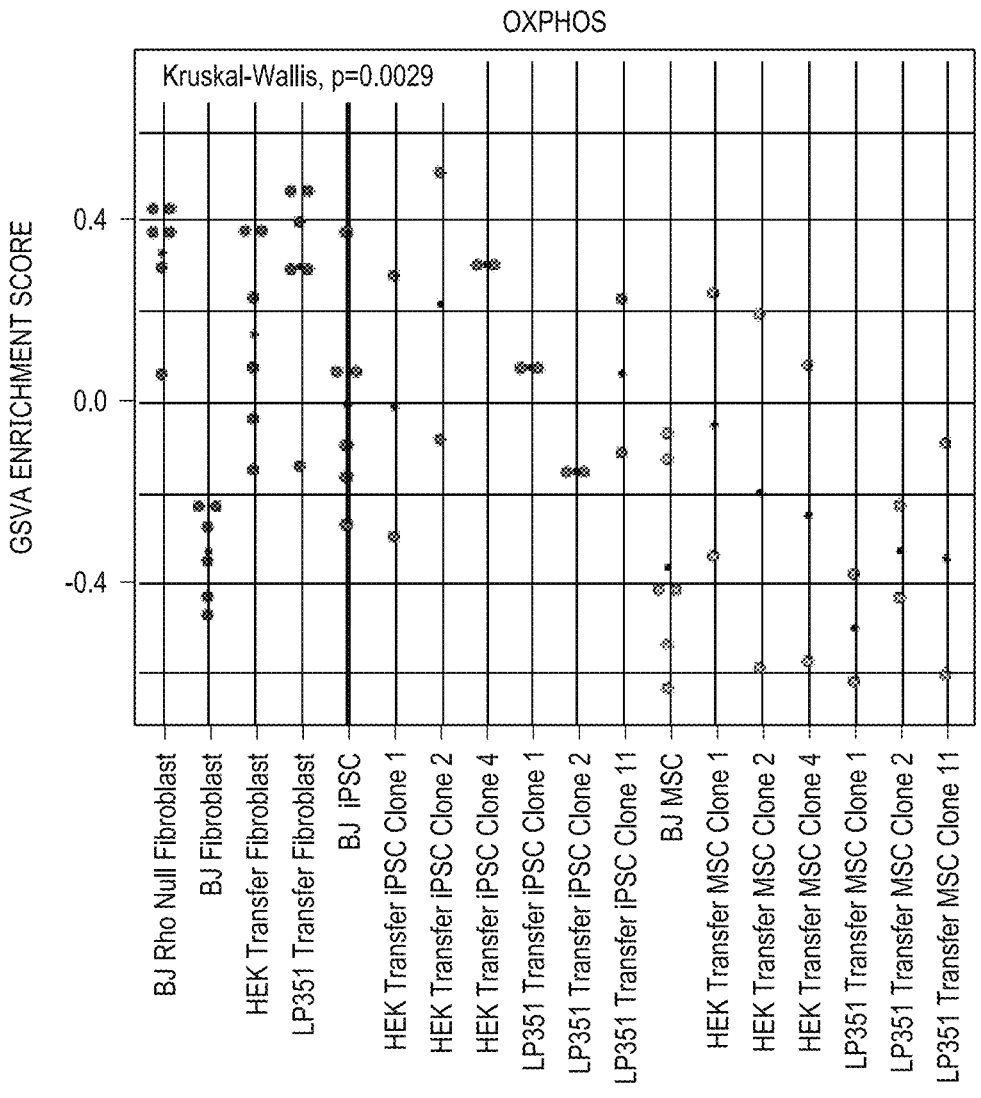
Figure 31D:
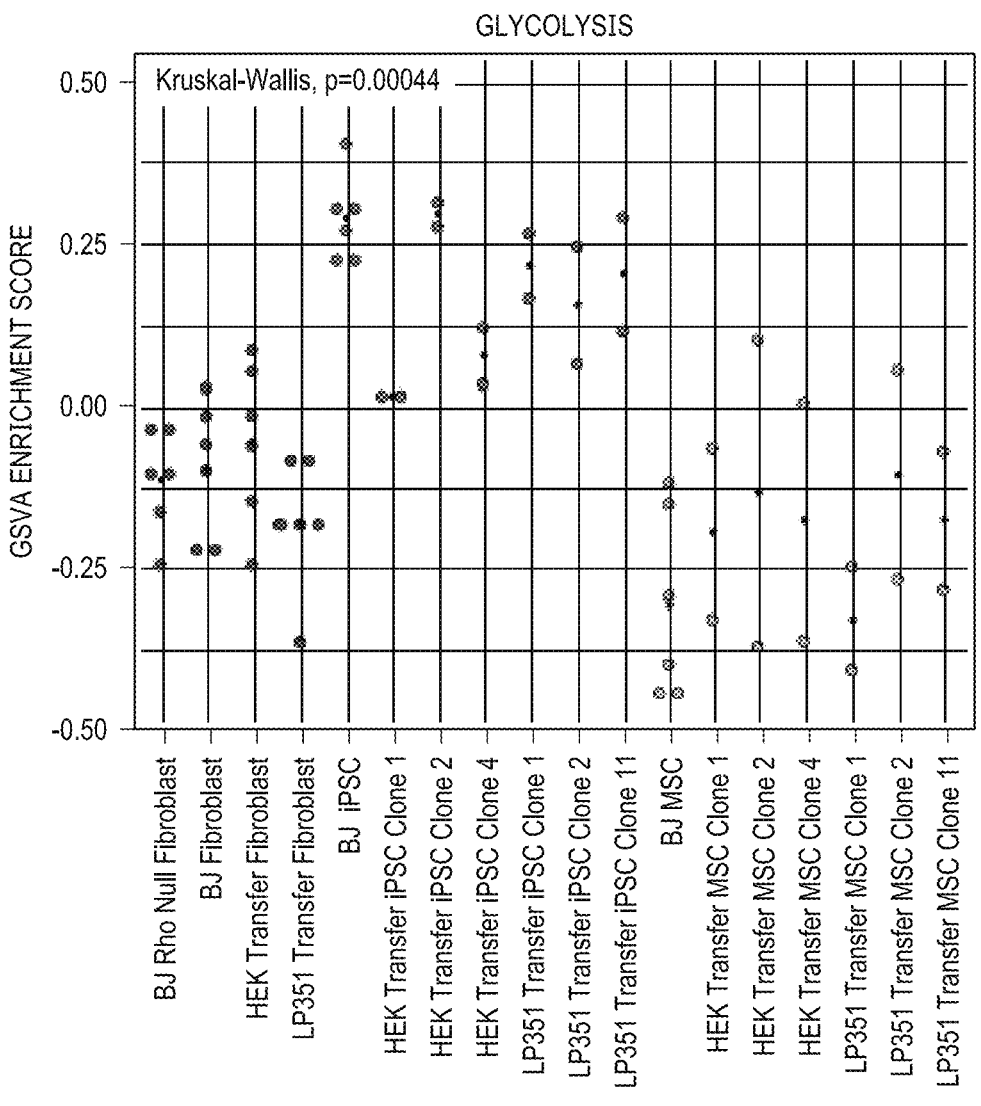
Figure 31E:
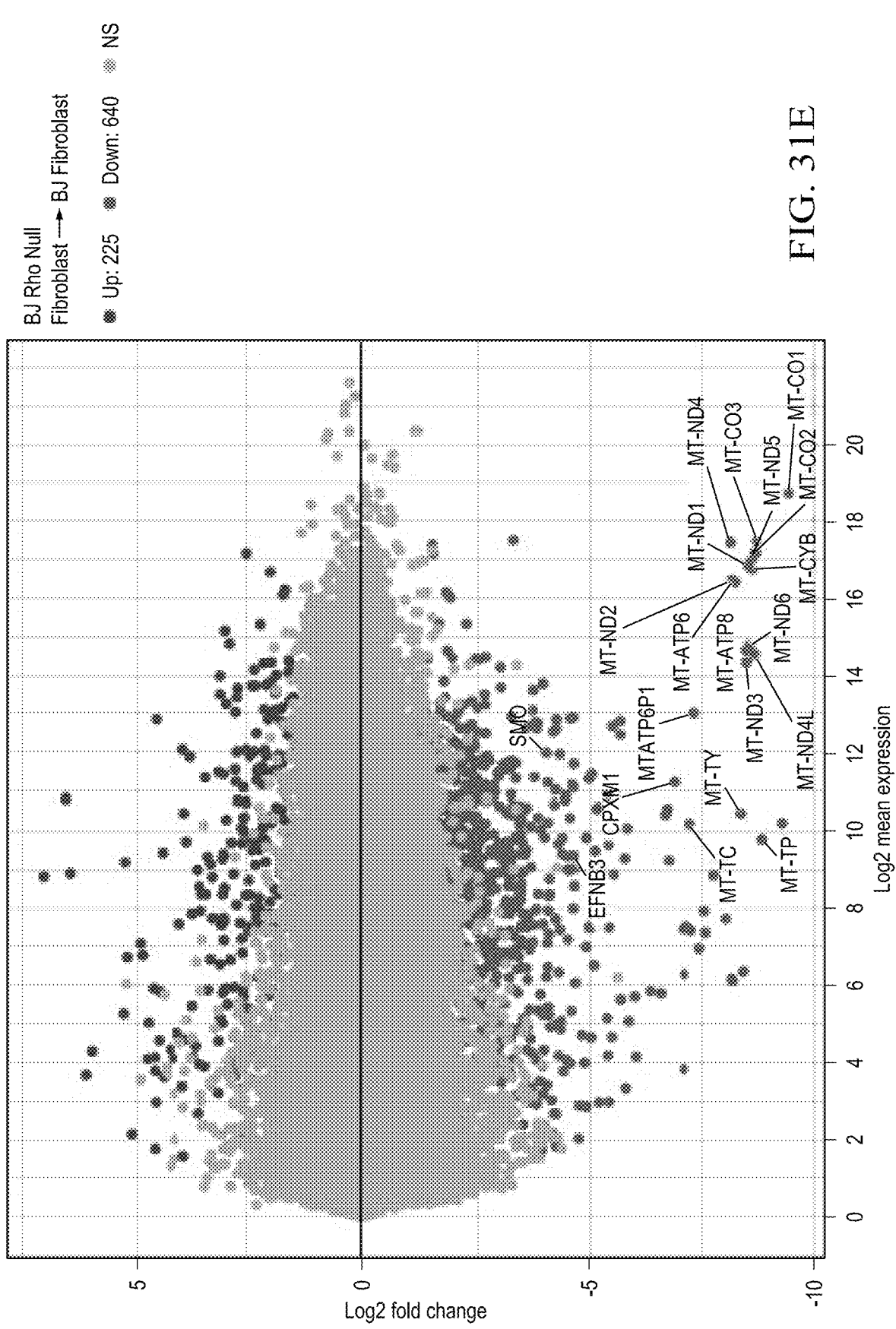

FIG. 31B shows PCA of mitochondrial (mtDNA) transcript gene-level expression, as derived from mitochondrial localization evidence in MitoMiner v4.0. Samples are labeled and plotted as FIG. 25A. FIGS. 31C-31E show individual GSVA scores mean averaged across all samples and clones (n=6 for BJ samples; n=2 for each transfer clone) for enrichment of the Oxidative Phosphorylation.

FIG. 31C-31D show Glycolysis-Gluconeogenesis.

FIG. 31E shows KEGG pathways. Lines represent mean±range. P values indicate Kruskal-Wallis one-way analysis of variance across sample cell fate and transfer condition. FIG. 31E shows a MA plot of gene expression alterations between BJ p0 (numerator) and BJ (denominator) fibroblasts (n=3 each condition; 6 total). X-axis indicates based mean value of gene level transcripts across all samples; y-axis indicates $\log_2$ transformed fold change (BJ p0/BJ) fibroblast gene expression. Differentially expressed genes with an absolute $\log_2$ fold change threshold of 1 and Benjamini-Hochberg adjusted P value threshold below 0.05 are colored in red (upregulated in BJ p0) and blue (down-regulated in BJ p0).

Figure 32A:
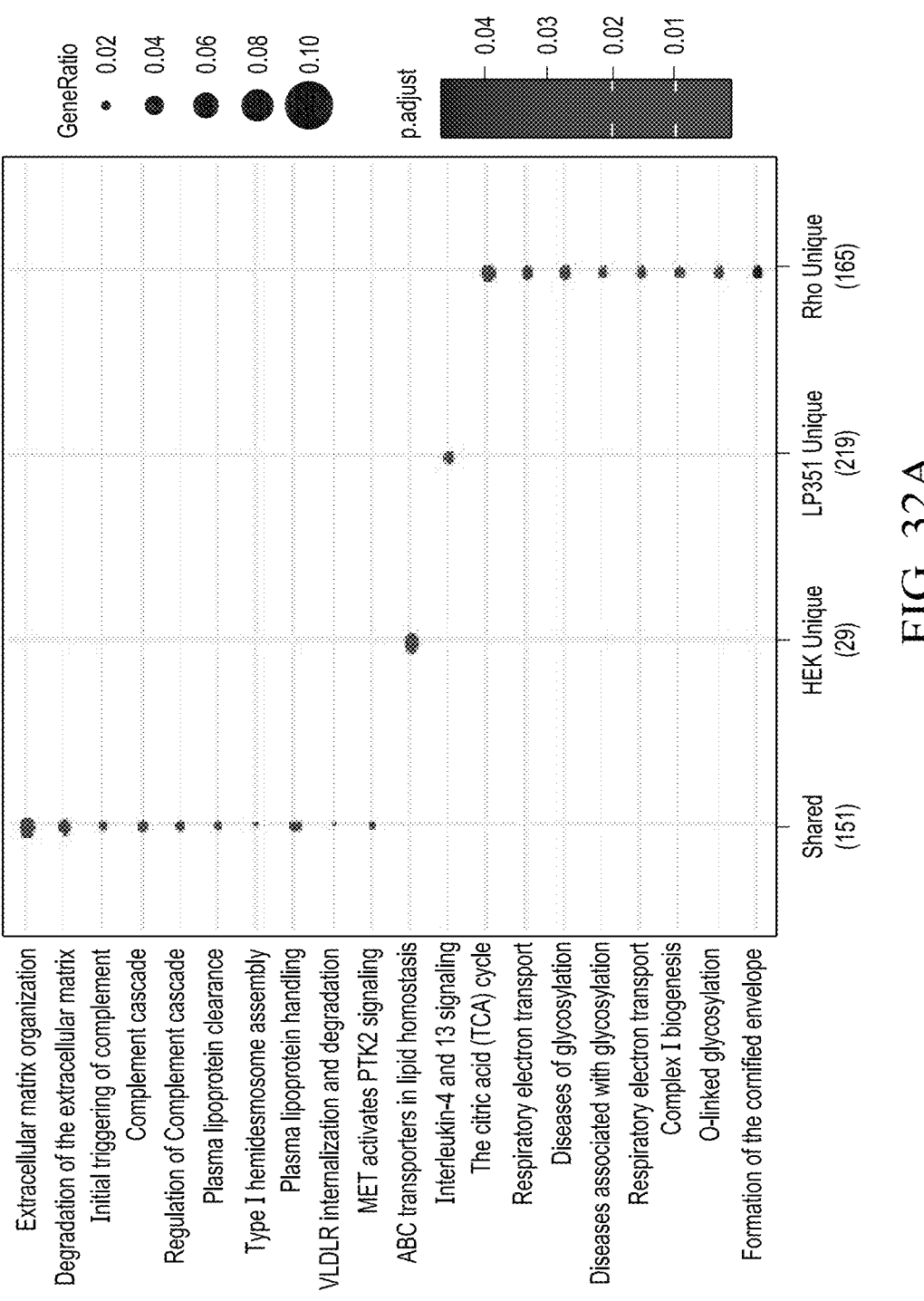
Figure 32B:
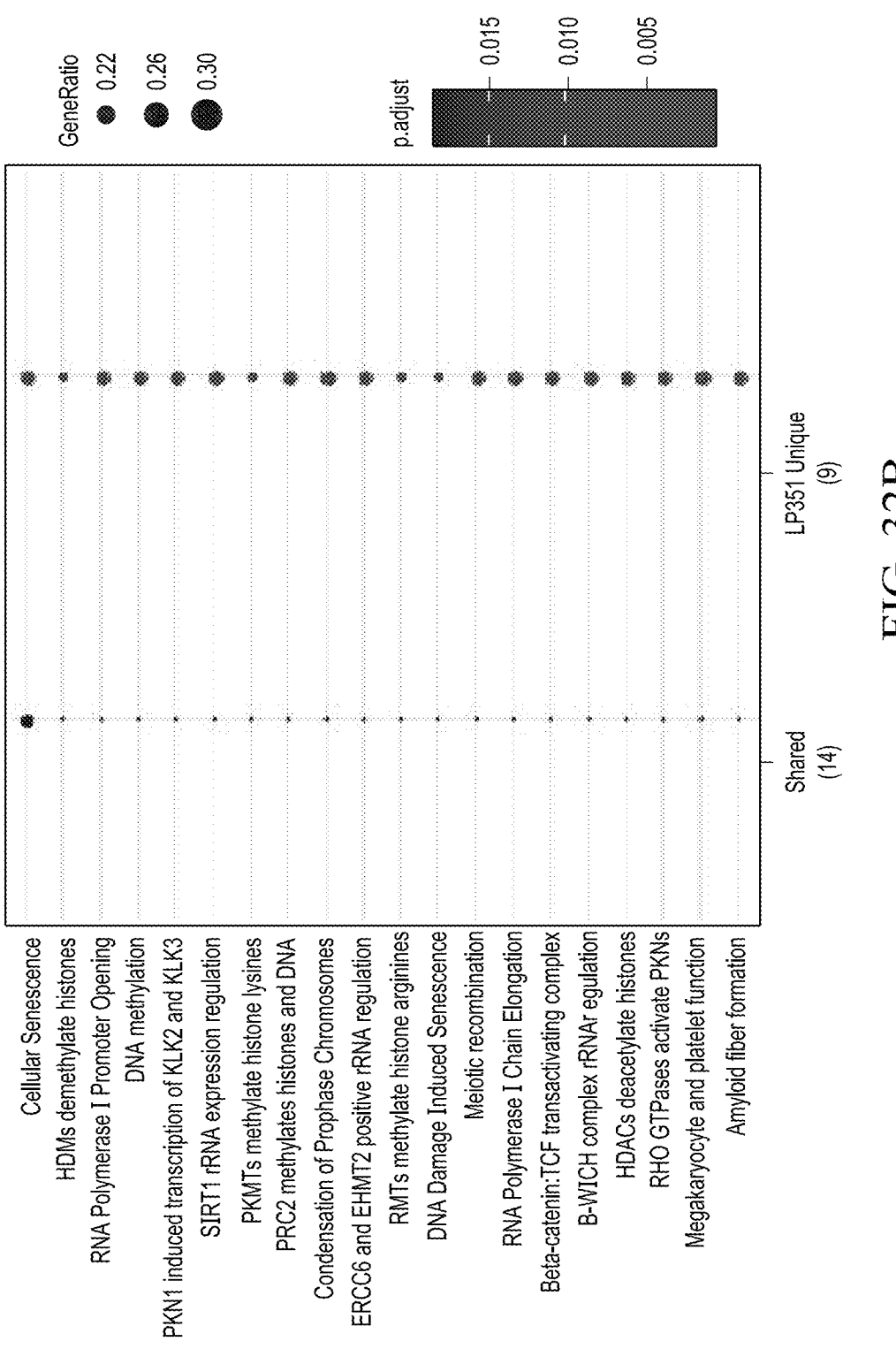
Figure 32C:
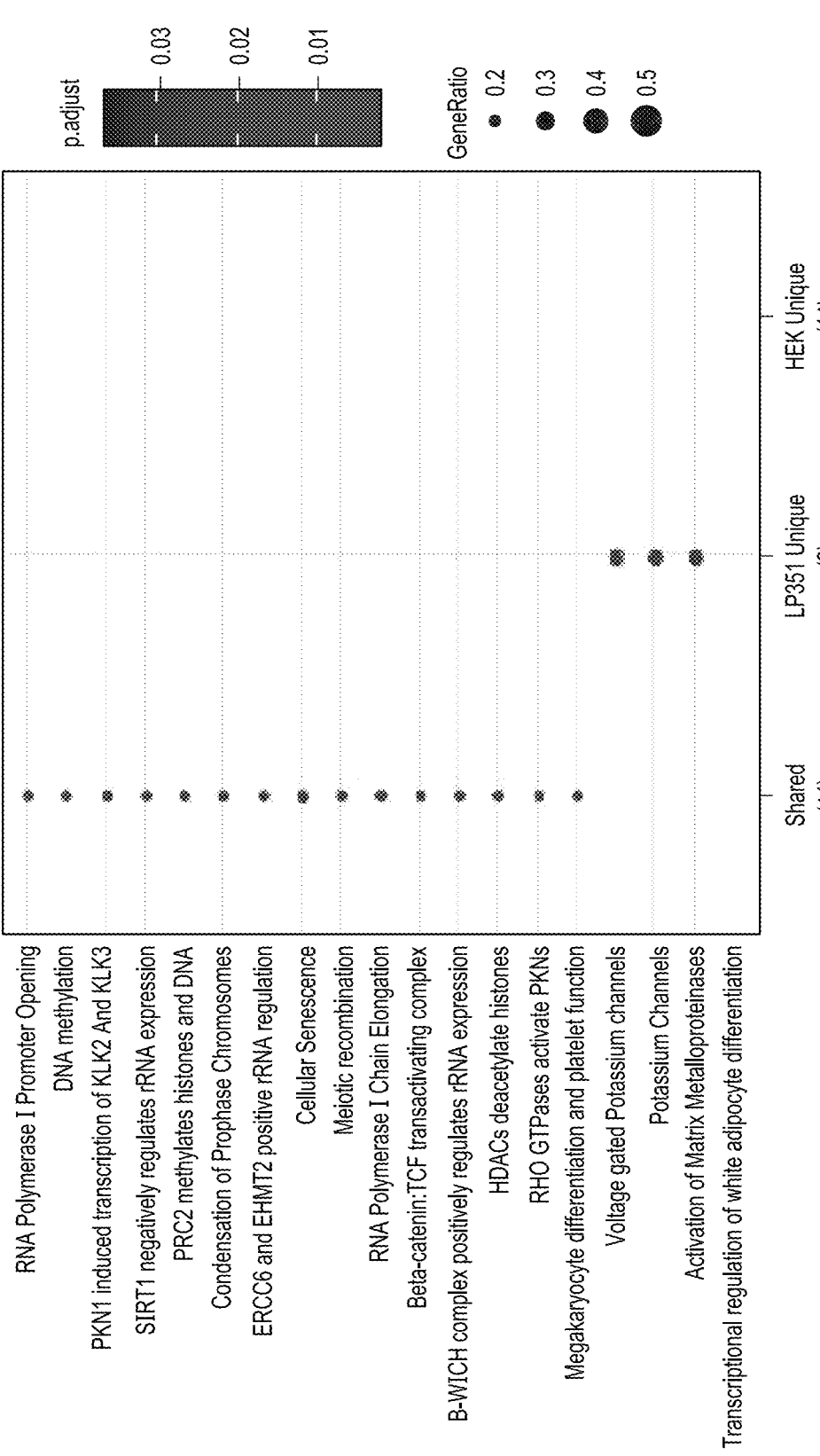

FIGS. 32A-32C show reactome overrepresentation analysis of transfer-type specific DEGs across cell fates. Related to FIG. 26A-26G. Reactome ORA performed with DEGs identified as HEK Unique, LP351 Unique, p0 Unique, or Transfer Unique, across fibroblasts as shown in FIG. 32A, iPSCs as shown in FIG. 32B, and MSCs as shown in FIG. 32C relative to BJ control. HEK Unique, p0 Unique, and LP351 Unique are denoted as cell type DEGs that are only differentially expressed in either BJ p0 (for fibroblast comparisons), BJ p0+HEK293 mitochondria; or BJ p0+LP351 mitochondrial transfers relative to BJ control. Transfer Unique refers to cell type DEGs that are differentially expressed in both BJ p0+HEK293 mitochondrial and BJ p0+LP351 mitochondrial transfers relative to BJ control.

The examples presented herein are not intended to be limiting. It is understood that many different variations of these examples are disclosed within the application, and that all such embodiments fall within the scope of the embodiments disclosed herein.

DETAILED DESCRIPTION

Methods and transfection devices are presented for delivery of various macrostructures into cells, such as depleted cells as further described below. Typically, movement of the cells is at least temporarily restrained (or adherent cells are employed), and the cells are initially separated from the macrostructures by a porous membrane. A force is applied onto a deformable fluid reservoir containing the macrostructures in a solution, which deforms the fluid reservoir and generates an applied pressure causing the macrostructures to pass through the pores to the at least temporarily immobilized cells, triggering uptake of at least some of the macrostructures into the cells to produce transfected cells.

High-throughput transfection techniques and devices are presented herein and may also be used as part of a process to replace defective mtDNA with corrected mtDNA to generate engineered cells, for example, for use in generate cellular-based therapeutics for administration to a patient. In general, recipient cells comprising one or more mtDNA mutations can be depleted of endogenous mtDNA to produce depleted cells, the depleted cells can be transfected with corrected mtDNA to produce transfected cells, the transfected cells can be reprogrammed into induced pluripotent stem cells, and the induced pluripotent stems can be differentiated into engineered cells.

Voice coil actuators, unlike other types of actuators, respond in a linear manner to an applied voltage. This response characteristic provides numerous customizable configuration options to tailor transfection processes to particular cell lines and specific types of macromolecules.

In other embodiments, planar magnetic speaker elements may be used in lieu of a voice coil actuator. With this type of speaker, a diaphragm with a circuit (e.g., foil strips and/or thin conductive wires attached to a sheet of Mylar) may be placed in a magnetic field created by a vertical array of magnets. Such diaphragms are thin and lightweight as compared to their typically heavier voice coil counterparts. Amplified electrical signals may be applied to the circuit on the diaphragm, and the resultant electrical forces react with the magnetic field to generate an electromagnetic force that creates sound. Planar speaker elements typically have a wide frequency response, durability, low distortion and high levels of responsiveness. Any suitable type of speaker element, which produces a range of sounds at a sufficient magnitude, are contemplated for use herein.

Machine learning techniques also may be utilized to optimize transfection parameters for particular types of cells. By analyzing successful transfections with high yields with regard to one or more parameters including but not limited to: the type of cell, applied force, size of the cargo, characteristics of the actuator, shape of the waveform, etc., the machine learning system may identify parameters to optimize or at least improve transfection yield.

Cell culture techniques and incubators may be used to optimize the transfected cells, such that one or more characteristics of the transfected cells are similar to or the same as wt cells absent mtDNA mutation(s). The devices and methods are described in further detail as follows.

1. Transfection Device and Use Thereof

Figure 1:
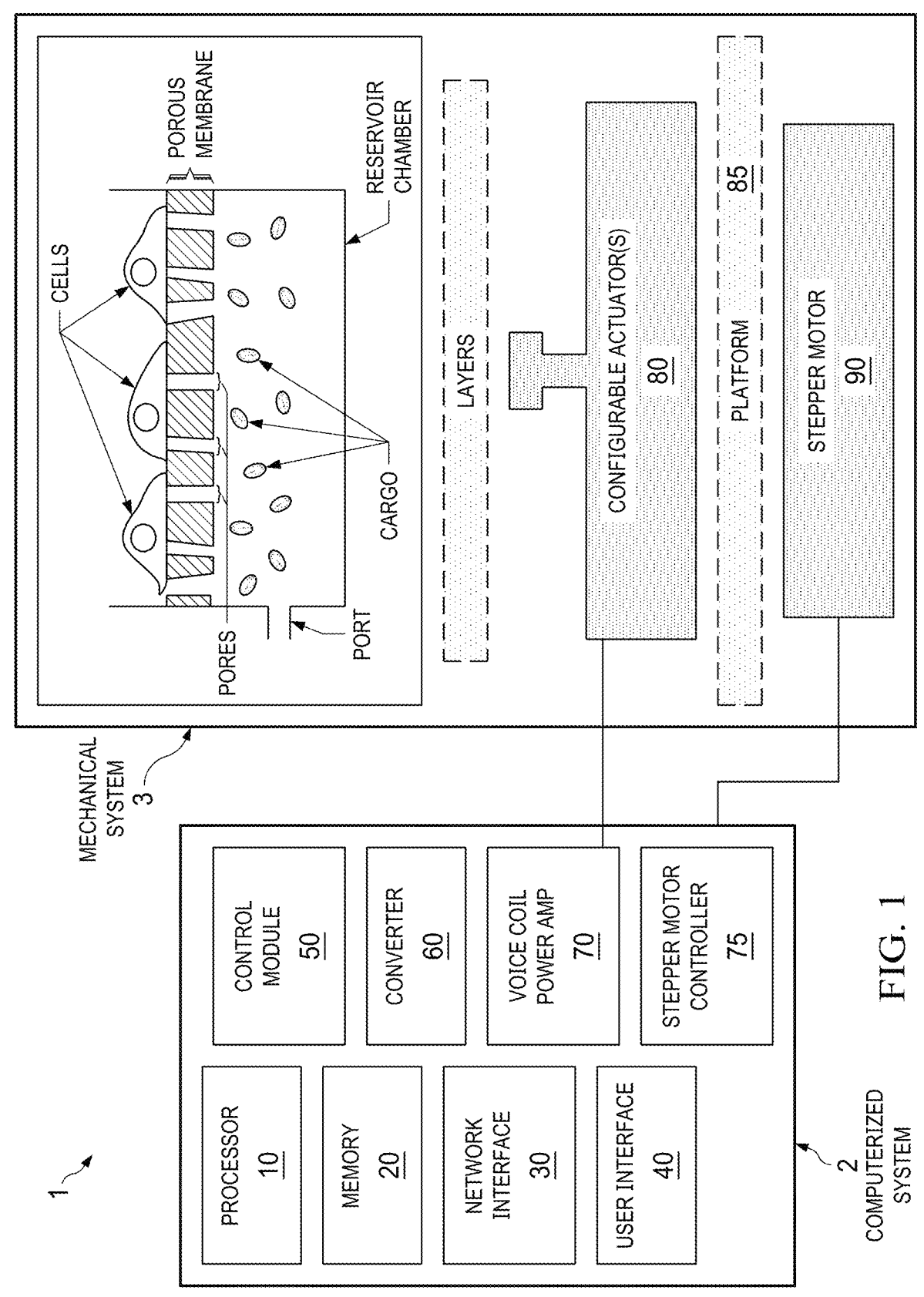
FIG. 1 is a schematic of an exemplary transfection device according to the embodiments presented herein.

FIG. 1 shows an example of a transfection device 1 (also referred to as a mitoPUNCH device), including a computerized system 2 for configuring and controlling the mechanical system 3 of the device, wherein the mechanical component 3 comprises components for receiving cells and movable parts for transfection of the received cells. Although depicted within a single housing, the various modules and components of computerized system 2 may be distributed across multiple computing systems that are spatially separated from each another. Additionally, any of the modules of the computerized system 2 may be combined into a single module or separated into other modules. Many such configurations are possible, and all such configurations are contemplated by the devices presented herein.

The computerized system 2 at least comprises one or more processors or microprocessors 10 configurable to execute software instructions stored in a non-transitory computer readable memory 20, one or more non-transitory computer readable memories 20 for storing instructions that are executed by processor 10, one or more optional network interfaces 30 for sending and receiving information, e.g., to a remote computing device, and one or more user interfaces 40 (e.g., a graphical user interface, a command line interface, a LCD touchscreen interface, etc.) for providing configuration settings to the computerized system. In some aspects, the processor 10 may have a processor speed of at least 50 MHz, at least 75 MHz, or at least 100 MHz.

The computerized system 2 may also comprise a control module 50 (also referred to as a mitoPUNCH control module), which controls the transfection process and may include (or interface with) a machine learning component for identifying optimal transfection parameters. The control module 50 may execute software instructions based on received parameters for generating a waveform (e.g., a voltage-based waveform) that is provided to one or more configurable actuator(s) 80, such as voice coil actuator(s), and may control the operation of the configurable actuator(s) 80.

Control module 50 may generate a waveform, e.g., in the form of a voltage, to be provided to a configurable actuator 80, such as a voice coil actuator, based upon received parameters from user interface 40. Parameters to generate the waveform include but are not limited to a duration of time over which the waveform is applied, shape of the waveform, frequency of the waveform, stroke/travel distance of the configurable actuator 80 (e.g., voice coil actuator), as well as the rise time and magnitude of the applied waveform. In some embodiments, duration of time in which the wavefrom is applied can be at least about 1 minute, at least about 5 minutes, at least about 10 minutes, at least about 20 minutes, at least about 30 minutes, at least about 40 minutes, at least about 50 minutes, or at least about 60 minutes; or from about 1 to about 60 minutes, about 5 to about 40 minutes, or about 10 to about 30 minutes. In some embodiment, frequency of waveform can be at least about 100 Hz, at least about 250 Hz, at least about 500 Hz, at least about 750 Hz, about 1 kHz; or from about 100 Hz to about 1 kHz, about 100 Hz to about 750 Hz, or about 100 Hz to about 500 Hz. In some embodiments, the waveform can be a ramp, step, sinusoid, or combination thereof. In some configurations, multiple configurable actuator(s) 80 (e.g., voice coil actuators) may be present, housed within mechanical system 3, with each being in contact with a different deformable fluid reservoir 120 (see FIG. 2A). The system may be configured to apply different waveforms to different deformable fluid reservoir(s) 120. Settings may be stored in non-erasable memory, for use with subsequent transfection runs. Such settings may include pre-defined waveforms, parameters for selecting a particular deformable fluid reservoir, and selection of a peak voltage output or magnitude. In some aspects, the control module 50 may monitor applied pressure/force as a function of time for specific cells, and may store this data as training data in a machine learning system to identify optional transfection conditions/parameters.

Control module 50 may also be configured to monitor the states of the various components of the system, including sensors which may monitor the position of the stepper motor, sensors which may monitor the position of the voice coil actuator(s), etc. as well as monitor the system for various error states (e.g., system errors, system resets, etc.) and other malfunctions. The control module 50 may also receive user inputs or other inputs, which may correspond to various trigger conditions that may cause the system to produce a signal that leads to a corresponding action of the mechanical system 3.

The computerized system 2 may also comprise a converter 60, such as a digital-to-analog converter (DAC) (e.g., a 12 bit DAC, a 24 bit DAC, etc.), which receives inputs from the control module 50. In some aspects, converter 60 may receive instructions in the form of a digital signal from the control module 50 regarding generation of waveforms with particular characteristics. Converter 60 converts the digital signal to an analog signal at a suitable resolution. The resolution of the signal may be increased, as needed, by using a higher bit resolution DAC. In some aspects, a MCP4728 (commercially available from Microchip Technology, Inc., Chandler, Arizona) may be selected as the DAC. To reduce latency between the time that the analog signal is generated and applied to the voice coil actuator, the MCP4728 hardware library, may be modified, e.g., by adjusting default latency settings in order to achieve the desired voltage rise. In some aspects, converter 60 may operate at a period of less than or equal to about $2.5\times10^{-6}$ sec, less than or equal to about $2.0\times10^{-6}$ sec, less than or equal to $1.5\times10^{-6}$ sec, or less than or equal to $1.0\times10^{-6}$ sec. Additionally or alternatively, converter 60 may operate at frequencies of greater than or equal to about 400 kHz, greater than or equal to about 600 kHz, greater than or equal to about 800 kHz, and so on.

Converter 60 may provide the analog waveform to voice coil power amplifier 70, which amplifies the strength of the signal (e.g., converts a low power signal to a higher power signal) capable of powering or driving one or more voice coil actuators) such as configurable actuator(s) 80. Converter 60 may be configured to prevent overheating.

Figure 2A:
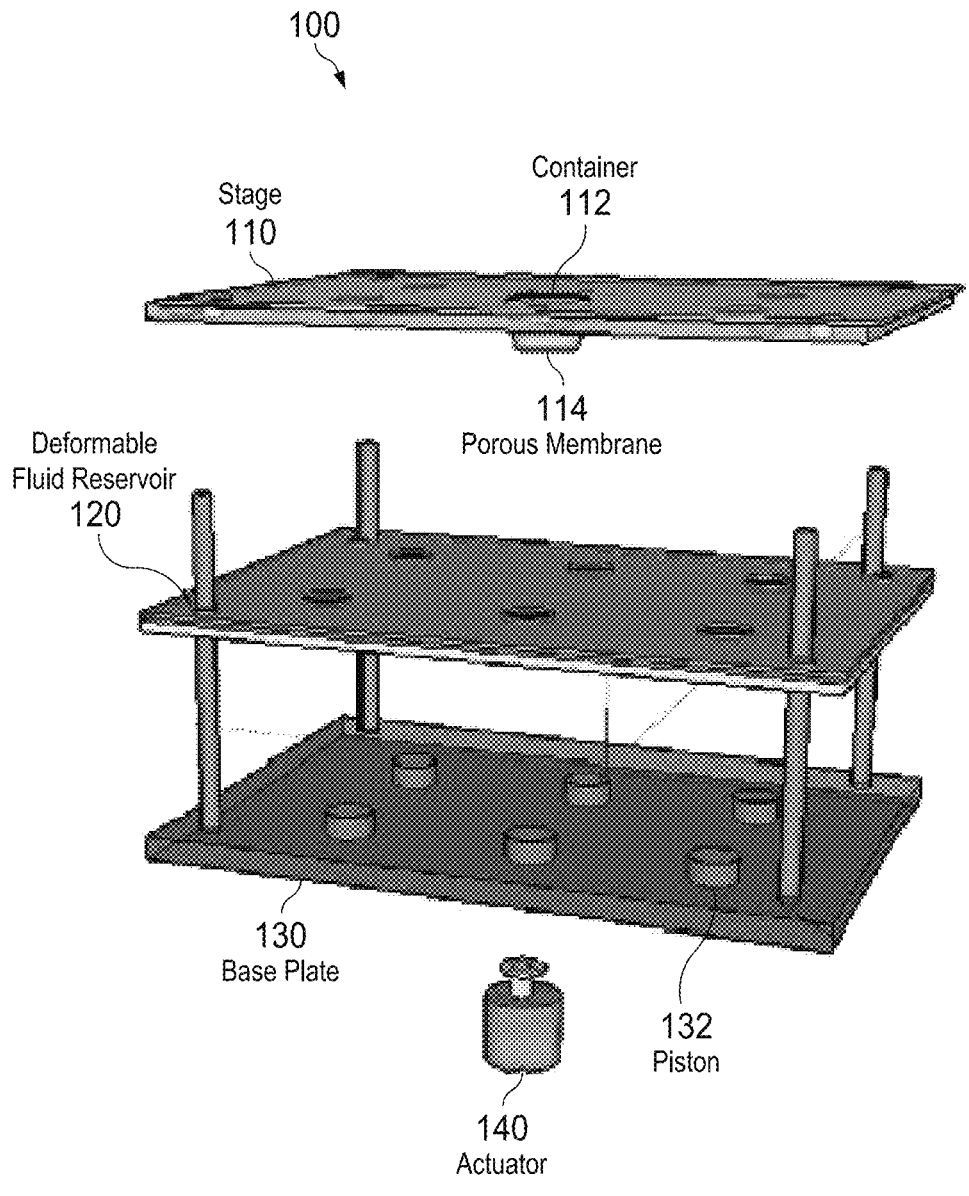

In other aspects, a stepper motor controller 75 may be used to control the positioning of the configurable actuator (s) 80 (e.g., voice coil actuator) at a set position relative to the deformable fluid reservoir 120 (see FIG. 2A). In some aspects, the stepper motor may raise and lower the position of the platform 85 on which the configurable actuator(s) 80 may be situated. For example, one or more configurable actuator(s) 80 80 (e.g., voice coil actuator) may be positioned on a platform 85, the position of which is controlled by a stepper motor 90. The stepper motor 90 may raise or lower the position of the platform 85 via screw drives to a specified height, in order to position the configurable actuator(s) 80 (e.g., voice coil actuator) to deform the reservoir chamber. Operation of stepper motors are known in the art, e.g., and may include positioning and configuration of limit switches to establish boundaries (e.g., upper position and lower position of the platform). The stepper motor 90 may also be configured to prevent overheating.

The configurable actuator(s) 80 used in the transfection devices described herein differ from previous transfection devices that use solenoid actuators in at least two regards. First, solenoid actuators have a fixed (On-Off) force generation profile, which cannot be tuned. In contrast, voice coil actuators and other configurable actuators can be tuned to generate particular force profiles over a finite period of time by controlling the input voltage, allowing a wide range of conditions to be applied to cells during transfection. Second, for a solenoid actuator, the amount of applied force increases with increasing stroke length. For example, when the sample is placed one mm away from the solenoid piston resting position, the force exerted on a sample is lower as compared to when the sample is placed three mm away. In contrast, the voice coil actuator has a constant force (under fixed voltage) over the entire length of the stroke distance. Accordingly, the distance from the actuator to the sample has to be precisely controlled when using a solenoid actuator, whereas voice coil actuators do not have this requirement.

Various voice coil actuators generating different magnitudes of forces are contemplated for use herein. In some aspects, small voice coils have a smaller maximum force but a faster speed (or shorter rise time). Large voice coils have a larger maximum force but a slower speed (or longer rise time). It is contemplated that the voice coil actuator (and thus the resultant speed and force) may be selected based upon the application and/or cell types. For example, for mitochondria delivery, small voice coils with fast speeds and small to moderate forces may be selected, to generate optimal results. However, large voice coils under conditions suitable to generate shorter travel distances and lower forces may also be selected. For RNA/DNA transfection, larger forces are generally needed, and therefore, larger voice coils are typically selected. In some regards, large voice coils may be selected by default for inclusion into the device, due to their flexibility with regard to both applications, e.g., mtDNA transfection via mitochondria transfer and RNA/DNA transfection. In some embodiments, a voice coil actuator can produce a speed of greater than or equal to about 0.5 m/s, greater than or equal to about 1 m/s, greater than or equal to about 1.5 m/s, or about 2 m/s; or from about 0.5 m/s to about 2 m/s, about 1 m/s to about 2 m/s or about 1.5 m/s to about 2 m/s. Additionally or alternatively, a voice coil actuator can produce a force of greater than or equal to about 0.1 N, greater than or equal to about 1 N, greater than or equal to about 2 N, greater than or equal to about 5 N, greater than or equal to about 10 N, greater than or equal to about 15 N, greater than or equal to about 20 N, greater than or equal to about 25 N, greater than or equal to about 30 N. or about 34 N; or from about 0.1 N to about 34 N, from about 1 N to about 34 N, about 2 N to about 34 N, or about 5 N to about 34 N.

A. Machine Learning

It is contemplated that cells with different mechanical properties and in view of different transfected materials (e.g., DNA, RNA, mtDNA, etc.) will have different optimal transfection conditions. For instance, optimal conditions, including but not limited to the voltage waveform and voltage magnitude, rise time, type of actuator, travel distance of actuator components (e.g., plunger), force applied by actuator, amount of applied pressure, the duration of applied pressure, etc., may vary between different cell lines and macrostructures.

Accordingly, a machine learning system may be trained on previous experimental data of transfections, including the parameters of the transfection and the outcome for particular cell types, and may be used to predict optimal conditions for particular cell types with certain macrostructures. Accordingly, the computerized system 2 (e.g., including the control module 50) may also comprise or interface with a machine learning system in order to determine optimal parameters/conditions for delivering particular types of macromolecules to particular types of recipient cells.

In other aspects, the machine learning system may utilize common features between cell types, e.g., size of cell, type of cell, mechanical properties of cells, etc., to predict optimal parameters for new types of cells to be transfected based on similarities to cells that have been transfected.

B. Mechanical System

The mechanical system 3 houses and applies pressure to the cells for transfection. This system includes a stage which receives a container comprising the porous membrane onto which cells are placed (e.g., depleted cells). The opposing surface of the porous membrane may be positioned facing a deformable fluid reservoir, wherein the reservoir comprises a solution containing the macrostructures to be transfected into the cell, using a process described herein. In this process, a configurable actuator, for example, a voice coil actuator, moves in response to applied voltage, and the resultant movement or displacement by a component of the configurable actuator, e.g., such as a plunger, etc., acts to generate a pressure by deforming the reservoir chamber. The resultant pressure brings the macrostructures into contact with the surface of the cells, which are in fluid communication with the solution of the reservoir chamber. Once contacting the cells, the macrostructures may pass through the cell membranes, e.g., via endocytosis, to enter the cell and produce transfected cells.

An exemplary device is schematically illustrated in FIG. 2A. Housing 100 comprises a stage 110 that is configured to removably retain one or more containers 112 that comprise a porous membrane 114 and contain cells to be transfected (e.g., depleted cells). As shown in FIG. 2A, the bottom surface of container 112 comprises a porous membrane 114, with the lower portion of the container 112 configured to sealingly engage with a mating portion of deformable fluid reservoir 120. Base plate 130 is disposed below the deformable fluid reservoir 120 and includes one or more pistons 132. A configurable actuator 140, such as a voice coil actuator, (or in other embodiments, a plurality of voice coil actuators-one for each fluid reservoir 120) is disposed below base plate 130 and exerts an upwards force onto base plate 130 such that the pistons engage with a lower surface of the deformable fluid reservoir 120 to generate pressure.

Figure 2B:
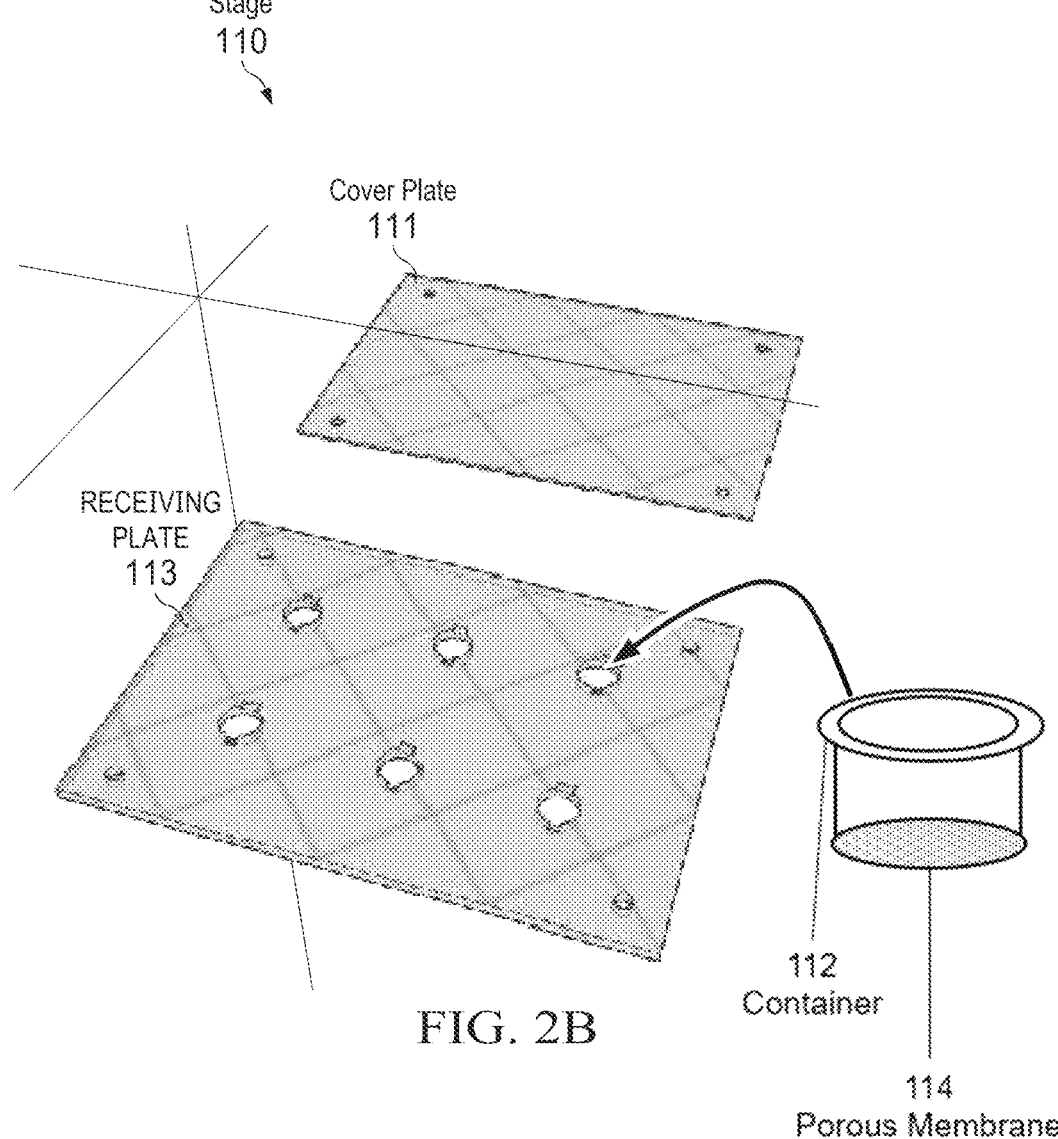

FIG. 2B provides a more detailed view of an exemplary stage 110. Here, the stage includes a receiving plate 113 having one or more openings to removably receive one or more containers 112 that have a porous membrane 114 at their lower surface. Container 112 is retained in the openings of the receiving plate via cover plate 111 such that when the configurable actuator 140 exerts force upon the deformable fluid reservoir 120, the container 112 remains in a fixed position relative to the stage.

FIG. 2C shows a detailed view of an exemplary deformable fluid reservoir 120 where the deformable fluid reservoir 120 comprises multiple layers. Here, the top layer 121 comprises a pliable material that allows for sealing and retaining engagement with the container. Without intending to be limited to a particular configuration, the top layer may have cutouts and a thickness that is selected so as to provide sufficient volume for a fluid that contains the macrostructures when the container is sealingly engaged with the deformable fluid reservoir 120. Thus, it should be appreciated that the fluid that contains the macrostructures is contained by both the deformable fluid reservoir and the porous membrane of the container.

Middle layer 122 is typically made from a deformable material that together with the cutouts in the top layer form a well for the liquid containing the macrostructures. In especially preferred aspects, the material for the middle layer is selected such as to allow a compressive force to act on the middle layer to thereby produce a fluid pressure of at least about 50 hPa, or at least about 100 hPa, or at least about 200 hPa, or at least about 400 hPa or more, for example, about 50 hPa to about 400 hPa, about 100 hPa to about 400 hPa or about 50 hPa to about 200 hPa, when the container is sealingly engaged with the container. The bottom layer 123 of the deformable fluid reservoir typically provides a rigid support platform for the middle and top layers and will typically include one or more openings for the actuator or piston 132 of the base plate 130.

FIG. 2D schematically illustrates a container 112 sealingly engaged (typically via press fit) with the top layer 121 such that the porous membrane 114 at the bottom of the container 112 is in fluid contact with the suspension 170 formed from the fluid and the macrostructures. Direct or indirect actuation (e.g., via piston 132) exerts mechanical force 141 onto the deformable middle layer 122. The middle layer and the top layer are both supported by bottom layer 123. Thus, it should be appreciated that by providing a force onto the pliable middle layer, pressure in the fluid space defined by the middle layer, the top layer, and the porous membrane increases, leading to migration of the macrostructures across the pores of the porous membrane into the container and cells. In the example of FIG. 1D, the cells may be retained at the bottom of the container (i.e., on the top side of the porous membrane) by a thin layer of CELL-TAK™ adhesive (polyphenolic proteins extracted from the marine mussel, *Mytilus edulis*, commercially available from Corning Inc., Bedford, MA).

Figure 2E:
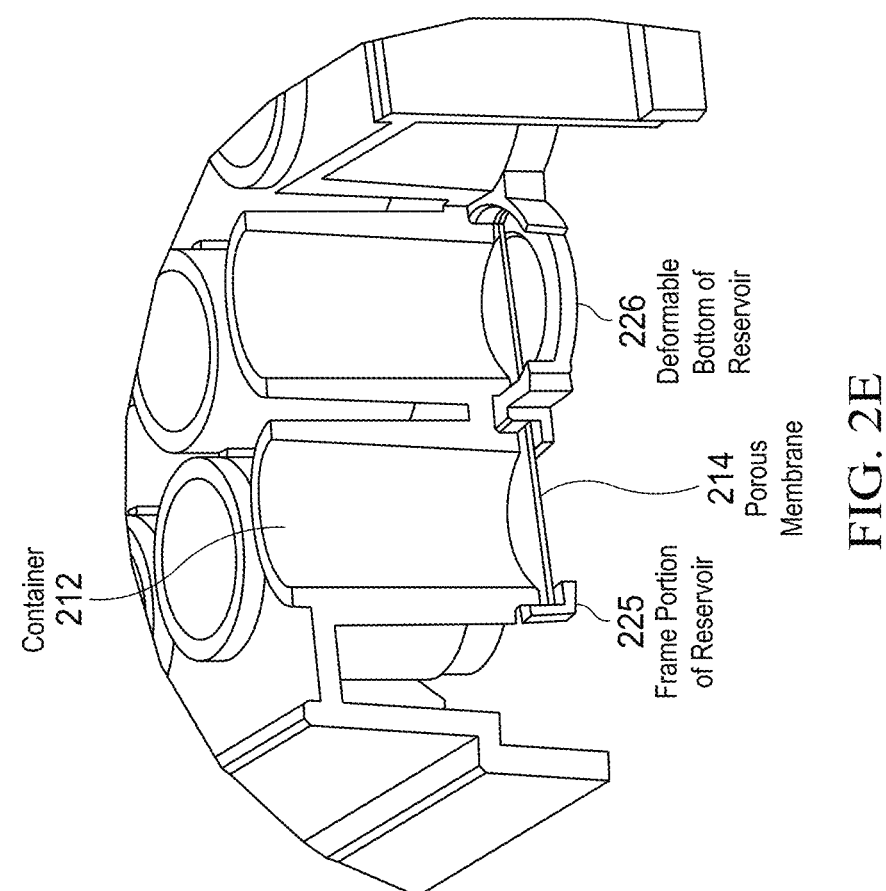
FIG. 2E illustrates another exemplary configuration of an assembly of the container and deformable fluid reservoir according to the embodiments presented herein.

Another exemplary device is schematically shown FIG. 2E where the container 212 is configured as a well of a multi well plate. The deformable fluid reservoir in this device may comprise a frame portion 225 that helps retain porous membrane 214. Also coupled to the frame portion 225 is a deformable bottom 226 of the reservoir. Thus, as noted previously, the porous membrane and a deformable portion of the fluid reservoir define the fluid reservoir that contains the macrostructure, and pressure onto the deformable portion will result in passage of the macrostructures through the pores of the porous membrane to the cells. Most typically, the fluid reservoir is preloaded, but the fluid reservoir may also include one or more fill and vent ports to fill the fluid reservoir before use.

Additional motors may be present to control ejection and retraction of the receiving plate, which house the containers 112.

Figures 3A, 3B, 3C, 3D, 3E, 3F:
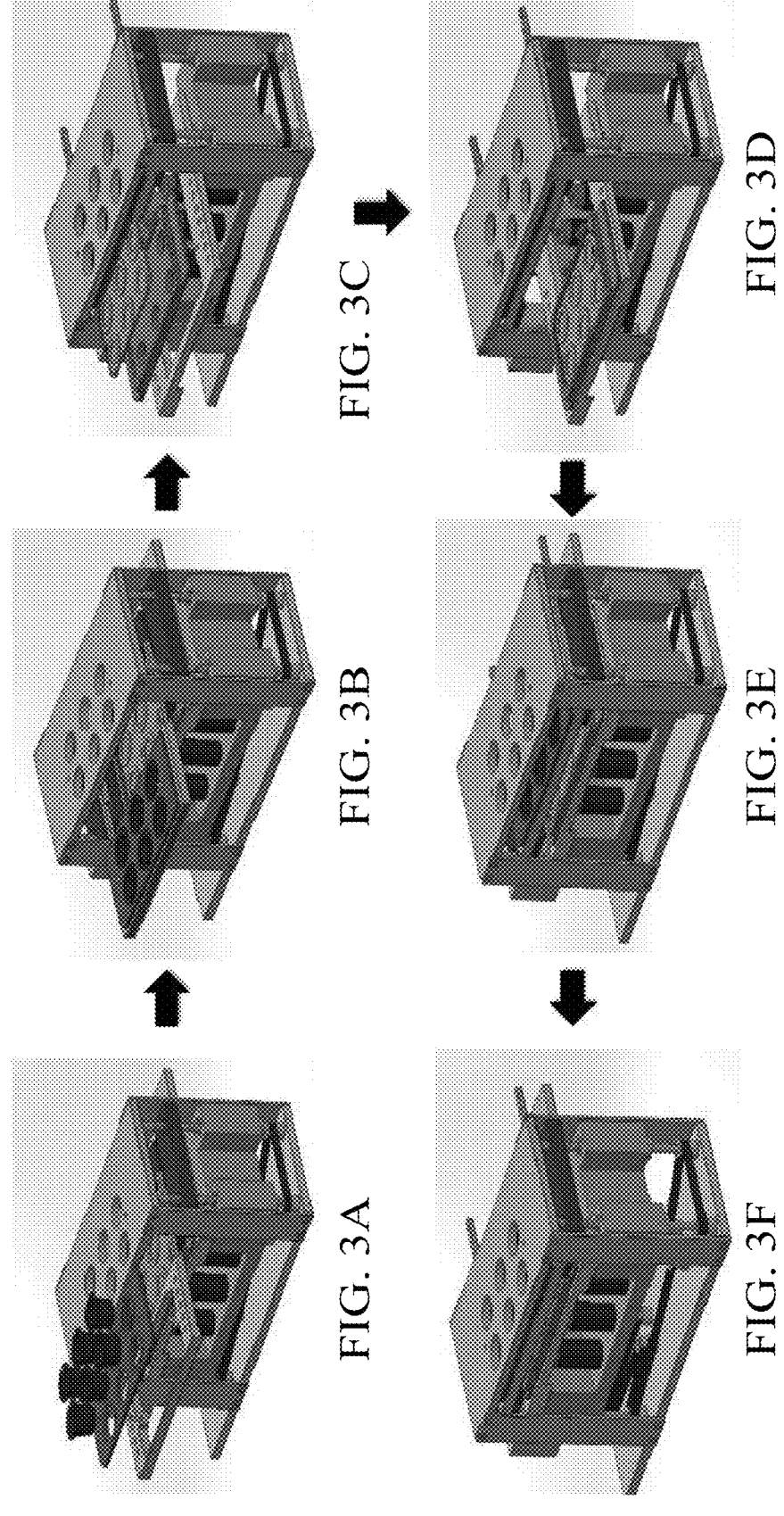
FIGS. 3A-3F show various stages for loading a mitoPUNCH device according to the embodiments presented herein.

FIG. 3 shows an example series of operations for loading the cells and macrostructures to be transfected into the device. FIGS. 3A-3B show placement of containers into the device. FIGS. 3C-3D show placement of the cargo reservoir. FIGS. 3E-3F show alignment and motorized clamping of the layers to create a seal.

C. Containers

With respect to suitable containers it is generally contemplated that the container 112 may be made from a variety of materials. Typically, materials are sterilizable by heat, radiation, and/or chemical treatment. Therefore, appropriate materials include but are not limited to various polymers (e.g., PE, PET, HDPE, PDMS, PC, etc.), glass, metals, and all reasonable combinations thereof. Regardless of the material, the container generally has a shape suitable for receiving and retaining mammalian recipient cells and is configured to allow culturing of the cells. Thus, containers contemplated herein will typically have a volume from about 0.1 mL to about 250 mL, or even higher. For example, where the container is configured as a multi well plate, suitable volumes will be between 0.1 and 20 mL. On the other hand, where the container is configured as a culture flask or culture beaker, suitable volumes will be about 10 mL to about 250 mL, or about to 250 mL to about 1000 mL. Thus, the shape of suitable containers is typically not limited and the shape considered suitable for use includes but is not limited to cup shapes, cell culture flask shapes, box shapes, cylinder shapes, Petri dish shapes, etc. In still further contemplated aspects, containers may be single use, disposable containers that are sterilized.

D. Porous Membrane

Regardless of the particular shape and volume of the container 112, it is contemplated that the container 112 will comprise (or be fluidly coupled to) at least one portion of a surface that includes the porous membrane 114. In some cases, the porous membrane 114 forms at least a portion of a bottom surface of the container 112. There are numerous porous membrane materials known in the art, and all such porous membranes are deemed suitable so long as such porous membranes are able to support and/or retain recipient cells during transfection. For example, contemplated porous membranes may be made from various materials, including nylon, polytetrafluoroethylene (PTFE), expanded polytetrafluoroethylene (ePTFE), polyetheretherketone (PEEK), expanded polyetheretherketone (ePEEK), polyethylene (PE), polypropylene (PP), polyvinylidene fluoride (PVDF), ethyl vinyl acetate (EVA), thermoplastic polyurethane (TPU), or polyethersulfone (PES) or any combination thereof.

The porous membrane 114 may be fabricated from any material compatible with the recipient cell, and with macrostructures that are to be delivered into the recipient cells. In some aspects, the porous membrane 114 may comprise a flexible porous membrane. Porous membranes may be formed from any of a variety of materials, including but not limited to, ethyl vinyl acetate (EVA), nylon/nylon mesh, polydimethylsiloxane (PDMS), polyetheretherketone (PEEK)/expanded polyetheretherketone (ePEEK), polyethylene (PE), polypropylene (PP), polytetrafluoroethylene (PTFE)/expanded polytetrafluoroethylene (ePTFE), polyvinylidene fluoride (PVDF), polyethersulfone (PES), thermoplastic polyurethane (TPU), etc. In other aspects, the porous membrane 114 may comprise an inflexible porous membrane, e.g., formed from porous rigid materials including but not limited to, e.g., porous ceramic, porous glasses, etc.

In further contemplated aspects, the porous membrane 114 will typically have a thickness of between 1 μm and 1 mm, or between 3 μm and 0.5 mm, or between 5 μm and 250 μm. Viewed from a different perspective, suitable membranes will generally have a thickness of at least 1 μm, or at least 3 μm, or at least 5 μm, or at least 10 μm. It should be noted that the membrane thickness will also be determined at least in part by the applied pressure from the deformable fluid reservoir. Accordingly, support structures (e.g., support grid or mesh) to avoid membrane failure are also expressly contemplated herein.

The average pore size of the porous membrane 114 will typically depend on various factors including the size and/or flexibility of the macrostructure. Therefore, it is contemplated that the average or median pore size of the porous membrane 114 may range from about 50 nm, or from about 100 nm, or from about 200 nm, or from about 300 nm, or from about 400 nm, or from about 500 nm, or from about 600 nm, or from about 700 nm, or from about 800 nm, or from about 900 nm, or from about 1 μm up to about 30 μm, or up to about 20 μm, or up to about 15 μm, or up to about 10 μm, or up to about 8 μm, or up to about 5 μm. In certain embodiments the median or average pore size in the porous membrane 114 is about 1 μm or about 3 μm, or about 5 μm or about 10 μm, or about 15 μm.

The pore density and pore size may vary based upon the type of cell undergoing transfection. With respect to the pore density of the porous membrane 114, it is contemplated that the density will be sufficiently high such that on average a cell will cover (or be located above) at least one pore, or at least 2 pores, or at least 3 pores, or at least 4 pores, or at least 5 pores, or at least 10 pores. Thus, the pore density in some embodiments will be about $1\times10^5$ pores/cm$^2$ to about $1\times10^7$ pores/cm$^2$, or about $5\times10^5$ pores/cm$^2$ to about $5\times10^6$ pores/cm$^2$, or at least about $1\times10^5$ pores/cm$^2$, or at least about $1\times10^6$ pores/cm$^2$, or at least about $1\times10^7$ pores/cm$^2$. Viewed from a different perspective, the porous membrane 114 comprises in some embodiments about a 1-10 μm diameter average pore size at about $1\times10^6$-107 pores/cm$^2$.

In still further contemplated aspects, additional elements may be included with the container 112 and porous membrane 114 to at least temporarily retain cells in a fixed position on the porous membrane. For example, additional elements may include microfluidic channels through which the cells may be fed/maintained on the porous membrane, a mesh to retain the cells on the membrane, or the porous membrane may be coated with an adhesive that temporarily retains the cells on the membrane. There are various adhesives known in the art, and all of them are deemed suitable for use herein, including collagen matrices, CELL-TAK™ adhesive, poly-L-lysine, extracellular matrix proteins (e.g., collagen, fibronectin, laminin, etc.), or other adherents. Alternatively, it is noted that where adherent cells are used, no additional elements to retain the cells may be needed.

E. Fluid Reservoir

A deformable fluid reservoir 120 contemplated herein will generally have a volume suitable for retaining sufficient macrostructures to transfect a desirable number of cells. Consequently, depending on the cell number, the transfection efficiency, the surface area of the porous membrane, and other factors, the volume of a deformable fluid reservoir 120 may vary considerably. However, it is generally contemplated that the volume will be about 10 μL to about 5 mL (in some cases even higher), or about 100 μL to about 1 mL, or about 50 μL to about 500 μL, or about 100 μL to about 1000 μL. Similarly, the shape of the deformable fluid reservoir 120 may vary considerably but it is generally contemplated that the particular shape will be at least in part determined by the shape of the container 112 and the size of the porous membrane 114. Consequently, it is contemplated that the deformable portion will preferably include a wall or wall portion, which may be homogenously or locally deformed, or the deformable portion may be replaced by a movable wall or wall portion (e.g., configured as a plunger).

Alternatively, the entire deformable fluid reservoir 120 may also be compressible. Moreover, it is contemplated that the deformable fluid reservoir 120 will sealingly engage with the container 112 such that the macrostructures will be able to flow from the fluid reservoir (typically within a solution) into the container 112 and to the cells on the porous membrane 114. In some aspects, sealing engagement of the deformable fluid reservoir 120 with the container 112 is maintained at pressures in the deformable fluid reservoir of at least 50 hPa, at least 100 hPa, at least 200 hPa, at least 400 hPa, or at least 800 hPa. Viewed from a different perspective, the sealing engagement may be maintained at pressures of about 1 to about 1000 hPa, about 10 to about 800 hPa, about 50 to about 600 hPa, or about 100 to about 1000 hPa.

In still further contemplated aspects, the deformable fluid reservoir 120 may be coupled to or include or one or more ports through which a fluid containing the macrostructures can be introduced, preferably using sterile techniques and sterile adapters (e.g., Luer lock adapters). Where desirable, vent and/or discharge ports may be included to facilitate loading and unloading of the deformable fluid reservoir. Most typically, the deformable fluid reservoir 120 will be removable. However, one or more permanently affixed deformable fluid reservoirs are also contemplated (in such case, the reservoirs may be prefilled with a fluid and macrostructures).

In some aspects, the deformable fluid reservoir 120 may be formulated of a polymer, for example, PDMS, using soft lithography techniques. A master mold corresponding to the inverse of the deformable fluid reservoir may be formed by any suitable technique known in the art, including but not limited to, a micromachining process, a photolithographic process, etc. Methods for making a master mold and for using soft lithography to generate polymeric structures, e.g., from PDMS are known in the art (see, e.g., Choudhury (1997) The Handbook of Microlithography, Micromachining, and Microfabrication, Soc. Photo-Optical Instru. Engineer., Bard & Faulkner, Fundamentals of Microfabrication).

A polymer, such as PDMS, may be poured over the master mold, allowed to polymerize, and cured to form the deformable fluid reservoir 120. The cured mold may be removed, trimmed, and modified (input or output ports are added) as needed. The polymer may be optionally treated with plasma and bonded to a glass substrate or any other suitable substrate. Plasma treatment alters the surface of PDMS, allowing PDMS to form an irreversible seal with its substrate. Numerous other materials including but not limited to polyolefin plastomers, perfluoropolyethylene, polyurethane, polyimides, and cross-linked phenol/formaldehyde polymer resins etc., may be used to form a deformable fluid reservoirs 120 of the device.

F. Macrostructures

Macrostructures suitable for use herein may include any suitable structure including cell organelles (e.g., nucleus, mitochondria, chloroplast, ribosomes, etc.), viruses and microorganisms (e.g., gram$^+$ and gram bacteria, etc.), various macromolecules, and recombinant and natural nucleic acids alone or in combination with a transfection agent (e.g., native, synthetic or artificial chromosomes, corrected mtDNA, DNA, RNA, miRNA, siRNA, plasmids, double minute chromosomes, etc.), proteins and/or protein complexes, and drug delivery particles.

G. Solutions

Fluids appropriate for mixing with macrostructures and movement through the porous membrane may vary considerably, but it is generally preferred that the fluids include physiologically acceptable solutions (e.g., isotonic and buffered solutions), growth media, etc. Examples of suitable fluids include experimental buffer, PBS, DMEM, HBSS, Opti-MEM, DMEM without Ca2+, or other media amenable to the nature of macrostructures. The macrostructures in the fluid can also comprise one or more lipid carriers. Example lipid carriers can include Lipofectamine, Transfectace, Transfectam, Cytofectin™, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho,-alanyl cholesterol; DCGS, DPPES, DCPE, DMAP, DMPE, DOGS, DOHME, DPEPC, Pluronic™. Tween®, BRIJ®, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis(dodecyaminocarbonylmethylene)-N, N'-bis((-N,N,N-trimethylammoniumethyl-aminocarbonylmethylene)ethylenediamine tetraiodide, N,N''-Bis(hexadecylaminocarbonylmethylene)-N,N', N''-tris((-N,N,N-trimethylammonium-ethylaminocarbonyl-methylenediethylenetriamine hexaiodide, N,N'-Bis(dodecy-laminocarbonylmethylene)-N,N''-bis((-N,N,N-trimethylam-moniumethylaminocarbonylmethylene)cyclohexylene-1,4-diamine tetraiodide, 1,7,7-tetra-((—N,N,N-tetramethylammoniumethylamino-carbonylmethylene)-3-hexadecylaminocarbonyl-methylene-1,3,7-triaazaheptane heptaiodide, or N,N,N',N'-tetra((—N,N,N-trimethylammo-nium-ethylaminocarbonylmethylene)-N'-(1,2-dioleoylglyc-ero-3-phosphoethanolaminocarbonylmethylene) diethylen-etriamine tetraiodide.

H. Configurable Actuators

As previously described, configurable actuator(s) 80 are capable of compressing the deformable fluid reservoir 120 to an extent that the macrostructures will move through the pores of the porous membrane 114 to contact the cells for transfection. Configurable actuator(s) 80, instead of operating in an on/off configuration (e.g., one speed) have various parameters that may be used to control aspects of transfection and are thus tunable, with regard to voltage waveforms, speed, force, applied pressure, duration of applied pressure, etc. These configurable parameters are described in additional detail below.

Figure 4A:
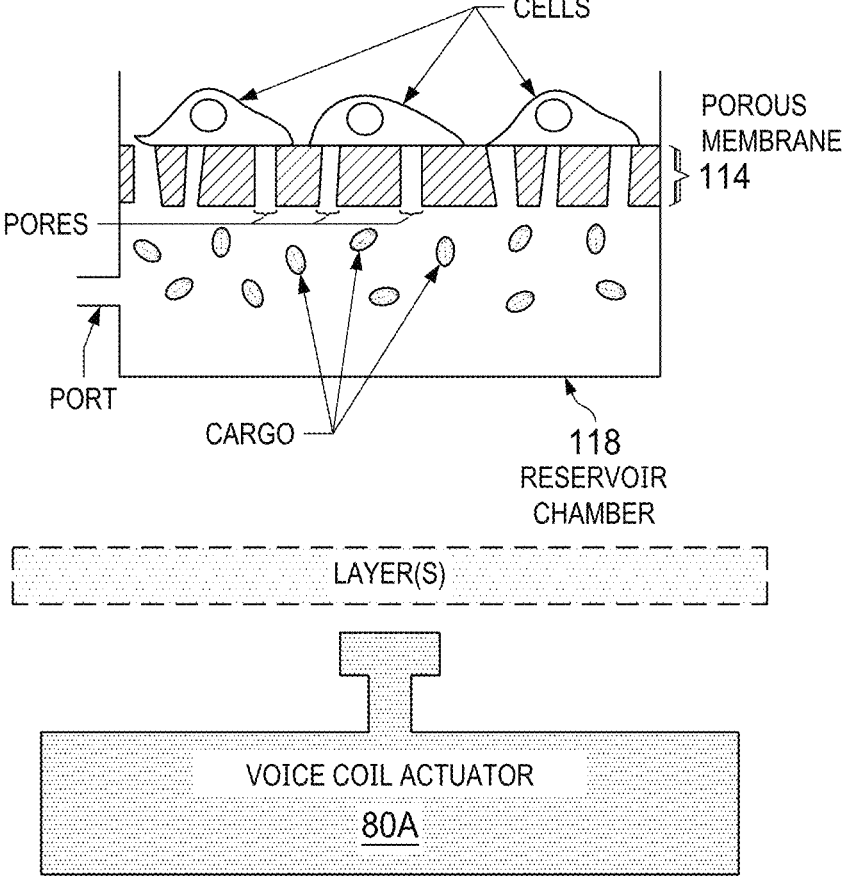
FIGS. 4A-4B are illustrations of an example fluid reservoir and applied force profiles, shown as a function of displacement and voltage, according to the embodiments presented herein.
Figure 4B:
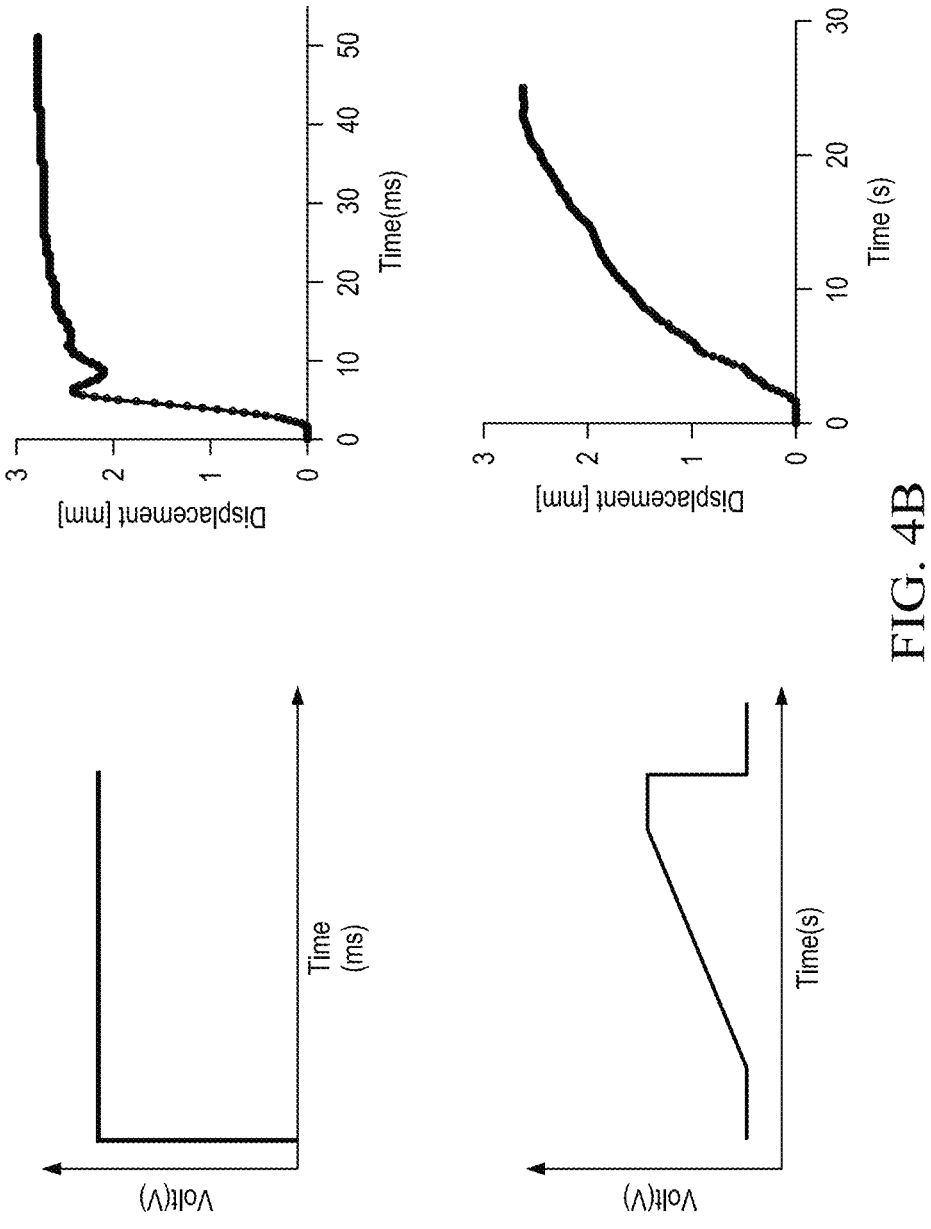

Configurable actuator(s) 80 may be voice coil actuator(s) 80a as shown in FIG. 4A, wherein the voice coil actuator 80a displaces layers (e.g., layers 121, 122, 123) comprising the deformable fluid reservoir to apply pressure to the macrostructures present in a reservoir chamber 118 defined in the deformable fluid reservoir 120 between a deformable portion of the deformable fluid reservoir 120 and the porous membrane 114. Voice coils may operate as bidirectional devices, and apply a constant force over a stroke (displacement). Typically, displacement is linear relative to applied voltage, as shown in FIG. 4B, wherein a step input results in a step displacement, and a ramp input results in a ramp displacement. Voice coil actuators offer direct control of force and speed for robust waveform inputs, and may be directly or indirectly in contact through one or more deformable layers with the fluid reservoir to transmit displacement into applied pressure.

The voice coil actuator may comprise a sliding component comprising an electric coil, such that the sliding component is positioned within a fixed portion comprising a permanent magnet of the voice coil, separated from the fixed component by an air gap. Changes in the magnetic flux path of the fixed component may drive movement in the sliding component. The displacement from this change in position may be applied to the reservoir chamber as applied force. Voice coil actuators may apply force over a variable range of speeds (at a velocity of about 0.1 to 200 mm/s) and provide a linear relationship between voltage and force (displacement).

In any embodiment, the a magnitude of a voltage-based waveform provided as input to the voice coil can range from about 0.1 volts to about 10 volts, about 0.5 volts to about 7.5 volts, about 1 volt to about 5 volts or about 1 volt to about 3 volts. Additionally, displacement of the component of the voice coil can range from about 0.1 mm to about 10 mm, about 0.1 mm to about 8 mm, about 0.5 mm to about 5 mm, or about 1 mm to about 3 mm.

In general, voice coil actuators may achieve velocities ranging from about 0.1 mm/s to about 2 m/s, with forces ranging from about 0.1 to about 35 N. For example, the velocity may be about 0.1 mm/s to about 1.5 m/s, about 0.1 mm/s to about 1 m/s, about 0.1 mm/s to about 500 mm/s, about 0.1 mm/s to about 250 mm/s, about 0.1 mm/s to about 150 mm/s, about 0.1 mm/s to about 100 mm/s, about 0.1 mm/s to about 50 mm/s, about 0.1 mm/s to about 25 mm/s, or about 0.1 mm/s to about 10 mm/s. The force may be about In some aspects, individual voice coils may be designed to operate within a subset of this range, e.g., such that larger voice coils may deliver higher forces at a lower velocity (e.g., about 35 N at about 45 mm/s) and smaller voice coils may deliver lower forces at a faster velocity (e.g., at about 200 mm/s at about 6 N). Other voice coils may operate in between these lower and upper ranges or outside these ranges. In some aspects, the voice coil can apply a continuous force of about 2.1 N with a displacement of about 3 mm or about 6.4 mm.

Actuator operation may be performed via the control module 50, which is configured to cause movement of the configurable actuator 80 to deform the deformable fluid reservoir 120, and as a result, pressurize the fluid comprising the macrostructures.

The control module 50 may be configured to apply pressure via the configurable actuator 80 for a period of time ranging from about 10 ms to about 30 s, or from about 20 ms to about 15 s, or from about 20 ms to about 300 ms. Thus, the controller will typically operate the plunger of the configurable actuator such that the deformable fluid reservoir is pressurized for at least about 10 ms, at least about 25 ms, at least about 50 ms, at least about 100 ms, or at least about 500 ms, or at least about 1 s, or at least about 5 s, and typically less than about 10 s, or less than about 20s, or less than about 30s, or less than about 60s. In some instances, pressurization may also last about 1 min, or up to and including about 1.5 min, or up to and including about 2 min, or up to and including about 2.5 min, or up to and including about 5 min. In some aspects, the control module 50 may be configured to effect pressurization for a period of time ranging from about 10 ms up to and including about 500 ms.

The control module 50 also may be configured to effect pressurization of the fluid in the deformable fluid reservoir 120 to a pressure of at least about 10 hPa, at least about 20 hPa, at least about 50 hPa, at least about 100 hPa, at least about 200 hPa, at least about 400 hPa, at least about 800 hPa, or at least about 1000 hPa. Therefore, suitable pressure ranges effected by the control module 50 may be from about 10 hPa to about 1000 hPa, or about 20 hPa to about 800 hPa, or about 40 hPa to about 400 hPa, or about 50 hPa to about 500 hPa. Additionally, it should be appreciated that the slope of pressure increase may vary considerably, and in most cases maximum pressure levels will be attained within less than or equal to about 10 s, or less than or equal to about 5 s, or less than or equal to about 1 s, or less than or equal to about 500 ms, or less than or equal to about 250 ms. Of course, it should be recognized that the control module 50 also may be programmable to a particular profile having any one or more of the following features: a predetermined maximum pressure, a predetermined minimum pressure, a predetermined pressure duration, a predetermined rise time to achieving maximum pressure, a predetermined voltage waveform, a predetermined frequency, and a predetermined distance of which the porous membrane 114 is distended. Wherein feedback mechanisms are contemplated, it is typically preferred that the control module 50 receives information from at least one pressure sensor in the device, typically located in the deformable fluid reservoir 120.

In other embodiments, planar magnetic speaker elements or any suitable type of speaker element, which produces a range of sounds at a sufficient magnitude, may be used in lieu of a voice coil actuator.

There are a number of formats, materials, and size scales that may be used in the construction of the transfection devices described herein and in microfluidic devices that may include or connect to such devices. All such configurations are contemplated for use herein.

II. Generation of Engineered Cells and Therapeutic Uses

Methods of generating engineered cells are also provided herein. The methods include depleting, transfecting, reprogramming, and differentiating steps.

A. Depletion of Endogenous mtDNA

In some aspects, recipient cells are depleted of endogenous mtDNA to produce depleted cells. The term "endogenous mtDNA" refers to mtDNA, which is found naturally in the recipient cells. The endogenous mtDNA may include at least one genetic mutations. Recipient cells may be differentiated cells or undifferentiated cells and depleted cells may be depleted differentiated cells or depleted undifferentiated cells. In any embodiment, the recipient cells may be contacted with a reverse transcriptase inhibitor to deplete endogenous mtDNA. Any suitable reverse transcriptase inhibitor may be used Any suitable reverse transcriptase inhibitor may be used to deplete endogenous mtDNA. For example, nucleoside analog reverse-transcriptase inhibitors (e.g., AZT, ddI, ddC, d4T, 3TC, ABC, FTC, ETV, etc.), nucleotide analog reverse-transcriptase inhibitors (e.g., TDF, ADV, AZT, d4T, ddC, 3TC, FTC, ABC, ETV, ddI, etc.), non-nucleoside reverse-transcriptase inhibitors (e.g., efavirenz, nevirapine, delavirdine, etravirine and rilpivirine, etc.) may be used to inhibit mitochondrial replication. In general, the reverse transcriptase inhibitor is capable of depleting mtDNA from the recipient cell (e.g., differentiated cells, such as primary and established fibroblasts), does not introduce high levels of secondary mutations, chromosomal breaks, or DNA copy number to the nuclear genome, and creates a suitable and clean environment for transfection. In some embodiments, the reverse transcriptase inhibitor can be 2',3'-dideoxycytidine (ddC). ddC-treated cells, as revealed by whole genome sequencing, had a low abundance of non-synonymous mutations, no chromosomal breaks, and no changes in DNA copy number (see, Example 22).

In some aspects, the amount of reverse transcriptase inhibitor added to the recipient cells may include an amount sufficient to produce depleted cells having less than 6% of endogenous mitochondrial DNA, to less than 5% of endogenous mitochondrial DNA, to less than 4% of endogenous mitochondrial DNA, to less than 3% of endogenous mitochondrial DNA, or to less than 2% of endogenous mitochondrial DNA. In other aspects, the amount of reverse transcriptase inhibitor may range from about 1 μM to about 10 μM, from about 2.5 μM to about 7.5 μM, from about 2.5 μM to about 5 μM or any amount in between.

In some aspects, the cells may be contacted or treated with a reverse transcriptase inhibitor for a period of time that is from about 1 day to about 60 days, about 7 days to about 30 days, about 15 days to about 30 days or about 16 days to about 21 days, or any amount in between.

Other techniques for depletion of mtDNA, e.g., selection based on drug resistance or selection under growth conditions, are known in the art and are contemplated for use herein.

B. Transfection of mtDNA

Once the endogenous mtDNA of the cells has been sufficiently depleted, e.g., to a level of about 0.1% or lower of endogenous mtDNA, the depleted cells may be transfected with corrected mtDNA using the transfection devices (see, e.g., FIG. 1) as described herein and parameters described herein to produce transfected cells. Such transfection devices comprise configurable actuators, including voice coil actuators, and have demonstrated results of over 2.3× delivery rates of other transfection techniques.

In a non-limiting example, the depleted cells (e.g., depleted differentiated cells), are placed on a porous membrane 114. The pores of the porous membrane may span the entire width of the porous membrane 114 to allow the depleted cells placed on a surface of the porous membrane 114 to contact underlying solutions and materials to be transfected. In other non-limiting aspects, the depleted cells (e.g., depleted differentiated cells), may be cultured on the porous membrane.

In some aspects, the depleted cells may adhere, adsorb, or may be deposited onto the porous membrane 114. The depleted cells may attach to the porous membrane 114 using various adhesion molecules (e.g., integrins, cadherins, selectins, etc.), and/or synthetic linkers (e.g., heterobifunctional or homobifunctional peptide linkers), or using adhesive materials that bind the depleted cells to the porous membrane 114 (e.g., a gel matrix, a collagen gel, a hydrogel, etc.).

The macrostructures to be transfected into the depleted cells are mixed with a solution, and the solution is placed in a deformable fluid reservoir 120 underlying the porous membrane 114. Relative to the opposing side of the porous membrane 114 as the depleted cells, there is a fluid connection between the depleted cells and the deformable fluid reservoir 120 comprising a solution of mitochondria containing desired mtDNA or other macromolecules to be transfected. Pressure is applied to the deformable fluid reservoir 120, which causes the macrostructures to flow through the membrane pores and make contact with the depleted cells. Once contacting the cells, the macrostructures may enter the cell, e.g., via endocytosis, etc.

In some aspects, the porous membrane 114 may deform due to the applied pressure. In other aspects, the depleted cells that are adhered or otherwise bound to the porous membrane 114 may undergo deformation, while generally remaining attached to the porous membrane 114. In still other aspects, both the depleted cells and the porous membrane 114 may undergo deformation in response to applied pressure.

The applied pressure may be applied for period(s) of time ranging from about 1 msec, from about 10 msec, from about 20 msec, from about 50 msec, from about 75 msec, from about 100 msec, from about 500 msec, from about 1 sec, from about 5 sec, from about 10 sec and up to and including about 20 sec, up to and including about 50 sec, up to and including about 1 min, up to and including about 2 min, up to and including about 5 min, or up to and including about 10 min or any amount in between. In certain embodiments, the pressure is applied for a period of time ranging from about 100 msec to about 1 min. In some aspects, the pressure may be applied continuously, or cyclically. For example, the pressure may be applied during an entire period of time (e.g., a constant applied pressure) or may be applied cyclically within a period of time (e.g., an applied pressure that may cycle between a high pressure and a low pressure, or between a high pressure and atmospheric pressure over a period of time).

For the purposes of this application, it is understood that corrected mtDNA includes any mtDNA that is different from the endogenous mtDNA. In some aspects, corrected mtDNA includes mtDNA that is free of genetic mutations, and is designed to correct mutation(s) present in endogenous mtDNA. In other aspects, corrected mtDNA includes modified mtDNA comprising one or more mutations conferring superior properties as compared to wt mtDNA.

In some aspects, subsequent isolation and characterization of mtDNA present in cells that have undergone depletion and transfection show the presence of only the corrected mtDNA and not the endogenous mtDNA. During depletion, the endogenous mtDNA is typically not completely eliminated, but is at a sufficiently low concentration such that transfected mtDNA is able to outcompete endogenous mtDNA during cell culture. In some aspects, the range of experimental conditions leading to replacement of endogenous mtDNA may be narrow. Conditions which deplete cells of all or nearly all of the endogenous mtDNA may lead to nonviable cells. Other conditions which do not sufficiently deplete mtDNA, such that the transfected mtDNA is able to outcompete the endogenous mtDNA, may lead to cells with mixed populations of mtDNA, both endogenous mtDNA and corrected mtDNA.

Pressure may be controlled by a voice coil actuator. Unlike other pressure generating devices, such as solenoid actuators that are not customizable or configurable, voice coil actuators linearly relate voltage to force, and offer a range of speeds in combination with a variety of waveforms and other parameters. This allows transfections to be highly customizable, and transfection parameters may be optimized per cell line and per macrostructure that is being transfected.

C. Reprogramming Cells with Transfected mtDNA

Once the cells have been transfected with the corrected mtDNA to produce transfected cells, the transfected cells may be reprogrammed to induced pluripotent stem cells (iPSCs). Techniques for reprogramming differentiated cells to stem cells (e.g., iPSCs) are known in the art, and any such method is contemplated for use herein. Such techniques may include a second round of transfection using reprogramming mRNAs including but not limited to OCT4, SOX2, KLF4, cMYC, NANOG, and LING28 in combination with immune evasion mRNAs including but not limited to E3, K3, B18R and also miRNAs: 302/367. These reprogramming and immune mRNAs may be introduced into cells using techniques described herein, or in U.S. Publication No. 2017/0175139, or by Takahashi, K. & Yamanaka, S. "Induction of pluripotent stem cells from mouse embryonic and adult fibroblast cultures by defined factors", Cell (2006) 126:663-676, both of which are incorporated by reference in their entirety. By using mRNAs encoding these respective reprogramming factors, iPSCs can be generated without leaving a genetic footprint in the reprogrammed cells (e.g., Warren, L. et al. "Highly Efficient Reprogramming to Pluripotency and Directed Differentiation of Human Cells with Synthetic Modified mRNA", Cell Stem Cell 7, 618-630 (2010); and Mandal, P. K. & Rossi, D. J. "Reprogramming human fibroblasts to pluripotency using modified mRNA", Nature Protocols (2013) 8:568-582). Other suitable techniques may include protocols for reprogramming human fibroblasts into induced pluripotent cells as described by P. Mandal and D. Rossi Nature Protocols (2013) 8:568-582, which is incorporated herein by reference in its entirety.

In some aspects, the iPSCs are are analyzed after reprogramming. In such reprogrammed cells, hypervariable regions of mtDNA may be analyzed, wherein the hypervariable region of the corrected mtDNA has at least one, at least two, at least three, at least four, or at least five mutations as compared to the endogenous DNA. Accordingly, the hypervariable region may be used to track changes in mtDNA.

D. Differentiation after Transfection

Once the transfected cells are reprogrammed to produce iPSCs, the iPSCs cells may be differentiated into engineered cells. Techniques for differentiating iPSCs to engineered cells are known in the art, and all such techniques are contemplated for use herein, e.g., Sheyn et al., Stem Cells Transl Med (2016) 5:1447-1460, which is incorporated herein by reference in its entirety. In other aspects, specific vendor protocols are available for differentiation of iPSCs, and any such protocol may be used. Examples of engineered cells include, but are not limited to cardiomyocyte cells, retinal epithelial cells, neural progenitor cells, and mesenchymal stem cells.

E. Patient Specific Therapeutic Use

Once the iPSCs have been differentiated into engineered cells, the engineered cells may be administered to a patient as part of a therapeutic treatment. In some aspects, the iPSCs may be directly delivered to a patient. However, in general, it is contemplated that the iPSCs will undergo differentiation into engineered cells (e.g., mesenchymal cells) or other progenitor or terminal cell types before administration to a patient.

In some aspects, the transfected cells, IPSCs, engineered cells, or a combination thereof may be cultured and the cells may be grown until meeting an acceptable profile before administration to a patient. The transfected cells, IPSCs, engineered cells, or a combination thereof can be cultured in a bioreactor, a closed reactor, a closed system as described in U.S. Patent Publication No. 2017/0037357, which is incorporated by reference in its entirety, etc. For example, the transfected cells, IPSCs, engineered cells, or a combination thereof may be cultured in a closed system until differences between the cells comprising the corrected mtDNA (transfected cells, IPSCs, engineered cells, or a combination thereof) and the corresponding wt DNA have been minimized. In some aspects, the cells comprising the corrected mtDNA (transfected cells, IPSCs, engineered cells, or a combination thereof) have the same or similar profile as the corresponding wt cells. In particular, the mesenchymal stem cells have the same or similar profile as the wt mesenchymal stem cells. Characteristics may include any condition that may be measured by a bioreactor, including but not limited to oxygen consumption, pH, galvanic response, $CO_2$ resistance, temperature, oxygen level, etc. Thus, in some aspects, the cells comprising the corrected mtDNA (transfected cells, IPSCs, engineered cells, or a combination thereof) are able to adapt under certain conditions, thereby optimizing characteristics such as oxygen consumption to be at or near wt characteristics.

Present techniques provide a way in which to deliver patient specific therapy to a patient. Such therapies may be used to repair injured tissue, cardiac tissue, immune cells, or any other disease associated with defective mtDNA.

F. Recipient Cell Types

The present techniques may be applied to a variety of different recipient cell types to correct defects in mtDNA and may include any type of cell for which correction of mtDNA is desirable. The present techniques may be used to transfer large macrostructures, such as mtDNA into cells, with high efficacy.

The recipient cell types provided herein are intended to be illustrative and non-limiting. The recipient cells can be any eukaryotic cell, including but not limited to mammalian cells, such as differentiated somatic cells, stem cells, fibroblasts, lymphocytes, epithelial cells, NK cells, EC-7 cells, T cells, embryonic cells, stem cells, macrophages, and gamete cells.

The term 'about', unless otherwise indicated, when used in conjunction with a numeral refers to a range spanning+/− 10%, inclusive, around that numeral. For example, the term 'about 10 µm refers to a range of 9 to 11 µm, inclusive.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context.

The use of any and all examples, or exemplary language (e.g. "such as") provided with respect to certain embodiments herein is intended merely to better illuminate the invention and is not intended to pose a limitation on the embodiments disclosed herein. No language in the specification should be construed as indicating any non-claimed element essential to the practice of the invention.

It should be apparent to those skilled in the art that many more modifications besides those already described are possible. The systems, methods and devices disclosed herein are not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

EXAMPLES

The following examples are offered to illustrate but not to limit the methods, compositions, and systems disclosed herein.

The following experiments provide exemplary guidance on certain aspects of the device and methods of use, but should not be construed to be limiting in any manner. Unless specified otherwise, all transfection experiments were performed with the devices described herein.

Example 1. Experimental Protocols for Transfection Using Voice Coil Actuators

Recipient cells were cultured or immobilized on top of a 10 µm-thick polycarbonate porous membrane. For mitochondria delivery, membranes with a 3 µm pore diameter and a density of about $2 \times 10^6$ pores/cm$^2$ were used. Macrostructures suspension containing the mtDNA in a solution was loaded into a deformable fluid reservoir made by stacking two layers of polydimethylsiloxane (PDMS). The bottom layer has a thickness of about 0.5 mm and the top layer has a thickness of about 1 mm. The fluid reservoir volume is about 100 µL. The porous membrane was clamped and sealed onto the PDMS fluid reservoir which connected the recipient cells with macrostructures in solution via pores of the porous membrane. A motorized configurable actuator (e.g., voice coil) is affixed to the bottom of the PDMS fluid reservoir. For delivery, the configurable actuator was activated to deform the fluid reservoir and subsequently pump the macrostructure suspension into proximity of the recipient cells. After delivery, recipient cells may be cultured on the porous membrane or re-plated onto other substrates for expansion or analyses.

Figure 5:
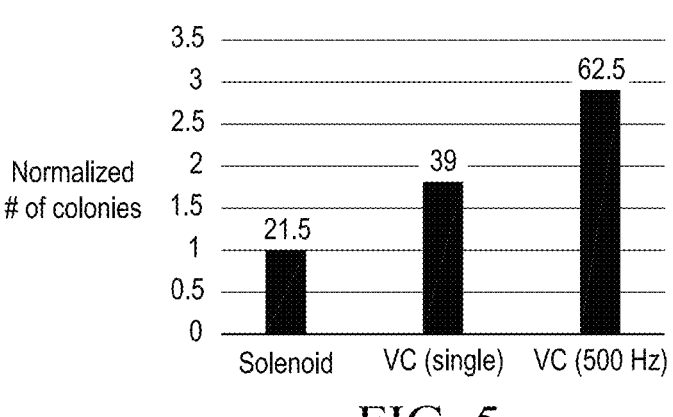
FIG. 5 shows results of a small voice coil actuator for delivering isolated, whole mitochondrion carrying mtDNA using a transfection process, according to the embodiments provided herein.

FIG. 5 shows the results of a small voice coil actuator used to transfect mtDNA into recipient cells. As shown by the graph, the small voice coil outperformed the solenoid actuator, regardless of whether a single waveform was used or a 500 Hz waveform was used. The higher frequency waveform performed better than the single waveform, and showed a 2.36× improvement over non-customizable actuators such as the solenoid actuators used in other protocols. In this case, parameters of the voice coil actuator included a voltage of 2 V, and a travel distance of the actuator plunger of 3 mm.

The voice coil actuator resulted in a higher colony yield of transformants with a normalized number of 62.5 colonies for a 500 Hz waveform, and a normalized number of 39 colonies for a single step waveform. The voice coil actuator regardless of frequency outperformed the solenoid device, which had a lower number of normalized colonies (21.5). The small mass of the voice coil plunger allowed quick actuation with a small force (low voltage). However, these conditions were found not to be sufficient for reprogramming with RNA transfection (data not shown).

Figure 6:
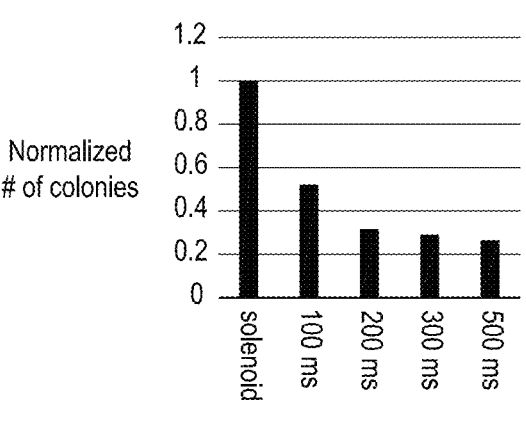
FIG. 6 shows results of a medium voice coil actuator for delivering isolated, whole mitochondrion carrying mtDNA using a transfection process, according to the embodiments provided herein.

FIG. 6 shows the results of a medium voice coil actuator used to transfect mtDNA into recipient cells. As shown by the graph, the medium voice coil actuator under certain conditions underperformed the solenoid actuator, with the number of colonies decreasing as the rise time of the applied voltage increased. The voltage was set at 8V with a 3 mm travel distance.

Figures 7A, 7B:
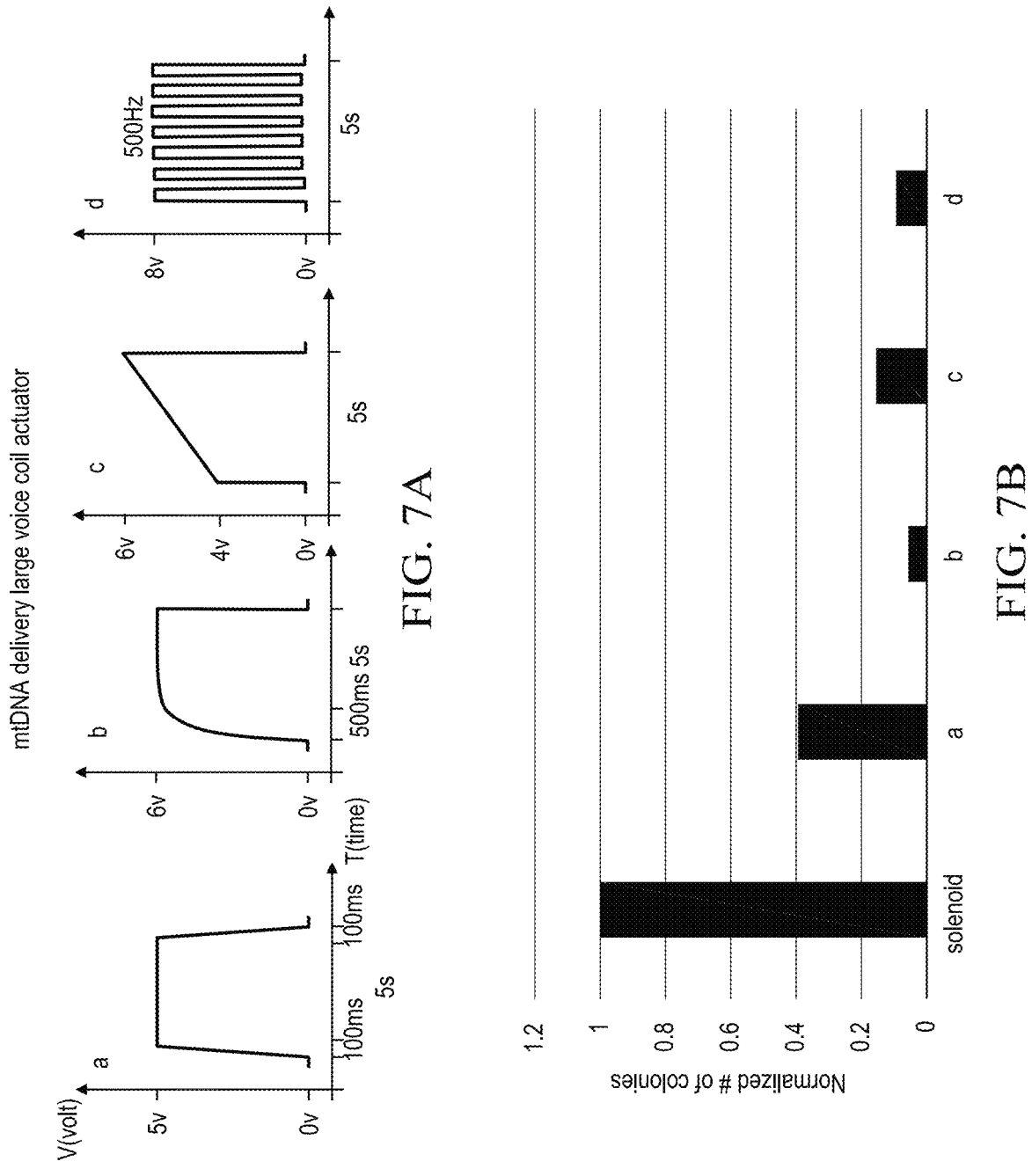
FIGS. 7A-7B show input waveforms and results of a large voice coil actuator for mtDNA transfection, according to the embodiments provided herein.

FIGS. 7A-7B show the results of a large voice coil actuator used to transfect mtDNA into recipient cells. Various waveforms are shown in FIG. 7A, and the corresponding results are shown in FIG. 7B. The large voice coil underperformed the solenoid actuator under certain conditions, with the number of colonies decreasing (using voltages of between 5-8V). Under these conditions, increasing force to improve ramp times was found to worsen delivery of mtDNA using large actuators.

Figures 8A, 8B, 8C, 8D, 8E, 8F, 8G:
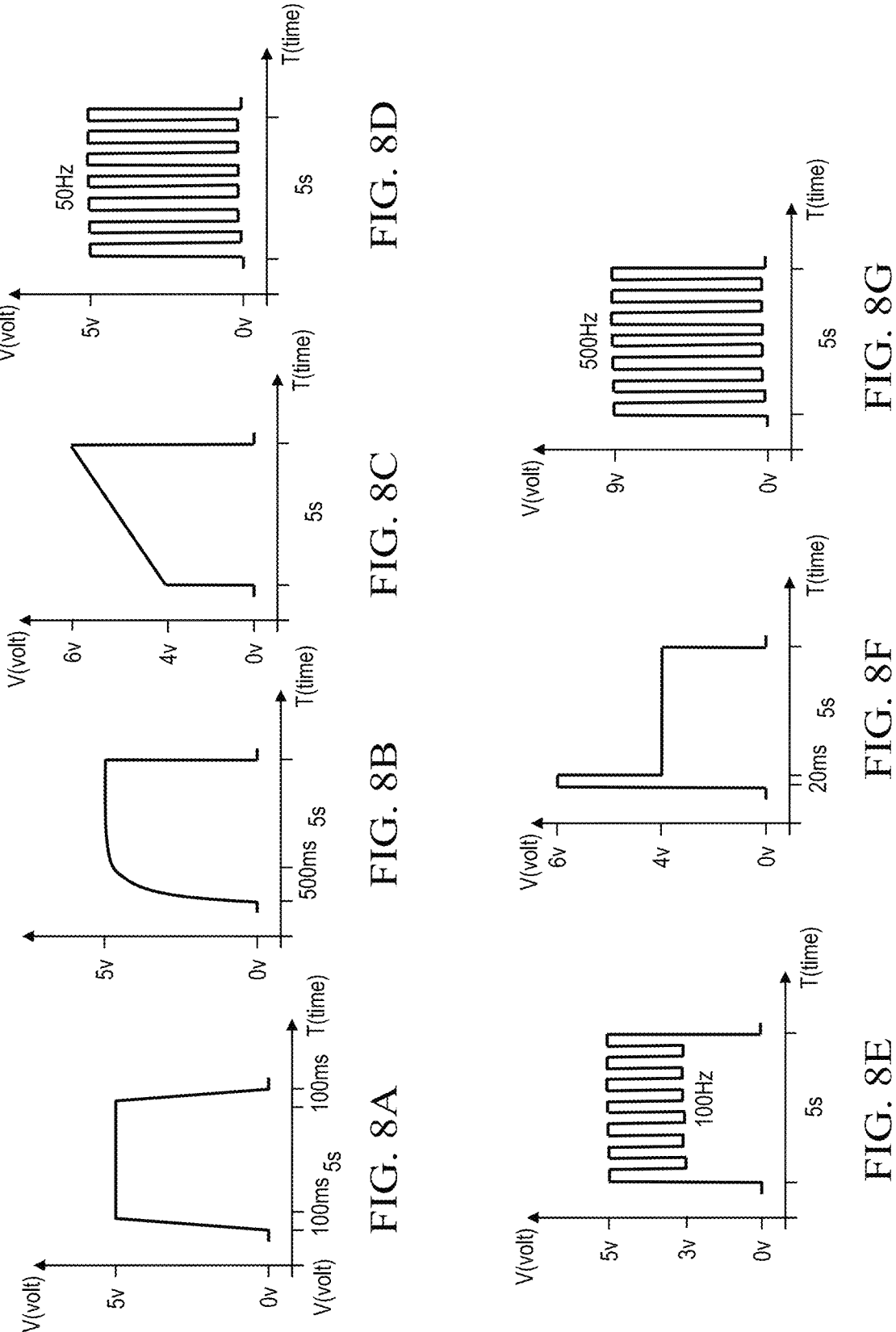
FIGS. 8A-8H show the input waveforms and results of various input waveforms on transfection efficiency, according to the embodiments provided herein.
Figure 8H:
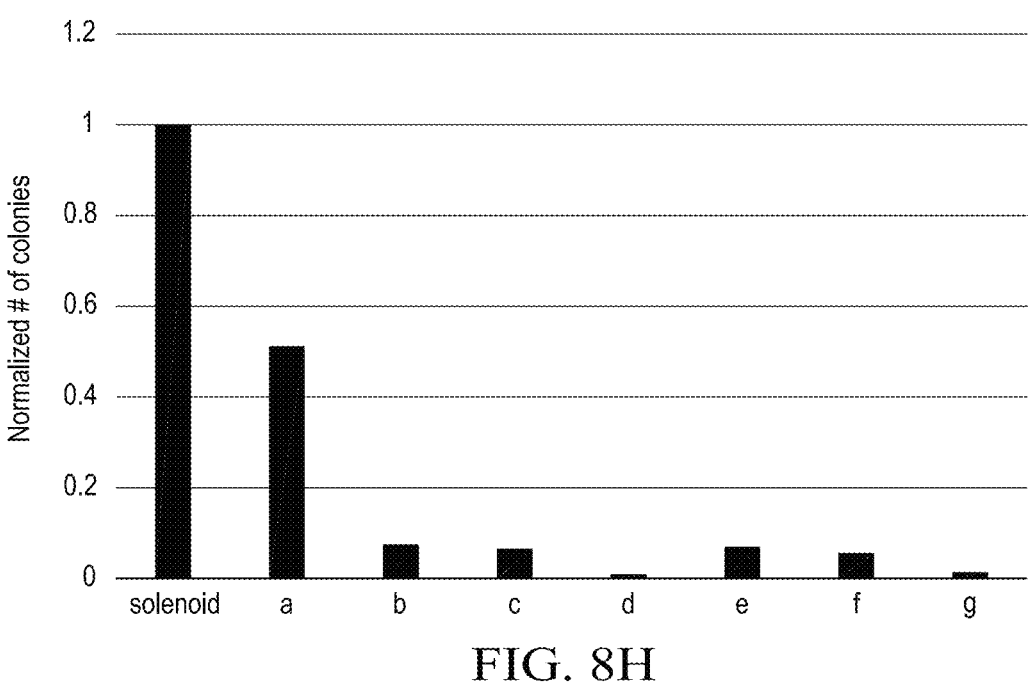

Similar to FIGS. 7A-7B, FIGS. 8A-8G show various waveforms applied to recipient cells using large solenoids, with the corresponding results shown in FIG. 8H. In each case under these conditions, the large voice coil underperformed the solenoid actuator, with the number of colonies decreasing with voltages of between 5-9V. Under these conditions, increasing force to improve ramp times was found to worsen delivery of mtDNA using large actuators.

In some embodiments, a simple step function was found to be optimal, e.g., for 143BTK rho (0) cells, which are cells depleted of mtDNA. However, it is contemplated that other cell types may show optimal efficiencies under voltage waveforms that are not simple step functions, e.g., such as those shown in FIGS. 8B-8G. In this regard, a voice coil actuator has the capability to generate custom waveforms, and using machine learning or other suitable techniques, optimal transfection parameters for particular types of cells may be determined.

Figure 9:
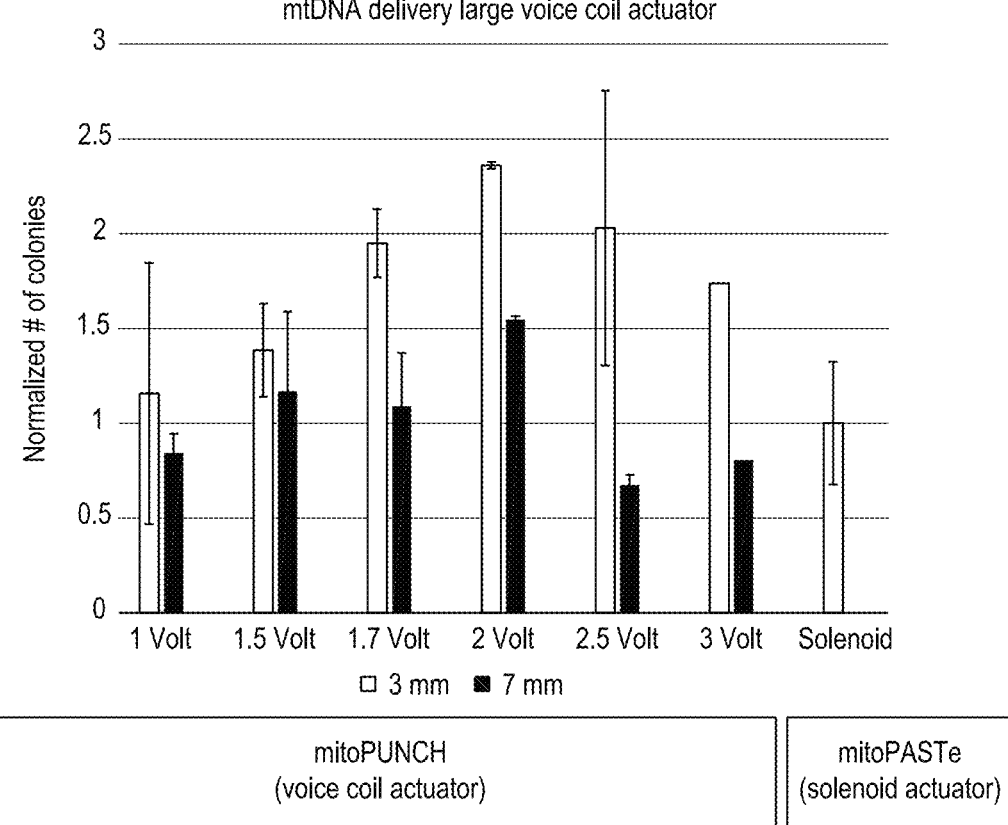
FIG. 9 shows results of varying the actuator stroke of a large voice coil actuator used for mtDNA transfection, according to the embodiments provided herein.

FIG. 9 reveals that delivery of mtDNA using a large actuator may be improved at lower voltages (e.g., 1-3V) and shorter travel distances of the plunger (3 mm). In this set of experiments, 143-BTK p (0) cells were transfected using a large voice coil actuator (GVCM-025-038-01) for mtDNA delivery, with superior results as compared to the solenoid.

These series of experiments, as shown in FIGS. 6-9 show that the rise time, voltage, and amount of force delivered by the voice coil actuator each impact efficiency of mtDNA transfection. In general, lower voltages and shorter travel distances (at higher frequencies) using configurable actuators outperformed solenoids for mtDNA delivery.

Example 2. Generation of mtDNA-Engineered Mesenchymal Stem Cells

Unless otherwise indicated, the following human cell lines were used: HEK293T expressing mitochondrial-targeted DsRed protein (Human Embryonic Kidney, pMitoDsRed, Clontech Laboratories) were generated as previously described (Miyata et al., 2014). BJ (Human Foreskin Fibroblast, CRL-2522), ADF (Adult Dermal Fibroblast, PCS-201-012), NDF (Neonatal Dermal Fibroblast, PCS-201-010). BJ, NDF, ADF, and HEK293T DsRed cells were cultured in "complete media" containing DMEM (Corning, Cat. #10013CV) supplemented with 10% Fetal Bovine Serum (FBS, Hyclone, Cat. #SH30088.03HI0), penicillin-streptomycin (Corning, Cat. #30-002-CI), GlutaMax (ThermoFisher, Cat. #35050-061), and non-essential amino acids (MEM NEAA, ThermoFisher, Cat. #11-140-050). BJ p0, NDF p0, and ADF p0 fibroblasts were cultured in complete media supplemented with 50 μg/ml uridine (Sigma, Cat. #U3003). IPSCs were cultured on matrigel (Corning, Cat. #356234) coated plates in mTeSRI media (StemCell Technologies, Cat. #85850) according to manufacturer's protocol. MSCs were cultured in defined, MesenCult-ACF media (StemCell Technologies, Cat. #05449) following manufacturer's protocol. Cells were tested frequently for *mycoplasma* using a universal *mycoplasma* detection kit (ATCC, Cat. #30-1012K).

Unless otherwise indicated, the following human tissues were used: LP351 (PBMCs from leukopak donor 351, Caucasian female, 42 year old, Donor ID: D326351 Hema- Care Corp), LP298 (PBMCs from leukopak donor 298, Hispanic/Latino male, 25 year old, Donor ID: D316153 HemaCare Corp)

FIGS. 10A-10E are illustrations showing an example process which was performed for generating patient-specific mtDNA-engineered mesenchymal stem cells, according to embodiments presented herein. FIG. 10A shows an illustration of fibroblasts comprising a mtDNA mutation/deletion. FIG. 10B shows an illustration of the fibroblasts depleted of the mutated endogenous mtDNA. FIG. 10C shows an illustration of the fibroblasts with corrected mtDNA after transfection of the corrected mtDNA, using the device of FIG. 1. FIG. 10D shows an illustration of the fibroblasts that have been reprogrammed to become iPSCs. FIG. 10E shows an illustration of iPSCs that have undergone differentiation into mesenchymal stem cells.

Figure 11A:
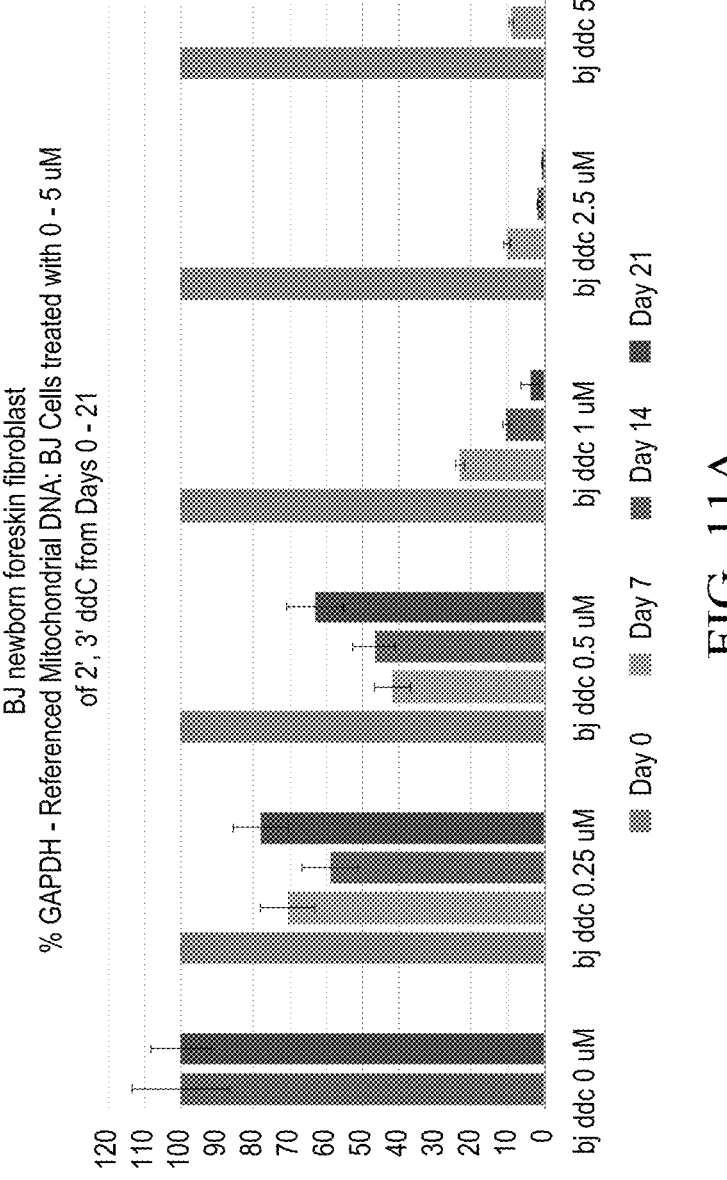
FIGS. 11A-11B show generation of mtDNA depleted primary fibroblast lines in BJ cells, according to the embodiments presented herein.
Figure 11B:
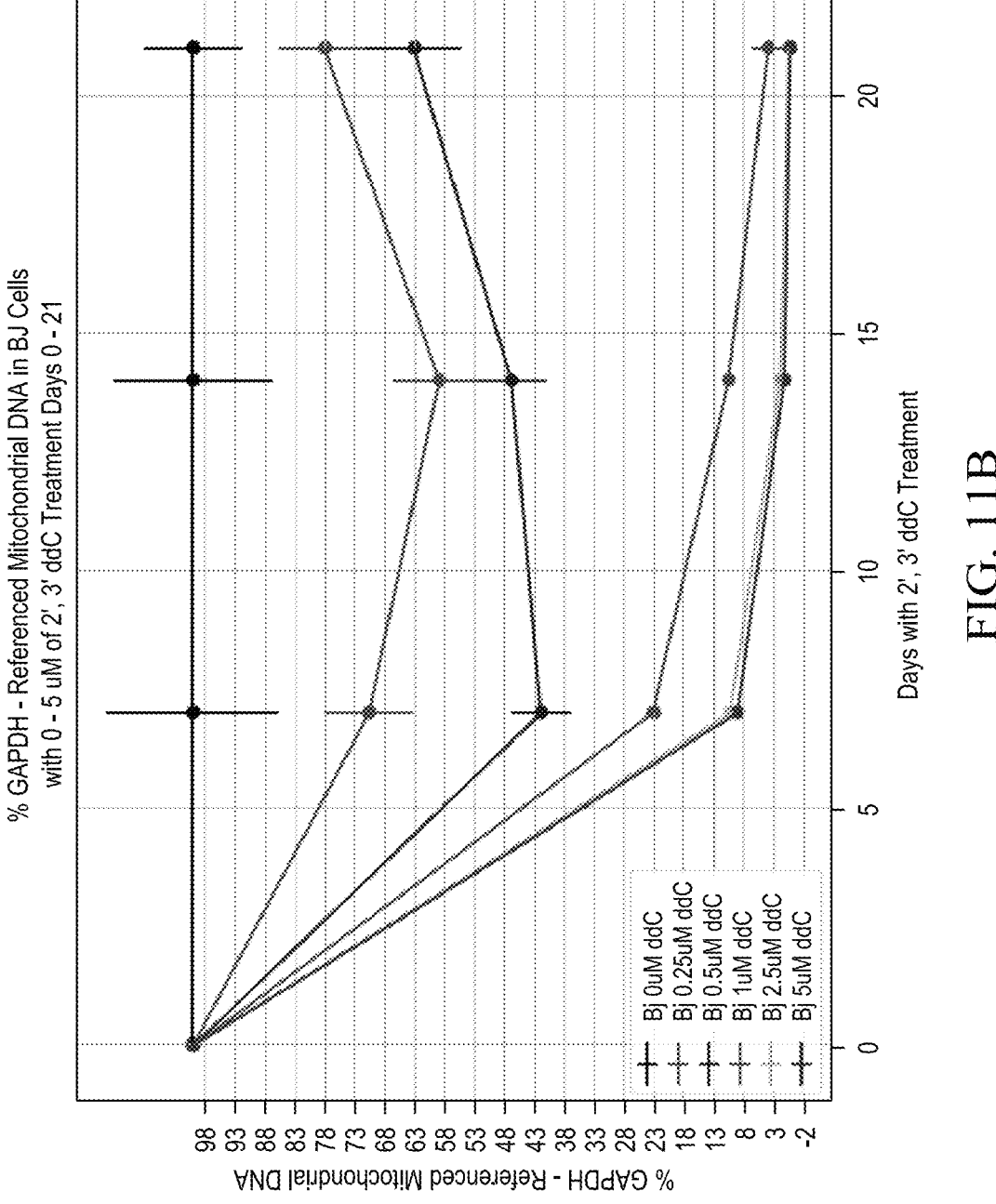
Figure 11C:
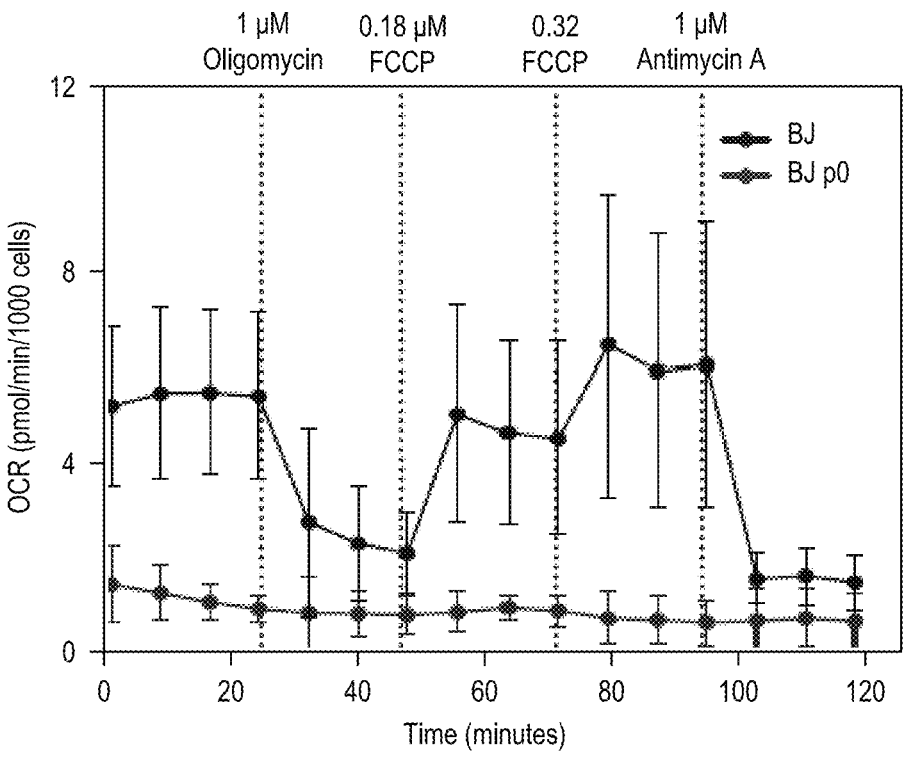
FIG. 11C shows quantification by a seahorse XF96 analyzer to quantify a measure of the respiratory capacity, the oxygen consumption rate (OCR), of ~20,000 15 BJ and BJ p0 fibroblasts. The dotted lines denote drug injection points. Data is presented as 16 mean±standard deviation from five technical replicates.

FIGS. 11A-11B show generation of mtDNA depleted primary fibroblast lines in BJ cells. FIG. 11A is a bar chart showing that a minimum concentration of 2.5 μM of 2',3' dideoxycytidine (ddC), a reverse transcriptase inhibitor, was required to deplete mtDNA to below 5% of the original level, three weeks from initiation of treatment. Concentrations of 2', 3' ddC of 2.5 μM or 5 μM showed that mtDNA levels were below 2% of initial untreated levels at two weeks, and were below 0.5% at three weeks from initiation of treatment. FIG. 11B is a line plot showing the information of FIG. 11A.

Figure 12A:
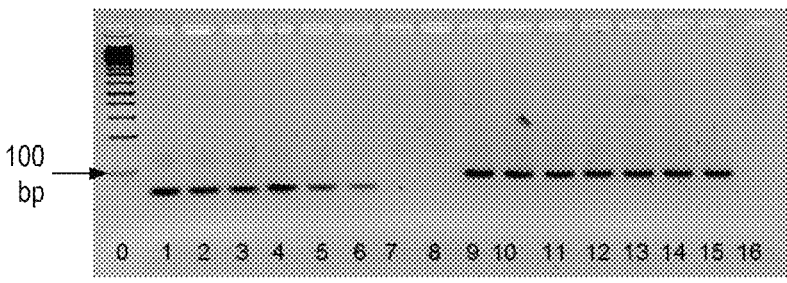
FIGS. 12A-12C show generation of mtDNA depleted human dermal fibroblasts cells, according to the embodiments presented herein.
Figures 12B, 12C:
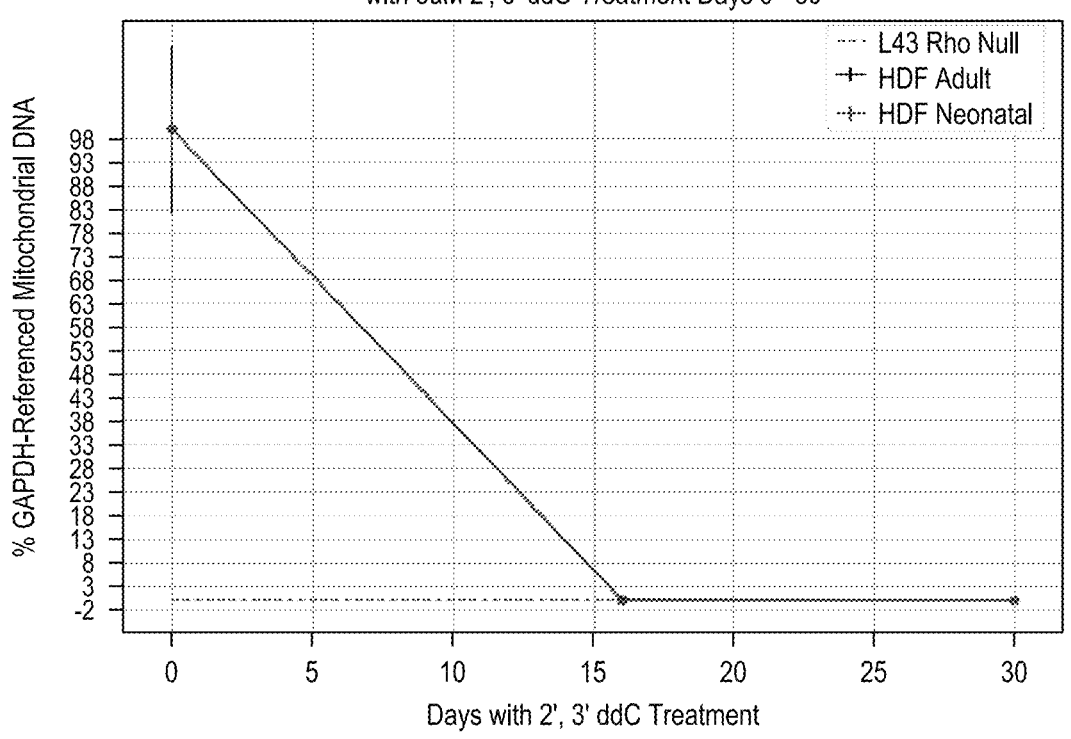

FIGS. 12A-12C show generation of mtDNA depleted human dermal fibroblasts cells. FIG. 12A shows results of various cells treated with 5 μM ddC at days one (1), sixteen (16) and thirty (30). 143 Rho Null (lacking mtDNA) and a control are also shown. Adult and neonatal human dermal fibroblast (HDF) cells showed mtDNA depletion after sixteen days of 2', 3' ddC treatment at 5 μM, according to embodiments presented herein. GAPDH expression, used as a reference gene, was also shown in adult and neonatal human dermal fibroblast (HDF) cells. FIG. 12B is a table showing depletion of mtDNA in HDF adult and HDF neonatal cells at days sixteen and thirty. FIG. 12C is a line plot showing the data of FIG. 12B.

Figures 13A, 13B, 13C:
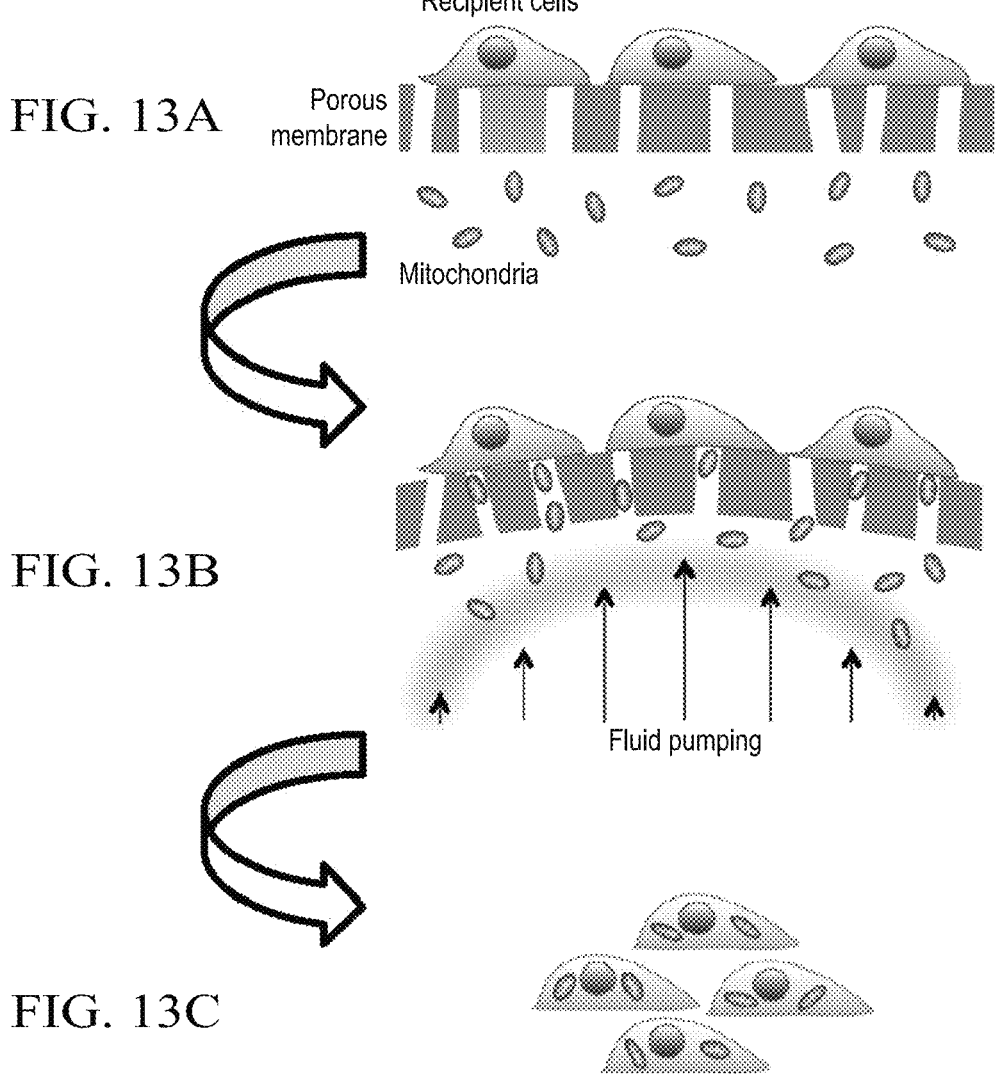
Figures 13D, 14A:
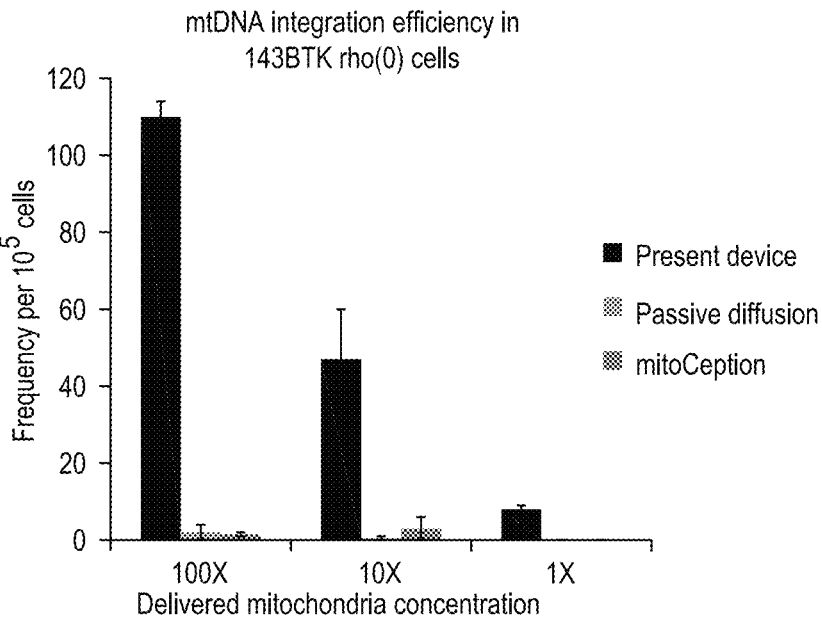

FIGS. 13A-13D show high-efficiency mtDNA integration by the devices provided herein. In FIG. 13A, recipient cells depleted of mtDNA may be placed on a porous membrane. Mitochondria (e.g., corrected mtDNA) to be transfected into the recipient cells are provided within a deformable fluid reservoir, such that the corrected mtDNA is in fluid communication with the recipient cells. FIG. 13B shows a deformable membrane that deforms in response to applied pressure from the pump/voice coil actuator provided herein, to place the macrostructures for transfection proximal to the recipient cells. FIG. 13C shows the transfected cells including cells transfected with mtDNA, according to embodiments presented herein. FIG. 13D shows a bar graph of mtDNA integration efficiency into a mtDNA deficient strain (143BTK rho (0) cells), according to multiple techniques at various concentrations. Passive diffusion includes co-incubation of cells with mitochondria, which relies on passive endocytic uptake. mitoCeption (see, https://www.ncbi.nlm-.nih.gov/pubmed/28287607) involves adding isolated mitochondria to the recipient cell culture followed by a centrifugation step to direct the mitochondrion towards recipient cells. As shown by the chart, the novel devices provided herein transfect mtDNA at a much higher frequency and clearly outperform the other techniques.

Figure 14B:
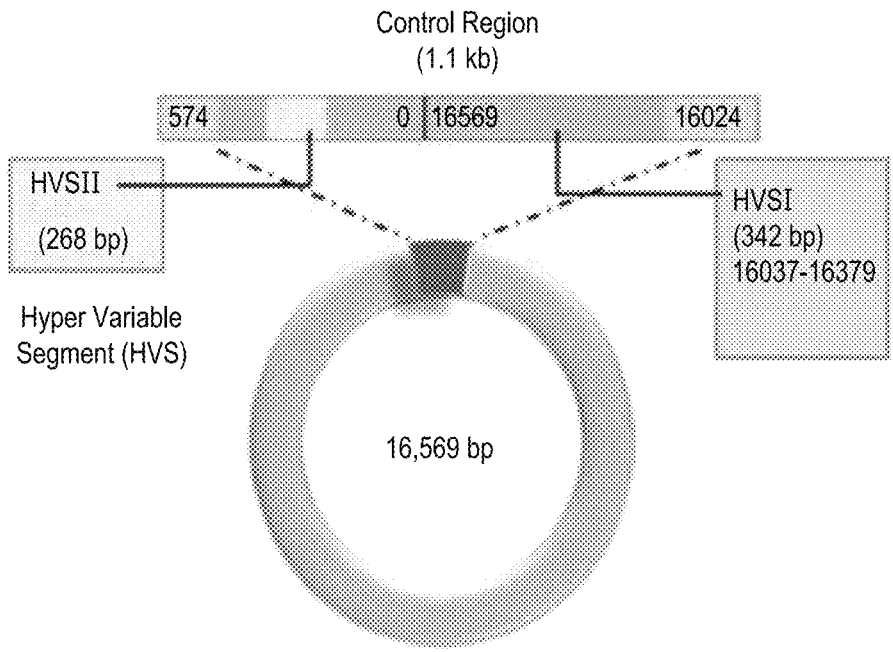
Figures 14C, 14D:
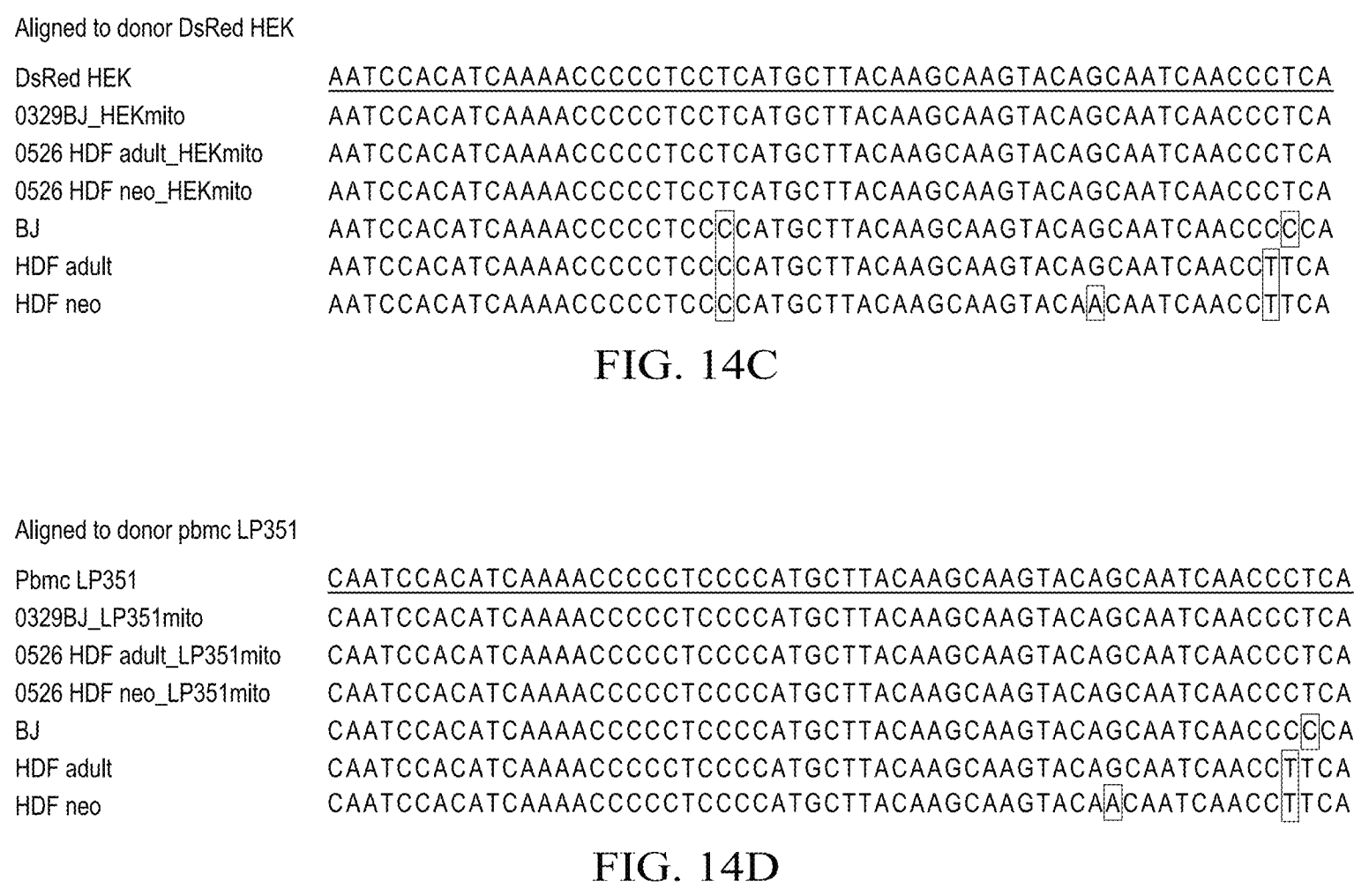
Figures 14G, 14H, 14I, 14J, 14K, 14L:
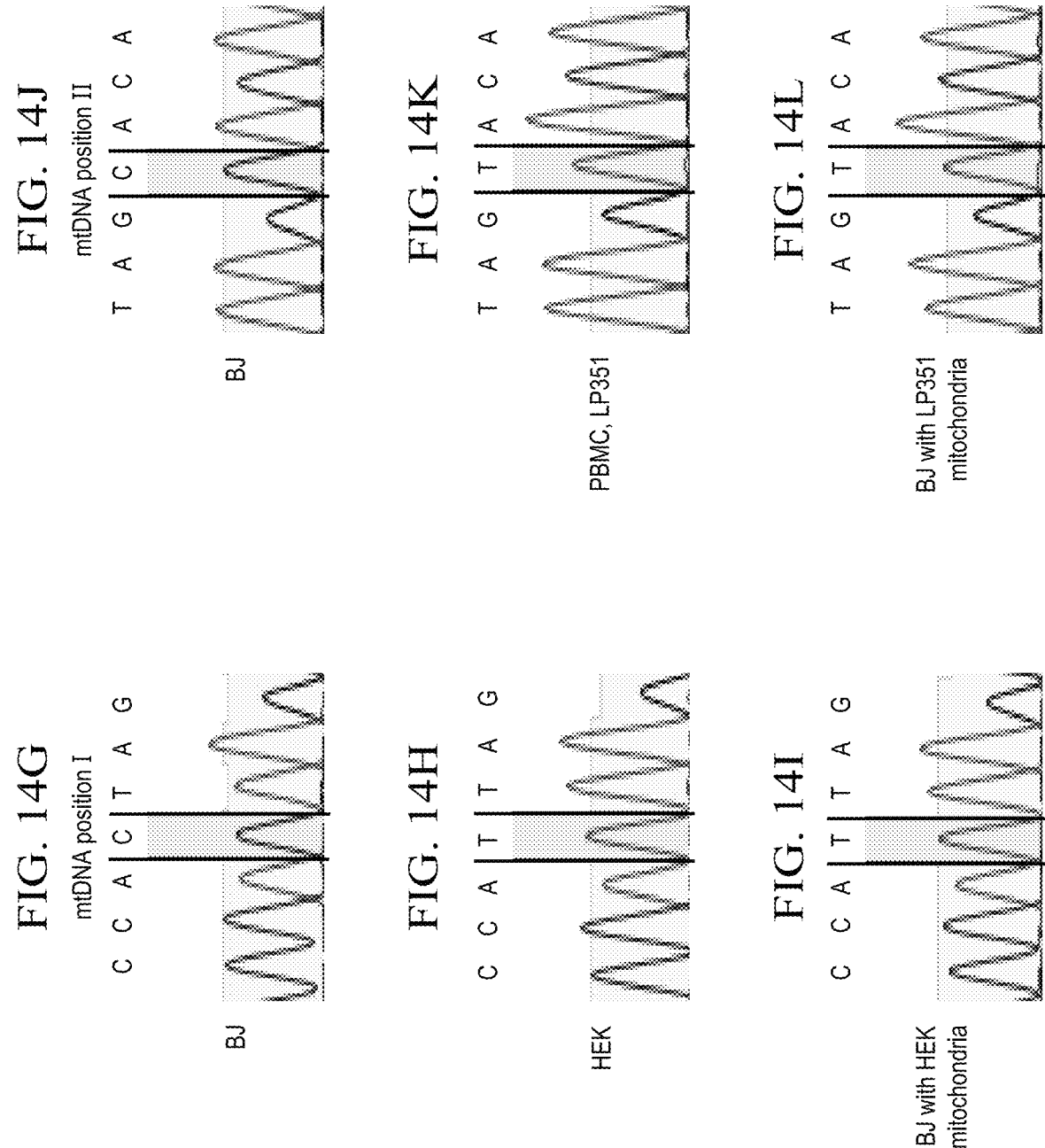

FIGS. 14A-14L shows various recipient cells that have been transformed with mtDNA. Sequences are shown illustrating that the endogenous mtDNA has been replaced with the donor mtDNA (e.g., the corrected mtDNA). FIG. 14A is a table showing various recipient cells (BJ, HDF neonatal, HDF adult) along with donor mtDNA (HEK mtDNA, PBMC LP351, and PBMC LP298). FIG. 14B is an illustration of mtDNA, showing hypervariable regions (HVSI and HVSII), which may be used to track the lineage of mtDNA strains. FIG. 14C shows wild type strains (BJ (SEQ ID NO: 11), HDF adult (SEQ ID NO: 12), HDF neonatal (SEQ ID NO: 13)) without transfected mtDNA (DsRed HEK (SEQ ID NO: 7) and transformed strains (0329BJ_HEKmito (SEQ ID NO: 8), 0526 HDF adult HEKmito (SEQ ID NO: 9), 0526 HDF neonatal HEKmito (SEQ ID NO: 10)) with transfected mtDNA from HEK mtDNA. As shown by the sequences, the transformed cells have acquired the sequence of the transfected mtDNA, and do not show the sequences of endogenous mtDNA. Similarly, FIGS. 14D and 14E show wild type strains (BJ (SEQ ID NOs: 18 and 24), HDF adult (SEQ ID NOs: 19 and 25), HDF neonatal (SEQ ID NOs: 20 and 26)) without transfected mtDNA (SEQ ID NOs: 16, 17, and 23) and transformed strains with transfected mtDNA from PBMC LP351 (SEQ ID NOs: 14 and 21) or PBMCLP298 (SEQ ID NOs: 15 and 22), respectfully. As shown by the corresponding sequences, the transformed cells have acquired the sequence of the transfected mtDNA, and do not show the endogenous mtDNA. FIGS. 14F-14L show additional transformation results, wherein BJ cells were transformed with HEK mtDNA or LP351 mtDNA. A sequence alignment showing that endogenous mtDNA has been replaced with transfected mtDNA (SEQ ID NOs: 27-31) is shown in FIG. 14F, with corresponding sequence runs shown in FIGS. 14G-14L. As shown in these figures, the endogenous mtDNA is not detected.

Figure 15A:
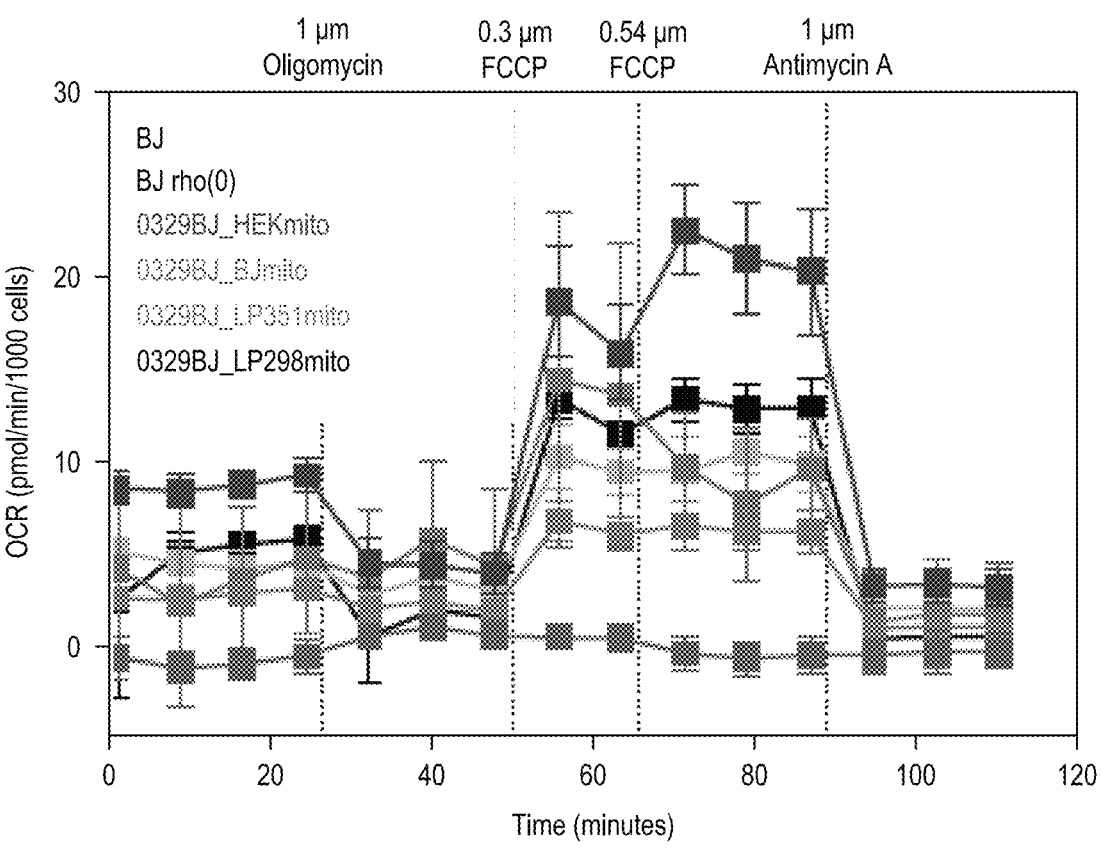
FIGS. 15A-15B show mitochondrial respiration in various transfected fibroblast lines, according to the embodiments presented herein.
Figure 15B:
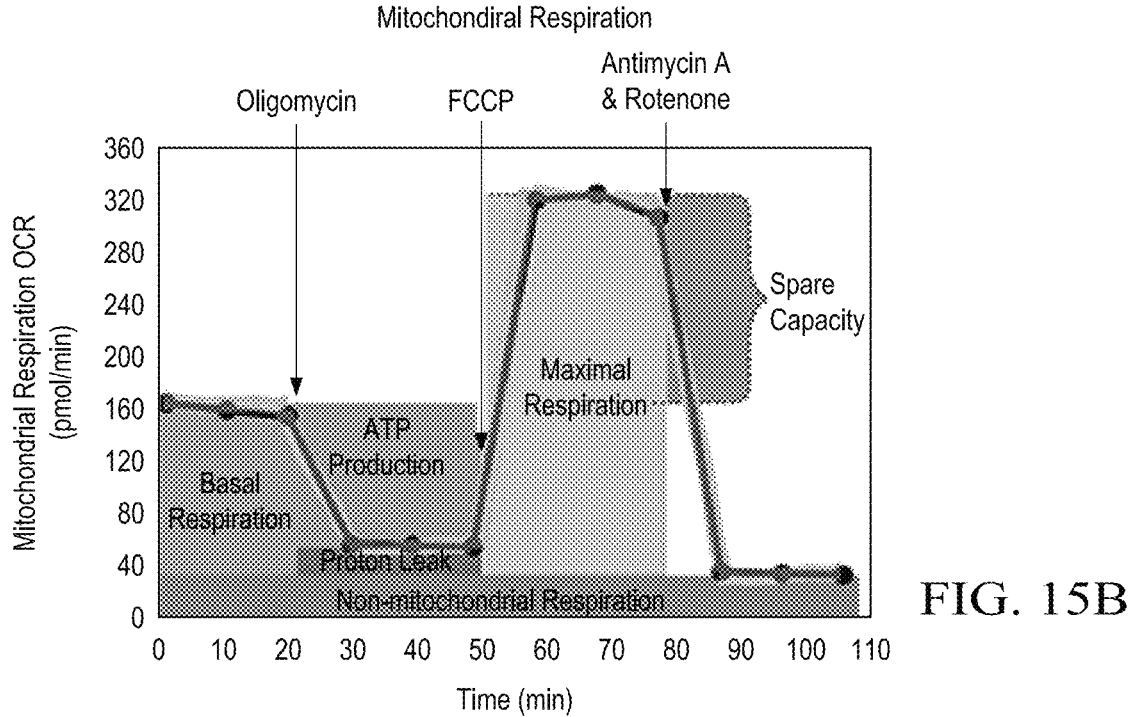

FIGS. 15A-15B show aspects of mitochondrial respiration in transformed fibroblast lines. The transformed cells (0329BJ_HEKmito, 0329BJ_BJmito, 0329BJ_LP351mito, 0329BJ_LP298mito) showed partial restoration of respiratory capacity as compared to wt strain BJ. Strains may be cultured to be the same as or similar to wt strains.

Figures 16A, 16B:
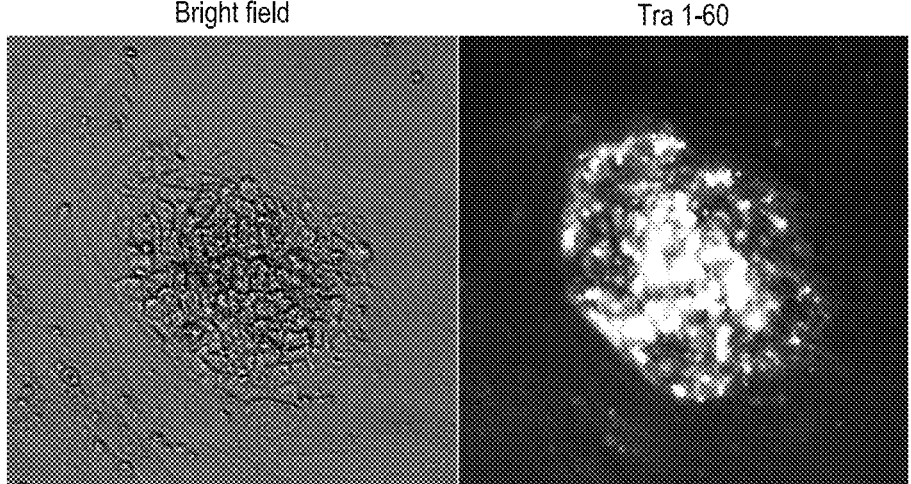
Figure 16E:
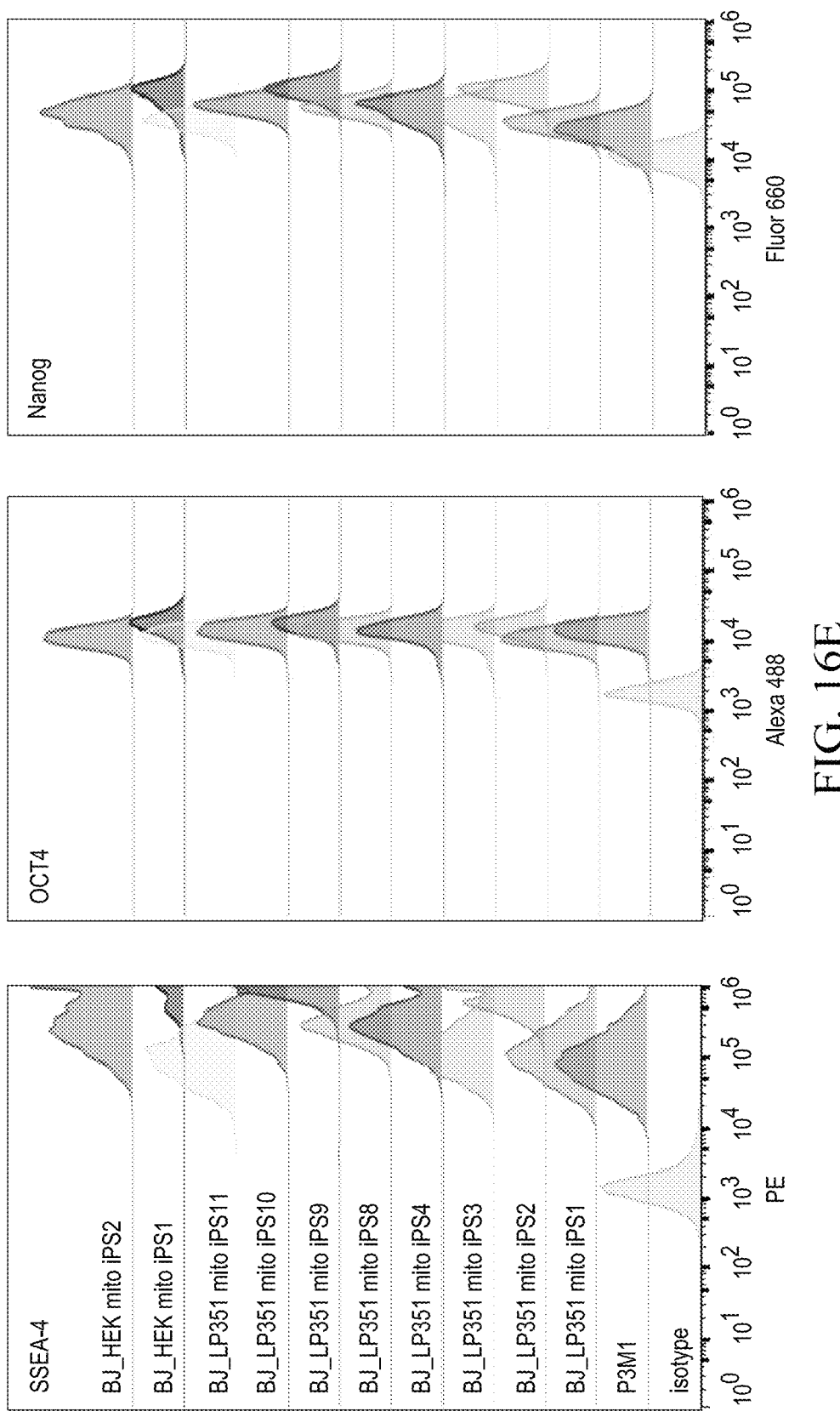

FIGS. 16A-16E show aspects of reprogramming fibroblasts to induced pluripotent stem cells (iPSCs). FIG. 16A shows a table summarizing two trials, in which various strains were reprogrammed to iPSCs. FIG. 16B shows a bright field and a fluorescent image of a fibroblast after reprogramming. Reprogramming may be achieved by any suitable technique known in the art, e.g., by utilizing reprogramming mRNAs including but not limited to: OCT4, SOX2, KLF4, cMYC, NANOG, and LIN28. In some aspects, the reprogramming rRNAs may be combined with immune evasion mRNAs including but not limited to: E3, K3, and B18R as well as miRNAs. FIGS. 16C-16E show sequences confirming the presence of donor mtDNA in the reprogrammed fibroblasts. FIG. 16C shows that the endogenous mtDNA in BJ-derived iPS strain (BJ iPS P3M1 (SEQ ID NO: 33)) was successfully replaced with donor HEK mtDNA (SEQ ID NO: 32) during depletion and transfection, and was retained during reprogramming (032917BJ_HEKmito_iPS 1-5 (SEQ ID NOs: 34-37)). FIG. 16D similarly shows that the endogenous mtDNA in BJ-derived iPS strain (BJ iPS P3M1 (SEQ ID NO: 39)) was successfully replaced with another donor mtDNA (LP351mito) (SEQ ID NO: 38) during depletion and transfection, and was retained during reprogramming (032917BJ_LP351mito_iPS 1-4, 8-11 (SEQ ID NOs: 40-47)). FIG. 16E shows expression of proteins SSEA-4, OCT4 and NANOG, proteins known to be associated with undifferentiated stem cells, in the various reprogrammed BJ cells comprising donor mtDNA.

Figure 17:
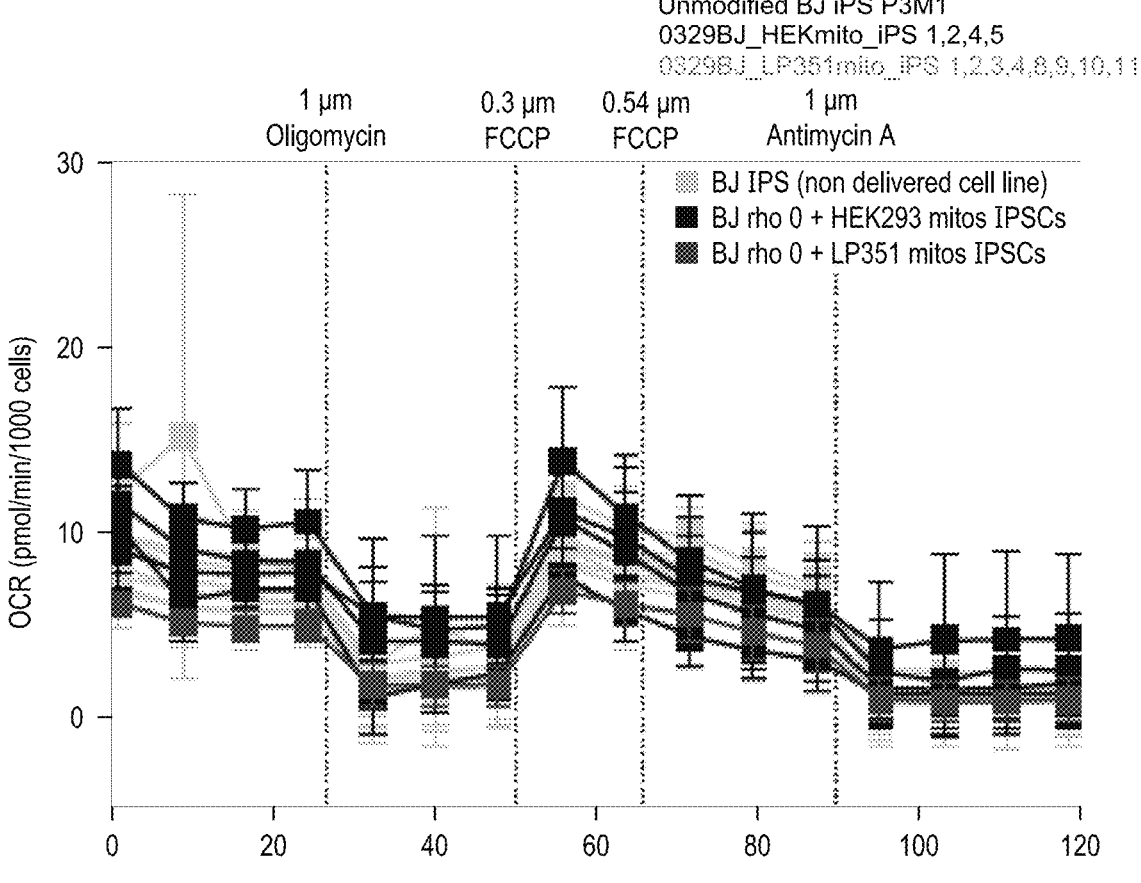
FIG. 17 shows a graph of mitochondrial respiration in iPS cell lines derived from reprogrammed fibroblasts, according to the embodiments presented herein.

FIG. 17 shows a graph of mitochondrial respiration in iPS cell lines derived from reprogrammed fibroblasts. The reprogrammed cells comprising donor mtDNA have improved mitochondrial respiration as compared to the unmodified BJ-derived iPS strain.

Figures 18A, 18B:
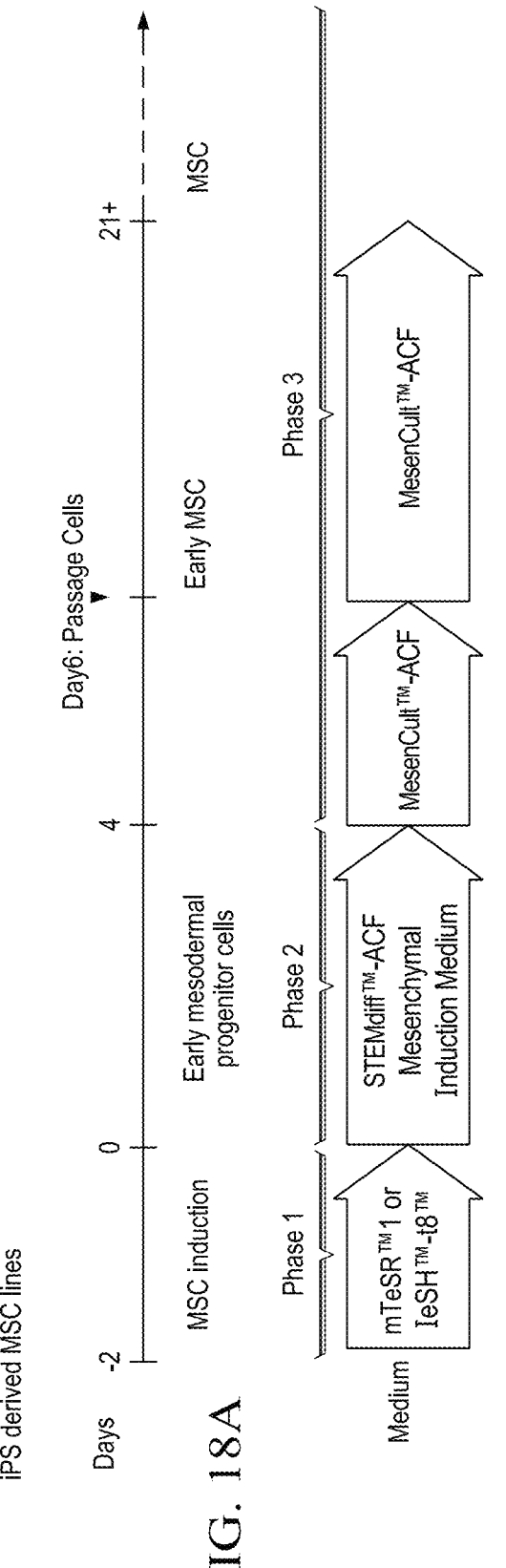
Figure 18C:
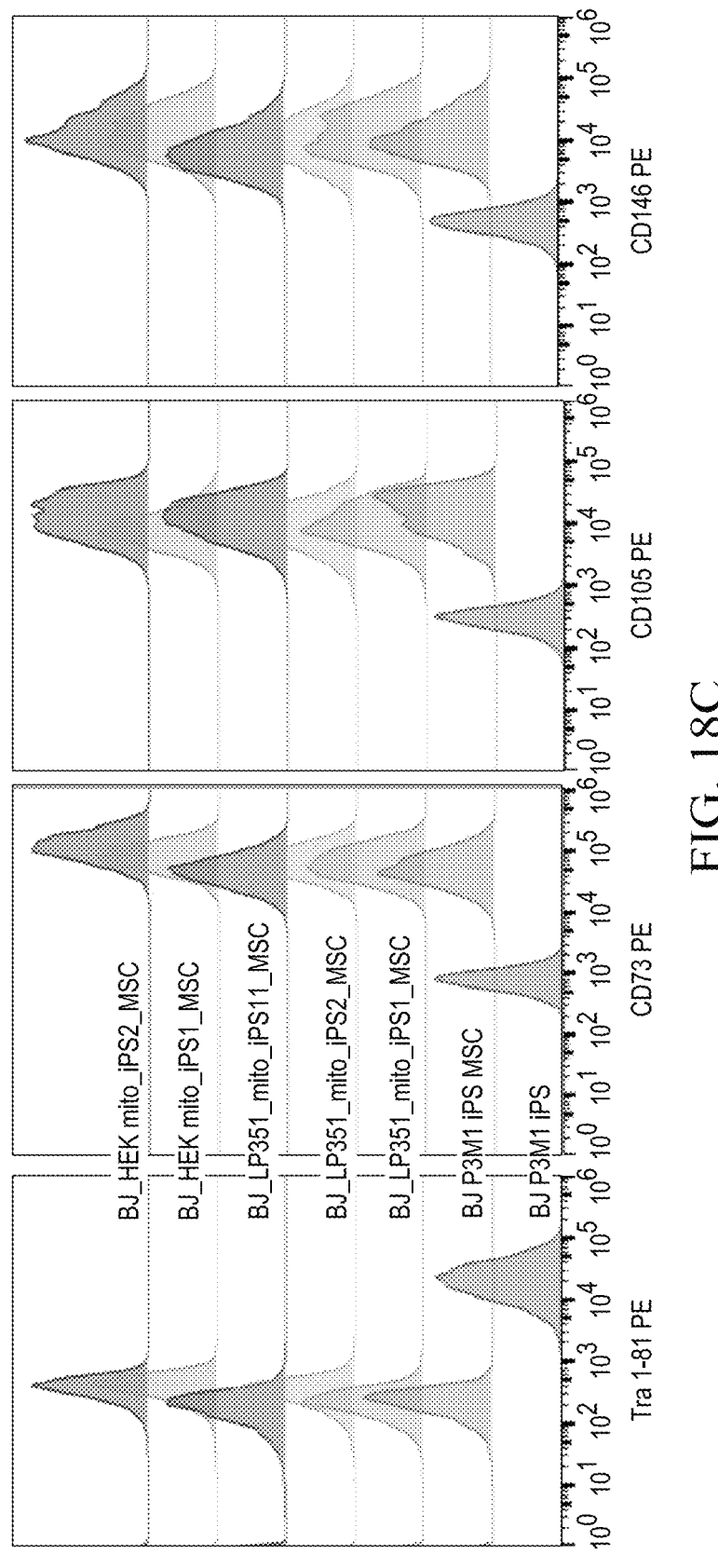
Figures 18E, 18F:
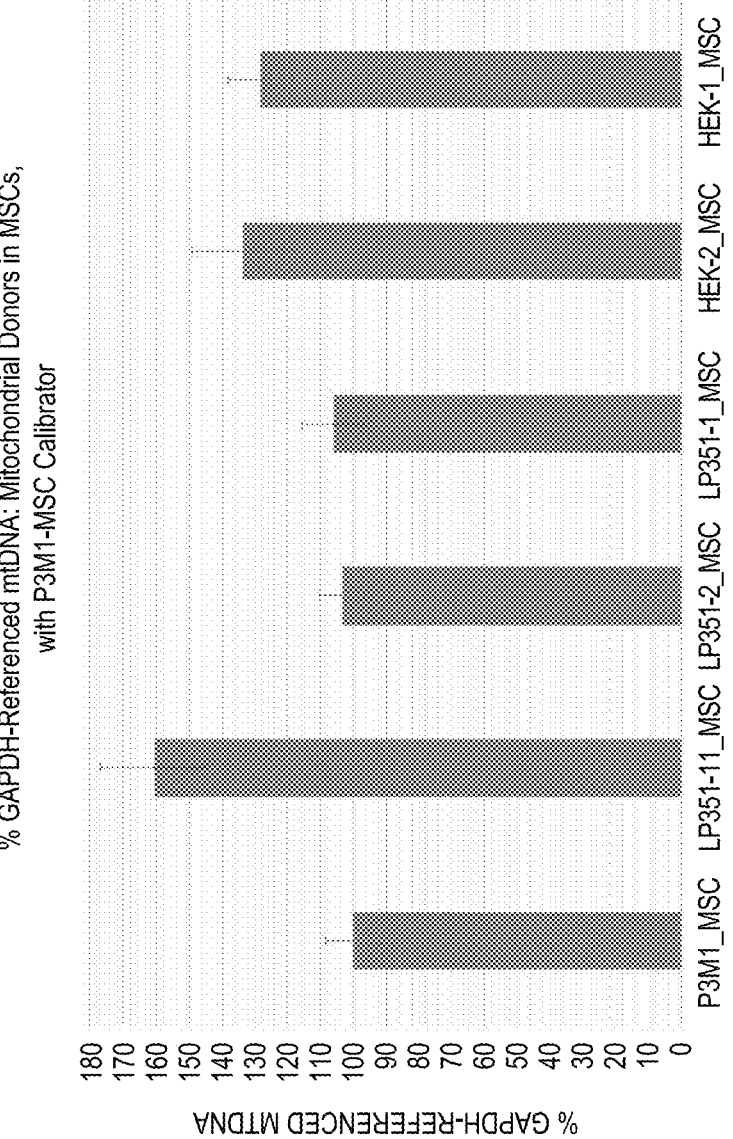

FIGS. 18A-18F show aspects of differentiating iPSCs into mesenchymal cells (MSC). FIG. 18A shows a flowchart summarizing the process for differentiating iPSCs into MSCs, including passaging for about three or more weeks. FIG. 18B is a table showing various strains that were differentiated into MSC cells. Differentiation may be achieved by any suitable technique known in the art. FIG. 18C shows expression of various proteins including CD73, CD105, and CD146, which are proteins associated with mesenchymal stem cells, in various differentiated BJ-derived iPS cells, some of which comprise donor mtDNA from HEK or LP351 strains. FIG. 18D shows that the endogenous mtDNA in BJ-derived iPS and differentiated cells (BJ (SEQ ID NOs: 53 and 58) or BJ iPS P3M1 (SEQ ID NOs: 52 and 57)) was successfully replaced with donor HEK mtDNA (SEQ ID NO: 54) or LP351mtDNA (SEQ ID NO: 48) during depletion and transfection, and was retained during reprogramming and differentiation (032917BJ_HEKmito_iPS 1-2 MSC (SEQ ID NOs: 55-56) and 032917BJ_LP351mito_iPS 1-2,11 MSC (SEQ ID NOs: 49-51)). FIGS. 18E and 18F show a graph and table, respectfully, illustrating % GAPDH-referenced mtDNA (mitochondrial donors in MSCs, with P3M1-MSC as a calibrator).

Example 3. mtDNA Depletion and qPCR Verification

A 1000× stock of 2',3'-dideoxycytidine (ddC, Sigma, Cat. #D5782) was prepared in water. BJ, ADF, and NDF cells cultured in complete media with 50 g/ml uridine were added ddC to an appropriate final concentration. Cells were passaged every 3-4 d and fresh ddC was added over the course of 3 weeks. After ddC treatment, total DNA was extracted (Qiagen, Cat. #69504) and mtDNA quantified using SYBR Select Master Mix for CFX (Life Technologies, Cat. #4472942). mtDNA-encoded ND1 was probed with the following primers: forward: CCCTAAAACCCGCCA-CATCT (SEQ ID NO: 1); reverse: CGATGGT-GAGAGCTAAGGTC (SEQ ID NO: 2). mtDNA levels were normalized to nuclear-encoded GAPDH using the following primers: forward: TGCACCACCAACTGCTTAGC (SEQ ID NO: 3); reverse: GGCATGGACTGTGGTCATGAG (SEQ ID NO: 4). qPCR was run on a BioRad CFX Thermal Cycler using the following protocol: 1) 50° C. for 2 min, 2) 95° C. for 2 min, 3) 40 cycles-95° C. for 10 s and 60° C. for 45 s. Samples were compared by calculating ΔΔCT and fold differences.

Example 4. Mitochondrial Isolation and Delivery into 00 Fibroblasts

Mitochondria were harvested from DsRed HEK293T, LP351 PBMC, or LP298 PBMC using a Qproteome Mitochondria Isolation Kit (Qiagen, Cat. #37612) following manufacturer's protocol. Mitochondrial pellets were resuspended in PBS at a concentration ~ 1 mg total protein/mL. Mitochondrial suspensions were delivered into p0 fibroblast cells using the device described herein. Transferred fibroblasts were cultured in complete media with 50 μg/mL uridine for 4 days following mitochondria delivery. On day 5, cells were shifted to uridine-free complete media prepared with 10% dialyzed FBS (Life Technologies, Cat. #26400-044). On day 8, cells were shifted to glucose-free, galactose-containing medium (DMEM without glucose (Gibco, Cat. #11966025) supplemented with 10% dialyzed FBS and 4.5 g/l galactose). Colonies emerged ~10 d post-delivery and cells were shifted back to uridine-free medium before colonies were counted by microscopy or isolated using cloning rings.

Example 5. iPSC Reprogramming

Fibroblast lines were reprogrammed to iPSCs using StemRNA-NM Reprogramming kit (Stemgent, Cat. #00-0076) following manufacturer's protocol. Briefly, fibroblasts were plated on a matrigel (Corning, Cat. #356234) coated 6-well plate at $2\times10^5$ cells/well on Day 0. Daily transfections of non-modified (NM)-RNA reprogramming cocktail were carried out from days 1~4 using Lipofectamine RNAiMAX (ThermoFisher, Cat. #13778100. On days $10^{-12}$, iPSC colonies were identified by staining with Tra 1-60 antibody (Stemgent, Cat. #09-0068). Tra 1-60+iPSC colonies were picked and re-plated on matrigel coated 12-well plates and maintained in mTeSR 1 (Stemcell Technologies, 85850).

Example 6. MSC Differentiation

MSC lines were generated from iPSCs using STEMdiff Mesenchymal Progenitor Kit (Stemcell Technologies, Cat. #05240) following manufacturer's protocol.

Example 7. Human mtDNA D-Loop Sequencing

Total DNA was extracted from $1\times10^6$ cells using the Qiagen DNasy Blood and Tissue kit. PCR was performed using Phusion high-fidelity PCR master mix with HF buffer (NEB, Cat. #M0531S) and the following primers: forward-TTCCAAGGACAAATCAGAGAAAAAGT (SEQ ID NO: 5), reverse-AGCCCGTCTAAACATTTTCAGTGTA (SEQ ID NO: 6). PCR was run on an Eppendorf vapo.protect thermal cycler at 1) 98° C. for 2 min, 2) 30 cycles –98° C. for 15 s, 58° C. for 30 s, 72° C. for 30 s, and 3) 72° C. for 5 min. PCR products were run on a 0.8-1% agarose TAE gel, extracted with the QIAGEN QIAQuick Gel Extraction kit (Qiagen, Cat. #28704), and Sanger sequenced using the same PCR primers.

Example 8. iPSC Flow Cytometry iPSCs were harvested by 15 min room temperature incubation with Gentle Cell Dissociation Reagent (Stem Cell Technologies, Cat. #07174). Cells were centrifuged at 300×g for 5 minutes, washed in 1 ml DPBS+10% FBS, and resuspended in 100 μl BD Perm/Fix Buffer (BD Bioscience). Cells were incubated at 4 degrees for 15 minutes and washed twice in DPBS+10% FBS. Following the second wash, cells were incubated in 50 μl DPBS+10% FBS containing conjugated antibodies (OCT3/4 AlexaFluor488 BD Bioscence 561628 1:10, SOX2 V450 BD Bioscience 561610 1:10, Mouse IgG1 κ Isotype Control AlexaFluor488 BD Biosciences 557782 1:10, Mouse IgG1, K Isotype Control V450 BD Bioscience 560373 1:10, CD44 PE BD Bioscience 562245 1:21)) for 30 minutes and then washed twice in DPBS+10% FBS. Data was acquired on LSRFortessa (BD Bioscience), and analyzed using FlowJo software (FlowJo, LLC).

Example 9. MSC Flow Cytometry

MSCs were harvested by 5 min 37° C. incubation with Accutase (BD Biosciences). Cells were centrifuged at 300 rcf for 5 minutes, washed in 1 ml DPBS+10% FBS, and resuspended in DPBS+10% FBS at 5×10^6 cells/ml. Cells were incubated in 100 μl DPBS +10% FBS for 30 minutes at 4 degrees with the appropriate antibodies indicated in the Human MSC Analysis Kit (BD Biosciences, Cat #562245) for 30 minutes and then washed twice in DPBS+10% FBS. Data was acquired on LSRFortessa (BD Bioscience), and analyzed using FlowJo software (FlowJo, LLC).

Example 10. Mitochondrial Oxygen Consumption Measurements

Oxygen consumption rates (OCR) were quantified using a Seahorse XF96 Extracellular Flux Analyzer (Agilent). For fibroblasts or MSCs, 15,000-20,000 cells per well were seeded onto a V3 96-well plate (Agilent, Cat. #101085-004) and cultured overnight before analysis. iPSCs were treated similarly but plated on matrigel-coated V3 plates. A mitochondrial stress test quantified the OCR at basal respiration and after the sequential addition of mitochondrial inhibitors oligomycin, carbonyl cyanide-p-trifluoromethoxyphenylhydrazone (FCCP), and rotenone.

Example 11. Fluorescence Microscopy iPSCs were cultured on matrigel-coated 6 well plates and fixed with 4% paraformaldehyde for 10 min. Blocking was done for 1 h in PBS with 5% FBS and 0.3% Triton X-100. Cells were stained with SSEA4 (eBioscience, Cat. #12-8843-42), OCT4 (eBioscience, Cat. #53-5841-82), and Hoechst 33342 (ThermoFisher, Cat. #R37605) overnight at 4° C. in blocking buffer. Phase contrast and fluorescence images were taken with a Zeiss Axio Observer Z1 microscope and Hamamatsu EM CCD camera (Cat. #C9100-02).

Example 12. MSC Immunosuppression Assay

MSC inhibition of T cell proliferation was performed similarly to (Hsu et al., J Vis Exp (2015) e53265). Briefly, MSCs were plated in a 12 well plate the day before assay. PBMCs were isolated by Ficoll gradient from a healthy leukopak donor. CD4+ T cells were isolated from PBMCs using the CD4+ T cell isolation kit (Miltenyi Biotec, Cat. #130-096-533) and labeled with CFDA SE (ThermoFisher, Cat. #V12883). Labeled CD4+ T cells were stimulated with Dynabeads Human T-activator CD3/CD28 (Thermo Fisher, Cat. #11131D) at a ratio of one bead per T cell. T cells were added into MSC culture at the following T cell: MSC ratios: 1:2, 1:1, 5:1, and 10:1. After 5 days of co-culture, T cell proliferation was measured using CFSE signature by flow cytometry.

Example 13. Trilineage Differentiation

Adipocytes, osteocytes, and chondrocytes were generated from MSCs. For adipogenic lineage differentiation, MSCs between passages 3-4 were plated on 6-well plates with MesenCult-ACF Basal Medium (Stem Cell Technologies, Cat. #05449) at 4-5×10^5 cells per well. Differentiation was performed using the MesenCult Adipogenic Differentiation Kit (Stem Cell Technologies, Cat. #05412) according to manufacturer's protocol. Media changes were conducted every 3-4 days until day 13. For osteogenic lineage differentiation, MSCs between passages 3-4 were plated on a 6-well plate with MesenCult-ACF Basal Medium (Stem Cell Technologies) at 3-4×10^4 cells per well. Differentiation was performed using the MesenCult Osteogenic Differentiation medium (Stem Cell Technologies, Cat. #05465) according to manufacturer's protocol. Medium changes were conducted every 3-4 days until day 13. For 3D pellet chondrogenic differentiation, MSCs were first released from T25 flasks using ACF Enzymatic Dissociation/Inhibition Solutions (Stem Cell Technologies, Cat. #05426) and collected in polypropylene tubes at $2.5-3\times10^6$ cells per tube with MesenCult-ACF Chondrogenic Differentiation Medium (Stem Cell Technologies, Cat. #05455) according to manufacturer's protocol. Medium changes were conducted every 3-4 days until day 13.

Example 14. UPHLC-MS-based Metabolomics Processing

Ultra high-performance liquid chromatography mass spectrometry (UHLPC-MS) experiments were performed as described previously (Xiao et al., Cell (2018) 173, 470-484 e418) to quantify metabolites from approximately $\sim7\times10^5$ cells. Briefly, cells were rinsed with cold 150 mM ammonium acetate (pH 7.3), followed by addition of ice-cold 80% methanol. Cells were detached with scrapers, transferred into microcentrifuge tubes, and 1 nmol D/L-norvaline added. After vortexing, the suspension was centrifuged at 4° C. at maximum speed. The supernatant was transferred into a glass vial, metabolites dried down under vacuum using an EZ-2Elite evaporator at 30° C., and resuspended in 70% acetonitrile. To normalize samples, pellets were resuspended in 58 mM Tris-HCl, pH 6.8, 5% glycerol, and 17 mg/ml sodium dodecyl sulfate and quantified by BCA protein assay (Thermo Fisher, Cat. #23225).

Metabolites were separated on a Luna $NH_2$ (150 mm×2 mm, Phenomenex) column using 5 mM $NH_4AcO$ (pH 9.9) (buffer A), acetonitrile (buffer B), and the following gradient: initially at 15% buffer B, 18 min gradient to 90% buffer B, 9 min isocratic at 90% buffer B. 7 min isocratic at 15% buffer B. Samples were analyzed with an UltiMate 3000RSLC (Thermo Scientific) coupled to a Q Exactive mass spectrometer (Thermo Scientific) run with polarity switching (+3.50 kV/-3.50 kV) in full scan mode and m/z range of 65-975. Metabolites were quantified with TraceFinder 3.3 using accurate mass measurements ($\leq3$ ppm) and retention times of pure standards.

Example 15. RNA Extraction

Fibroblasts, iPSCs, and MSCs were grown in biological triplicates and technical duplicates to 70-80% confluence and purified using the RNeasy Mini Kit (Qiagen, Cat. #74104) and RNase-free DNase (Qiagen, Cat. #79254) following manufacturer's protocols. All samples showed a A260/280 ratio >1.99 (Nanodrop; Thermo Scientific). Prior to library preparation, quality control of the RNA was performed using the Advanced Analytical Technologies Fragment Analyzer (Advanced Analytical, Inc.) and analyzed using PROSize 2.0.0.51 software. RNA Quality Numbers (RQNs) were computed per sample, indicating fully intact total RNA per sample prior to library preparation.

Example 16. RNA-Seq Library Preparation

Strand-specific ribosomal RNA (rRNA) depleted RNA-Seq libraries were prepared from 1 µg of total RNA using the KAPA Stranded RNA-Seq Kit with Ribo-Erase (Kapa Biosystems, Roche). Briefly, rRNA was depleted from total RNA samples, the remaining RNA was heat fragmented, and strand-specific cDNA was synthesized using a first strand random priming and second strand dUTP incorporation approach. Fragments were then A-tailed, adapters were ligated, and libraries were amplified using high-fidelity PCR. All libraries were prepared in technical duplicates per sample (n=60 samples, 120 libraries total), and resulting raw sequencing reads merged for downstream alignment and analysis. Libraries were paired-end sequenced at 2×125 bp on an Illumina HiSeq.

Example 17. Quantification and Statistical Analysis for Metabolomics Data Analysis Data analysis, including principal components analysis and clustering, was performed using the statistical language R v3.4.4 and Bioconductor v3.6.0 packages (Huber et al., Nat Methods (2015) 12, 115-121; R Core Team, A language and environment for statistical computing (2017) Vienna, Austria). Metabolite abundance was normalized per µg of protein content per metabolite extraction, and metabolites not detected were set to zero. Metabolite normalized amounts were scaled and centered into Z-scores across all samples for relative comparison using R base function scale ( ) with parameters "scale=TRUE, center=TRUE". Heatmaps and Euclidean distance similarity plots were created using the Z-scores in R package pheatmap v1.0.8, and hierarchical clustering was performed using the Euclidean distance measure.

Principal components analysis (PCA) was performed using R packages FactoMineR v1.34 and factoextra v1.0.5. Normalized metabolite amounts were standardized using a $\log_2$ (normalized amounts+1) transformation, and PC scores computed with function PCA( ) using parameters "scale.unit=TRUE, ncp=10, graph=FALSE". PCA individual score plots were plotted using function fviz_pca( ). PCA variable loadings plots were generated using function fviz_pca_var( ) extracting metabolite scores for contributions to the top ten principal components, strength of representation on the factor map ($cosine^2$) and variable coordinates indicating Pearson correlation coefficient r of each metabolite to the top ten principal components. Variable loadings were classified into k=3 separate clusters using k-means clustering in function kmeans ( ) using parameters "set.seed(123), centers=3, nstart25".

Metabolite trajectory clustering was performed using R Bioconductor package Mfuzz v2.38.0, soft clustering 6 supervised pattern trajectories of metabolites over control BJ development from fibroblast, iPSC, to MSC (Kumar and M, Bioinformation (2007) 2, 5-7). Prior to clustering, total metabolites were subset to metabolites that differentially fluctuate over any comparison of cell fate and transfer condition using R Bioconductor package limma v3.34.9, fitting a linear model to each metabolite and assessing differences in normalized abundance using an empirical Bayes moderated F-statistic with an adjusted P value threshold of 0.05, using the Benjamini-Hochberg false discovery rate of 0.05 (Benjamini and Hochberg, J Roy Stat Soc B Met (1995) 57, 289-300; Ritchie et al., Nucleic Acids Res (2015) 43, e47). Clustered metabolites were then ranked based on membership value to each cluster (Pearson correlation coefficient r). Sample metabolite Z-scores were then calculated and averaged across cell fate and condition for each trajectory, and boxplots generated using R package ggplot2 v2.2.1 for comparison. Significance testing across cell fate and transfer condition for each trajectory was calculated using the Kruskal-Wallis one-way analysis of variance (ANOVA).

Pathway-level metabolite set enrichment analysis was performed using R Bioconductor package GSVA v1.26.0

(Hanzelmann et al., BMC Bioinformatics (2013) 14, 7). Metabolite normalized abundances were standardized using a $\log_2$ (normalized amounts+1) transformation, and metabolites per sample were converted to a pathways per sample matrix using function gsva ( ) with parameters "method=gsva, rnaseq=FALSE, abs.ranking=FALSE, min.sz=5, max.sz=500". GSVA pathway enrichments scores were then extracted and significance testing across sample conditions was calculated using R Bioconductor package limma v3.34.9, as described above. Pathway metabolite sets were constructed using the KEGG Compound Database and derived from the existing Metabolite Pathway Enrichment Analysis (MPEA) toolbox (Kanehisa et al., Nucleic Acids Res (2012) 40, D109-114; Kankainen et al., Bioinformatics (2011) 27, 1878-1879).

Example 18. RNA-Seq Pre-Processing

Fibroblasts, iPSCs, and MSCs were each sequenced in biological triplicates and technical duplicates (n=60 total samples) to account for variation in extraction and culturing. Raw sequencing reads were converted into fastq files and filtered for low quality reads and Illumina sequencing adapter contamination using bcl2fastq (Illumina). Reads were then quasi-mapped and quantified to the *Homo sapiens* GENCODE 28 (GRCh38.p12, Ensembl 92, April 2018) transcriptome using the alignment-free transcript level quantifier Salmon v0.9.1 (Harrow et al., Genome Res (2012) 22, 1760-1774; Mudge and Harrow, Mamm Genome (2015) 26, 366-378; Patro et al., Nat Methods (2017) 14, 417-419). A quasi-mapping index was prepared using parameters "salmon index-k 31-type quasi", and comprehensive transcript level estimates were calculated using parameters "salmon quant-lA-seqBias-gcBias—discardOrphansQuasi". Transcript level counts were collapsed to gene level (HGNC) counts, transcripts per million abundances (TPM) and estimated lengths using R Bioconductor package tximport v1.6.0 (Soneson et al., F1000 Res (2015) 4, 1521).

Example 19. Differential Gene Expression Analysis

The resulting sample gene count matrix was size factor normalized and analyzed for pairwise differential gene expression using R Bioconductor package DESeq2 v1.18.1. Expression changes were estimated using an empirical Bayes procedure to generate moderated fold change values with design "~ Batch+Sample", modeling batch effect variation due to day of RNA extraction (Huber et al., Nat Methods (2015) 12, 115-121; Love et al., Genome Biol (2014) 15, 550). Significance testing was performed using the Wald test, and resulting P values were adjusted for multiple testing using the Benjamini-Hochberg procedure (Benjamini and Hochberg, J Roy Stat Soc B Met (1995) 57, 289-300). DEGs were filtered using an adjusted false discovery rate (FDR) q value <0.05 and an absolute $\log_2$ transformed fold-change >1.

Example 20. Gene Expression PCA

Variance stabilized transform (VST) values in the gene count matrix were calculated and plotted for principal component analysis (PCA) using R Bioconductor packages DESeq2, FactoMineR, and factoextra, as described in the metabolomics methods (Huber et al., Nat Methods (2015) 12, 115-121; Love et al., Genome Biol (2014) 15, 550). PCA of nuclear-encoded mitochondrial protein and mtDNA transcripts were extracted using localization evidence derived from MitoMiner v4.0, subsetting VST matrices using genes listed in MitoCarta 2.0 (Calvo et al., Nucleic Acids Res (2016) 44, D1251-1257; Smith and Robinson, Nucleic Acids Res (2017) 44, D1258-1261). Scatterplots and MA plots of gene expression fold-changes between fibroblasts, iPSCs, and MSCs were performed, and Pearson/Spearman correlation coefficients calculated, using R package ggpubr v0.1.6 (https://cran.r-project.org/web/packages/ggpubr/index-.html). Genes of interest were extracted and averaged clonal heatmaps were prepared using R Bioconductor packages pheatmap v1.0.8 and gplots v3.0.1. Venn diagram intersections of DEG lists were generated using Venny 2.1.0 (http://bioinfogp.cnb.csic.es/tools/venny/index.html)

Example 21. Metabolic Transcript Gene Set Variation Analysis (GSVA)

GSVA on metabolic transcripts were performed similarly to metabolomics data as noted above. Pathway-level metabolic gene set enrichment analysis was performed using R Bioconductor package GSVA v1.26.0 function gsva ( ) with parameters "method=gsva, rnaseq=FALSE, abs.ranking=FALSE, min.sz=5, max.sz=500" using a $\log_2$ (TPM+1) transformed gene expression matrix (Hanzelmann et al., BMC Bioinformatics (2013) 14, 7). GSVA pathway enrichment scores per sample were extracted and assessed for significance using R Bioconductor package limma v3.34.9, as described above except with a Benjamini-Hochberg adjusted P value threshold=0.01. Pathway metabolite sets were constructed using the KEGG PATHWAY Database, utilizing gene sets annotated to the metabolic pathways overview map HSA01100 (Kanehisa et al., Nucleic Acids Res (2012) 40, D109-114). Significance testing across clones and conditions for each gene set were calculated using Kruskal-Wallis ANOVA.

Example 22. Gene Set Overrepresentation Analysis (ORA)

DEGs were extracted and analyzed for pathway/gene ontology (GO) term overrepresentation using the R Bioconductor package clusterProfiler v3.6.0 and ReactomePA v1.22.0, using a background gene set of all genes expressed with at least one read count in the sample gene count matrix (Yu and He, Mol Biosyst (2016) 12, 477-479; Yu et al., OMICS (2012) 16, 284-287). Overrepresented Reactome/KEGG pathways and GO terms were identified across DEG lists and conditions using clusterProfiler function compareCluster ( ) with significance testing cutoffs of P<0.05, and an adjusted FDR <0.25.

Example 23. Mutation Signature Comparison

A comparison of mutation signatures between 5 μM-ddC treated BJs and the BJ parent with 30× whole genome sequencing.

TABLE 1

| | Non-synonymous mutations | Mutation rate |
| --- | --- | --- |
| ddC-treated BJs vs. BJ parent | 26 | 0.6/MB |

TABLE 2

| A comparison of mutation signatures between 5 μM- ddC treated BJs and the BJ parent with 30X whole genome sequencing. | | | | |
|---|---|---|---|---|
| Signature | # SNVs | % of Total | Caused by | Associated with | Common tumor types |
| Signature 5 | 2,230 | 42.0 | Unknown | Transcriptional strand bias for T > C mutations | All |
| Signature 8 | 873 | 16.0 | Unknown | Weak strand bias for C > A mutations | Breast, Medulloblastoma |
| Signature 9 | 854 | 16.0 | DNA repair by polymerase eta | Activity of AID during somatic hypermutations | CLL, B-Cell Lymphoma |
| Signature 18 | 471 | 9.0 | Unknown | — | Neuroblastoma |
| Signature 16 | 200 | 4.0 | Unknown | Strong transcriptional strand bias for T > C mutations | Liver |

Example 24. Metabolic Analysis

In other studies, it has been shown that 1 of 3 generated mitochondrial recipient clones failed to reset its metabolic profile from the p0 cell line to the parental phenotype (Wu et al., Cell Metab. (2016) v 23, p921-929). In the present application, the metabolic resetting potential of p0 fibroblast cells, as opposed to established cancer lines, was investigated, and a high throughput transfer platform was used to study the degree of metabolic heterogeneity after mitochondrial rescue. The metabolic profiles of BJ p0+HEK293T and BJ p0+LP351 cells at the fibroblast, iPSC, and MSC fates were quantified and compared to the BJ parental cell line to determine whether introducing exogenous mtDNA produces deleterious phenotypes. An analysis of the steady-state levels of 154 metabolites showed unique profiles for fibroblast, iPSC, and MSC fates regardless of mitochondrial transfer condition (FIG. 23A). A principal component analysis (PCA) of the metabolites among the transfer conditions and cell fates showed three main clusters representing the fibroblast, iPSC, and MSC cell fates (FIG. 23B). The clones from transferred cell lines were clustered with the BJ control across all cell fates, with the exception of BJ p0+HEK293T iPSC clones 1 and 2, which segregated into their own distinct cluster (FIG. 23B, FIG. 30A-30B). These two clones clustered with the BJ control again following differentiation to the MSC fate, suggesting that metabolism may be further reset during differentiation.

The specific metabolites that drive the principal component separation of samples into their respective clusters were identified. Analysis of the metabolite contributions correlating to each principal component dimension segregated metabolites into three distinct groups that corresponded to cell fate (FIG. 23C). Fibroblasts were shown to exhibit elevated levels of amino acid, fatty acid, polyol pathway, and TCA cycle metabolites in comparison to iPSCs and MSCs (FIGS. 23A, 23C, 30A-30B). When compared to other conditions and fates, BJ p0+HEK293T fibroblasts showed a dramatic accumulation of the pyrimidine precursors carbamoyl aspartate and dihydroorotate, molecules dependent on a functioning ETC complex III for further processing (Acin-Perez et al., Mol Cell (2004) v. 13, p. 805-815). In BJ p0 fibroblasts with a severely impaired ETC, levels of the glycolytic intermediate glycerol 3-phosphate and TCA metabolites succinate and 2-hydroxyglutarate were higher in comparison to the other fates. In contrast to fibroblasts and MSCs, iPSCs derived from BJ, BJ p0+HEK293T clone 4, and all BJ p0+LP351 clones exhibited increased levels of deoxynucleotide and glycolytic metabolites, in addition to epigenetic-associated molecules such as S-adenosylmethionine, 5-methylthioadenosine, and acetyl-CoA. BJ p0+HEK293T iPSC clones 1 and 2 have decreased levels of these metabolites and instead exhibited increased levels of metabolites associated with the pentose phosphate pathway (ribulose-5-phosphate and sedoheptulose 7-phosphate), the TCA cycle/Krebs bicycle (arginine, fumarate and malate), and reactive oxygen damage (methionine sulfoxide).

Finally, MSCs were distinguished by high levels of nucleobase-derivatives, the ρ-fatty acid oxidation inhibitor malonyl-CoA and asparagine (FIG. 23A). In summary, this steady-state metabolomic analysis suggests mitochondrial transfer may generate heterogenous metabolic rescues depending on the delivered mtDNA.

The cell lines were further characterized by identifying and grouping metabolites whose abundances followed similar patterns of fluctuation through reprogramming and differentiation. Out of a total of 154 metabolites analyzed, 103 metabolites were identified with differential abundance across cell fates in the different transfer conditions (see, FIGS. 24A-24C). Six metabolite trajectories were characterized by distinct sets of metabolites elevated or reduced in only one cell fate relative to the other two (see, FIGS. 24A-24C). In comparison to the BJ control, BJ p0+LP351 cells had similar metabolite abundances across all six defined trajectories (see, FIGS. 24A-24C). However, BJ p0+HEK293T cells in general showed aberrant trajectories compared to the BJ parental line, as shown in trajectories 3, 4, and 6 that show no significant alteration in metabolites across fate (see, FIGS. 24A-24C). As previously observed, BJ p0+HEK293T iPSC clone 4 was significantly different from clones 1 and 2 and was the only one to resemble the BJ parental trajectories. In conclusion, this metabolomics data suggested that despite rescuing respiration and supporting reprogramming and differentiation, HEK293T mitochondrial delivery generated clones with inconsistent metabolism, which was not observed for BJ p0+LP351 cells.

Example 25. Transcriptomic Comparison of Transfer Cell Lines

Due to the metabolic differences observed in mitochondrial recipient clones, differences in the transcriptomes were quantified to assess the extent of exogenous mtDNA integration into p0 cells across fate. Analysis of total RNA transcripts by PCA and hierarchical clustering showed three distinct populations representing the fibroblast, iPSC, and MSC cell fates (see, FIG. 25A, 31A). Within each cluster, no significant differences were observed between mitochondrial and control cell lines. Closer examination of the genes associated with specific cell fates showed that expression levels of common pluripotency markers, including LIN28A (a reprogramming factor used in this study), POU5F1 (OCT4), SOX2, NANOG, and DNMT3B (Bharathan et al., Biol Open (2017) v6, p100-108; David and Polo, Stem Cell Res (2014) v12, p754-761), were highly expressed in iPSCs in comparison to all fibroblasts and MSCs (e.g., FIG. 25B). The expression of MMP1/3, SRGN, SHOX, TBX5, THY1, VSIR, ICAM1, ANPEP, S100A6, COL1A1, and COL1A2 was highly elevated in fibroblasts in comparison to the iPSC and MSC fates. Differentiating MSCs from fibroblasts is challenging due to the similarity in their marker expression (Denu et al., Acta Haematol (2016), v136, p85-97; Halfon et al., Stem Cells Dev (2011) v20, p53-66; Lv et al., Stem Cells (2014) v32, p1408-1419). However, expression of recognized markers in support of the MSC fate, including alkaline phosphatase (ALPL) CD44, CD73 (NT5E), and CD105 (ENG), were elevated in MSCs (Billing et al., Sci Rep (2016) v6, p21507; Jaiswal et al., J Biol Chem (2000), v275, p9645-9652). These data further validate the identity of the iPSC and MSC lines generated from mitochondrial recipient BJ p0 cells.

In-depth analysis of nuclear-encoded mitochondrial transcripts showed three distinct expression patterns represented by clusters corresponding to the fibroblast, iPSC, and MSC fates (see, FIG. 25C). nDNA-encoded mitochondrial transcript levels were reduced in BJ fibroblasts in comparison to BJ p0, BJ p0+HEK293T, and BJ p0+LP351 cells of the same fate (FIG. 25C). The levels of mtDNA transcripts were quantified among the different conditions and fates. mtDNA transcripts in BJ p0 transcripts were negligible for all 37 genes in comparison to the cell lines containing transferred or native mtDNA (see, FIG. 23D). PCA analysis of mtDNA transcripts further verified that BJ p0 were different from the other conditions and fates (FIG. 31B). Additionally, most tRNA transcripts encoded by the light strand were elevated in comparison to the heavy strand as previously reported (FIG. 25D) (Mercer et al., Cell (2011) 146, 645-658).

Metabolic pathway differences in these cell conditions and fates were elucidated. The expression of oxidative phosphorylation transcripts was significantly elevated in BJ p0, BJ p0+HEK293T, and BJ p0+LP351 fibroblasts in comparison to the BJ parental line (see, FIG. 25E, 31C-31D). The reprogramming of differentiated cells to pluripotent cells is reflected by a shift away from oxidative phosphorylation, which is demonstrated in all our iPSC lines by elevated glycolytic transcripts (FIG. 25E, 31C-31D). Metabolic pathways related to epigenome regulation and maintenance of pluripotency are also elevated, including the one carbon, methionine, folate, and CoA biosynthesis pathways. Interestingly, BJ p0+HEK293T iPSCs exhibited increased variance in several pathways in comparison to BJ p0+LP351 iPSCs, particularly retinol, arginine/proline, and glycerolipid metabolism. In contrast to iPSCs and fibroblasts, elevated levels of transcripts associated with glycosaminoglycan-related pathways were observed, which are important for MSC extracellular matrix production, commitment, and growth.

The differentially regulated molecular pathways in mitochondrial recipient cells of each fate were characterized to identify specific pathways affected by mitochondrial transfer. A PCA comparison of fibroblast transcripts showed BJ and BJ p0 cells were distinct and did not cluster together (FIG. 26A). In the BJ p0 line, a total of 225 genes were upregulated and 640 genes were downregulated, especially mtDNA-encoded ETC genes, in comparison to the BJ parental line (FIG. 31E). The BJ p0+HEK293T clusters close to the BJ p0 line, while the BJ p0+LP351 is distant from both the BJ and BJ p0 clusters. PCA analysis at iPSC reprogrammed fate showed that the distinction between mitochondrial recipient lines was lost during reprogramming, while the mitochondrial transfer lines still clustered independently of the BJ iPSC (FIG. 26A). Finally, separate clustering of the BJ p0, BJ p0+HEK293T, and BJ p0+LP351 conditions at the MSC fate was not observed (FIG. 26A).

A more detailed pathway analysis revealed that 173, 0, and 122 genes identified in overrepresented reactome pathways were upregulated, and 278, 205, and 315 genes were downregulated in the BJ p0, BJ p0+HEK293T, and BJ p0+LP351 conditions, respectively, at the fibroblast fate in comparison to the BJ (FIG. 26B). Both BJ p0 and BJ p0+LP351 upregulated pathways associated with extracellular matrix production, while only the BJ p0+LP351 line upregulated receptor tyrosine kinase signaling. In contrast, BJ p0, BJ p0+HEK293T, and BJ p0+LP351 lines all downregulated the complement cascade, with only the BJ p0+LP351 also downregulating the IGF transport pathway. A smaller number of genes were identified to be overrepresented in reactome pathways at the iPSC fate, with 19 and 1 genes upregulated and downregulated in the BJ p0+LP351, respectively, in comparison to the BJ iPSC (FIG. 26G). Likewise, 14 and 3 genes were upregulated and downregulated in the BJ p0+HEK293T iPSCs, respectively (FIG. 26B, 26D, 26F). Identical pathways were upregulated in the mitochondrial recipient iPSCs and included those associated with histone protein modifications and epigenome remodeling. However, genes associated with bone development were only downregulated in BJ p0+HEK293T. Finally, 13 and 3 genes were upregulated and downregulated in the BJ p0+LP351 MSCs, respectively, in comparison to the BJ MSCs (FIG. 26B, 26D, 26F). Furthermore, 19 and 0 genes were upregulated and downregulated in the BJ p0+LP351 MSCs, respectively. Both mitochondrial recipient lines upregulated pathways associated with transcription and epigenome regulation similar to the iPSCs, while BJ p0+LP351 also downregulated pluripotency pathways.

Finally, shared patterns of differentially expressed genes were quantified in the BJ p0+HEK293T and BJ p0+LP351 lines in comparison to the BJ parent to identify potential transfer signatures in mitochondria recipients (FIG. 26G, 32A-32C). At the fibroblast, iPSC, and MSC fates, a total of 91, 29, and 35 genes, respectively, were similarly altered in the p0+HEK293T and BJ p0+LP351 lines. Of these, no differentially expressed genes were shared between the fibroblast-iPSC or fibroblast-MSC fates. However, 14 differentially expressed genes were shared between the iPSC and MSC fates. Among these genes were histones (HIST1H1A, HIST2H2BA, HIST1H3A, HIST1H4A), zinc finger proteins (ZNF560, ZNF662), non-coding RNAs (FLG-AS1, SVIL-AS1, LINC01535, MEG3), filaggrin (FLG), and glutathione S-transferase Mu 5 (GSTM5) (data not shown). In summary, the transcriptomics data demonstrate that initial large differences in transcription among mitochondrial recipients dissipate with reprogramming and differentiation. Furthermore, many of the genes shared among mitochondrial recipient lines at the iPSC and MSC fate are associated with remodeling of the nuclear genome.

Present techniques have the capability of successfully transferring mitochondria into a clinically-relevant mtDNA-deficient cell line, and integrating the isolated, exogenous mitochondria into cells to generate functionally reprogrammed and differentiated cell types that are difficult to obtain otherwise. These techniques use a high-throughput mitochondrial delivery platform to transfer mitochondria isolated from an established cancer cell line or primary PBMCs into a p0 fibroblast. BJ p0 cells receiving HEK293T mitochondria produce approximately twice as many colonies as those transferred PBMC mitochondria, which may be due to nDNA-mtDNA incompatibilities that adjust metabolism (Latorre-Pellicer et al., Nature (2016) 535, 561-565). Interestingly, the BJ p0, BJ p0+HEK293T, and BJ p0+LP351 fibroblasts cluster together by PCA and each condition shows downregulated elements of the classical complement cascade relative to BJ fibroblasts with their original mtDNA. The complement cascade is a primary component of the innate immune system that is able to opsonize and degrade pathogens. Importantly, the complement pathway may recognize extracellular mitochondria to initiate an immune response, and cybrids containing mutant mtDNA display an intracellular complement response to the detrimental mitochondria (Brinkmann et al., Biol Chem (2013) 288, 8016-8027; Kenney et al., Hum Mol Genet (2014) 23, 3537-3551; Nashine et al., PLOS One (2016) 11, e0159828). In our study, complement may be an important mechanism to ensure efficient mtDNA-nDNA integration.

The present techniques may be used to perform transcriptomic analysis on a mitochondrial transfer line and demonstrate resetting with fate, which reduces the variance caused by mtDNA identity at the iPSC fate and becomes indistinguishable in MSCs. Replacing the variety of differentially expressed genes at the fibroblast fate, mitochondrial recipient iPSCs and MSCs have similar nDNA-encoded mitochondria transcript levels and strictly increase the expression of pathways associated with epigenome remodeling compared to the BJ control. An analysis of genes differentially expressed from the BJ line across mitochondrial identities and cell fates did not identify genes shared between the iPSC and MSC fates with fibroblasts. In contrast, mitochondrial transfer iPSCs and MSCs share 14 genes that are differentially expressed, including histones H1.1, H2A pseudogene, H3, and H4, in addition to zinc finger nucleic acid binding proteins. mtDNA in these conditions may facilitate increased gene expression and epigenetic plasticity in comparison to the BJ control due to potential mtDNA-and nDNA-encoded mitochondrial complex interactions and consequential modulation of metabolite production (Venkatesh and Workman, Nat Rev Mol Cell Biol (2015) 16, 178-189).

Despite relative transcriptomic similarity among the conditions, BJ p0+HEK293T clones exhibit significant metabolic variation in comparison to the BJ p0+LP351 at all observed fates. Although trilineage differentiation into adipocytes, chondrocytes, and osteocytes was successful for MSCs regardless of mtDNA, BJ p0+HEK293T adipocytes and osteocytes appeared to be less mature measured by fewer lipid droplets and calcium deposits compared to those derived from BJs. Furthermore, although the BJ control produced the largest chondrocytes, the BJ p0+LP351 osteocytes produced the most calcium. These data support other studies that suggest mtDNA, mitochondrial oxidative phosphorylation, and metabolic byproducts are important for MSC differentiation.

Thus, the transcriptomes of transferred cells were distinct at the fibroblast fate and exhibited downregulated complement cascade but were indistinguishable from nDNA-matched control cells when converted to MSCs. Furthermore, HEK293T and PBMC transferred lines had unique metabolomic profiles and produced adipocyte, osteocyte, and chondrocytes of different maturity. Transcriptomic variation in transfer recipients may be removed by reprogramming.

High-throughput, novel mitochondrial transfer techniques are presented to generate cells of different fates with specific nDNA-mtDNA combinations. Although these techniques focus on mtDNA without pathogenic mutations, these techniques may be applied to transfer mutant mtDNA to generate patient specific disease and drug screening models for mtDNA disease in otherwise difficult to obtain cell types, such as cardiomyocytes and astrocytes.

Additionally, mitochondrial transfer has the potential to expand upon the repertoire of genomic combinations present in the human population and generate a library of cells at various fates with defined mtDNA-nDNA combinations and unique functional properties for research and therapeutic applications. The present techniques may be used to generate rescued cell lines from primary cells. Transfer recipients may integrate mtDNA to allow iPSC and MSC generation.

Patient-derived differentiated and multipotent cell lines with specific nDNA-mtDNA combinations enables the quantification of mtDNA pathologies in cell types that are hard to obtain or that have limited lifespans. The present techniques also facilitate the elucidation of biomarkers for mitochondrial disorders (Pfeffer et al., Nat Rev Neurol (2013) 9, 474-481) and the establishment of patient-specific models for drug discovery and individualized medicine (Lorenz et al., Cell Stem Cell (2017) 20, 659-674 e65).

What is claimed is:

1. A method of transfecting cells comprising:

transfecting a macrostructure comprising RNA, DNA, or a combination thereof into the cells to produce transfected cells, wherein the cells are transfected with the macrostructure using a device that generates pressure from displacement of a configurable actuator, wherein the configurable actuator is a voice coil actuator or a planar magnetic speaker.

2. The method of claim 1, further comprising reprogramming the transfected cells into induced pluripotent stem cells, and differentiating the induced pluripotent stem cells into engineered cells.

3. The method of claim 2, wherein the engineered cells are selected from the group consisting of cardiomyocyte cells, retinal epithelial cells, neural progenitor cells, and mesenchymal stem cells.

4. The method of claim 1, wherein the cells are selected from the group consisting of fibroblasts, epithelial cells, lymphocytes, NK cells, EC-7 cells, T cells, embryonic cells, stem cells, macrophages, and gamete cells.

5. The method of claim 1, wherein the configurable actuator generates a force that is applied to a deformable fluid reservoir comprising the macrostructure, and wherein the force has a linear relationship with regard to an input voltage of the configurable actuator.

6. The method of claim 1, wherein a machine learning system is utilized to determine optimal transfection parameters for transfecting cells with the macrostructure.

7. The method of claim 6, wherein the transfection parameters include one or more of a displacement of a component of the voice coil actuator, a frequency and a magnitude of a voltage-based waveform for input to the voice coil actuator, and a duration of applied pressure by the voice coil actuator.

8. The method of claim 7, wherein the magnitude of the voltage-based waveform provided as input to the voice coil actuator ranges from about 0.1 volts to about 10 volts and the displacement of the component of the voice coil actuator is about 0.1 mm to about 10 mm.

9. The method of claim 8, wherein the magnitude of the voltage-based waveform provided as input to the voice coil actuator ranges from about 1 volt to about 3 volts and the displacement of the component of the voice coil actuator is about 1 mm to about 3 mm.

10. The method of claim 1, wherein the voice coil actuator applies a continuous force of about 0.1 N to about 34 N with a displacement of about 1 mm to about 10 mm.

* * * * *

SEQUENCE LISTING

```
Sequence total quantity: 77
SEQ ID NO: 1           moltype = DNA  length = 20
FEATURE                Location/Qualifiers
misc_feature           1..20
                       note = ND1 forward
source                 1..20
                       mol_type = other DNA
                       organism = synthetic construct
SEQUENCE: 1
ccctaaaacc cgccacatct                                        20

SEQ ID NO: 2           moltype = DNA  length = 20
FEATURE                Location/Qualifiers
misc_feature           1..20
                       note = ND1 reverse
source                 1..20
                       mol_type = other DNA
                       organism = synthetic construct
SEQUENCE: 2
cgatggtgag agctaaggtc                                        20
```

-continued

```
SEQ ID NO: 3               moltype = DNA   length = 20
FEATURE                    Location/Qualifiers
misc_feature               1..20
                           note = GAPDH forward
source                     1..20
                           mol_type = other DNA
                           organism = synthetic construct
SEQUENCE: 3
tgcaccacca actgcttagc                                            20

SEQ ID NO: 4               moltype = DNA   length = 21
FEATURE                    Location/Qualifiers
misc_feature               1..21
                           note = GAPDH reverse
source                     1..21
                           mol_type = other DNA
                           organism = synthetic construct
SEQUENCE: 4
ggcatggact gtggtcatga g                                          21

SEQ ID NO: 5               moltype = DNA   length = 26
FEATURE                    Location/Qualifiers
misc_feature               1..26
                           note = D-Loop sequencing primer - forward
source                     1..26
                           mol_type = other DNA
                           organism = synthetic construct
SEQUENCE: 5
ttccaaggac aaatcagaga aaaagt                                     26

SEQ ID NO: 6               moltype = DNA   length = 25
FEATURE                    Location/Qualifiers
misc_feature               1..25
                           note = D-Loop sequencing primer - reverse
source                     1..25
                           mol_type = other DNA
                           organism = synthetic construct
SEQUENCE: 6
agcccgtcta aacattttca gtgta                                      25

SEQ ID NO: 7               moltype = DNA   length = 57
FEATURE                    Location/Qualifiers
misc_feature               1..57
                           note = DsRed HEK
source                     1..57
                           mol_type = other DNA
                           organism = synthetic construct
SEQUENCE: 7
aatccacatc aaaacccct cctcatgctt acaagcaagt acagcaatca accctca    57

SEQ ID NO: 8               moltype = DNA   length = 57
FEATURE                    Location/Qualifiers
misc_feature               1..57
                           note = 0329BJ_HEKmito
source                     1..57
                           mol_type = other DNA
                           organism = synthetic construct
SEQUENCE: 8
aatccacatc aaaacccct cctcatgctt acaagcaagt acagcaatca accctca    57

SEQ ID NO: 9               moltype = DNA   length = 57
FEATURE                    Location/Qualifiers
misc_feature               1..57
                           note = 0526 HDF adult_HEKmito
source                     1..57
                           mol_type = other DNA
                           organism = synthetic construct
SEQUENCE: 9
aatccacatc aaaacccct cctcatgctt acaagcaagt acagcaatca accctca    57

SEQ ID NO: 10              moltype = DNA   length = 57
FEATURE                    Location/Qualifiers
misc_feature               1..57
                           note = 0526 HDF neo_HEKmito
source                     1..57
                           mol_type = other DNA
                           organism = synthetic construct
SEQUENCE: 10
```

```
aatccacatc aaaacccct cctcatgctt acaagcaagt acagcaatca accctca         57

SEQ ID NO: 11              moltype = DNA  length = 57
FEATURE                    Location/Qualifiers
misc_feature               1..57
                           note = BJ
source                     1..57
                           mol_type = other DNA
                           organism = synthetic construct
SEQUENCE: 11
aatccacatc aaaacccct ccccatgctt acaagcaagt acagcaatca accccca         57

SEQ ID NO: 12              moltype = DNA  length = 57
FEATURE                    Location/Qualifiers
misc_feature               1..57
                           note = HDF adult
source                     1..57
                           mol_type = other DNA
                           organism = synthetic construct
SEQUENCE: 12
aatccacatc aaaacccct ccccatgctt acaagcaagt acagcaatca accttca         57

SEQ ID NO: 13              moltype = DNA  length = 57
FEATURE                    Location/Qualifiers
misc_feature               1..57
                           note = HDF neo
source                     1..57
                           mol_type = other DNA
                           organism = synthetic construct
SEQUENCE: 13
aatccacatc aaaacccct ccccatgctt acaagcaagt acaacaatca accttca         57

SEQ ID NO: 14              moltype = DNA  length = 58
FEATURE                    Location/Qualifiers
misc_feature               1..58
                           note = Pbmc LP351
source                     1..58
                           mol_type = other DNA
                           organism = synthetic construct
SEQUENCE: 14
caatccacat caaaacccc tccccatgct tacaagcaag tacagcaatc aaccctca       58

SEQ ID NO: 15              moltype = DNA  length = 58
FEATURE                    Location/Qualifiers
misc_feature               1..58
                           note = 0.29BJ_LP351mito
source                     1..58
                           mol_type = other DNA
                           organism = synthetic construct
SEQUENCE: 15
caatccacat caaaacccc tccccatgct tacaagcaag tacagcaatc aaccctca       58

SEQ ID NO: 16              moltype = DNA  length = 58
FEATURE                    Location/Qualifiers
misc_feature               1..58
                           note = 0526 HDF adult_LP351mito
source                     1..58
                           mol_type = other DNA
                           organism = synthetic construct
SEQUENCE: 16
caatccacat caaaacccc tccccatgct tacaagcaag tacagcaatc aaccctca       58

SEQ ID NO: 17              moltype = DNA  length = 58
FEATURE                    Location/Qualifiers
misc_feature               1..58
                           note = 0526 HDF neo_LP351mto
source                     1..58
                           mol_type = other DNA
                           organism = synthetic construct
SEQUENCE: 17
caatccacat caaaacccc tccccatgct tacaagcaag tacagcaatc aaccctca       58

SEQ ID NO: 18              moltype = DNA  length = 58
FEATURE                    Location/Qualifiers
misc_feature               1..58
                           note = BJ
source                     1..58
                           mol_type = other DNA
                           organism = synthetic construct
```

-continued

```
SEQUENCE: 18
caatccacat caaaacccc tccccatgct tacaagcaag tacagcaatc aacccccca      58

SEQ ID NO: 19            moltype = DNA  length = 58
FEATURE                  Location/Qualifiers
misc_feature             1..58
                         note = HDF adult
source                   1..58
                         mol_type = other DNA
                         organism = synthetic construct
SEQUENCE: 19
caatccacat caaaacccc tccccatgct tacaagcaag tacagcaatc aaccttca       58

SEQ ID NO: 20            moltype = DNA  length = 58
FEATURE                  Location/Qualifiers
misc_feature             1..58
                         note = HDF neo
source                   1..58
                         mol_type = other DNA
                         organism = synthetic construct
SEQUENCE: 20
caatccacat caaaacccc tccccatgct tacaagcaag tacaacaatc aaccttca       58

SEQ ID NO: 21            moltype = DNA  length = 59
FEATURE                  Location/Qualifiers
misc_feature             1..59
                         note = Pbmc LP298
source                   1..59
                         mol_type = other DNA
                         organism = synthetic construct
SEQUENCE: 21
caatccacat caaaaccctc tccccatgct tacaagcaag tacagcaatc aaccttcaa     59

SEQ ID NO: 22            moltype = DNA  length = 59
FEATURE                  Location/Qualifiers
misc_feature             1..59
                         note = 0329BJ_LP298mito
source                   1..59
                         mol_type = other DNA
                         organism = synthetic construct
SEQUENCE: 22
caatccacat caaaaccctc tccccatgct tacaagcaag tacagcaatc aaccttcaa     59

SEQ ID NO: 23            moltype = DNA  length = 59
FEATURE                  Location/Qualifiers
misc_feature             1..59
                         note = 0526 HDF neo_LF298mito
source                   1..59
                         mol_type = other DNA
                         organism = synthetic construct
SEQUENCE: 23
caatccacat caaaaccctc tccccatgct tacaagcaag tacagcaatc aaccttcaa     59

SEQ ID NO: 24            moltype = DNA  length = 59
FEATURE                  Location/Qualifiers
misc_feature             1..59
                         note = BJ
source                   1..59
                         mol_type = other DNA
                         organism = synthetic construct
SEQUENCE: 24
caatccacat caaaacccc tccccatgct tacaagcaag tacagcaatc aacccccaa      59

SEQ ID NO: 25            moltype = DNA  length = 59
FEATURE                  Location/Qualifiers
misc_feature             1..59
                         note = HDF adult
source                   1..59
                         mol_type = other DNA
                         organism = synthetic construct
SEQUENCE: 25
caatccacat caaaacccc tccccatgct tacaagcaag tacagcaatc aaccttcaa      59

SEQ ID NO: 26            moltype = DNA  length = 59
FEATURE                  Location/Qualifiers
misc_feature             1..59
                         note = HDF neo
source                   1..59
                         mol_type = other DNA
```

```
                              organism = synthetic construct
SEQUENCE: 26
caatccacat caaaaccccc tccccatgct tacaagcaag tacaacaatc aaccttcaa      59

SEQ ID NO: 27                 moltype = DNA   length = 64
FEATURE                       Location/Qualifiers
misc_feature                  1..64
                              note = BJ
source                        1..64
                              mol_type = other DNA
                              organism = synthetic construct
SEQUENCE: 27
aagccacccc tcacccacta ggataccaac aaacctaccc acccttaaca gtacatagca      60
cata                                                                   64

SEQ ID NO: 28                 moltype = DNA   length = 64
FEATURE                       Location/Qualifiers
misc_feature                  1..64
                              note = HEK
source                        1..64
                              mol_type = other DNA
                              organism = synthetic construct
SEQUENCE: 28
aagtcacccc tcacccatta ggataccaac aaacctaccc acccttaaca gtacatagta      60
cata                                                                   64

SEQ ID NO: 29                 moltype = DNA   length = 64
FEATURE                       Location/Qualifiers
misc_feature                  1..64
                              note = BJ with HEK mitochondria
source                        1..64
                              mol_type = other DNA
                              organism = synthetic construct
SEQUENCE: 29
aagtcacccc tcacccatta ggataccaac aaacctaccc acccttaaca gtacatagta      60
cata                                                                   64

SEQ ID NO: 30                 moltype = DNA   length = 64
FEATURE                       Location/Qualifiers
misc_feature                  1..64
                              note = PBMC, LP351
source                        1..64
                              mol_type = other DNA
                              organism = synthetic construct
SEQUENCE: 30
aagccacccc tcacccacta ggataccaac aaacctaccc acccttaaca gtacatagta      60
cata                                                                   64

SEQ ID NO: 31                 moltype = DNA   length = 64
FEATURE                       Location/Qualifiers
misc_feature                  1..64
                              note = 032917BJ_HEKmito_iPS 1
source                        1..64
                              mol_type = other DNA
                              organism = synthetic construct
SEQUENCE: 31
aagccacccc tcacccacta ggataccaac aaacctaccc acccttaaca gtacatagta      60
cata                                                                   64

SEQ ID NO: 32                 moltype = DNA   length = 287
FEATURE                       Location/Qualifiers
misc_feature                  1..287
                              note = DsRed HEK (mito donor)
source                        1..287
                              mol_type = other DNA
                              organism = synthetic construct
SEQUENCE: 32
atcaaaaccc cctcctcatg cttacaagca agtacagcaa tcaaccctca actatcacac      60
atcaactgca actccaaagt caccccctcac ccattaggat accaacaaac ctacccaccc     120
ttaacagtac atagtacata aagccattta ccgtacatag cacattacag tcaaatccct      180
tctcgtcccc atggatgacc cccctcagat aggggtccct tggccaccat cctccgtgaa      240
atcaatatcc cgcacaagag tgctactctc ctcgctccgg gcccata                    287

SEQ ID NO: 33                 moltype = DNA   length = 287
FEATURE                       Location/Qualifiers
misc_feature                  1..287
                              note = BJ iPS P3M1
source                        1..287
                              mol_type = other DNA
```

-continued

```
                              organism = synthetic construct
SEQUENCE: 33
atcaaaaccc cctccccatg cttacaagca agtacagcaa tcaacccca actatcacac       60
atcaactgca actccaaagc cacccctcac ccactaggat accaacaaac ctacccaccc     120
ttaacagtac atagcacata aagccattta ccgtacatag cacattacag tcaaatccct     180
tctcgtcccc atggatgacc cccctcagat aggggtccct tgaccaccat cctccgtgaa     240
atcaatatcc cgcacaagag tgctactctc ctcgctccgg gcccata                   287

SEQ ID NO: 34             moltype = DNA  length = 287
FEATURE                   Location/Qualifiers
misc_feature             1..287
                          note = 032917BJ_HEKmito_iPS 1
source                    1..287
                          mol_type = other DNA
                          organism = synthetic construct
SEQUENCE: 34
atcaaaaccc cctcctcatg cttacaagca agtacagcaa tcaaccctca actatcacac       60
atcaactgca actccaaagt cacccctcac ccattaggat accaacaaac ctacccaccc     120
ttaacagtac atagtacata aagccattta ccgtacatag cacattacag tcaaatccct     180
tctcgtcccc atggatgacc cccctcagat aggggtccct tggccaccat cctccgtgaa     240
atcaatatcc cgcacaagag tgctactctc ctcgctccgg gcccata                   287

SEQ ID NO: 35             moltype = DNA  length = 287
FEATURE                   Location/Qualifiers
misc_feature             1..287
                          note = 032917BJ_HEKmito_iPS 2
source                    1..287
                          mol_type = other DNA
                          organism = synthetic construct
SEQUENCE: 35
atcaaaaccc cctcctcatg cttacaagca agtacagcaa tcaaccctca actatcacac       60
atcaactgca actccaaagt cacccctcac ccattaggat accaacaaac ctacccaccc     120
ttaacagtac atagtacata aagccattta ccgtacatag cacattacag tcaaatccct     180
tctcgtcccc atggatgacc cccctcagat aggggtccct tggccaccat cctccgtgaa     240
atcaatatcc cgcacaagag tgctactctc ctcgctccgg gcccata                   287

SEQ ID NO: 36             moltype = DNA  length = 287
FEATURE                   Location/Qualifiers
misc_feature             1..287
                          note = 032917BJ_HEKmito_iPS 4
source                    1..287
                          mol_type = other DNA
                          organism = synthetic construct
SEQUENCE: 36
atcaaaaccc cctcctcatg cttacaagca agtacagcaa tcaaccctca actatcacac       60
atcaactgca actccaaagt cacccctcac ccattaggat accaacaaac ctacccaccc     120
ttaacagtac atagtacata aagccattta ccgtacatag cacattacag tcaaatccct     180
tctcgtcccc atggatgacc cccctcagat aggggtccct tggccaccat cctccgtgaa     240
atcaatatcc cgcacaagag tgctactctc ctcgctccgg gcccata                   287

SEQ ID NO: 37             moltype = DNA  length = 287
FEATURE                   Location/Qualifiers
misc_feature             1..287
                          note = 032917BJ_HEKmito_iPS 5
source                    1..287
                          mol_type = other DNA
                          organism = synthetic construct
SEQUENCE: 37
atcaaaaccc cctcctcatg cttacaagca agtacagcaa tcaaccctca actatcacac       60
atcaactgca actccaaagt cacccctcac ccattaggat accaacaaac ctacccaccc     120
ttaacagtac atagtacata aagccattta ccgtacatag cacattacag tcaaatccct     180
tctcgtcccc atggatgacc cccctcagat aggggtccct tggccaccat cctccgtgaa     240
atcaatatcc cgcacaagag tgctactctc ctcgctccgg gcccata                   287

SEQ ID NO: 38             moltype = DNA  length = 184
FEATURE                   Location/Qualifiers
misc_feature             1..184
                          note = PBMC LP351 (mito donor)
source                    1..184
                          mol_type = other DNA
                          organism = synthetic construct
SEQUENCE: 38
atcaaaaccc cctccccatg cttacaagca agtacagcaa tcaaccctca actatcacac       60
atcaactgca actccaaagc cacccctcac ccactaggat accaacaaac ctacccaccc     120
ttaacagtac atagtacata aagccattta ccgtacatag cacattacag tcaaatcctt     180
tctc                                                                   184

SEQ ID NO: 39             moltype = DNA  length = 184
FEATURE                   Location/Qualifiers
```

```
misc_feature              1..184
                          note = BJ iPS P3M1
source                    1..184
                          mol_type = other DNA
                          organism = synthetic construct
SEQUENCE: 39
atcaaaaccc cctccccatg cttacaagca agtacagcaa tcaaccccca actatcacac    60
atcaactgca actccaaagc cacccctcac ccactaggat accaacaaac ctacccaccc   120
ttaacagtac atagcacata aagccattta ccgtacatag cacattacag tcaaatccct   180
tctc                                                              184

SEQ ID NO: 40             moltype = DNA   length = 184
FEATURE                   Location/Qualifiers
misc_feature              1..184
                          note = 032917BJ_LP351mito_iPS 1
source                    1..184
                          mol_type = other DNA
                          organism = synthetic construct
SEQUENCE: 40
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                              184

SEQ ID NO: 41             moltype = DNA   length = 184
FEATURE                   Location/Qualifiers
misc_feature              1..184
                          note = 032917BJ_LP351mito_iPS 2
source                    1..184
                          mol_type = other DNA
                          organism = synthetic construct
SEQUENCE: 41
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                              184

SEQ ID NO: 42             moltype = DNA   length = 184
FEATURE                   Location/Qualifiers
misc_feature              1..184
                          note = 032917BJ_LP351mito_iPS 3
source                    1..184
                          mol_type = other DNA
                          organism = synthetic construct
SEQUENCE: 42
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                              184

SEQ ID NO: 43             moltype = DNA   length = 184
FEATURE                   Location/Qualifiers
misc_feature              1..184
                          note = 032917BJ_LP351mito_iPS 4
source                    1..184
                          mol_type = other DNA
                          organism = synthetic construct
SEQUENCE: 43
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                              184

SEQ ID NO: 44             moltype = DNA   length = 184
FEATURE                   Location/Qualifiers
misc_feature              1..184
                          note = 032917BJ_LP351mito_iPS 8
source                    1..184
                          mol_type = other DNA
                          organism = synthetic construct
SEQUENCE: 44
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                              184

SEQ ID NO: 45             moltype = DNA   length = 184
FEATURE                   Location/Qualifiers
misc_feature              1..184
```

```
                              note = 032917BJ_LP351mito_iPS 9
source                        1..184
                              mol_type = other DNA
                              organism = synthetic construct
SEQUENCE: 45
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                               184

SEQ ID NO: 46                 moltype = DNA   length = 184
FEATURE                       Location/Qualifiers
misc_feature                  1..184
                              note = 032917BJ_LP351mito_iPS 10
source                        1..184
                              mol_type = other DNA
                              organism = synthetic construct
SEQUENCE: 46
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                               184

SEQ ID NO: 47                 moltype = DNA   length = 184
FEATURE                       Location/Qualifiers
misc_feature                  1..184
                              note = 032917BJ_LP351mito_iPS 11
source                        1..184
                              mol_type = other DNA
                              organism = synthetic construct
SEQUENCE: 47
atcaaaaccc cctccccatg cttacaagca agtacagcaa tcaaccctca actatcacac    60
atcaactgca actccaaagc cacccctcac ccactaggat accaacaaac ctacccaccc   120
ttaacagtac atagtacata aagccattta ccgtacatag cacattacag tcaaatcctt   180
tctc                                                               184

SEQ ID NO: 48                 moltype = DNA   length = 59
FEATURE                       Location/Qualifiers
misc_feature                  1..59
                              note = PBMC P351 (mito donor)
source                        1..59
                              mol_type = other DNA
                              organism = synthetic construct
SEQUENCE: 48
agtacatagt acataaagcc atttaccgta catagcacat tacagtcaaa tcctttctc    59

SEQ ID NO: 49                 moltype = DNA   length = 59
FEATURE                       Location/Qualifiers
misc_feature                  1..59
                              note = 032917BJ_LP351mito_iPs 1_MSC
source                        1..59
                              mol_type = other DNA
                              organism = synthetic construct
SEQUENCE: 49
agtacatagt acataaagcc atttaccgta catagcacat tacagtcaaa tcctttctc    59

SEQ ID NO: 50                 moltype = DNA   length = 59
FEATURE                       Location/Qualifiers
misc_feature                  1..59
                              note = 032917BJ_LP351mito_iPS 2_MSC
source                        1..59
                              mol_type = other DNA
                              organism = synthetic construct
SEQUENCE: 50
agtacatagt acataaagcc atttaccgta catagcacat tacagtcaaa tcctttctc    59

SEQ ID NO: 51                 moltype = DNA   length = 59
FEATURE                       Location/Qualifiers
misc_feature                  1..59
                              note = 032917BJ_LP351mito_iPS 11_MSC
source                        1..59
                              mol_type = other DNA
                              organism = synthetic construct
SEQUENCE: 51
agtacatagt acataaagcc atttaccgta catagcacat tacagtcaaa tcctttctc    59

SEQ ID NO: 52                 moltype = DNA   length = 59
FEATURE                       Location/Qualifiers
misc_feature                  1..59
```

-continued

```
                          note = BJ iPS P3M1 MSC
source                    1..59
                          mol_type = other DNA
                          organism = synthetic construct
SEQUENCE: 52
agtacatagc acataaagcc atttaccgta catagcacat tacagtcaaa tcccttctc     59

SEQ ID NO: 53             moltype = DNA   length = 59
FEATURE                   Location/Qualifiers
misc_feature              1..59
                          note = BJ
source                    1..59
                          mol_type = other DNA
                          organism = synthetic construct
SEQUENCE: 53
agtacatagc acataaagcc atttaccgta catagcacat tacagtcaaa tcccttctc     59

SEQ ID NO: 54             moltype = DNA   length = 59
FEATURE                   Location/Qualifiers
misc_feature              1..59
                          note = HEK (mito donor)
source                    1..59
                          mol_type = other DNA
                          organism = synthetic construct
SEQUENCE: 54
tacaagcaag tacagcaatc aaccctcaac tatcacacat caactgcaac tccaaagtc     59

SEQ ID NO: 55             moltype = DNA   length = 59
FEATURE                   Location/Qualifiers
misc_feature              1..59
                          note = 032917BJ_HEKmito_iPS1_MSC
source                    1..59
                          mol_type = other DNA
                          organism = synthetic construct
SEQUENCE: 55
tacaagcaag tacagcaatc aaccctcaac tatcacacat caactgcaac tccaaagtc     59

SEQ ID NO: 56             moltype = DNA   length = 59
FEATURE                   Location/Qualifiers
misc_feature              1..59
                          note = 032917BJ_HEKmito_iPS 2_MSC
source                    1..59
                          mol_type = other DNA
                          organism = synthetic construct
SEQUENCE: 56
tacaagcaag tacagcaatc aaccctcaac tatcacacat caactgcaac tccaaagtc     59

SEQ ID NO: 57             moltype = DNA   length = 59
FEATURE                   Location/Qualifiers
misc_feature              1..59
                          note = BJ iPS P3M1 MSC
source                    1..59
                          mol_type = other DNA
                          organism = synthetic construct
SEQUENCE: 57
tacaagcaag tacagcaatc aaccccaac tatcacacat caactgcaac tccaaagcc      59

SEQ ID NO: 58             moltype = DNA   length = 59
FEATURE                   Location/Qualifiers
misc_feature              1..59
                          note = BJ
source                    1..59
                          mol_type = other DNA
                          organism = synthetic construct
SEQUENCE: 58
tacaagcaag tacagcaatc aaccccaac tatcacacat caactgcaac tccaaagcc      59

SEQ ID NO: 59             moltype = DNA   length = 18
FEATURE                   Location/Qualifiers
misc_feature              1..18
                          note = BJ
source                    1..18
                          mol_type = other DNA
                          organism = synthetic construct
SEQUENCE: 59
gccacccctc acccacta                                                  18

SEQ ID NO: 60             moltype = DNA   length = 18
FEATURE                   Location/Qualifiers
```

-continued

```
misc_feature              1..18
                          note = HEK293T
source                    1..18
                          mol_type = other DNA
                          organism = synthetic construct
SEQUENCE: 60
gtcacccctc acccatta                                              18

SEQ ID NO: 61             moltype = DNA  length = 18
FEATURE                   Location/Qualifiers
misc_feature              1..18
                          note = LP351
source                    1..18
                          mol_type = other DNA
                          organism = synthetic construct
SEQUENCE: 61
gccacccctc acccacta                                              18

SEQ ID NO: 62             moltype = DNA  length = 18
FEATURE                   Location/Qualifiers
misc_feature              1..18
                          note = BJ p0+HEK293T
source                    1..18
                          mol_type = other DNA
                          organism = synthetic construct
SEQUENCE: 62
gtcacccctc acccatta                                              18

SEQ ID NO: 63             moltype = DNA  length = 18
FEATURE                   Location/Qualifiers
misc_feature              1..18
                          note = BJ p0+LP351
source                    1..18
                          mol_type = other DNA
                          organism = synthetic construct
SEQUENCE: 63
gccacccctc acccacta                                              18

SEQ ID NO: 64             moltype = DNA  length = 17
FEATURE                   Location/Qualifiers
misc_feature              1..17
                          note = BJ
source                    1..17
                          mol_type = other DNA
                          organism = synthetic construct
SEQUENCE: 64
gccacccctc acccact                                               17

SEQ ID NO: 65             moltype = DNA  length = 17
FEATURE                   Location/Qualifiers
misc_feature              1..17
                          note = BJ p0+HEK293T Clone 1
source                    1..17
                          mol_type = other DNA
                          organism = synthetic construct
SEQUENCE: 65
gtcacccctc acccatt                                               17

SEQ ID NO: 66             moltype = DNA  length = 17
FEATURE                   Location/Qualifiers
misc_feature              1..17
                          note = BJ p0 + HEK293T Clone 2
source                    1..17
                          mol_type = other DNA
                          organism = synthetic construct
SEQUENCE: 66
gtcacccctc acccatt                                               17

SEQ ID NO: 67             moltype = DNA  length = 17
FEATURE                   Location/Qualifiers
misc_feature              1..17
                          note = BJ p)+HEK293T Clone 4
source                    1..17
                          mol_type = other DNA
                          organism = synthetic construct
SEQUENCE: 67
gtcacccctc acccatt                                               17

SEQ ID NO: 68             moltype = DNA  length = 17
```

-continued

```
FEATURE                  Location/Qualifiers
misc_feature             1..17
                         note = BJ p0+LP351 Clone 1
source                   1..17
                         mol_type = other DNA
                         organism = synthetic construct
SEQUENCE: 68
gccacccctc acccact                                                    17

SEQ ID NO: 69            moltype = DNA   length = 17
FEATURE                  Location/Qualifiers
misc_feature             1..17
                         note = BJ p0+LP351 Clone2
source                   1..17
                         mol_type = other DNA
                         organism = synthetic construct
SEQUENCE: 69
gccacccctc acccact                                                    17

SEQ ID NO: 70            moltype = DNA   length = 17
FEATURE                  Location/Qualifiers
misc_feature             1..17
                         note = BJ p0+LP351 Clone 11
source                   1..17
                         mol_type = other DNA
                         organism = synthetic construct
SEQUENCE: 70
gccacccctc acccact                                                    17

SEQ ID NO: 71            moltype = DNA   length = 17
FEATURE                  Location/Qualifiers
misc_feature             1..17
                         note = BJ
source                   1..17
                         mol_type = other DNA
                         organism = synthetic construct
SEQUENCE: 71
gccacccctc acccact                                                    17

SEQ ID NO: 72            moltype = DNA   length = 17
FEATURE                  Location/Qualifiers
misc_feature             1..17
                         note = BJ p0+HEK293 Clone 1
source                   1..17
                         mol_type = other DNA
                         organism = synthetic construct
SEQUENCE: 72
gtcacccctc acccatt                                                    17

SEQ ID NO: 73            moltype = DNA   length = 17
FEATURE                  Location/Qualifiers
misc_feature             1..17
                         note = BJ p0+HEK293 Clone 2
source                   1..17
                         mol_type = other DNA
                         organism = synthetic construct
SEQUENCE: 73
gtcacccctc acccatt                                                    17

SEQ ID NO: 74            moltype = DNA   length = 17
FEATURE                  Location/Qualifiers
misc_feature             1..17
                         note = BJ p0+HEK293 Clone 4
source                   1..17
                         mol_type = other DNA
                         organism = synthetic construct
SEQUENCE: 74
gtcacccctc acccatt                                                    17

SEQ ID NO: 75            moltype = DNA   length = 17
FEATURE                  Location/Qualifiers
misc_feature             1..17
                         note = BJ p0+LP351
source                   1..17
                         mol_type = other DNA
                         organism = synthetic construct
SEQUENCE: 75
gccacccctc acccact                                                    17
```

-continued

```
SEQ ID NO: 76        moltype = DNA  length = 17
FEATURE              Location/Qualifiers
misc_feature         1..17
                     note = BJ p0+LP351
source               1..17
                     mol_type = other DNA
                     organism = synthetic construct
SEQUENCE: 76
gccacccctc acccact                                              17

SEQ ID NO: 77        moltype = DNA  length = 17
FEATURE              Location/Qualifiers
misc_feature         1..17
                     note = BJ p0+LP351 Clone 11
source               1..17
                     mol_type = other DNA
                     organism = synthetic construct
SEQUENCE: 77
gccacccctc acccact                                              17
```